US009714298B2

(12) United States Patent
Ohtsuka et al.

(10) Patent No.: US 9,714,298 B2
(45) Date of Patent: *Jul. 25, 2017

(54) ANTI-FGFR2 ANTIBODIES AND METHODS OF USE THEREOF FOR TREATING CANCER

(71) Applicant: Daiichi Sankyo Company, Limited, Chuo-ku, Tokyo (JP)

(72) Inventors: Toshiaki Ohtsuka, Tokyo (JP); Chigusa Yoshimura, Tokyo (JP); Toshinori Agatsuma, Tokyo (JP); Atsushi Urano, Tokyo (JP); Takako Kimura, Tokyo (JP); Yumi Matsui, Tokyo (JP); Tatsuji Matsuoka, Tokyo (JP); Jun Hasegawa, Tokyo (JP); Yasuki Kamai, Tokyo (JP); Reimi Kawaida, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/391,435

(22) PCT Filed: Apr. 9, 2013

(86) PCT No.: PCT/JP2013/061340
§ 371 (c)(1),
(2) Date: Oct. 9, 2014

(87) PCT Pub. No.: WO2013/154206
PCT Pub. Date: Oct. 17, 2013

(65) Prior Publication Data
US 2015/0125454 A1   May 7, 2015

(30) Foreign Application Priority Data
Apr. 9, 2012  (JP) .................. 2012-088299

(51) Int. Cl.
*C07K 16/40*  (2006.01)
*C07K 16/28*  (2006.01)
*A61K 39/395*  (2006.01)
*G01N 33/50*  (2006.01)
*G01N 33/574*  (2006.01)
*A61K 39/00*  (2006.01)

(52) U.S. Cl.
CPC ......... *C07K 16/40* (2013.01); *A61K 39/3955* (2013.01); *C07K 16/2863* (2013.01); *G01N 33/5011* (2013.01); *G01N 33/57419* (2013.01); *G01N 33/57446* (2013.01); *G01N 33/57492* (2013.01); *A61K 2039/505* (2013.01); *C07K 2317/14* (2013.01); *C07K 2317/24* (2013.01); *C07K 2317/33* (2013.01); *C07K 2317/40* (2013.01); *C07K 2317/41* (2013.01); *C07K 2317/55* (2013.01); *C07K 2317/565* (2013.01); *C07K 2317/732* (2013.01); *C07K 2317/76* (2013.01); *G01N 2333/71* (2013.01); *G01N 2500/04* (2013.01); *G01N 2800/52* (2013.01); *G01N 2800/54* (2013.01)

(58) Field of Classification Search
CPC ............ C07K 16/2863; C07K 2317/24; C07K 2317/33; C07K 2317/41; C07K 2317/55; C07K 2317/565; C07K 2317/732; C07K 2317/76; G01N 33/5011; G01N 33/57492; G01N 2333/71; G01N 2500/04; G01N 2800/52; G01N 2800/54; A61K 39/3955; A61K 2039/505
See application file for complete search history.

(56) References Cited

U.S. PATENT DOCUMENTS

2011/0305687 A1  12/2011  Weng et al.
2013/0142802 A1   6/2013  Chang et al.

FOREIGN PATENT DOCUMENTS

| JP | 2010-536384 A | 12/2010 |
|----|---------------|---------|
| JP | 2012-508184 A | 4/2012 |
| WO | WO 2009/026558 A1 | 2/2009 |
| WO | WO 2009/100105 A2 | 8/2009 |
| WO | WO 2010/054265 A2 | 5/2010 |
| WO | WO 2010/111367 A1 | 9/2010 |
| WO | WO 2011/143318 A2 | 11/2011 |
| WO | WO 2012/021841 A2 | 2/2012 |
| WO | WO 2014/160160 A2 | 10/2014 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Zhao et al., "Monoclonal Antibodies to Fibroblast Growth Factor Receptor 2 Effectively Inhibit Growth of Gastric Tumor Xenografts," Clin. Cancer Res., Jul. 29, 2010, 16(23):5750-5758.
Bai et al., "GP369, an FGFR2-IIIb-Specific Antibody, Exhibits Potent Antitumor Activity against Human Cancers Driven by Activated FGFR2 Signaling," Cancer Res., Oct. 1, 2010 (published online Aug. 13, 2010), 70(19):7630-7639.
Carstens et al., "Alternative splicing of fibroblast growth factor receptor 2 (FGF-R2) in human prostate cancer," Oncogene, Dec. 18, 1997, 15(25):3059-3065.
Chaffer et al., "Aberrant fibroblast growth factor receptor signaling in bladder and other cancers," Differentiation, Nov. 2007 (published online Aug. 14, 2007), 75(9):831-842.
Easton et al., "Genome-wide association study identifies novel breast cancer susceptibility loci," Nature, Jun. 28, 2007, 447(7148):1087-1095.
Eswarakumar et al., "Cellular signaling by fibroblast growth factor receptors," Cytokine & Growth Factor Reviews, Apr. 2005 (published online Feb. 1, 2005), 16(2):139-149.

(Continued)

*Primary Examiner* — Robert Landsman
(74) *Attorney, Agent, or Firm* — Foley & Lardner LLP

(57) ABSTRACT

The present invention provides an antibody which binds to a fibroblast growth factor receptor.

46 Claims, 79 Drawing Sheets

(56) References Cited

OTHER PUBLICATIONS

Hunter et al., "A genome-wide association study identifies alleles in FGFR2 associated with risk of sporadic postmenopausal breast cancer," Nature Genetics, Jun. 2007 (published online May 27, 2007), 39(6):870-874.
Katoh et al., "FGFR2-related pathogenesis and FGFR2-targeted therapeutics (Review)," International Journal of Molecular Medicine, Mar. 2009, 23(3):307-311.
Turner et al., "Fibroblast growth factor signaling: from development to cancer," Nature Reviews, Feb. 2010, 10(2):116-129.

\* cited by examiner

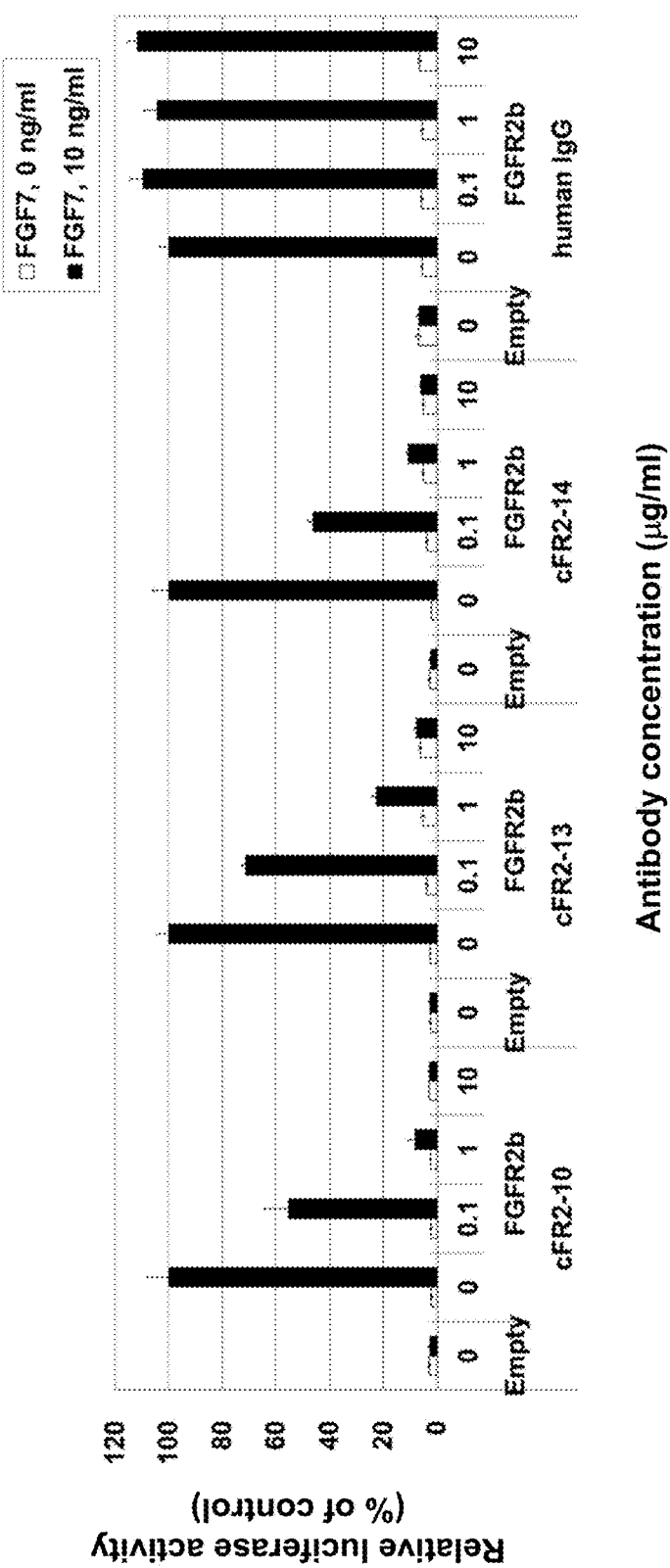

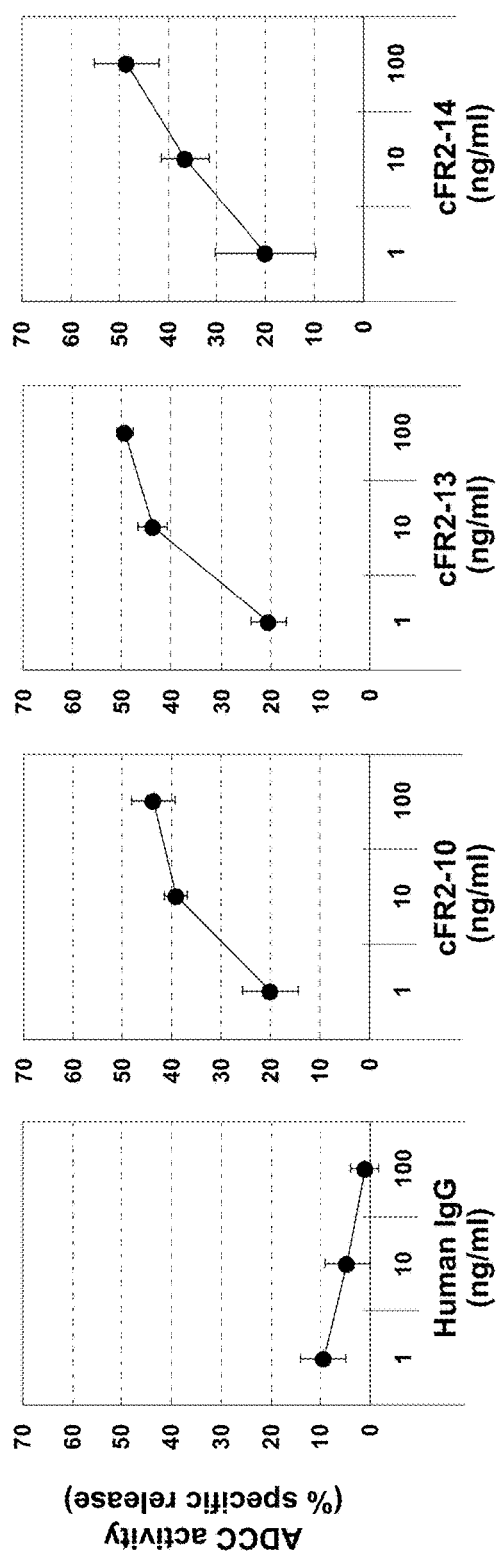

Figure 9

EVQLVESGGGLV
(SEQ ID NO: 1 of Sequence Listing)

Figure 10

DIQMTQSPSSLSA
(SEQ ID NO: 2 of Sequence Listing)

Figure 11

QVKLL
(SEQ ID NO: 3 of Sequence Listing)

Figure 12

DIQMTQSPASLSASLGE
(SEQ ID NO: 4 of Sequence Listing)

Figure 13

QVKLL
(SEQ ID NO: 5 of Sequence Listing)

Figure 14

DIQMTQSPASLSASLGE
(SEQ ID NO: 6 of Sequence Listing)

Figure 15

GAGTTACTTTTGAGAGCAGTTCCAGGAG
(SEQ ID NO: 7 of Sequence Listing)

Figure 16

GGTTCTCCCACTCAGTAATC
(SEQ ID NO: 8 of Sequence Listing)

Figure 17

CATATGATCAGTGTCCTCTC
(SEQ ID NO: 9 of Sequence Listing)

Figure 18

ATATGATCAGTGTCCTCTCC
(SEQ ID NO: 10 of Sequence Listing)

Figure 19 gaggtgcagctggtggagtctgggggaggcctggtgcagcctggaaggtctctgaaactatcctgtgtagcctctggatt
cagattcaatgacttttggatgacctggatccgccaggctccagggaaggggctggagtgggttgcatccattacttata
ctggtgataacacttactatgcaggctctgtgaagggccgaatcactatctccagagataatgcgaagagcaccctatac
ctgcaaatgaacagtctgaggtctgaggacacggccacttattactgtacaagagatgactacggaggatatagcccca
ctatatggatgcctggggtcaaggaacttcagtcactgtctcctca
Variable region (1-366)
(SEQ ID NO: 11 of Sequence Listing)

Figure 20

EVQLVESGGGLVQPGRSLKLSCVASGFRFNDFWMTWIRQAPGKGLEWVASITYTGDNTYYAGSVKGRITISRDNAKSTLY
LQMNSLRSEDTATYYCTRDDYGGYSPYYMDAWGQGTSVTVSS
Variable region (1-122)
(SEQ ID NO: 12 of Sequence Listing)

Figure 21 caggttaagctgctgcagtctggggctgagctggtaaaacctggtgcttcagtgaagttgtcctgcaagacttctggttt
taccttcagcactagctatatgagttggttgaagcaggtgcctggaccgagtattgagtggattggatggatttatgctg
gagatggtggtactaagtataatcagaagttcaagggcaaggccacactgacagtagacaaatcttctagcacagcatac
atggatctcagcagcctgacatctgaggacgctgcagtctattttgtgcaacggatggttatggggattggtttgctta
ctggggccaaggcactctggtcactgtctcttca
Variable region (1-354)
(SEQ ID NO: 13 of Sequence Listing)

Figure 22

QVKLLQSGAELVKPGASVKLSCKTSGFTFSTSYMSWLKQVPGPSIEWIGWIYAGDGGTKYNQKFKGKATLTVDKSSSTAY
MDLSSLTSEDAAVYFCATDGYGDWFAYWGQGTLVTVSS
Variable region (1-118)
(SEQ ID NO: 14 of Sequence Listing)

Figure 23 caggttaagctgctgcagtctggggctgagctggtaaaacctggtgcttcagtgaagttgtcctgcaagacttctggttt
tacattcagcactagttatatgagttggttgaagcaggtgcctggaccgagtactgagtggattggatggatttatgctg
gagatggtggtactaagtataatcagaagttcaagggcaaggccacactgacagtagacaaattttctagcacagcatac
atggatctcagcagcctgacatctgaggacgctgcagtctatttctgtgcaacggatggttatggggattggtttactta
ctggggccaaggcactctggtcactgtctcttca
Variable region (1-354)
SEQ ID NO: 15 of Sequence Listing

Figure 24

QVKLLQSGAELVKPGASVKLSCKTSGFTFSTSYMSWLKQVPGPSTEWIGWIYAGDGGTKYNQKFKGKATLTVDKFSSTAY
MDLSSLTSEDAAVYFCATDGYGDWFTYWGQGTLVTVSS
Variable region (1-118)
(SEQ ID NO: 16 of Sequence Listing)

Figure 25

TTCATGAGGCACACGACTGAGGCACCTCC
(SEQ ID NO: 17 of Sequence Listing)

Figure 26

TCCAGTTGCTAACTGTTCCG
(SEQ ID NO: 18 of Sequence Listing)

Figure 27

CAGTGGTATCAACGCAGAG
(SEQ ID NO: 19 of Sequence Listing)

Figure 28 gacatccagatgacccagtctccatcttccctgtctgcatttctgggagacagagtcactattacttgccgggcaagtca
agacattggaaattatttaagatggttccagcagaaaccggggaaatctcctaggcttatgatttatggtgcaaccaact
tggcaaatggggtcccatcaaggttcagtggcagtaggtctgggtcagattattctctgaccatcaacaacttggagtct
gaagacatggctatttattactgtctgaagcataatgagtatccattcacgttcggctcagggacgaagttggaaataaa
acgggct
Variable region (1-327)
(SEQ ID NO: 20 of Sequence Listing)

Figure 29

DIQMTQSPSSLSAFLGDRVTITCRASQDIGNYLRWFQQKPGKSPRLMIYGATNLANGVPSRFSGSRSGSDYSLTINNLES
EDMAIYYCLKHNEYPFTFGSGTKLEIKRA
Variable region (1-109)
(SEQ ID NO: 21 of Sequence Listing)

Figure 30

TACGTGCTGTCTTTGCTGTCCTGATCAG
(SEQ ID NO: 22 of Sequence Listing)

Figure 31 gacatccagatgacacagtctccagcttccctgtctgcatctctgggagaaactgtcaccatcgaatgtcgagcaagtga
ggacatttacagtaatttagcgtggtatcagcagaaaccagggaactctcctcagctcctgatctatgatgcaaatatct
tggcagatggggtcccatcacggttcagtggcagtgggtctggcacacagtattctctaaagataaacagcctgcaatct
gaagatgtcgcaagttatttctgtcaacagtataacaattatcctccgttcacgtttggagttgggaccaagctggaact
gaaacgggct
Variable region (1-330)
(SEQ ID NO: 23 of Sequence Listing)

Figure 32

DIQMTQSPASLSASLGETVTIECRASEDIYSNLAWYQQKPGNSPQLLIYDANILADGVPSRFSGSGSGTQYSLKINSLQS
EDVASYFCQQYNNYPPFTFGVGTKLELKRA
Variable region (1-110)
(SEQ ID NO: 24 of Sequence Listing)

Figure 33 gacatccagatgacacagtctccagcttccctgtctgcatctctgggagaaactgtcaccatcgaatgtcgagcaagtga
ggacatatacagtaatttagcgtggtatcagcagaaaccagggaactctcctcagctcctgatctatgatgcaaatatcc
tggcagatggggtcccatcacggttcagtggcagtgggtctggcacacagtattctctaaagataaacagcctgcaatct
gaagatgtcgcaagttatttctgtcaacagtataacaattatcctccgttcacgtttggagctgggaccaagctggaact
gaaacgggct
Variable region (1-330)
(SEQ ID NO: 25 of Sequence Listing)

Figure 34

DIQMTQSPASLSASLGETVTIECRASEDIYSNLAWYQQKPGNSPQLLIYDANILADGVPSRFSGSGSGTQYSLKINSLQS
EDVASYFCQQYNNYPPFTFGAGTKLELKRA
Variable region (1-110)
(SEQ ID NO: 26 of Sequence Listing)

Figure 35 gcctccggactctagagccaccATGGTGCTGCAGACCCAGGTGTTCATCTCCCTGCTGCTGTGGATCTCCGGCGCGTACG
GCGATATCGTGATGATTAAACGTACGGTGGCCGCCCCCTCCGTGTTCATCTTCCCCCCCTCCGACGAGCAGCTGAAGTCC
GGCACCGCCTCCGTGGTGTGCCTGCTGAATAACTTCTACCCCAGAGAGGCCAAGGTGCAGTGGAAGGTGGACAACGCCCT
GCAGTCCGGGAACTCCCAGGAGAGCGTGACCGAGCAGGACAGCAAGGACAGCACCTACAGCCTGAGCAGCACCCTGACCC
TGAGCAAAGCCGACTACGAGAAGCACAAGGTGTACGCCTGCGAGGTGACCCACCAGGGCCTGAGCTCCCCCGTCACCAAG
AGCTTCAACAGGGGGGAGTGTTAGgggcccgtttaaacgggggaggcta
(SEQ ID NO: 27 of Sequence Listing)

Figure 36

TATACCGTCGACCTCTAGCTAGAGCTTGGC
(SEQ ID NO: 28 of Sequence Listing)

Figure 37

GCTATGGCAGGGCCTGCCGCCCCGACGTTG
(SEQ ID NO: 29 of Sequence Listing)

Figure 38 gcctccggactctagagccaccATGAAACACCTGTGGTTCTTCCTCCTGCTGGTGGCAGCTCCCAGATGGGTGCTGAGCC
AGGTGCAATTGTGCAGGCGGTTAGCTCAGCCTCCACCAAGGGCCCAAGCGTCTTCCCCCTGGCACCCTCCTCCAAGAGCA
CCTCTGGCGGCACAGCCGCCCTGGGCTGCCTGGTCAAGGACTACTTCCCCGAACCCGTGACCGTGAGCTGGAACTCAGGC
GCCCTGACCAGCGGCGTGCACACCTTCCCCGCTGTCCTGCAGTCCTCAGGACTCTACTCCCTCAGCAGCGTGGTGACCGT
GCCCTCCAGCAGCTTGGGCACCCAGACCTACATCTGCAACGTGAATCACAAGCCCAGCAACACCAAGGTGGACAAGAGAG
TTGAGCCCAAATCTTGTGACAAAACTCACACATGCCCACCCTGCCCAGCACCTGAACTCCTGGGGGGACCCTCAGTCTTC
CTCTTCCCCCCAAAACCCAAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGACAAAGCCCCGGGAGGAGC
AGTACAACAGCACGTACCGGGTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGCCAGCCCCGGGAACCACAGGT
GTACACCCTGCCCCCATCCCGGGAGGAGATGACCAAGAACCAGGTCAGCCTGACCTGCCTGGTCAAAGGCTTCTATCCCA
GCGACATCGCCGTGGAGTGGGAGAGCAATGGGCAGCCCGAGAACAACTACAAGACCACCCCTCCCGTGCTGGACTCCGAC
GGCTCCTTCTTCCTCTACAGCAAGCTCACCGTGGACAAGAGCAGGTGGCAGCAGGGCAACGTCTTCTCATGCTCCGTGAT
GCATGAGGCTCTGCACAACCACTACACCCAGAAGAGCCTCTCCCTGTCTCCCGGCAAATGAgatatcgggcccgtttaaa
cggggaggcta
(SEQ ID NO: 30 of Sequence Listing)

Figure 39 atggtgctgcagacccaggtgttcatctccctgctgctgtggatctccggcgcgtacggcgacatccagatgacccagtc
tccatcttccctgtctgcatttctgggagacagagtcactattacttgccgggcaagtcaagacattggaaattattaa
gatggttccagcagaaaccggggaaatctcctaggcttatgatttatggtgcaaccaacttggcaaatggggtcccatca
aggttcagtggcagtaggtctgggtcagattattctctgaccatcaacaacttggagtctgaagacatggctatttatta
ctgtctgaagcataatgagtatccattcacgttcggctcagggacgaagttggaaataaaacgggctgtggccgcccct
ccgtgttcatcttcccccctccgacgagcagctgaagtccggcaccgcctccgtggtgtgcctgctgaataacttctac
cccagagaggccaaggtgcagtggaaggtggacaacgccctgcagtccgggaactcccaggagagcgtgaccgagcagga
cagcaaggacagcacctacagcctgagcagcaccctgaccctgagcaaagccgactacgagaagcacaaggtgtacgcct
gcgaggtgacccaccaggcctgagctcccccgtcaccaagagcttcaacaggggggagtgt
Signal sequence (1-60), Variable region (61-387), Constant region (389-702)
(SEQ ID NO: 31 of Sequence Listing)

Figure 40

MVLQTQVFISLLLWISGAYGDIQMTQSPSSLSAFLGDRVTITCRASQDIGNYLRWFQQKPGKSPRLMIYGATNLANGVPS
RFSGSRSGSDYSLTINNLESEDMAIYYCLKHNEYPFTFGSGTKLEIKRAVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFNRGEC
Signal sequence (1-20), Variable region (21-129), Constant region (130-234)
(SEQ ID NO: 32 of Sequence Listing)

Figure 41

ATCTCCGGCGCGTACGGCGACATCCAGATGACCCAGTCTCCATCTTCC
(SEQ ID NO: 33 of Sequence Listing)

Figure 42

GGAGGGGGCGGCCACAGCCCGTTTTATTTCCAACTTCGTCCCTG
(SEQ ID NO: 34 of Sequence Listing)

Figure 43 atgaaacacctgtggttcttcctcctgctggtggcagctcccagatgggtgctgagcgaggtgcagctggtggagtctgg
gggaggcctggtgcagcctggaaggtctctgaaactatcctgtgtagcctctggattcagattcaatgacttttggatga
cctggatccgccaggctccagggaaggggctggagtgggttgcatccattacttatactggtgataacacttactatgca
ggctctgtgaaggggccgaatcactatctccagagataatgccaagagcaccctatacctgcaaatgaacagtctgaggtc
tgaggacacggccacttattactgtacaagagatgactacggaggatatagccccactatatggatgcctggggtcaag
gaacttcagtcactgtcagctcagcctccaccaagggcccaagcgtcttcccctggcaccctcctccaagagcacctct
ggcggcacagccgccctgggctgcctggtcaaggactacttccccgaacccgtgaccgtgagctggaactcaggcgccct
gaccagcggcgtgcacacctlccccgctgtcctgcagtcctcaggactctactccctcagcagcgtggtgaccgtgccct
ccagcagcttgggcacccagacctacatctgcaacgtgaatcacaagcccagcaacaccaaggtggacaagagagttgag
cccaaatcttgtgacaaaactcacacatgcccaccctgcccagcacctgaactcctggggggaccctcagtcttcctctt
ccccccaaaacccaaggacaccctcatgatctcccggaccctgaggtcacatgcgtggtggtggacgtgagccacgaag
accctgaggtcaagttcaactggtacgtggacggcgtggaggtgcataatgccaagacaaagcccggaggagcagtac
aacagcacgtaccgggtggtcagcgtcctcaccgtcctgcaccaggactggctgaatggcaaggagtacaagtgcaaggt
ctccaacaaagccctcccagcccccatcgagaaaaccatctccaaagccaaaggccagccccgggaaccacaggtgtaca
ccctgccccatcccgggaggagatgaccaagaaccaggtcagcctgacctgcctggtcaaaggcttctatcccagcgac
atcgccgtggagtgggagagcaatggccagcccgagaacaactacaagaccacccctcccgtgctggactccgacggctc
cttcttcctctacagcaagctcaccgtggacaagagcaggtggcagcagggcaacgtcttctcatgctccgtgatgcatg
aggctctgcacaaccactacacccagaagagcctctccctgtctccggcaaa
Signal sequence (1-57), Variable region (58-423), Constant region (424-1413)
(SEQ ID NO: 35 of Sequence Listing)

Figure 44

MKHLWFFLLLVAAPRWVLSEVQLVESGGGLVQPGRSLKLSCVASGFRFNDFWMTWIRQAPGKGLEWVASITYTGDNTYYA
GSVKGRITISRDNAKSTLYLQMNSLRSEDTATYYCTRDDYGGYSPYYMDAWGQGTSVTVSSASTKGPSVFPLAPSSKSTS
GGTAALGCLVKDYFPEPVTVSWNSGALTSGVHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK
Signal sequence (1-19), Variable region (20-141), Constant region (142-471)
(SEQ ID NO: 36 of Sequence Listing)

Figure 45

CCAGATGGGTGCTGAGCGAGGTGCAGCTGGTGGAGTCTGGGGGAGGC
(SEQ ID NO: 37 of Sequence Listing)

Figure 46

CTTGGTGGAGGCTGAGCTGACAGTGACTGAAGTTCCTTGACCCCAGGC
(SEQ ID NO: 38 of Sequence Listing)

Figure 47 atggtgctgcagacccaggtgttcatctccctgctgctgtggatctccggcgcgtacggcgacatccagatgacacagtc
tccagcttccctgtctgcatctctgggagaaactgtcaccatcgaatgtcgagcaagtgaggacatttacagtaatttag
cgtggtatcagcagaaaccaggaactctcctcagctcctgatctatgatgcaaatatcttggcagatggggtcccatca
cggttcagtggcagtgggtctggcacacagtattctctaaagataaacagcctgcaatctgaagatgtcgcaagttattt
ctgtcaacagtataacaattatcctccgttcacgttgggagttgggaccaagctggaactgaaacgggctgtggccgccc
cctccgtgttcatcttcccccctccgacgagcagctgaagtccggcaccgcctccgtggtgtgcctgctgaataacttc
tacccagagaggccaaggtgcagtggaaggtggacaacgccctgcagtccgggaactcccaggagagcgtgaccgagca
ggacagcaaggacagcacctacagcctgagcagcaccctgaccctgagcaaagccgactacgagaagcacaaggtgtacg
cctgcgaggtgacccaccagggcctgagctcccccgtcaccaagagcttcaacagggggggagtgt
Signal sequence (1-60), Variable region (61-390), Constant region (391-705)
(SEQ ID NO: 39 of Sequence Listing)

Figure 48

MVLQTQVFISLLLWISGAYGDIQMTQSPASLSASLGETVTIECRASEDIYSNLAWYQQKPGNSPQLLIYDANILADGVPS
RFSGSGSGTQYSLKINSLQSEDVASYFCQQYNNYPPFTFGVGTKLELKRAVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVTKSFNRGEC
Signal sequence (1-20), Variable region (21-130), Constant region (131-235)
(SEQ ID NO: 40 of Sequence Listing)

Figure 49

ATCTCCGGCGCGTACGGCGACATCCAGATGACACAGTCTCCAGCTTCC
(SEQ ID NO: 41 of Sequence Listing)

Figure 50

GGAGGGGGCGGCCACAGCCCGTTTCAGTTCCAGCTTGGTCCCAAC
(SEQ ID NO: 42 of Sequence Listing)

Figure 51

```
atgaaacacctgtggttcttcctcctgctggtggcagctcccagatgggtgctgagccaggttaagctgctgcagtctgg
ggctgagctggtaaaacctggtgcttcagtgaagttgtcctgcaagacttctggttttaccttcagcactagctatatga
gttggttgaagcaggtgcctggaccgagtattgagtggattggatggatttatgctggagatggtggtactaagtataat
cagaagttcaagggcaaggccacactgacagtagacaaatcttctagcacagcatacatggatctcagcagcctgacatc
tgaggacgctgcagtctattttgtgcaacggatggttatggggattggtttgcttactggggccaaggcactctggtca
ctgtcagctcagcctccaccaagggcccaagcgtcttcccctggcaccctcctccaagagcacctctggcggcacagcc
gccctgggctgcctggtcaaggactacttccccgaacccgtgaccgtgagctggaactcaggcgccctgaccagcggcgt
gcacaccttcccgctgtcctgcagtcctcaggactctactccctcagcagcgtggtgaccgtgcctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctgggggacccagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccaccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctcccggcaaa
```
Signal sequence (1-57), Variable region (58-411), Constant region (412-1401)
(SEQ ID NO: 43 of Sequence Listing)

Figure 52

```
MKHLWFFLLLVAAPRWVLSQVKLLQSGAELVKPGASVKLSCKTSGFTFSTSYMSWLKQVPGPSIEWIGWIYAGDGGTKYN
QKFKGKATLTVDKSSSTAYMDLSSLTSEDAAVYFCATDGYGDWFAYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK
```
Signal sequence (1-19), Variable region (20-137), Constant region (138-467)
(SEQ ID NO: 44 of Sequence Listing)

Figure 53

CCAGATGGGTGCTGAGCCAGGTTAAGCTGCTGCAGTCTGGGGCTGAG
(SEQ ID NO: 45 of Sequence Listing)

Figure 54

CTTGGTGGAGGCTGAGCTGACAGTGACCAGAGTGCCTTGGCCCCAG
(SEQ ID NO: 46 of Sequence Listing)

Figure 55 atggtgctgcagacccaggtgttcatctccctgctgctgtggatctccggcgcgtacggcgacatccagatgacacagtc
tccagcttccctgtctgcatctctgggagaaactgtcaccatcgaatgtcgagcaagtgaggacatatacagtaatttag
cgtggtatcagcagaaaccagggaactctcctcagctcctgatctatgatgcaaatatcctggcagatggggtcccatca
cggttcagtggcagtgggtctggcacacagtattctctaaagataaacagcctgcaatctgaagatgtcgcaagttattt
ctgtcaacagtataacaattatcctccgttcacgtttggagctgggaccaagctggaactgaaacgggctgtggccgccc
cctccgtgttcatcttcccccctccgacgagcagctgaagtccggcaccgcctccgtggtgtgcctgctgaataacttc
tacccagagaggccaaggtgcagtggaaggtggacaacgccctgcagtccgggaactcccaggagagcgtgaccgagca
ggacagcaaggacagcacctacagcctgagcagcaccctgaccctgagcaaagccgactacgagaagcacaaggtgtacg
cctgcgaggtgacccaccagggcctgagctcccccgtcaccaagagcttcaacaggggggagtgt
Signal sequence (1-60), Variable region (61-390), Constant region (391-705)
(SEQ ID NO: 47 of Sequence Listing)

Figure 56

MVLQTQVFISLLLWISGAYGDIQMTQSPASLSASLGETVTIECRASEDIYSNLAWYQQKPGNSPQLLIYDANILADGVPS
RFSGSGSGTQYSLKINSLQSEDVASYFCQQYNNYPPFTFGAGTKLELKRAVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVTKSFNRGEC
Signal sequence (1-20), Variable region (21-130), Constant region (131-235)
(SEQ ID NO: 48 of Sequence Listing)

Figure 57

GGAGGGGGCGGCCACAGCCCGTTTCAGTTCCAGCTTGGTCCCAGC
(SEQ ID NO: 49 of Sequence Listing)

Figure 58

```
atgaaacacctgtggttcttcctcctgctggtggcagctcccagatgggtgctgagccaggttaagctgctgcagtctgg
ggctgagctggtaaaacctggtgcttcagtgaagttgtcctgcaagacttctggttttacattcagcactagttatatga
gttggttgaagcaggtgcctggaccgagtactgagtggattggatggatttatgctggagatggtggtactaagtataat
cagaagttcaagggcaaggccacactgacagtagacaaattttctagcacagcatacatggatctcagcagcctgacatc
tgaggacgctgcagtctatttctgtgcaacggatggttatggggattggtttacttactggggccaaggcactctggtca
ctgtcagctcagcctccaccaagggcccaagcgtctccccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctgggggaccctcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctcccggcaaa
```
Signal sequence (1-57), Variable region (58-411), Constant region (412-1401)
(SEQ ID NO: 50 of Sequence Listing)

Figure 59

```
MKHLWFFLLLVAAPRWVLSQVKLLQSGAELVKPGASVKLSCKTSGFTFSTSYMSWLKQVPGPSTEWIGWIYAGDGGTKYN
QKFKGKATLTVDKFSSTAYMDLSSLTSEDAAVYFCATDGYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK
```
Signal sequence (1-19), Variable region (20-137), Constant region (138-467)
(SEQ ID NO: 51 of Sequence Listing)

Figure 60

DFWMT
(SEQ ID NO: 52 of Sequence Listing)

Figure 61

SITYTGDNTYYAGSVKG
(SEQ ID NO: 53 of Sequence Listing)

Figure 62

DDYGGYSPYYMDA
(SEQ ID NO: 54 of Sequence Listing)

Figure 63

TSYMS
(SEQ ID NO: 55 of Sequence Listing)

Figure 64

WIYAGDGGTKYNQKFKG
(SEQ ID NO: 56 of Sequence Listing)

Figure 65

DGYGDWFAY
(SEQ ID NO: 57 of Sequence Listing)

Figure 66

TSYMS
(SEQ ID NO: 58 of Sequence Listing)

Figure 67

WIYAGDGGTKYNQKFKG
(SEQ ID NO: 59 of Sequence Listing)

Figure 68

DGYGDWFTY
(SEQ ID NO: 60 of Sequence Listing)

Figure 69

RASQDIGNYLR
(SEQ ID NO: 61 of Sequence Listing)

Figure 70

GATNLAN
(SEQ ID NO: 62 of Sequence Listing)

Figure 71

LKHNEYPFT
(SEQ ID NO: 63 of Sequence Listing)

Figure 72

RASEDIYSNLA
(SEQ ID NO: 64 of Sequence Listing)

Figure 73

DANILAD
(SEQ ID NO: 65 of Sequence Listing)

Figure 74

QQYNNYPPFT
(SEQ ID NO: 66 of Sequence Listing)

Figure 75

RASEDIYSNLA
(SEQ ID NO: 67 of Sequence Listing)

Figure 76

DANILAD
(SEQ ID NO: 68 of Sequence Listing)

Figure 77

QQYNNYPPFT
(SEQ ID NO: 69 of Sequence Listing)

Figure 78

MVSWGRFICLVVVTMATLSLARPSFSLVEDTTLEPEEPPTKYQISQPEVYVAAPGESLEVRCLLKDAAVISWTKDGVHLG
PNNRTVLIGEYLQIKGATPRDSGLYACTASRTVDSETWYFMVNVTDAISSGDDEDDTDGAEDFVSENSNNKRAPYWTNTE
KMEKRLHAVPAANTVKFRCPAGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSKYGPDGLPYLKVLKHSGINSS
NAEVLALFNVTEADAGEYICKVSNYIGQANQSAWLTVLPKQQAPGREKEITASPDYLEIAIYCIGVFLIACMVVTVILCR
MKNTTKKPDFSSQPAVHKLTKRIPLRRQVTVSAESSSSMNSNTPLVRITTRLSSTADTPMLAGVSEYELPEDPKWEFPRD
KLTLGKPLGEGCFGQVVMAEAVGIDKDKPKEAVTVAVKMLKDDATEKDLSDLVSEMEMMKMIGKHKNIINLLGACTQDGP
LYVIVEYASKGNLREYLRARRPPGMEYSYDINRVPEEQMTFKDLVSCTYQLARGMEYLASQKCIHRDLAARNVLVTENNV
MKIADFGLARDINNIDYYKKTTNGRLPVKWMAPEALFDRVYTHQSDVWSFGVLMWEIFTLGGSPYPGIPVEELFKLLKEG
HRMDKPANCTNELYMMMRDCWHAVPSQRPTFKQLVEDLDRILTLTTNEEYLDLSQPLEQYSPSYPDTRSSCSSGDDSVFS
PDPMPYEPCLPQYPHINGSVKT
(SEQ ID NO: 70 of Sequence Listing)

Figure 79

MVSWGRFICLVVVTMATLSLARPSFSLVEDTTLEPEEPPTKYQISQPEVYVAAPGESLEVRCLLKDAAVISWTKDGVHLG
PNNRTVLIGEYLQIKGATPRDSGLYACTASRTVDSETWYFMVNVTDAISSGDDEDDTDGAEDFVSENSNNKRAPYWTNTE
KMEKRLHAVPAANTVKFRCPAGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSKYGPDGLPYLKVLKAAGVNTT
DKEIEVLYIRNVTFEDAGEYTCLAGNSIGISFHSAWLTVLPAPGREKEITASPDYLEIAIYCIGVFLIACMVVTVILCRM
KNTTKKPDFSSQPAVHKLTKRIPLRRQVTVSAESSSSMNSNTPLVRITTRLSSTADTPMLAGVSEYELPEDPKWEFPRDK
LTLGKPLGEGCFGQVVMAEAVGIDKDKPKEAVTVAVKMLKDDATEKDLSDLVSEMEMMKMIGKHKNIINLLGACTQDGPL
YVIVEYASKGNLREYLRARRPPGMEYSYDINRVPEEQMTFKDLVSCTYQLARGMEYLASQKCIHRDLAARNVLVTENNVM
KIADFGLARDINNIDYYKKTTNGRLPVKWMAPEALFDRVYTHQSDVWSFGVLMWEIFTLGGSPYPGIPVEELFKLLKEGH
RMDKPANCTNELYMMMRDCWHAVPSQRPTFKQLVEDLDRILTLTTNEEYLDLSQPLEQYSPSYPDTRSSCSSGDDSVFSP
DPMPYEPCLPQYPHINGSVKT
(SEQ ID NO: 71 of Sequence Listing)

Figure 80 atggtgctgcagacccaggtgttcatctccctgctgctgtggatctccggcgcgtacggcgacatccagatgacccagag
ccccagcagcctgagcgccagcgtgggcgacagagtgaccatcacctgtcgggccagcgaggacatctacagcaacctgg
cctggtatcagcagaagcccggcaagagcccccagctgctgatctacgacgccaacatcctggccgacggcgtgcccagc
agattcagcggcagcggctccggcaccgactacaccctgaccatctccagcctgcagcccgaggacttcgccacctacta
ctgccagcagtacaacaactacccccattcacctcggccaggcaccaaggtggaaatcaagcgtacggtggccgccc
cctccgtgttcatcttcccccctccgacgagcagctgaagtccggcaccgcctccgtggtgtgcctgctgaataacttc
tacccagagaggccaaggtgcagtggaaggtggacaacgccctgcagtccgggaactcccaggagagcgtgaccgagca
ggacagcaaggacagcacctacagcctgagcagcaccctgaccctgagcaaagccgactacgagaagcacaaggtgtacg
cctgcgaggtgacccaccagggcctgagctcccccgtcaccaagagcttcaacagggggagtgt
Signal sequence (1-60), Variable region (61-390), Constant region (391-705)
(SEQ ID NO: 72 of Sequence Listing)

Figure 81

MVLQTQVFISLLLWISGAYGDIQMTQSPSSLSASVGDRVTITCRASEDIYSNLAWYQQKPGKSPQLLIYDANILADGVPS
RFSGSGSGTDYTLTISSLQPEDFATYYCQQYNNYPPFTFGQGTKVEIKRTVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVTKSFNRGEC
Signal sequence (1-20), Variable region (21-130), Constant region (131-235)
(SEQ ID NO: 73 of Sequence Listing)

Figure 82 atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggccagggactggaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgacggctacggcgactggttcacatactggggccagggcaccctggtga
ccgtgagctcagcctccaccaagggcccaagcgtcttccccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctgggggggaccctcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctcccggcaaa Signal sequence (1-57), Variable region (58-411), Constant region (412-1401)

(SEQ ID NO: 74 of Sequence Listing)

Figure 83

MKHLWFFLLLVAAPRWVLSQVQLVQSGAEVKKPGASVKVSCKASGFTFSTSYMSWVRQAPGQGLEWMGWIYAGDGGTKYN
QKFKGRVTLTVDKSTSTAYMELSSLRSEDTAVYYCATDGYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence (1-19), Variable region (20-137), Constant region (138-467)

(SEQ ID NO: 75 of Sequence Listing)

Figure 84 atgaaacacctgtggttcttcctcctgctggtggcagctcccagatgggtgctgagccaggtgcagctggtgcagtctgg
cgccgaagtgaagaaacctgggggctagcgtgaaggtgtcctgcaaggccagcggcttcaccttcagcaccagctatatga
gctgggtccgccaggctccaggccagggactggaatggatgggctggatctatgccggcgacggcggcaccaagtacaac
cagaaattcaagggcagagtgaccctgaccgccgacaagagcaccagcaccgcctacatggaactgagcagcctgcggag
cgaggacaccgccgtgtactactgcgccaccgacggctacggcgactggttcacatactggggccagggcaccctggtga
ccgtgagctcagcctccaccaagggcccaagcgtcttcccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctgggggaccctcagtcttcctcttccccccaaaacc
caaggacaccctcatgatctcccggaccctgaggtcacatgcgtggtggtggacgtgagccacgaagaccctgaggtca
agttcaactggtacgtggacggcgtggaggtgcataatgccaagacaaagcccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctcccggcaaa Signal sequence (1-57), Variable region (58-411), Constant region (412-1401)

(SEQ ID NO: 76 of Sequence Listing)

Figure 85

MKHLWFFLLLVAAPRWVLSQVQLVQSGAEVKKPGASVKVSCKASGFTFSTSYMSWVRQAPGQGLEWMGWIYAGDGGTKYN
QKFKGRVTLTADKSTSTAYMELSSLRSEDTAVYYCATDGYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence (1-19), Variable region (20-137), Constant region (138-467)

(SEQ ID NO: 77 of Sequence Listing)

Figure 86

```
atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggcccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgacggctacggcgactggttcacatactggggccagggcaccctggtga
ccgtgagctcagcctccaccaagggcccaagcgtcttccccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccacccctgcccagcacctgaactcctgggggggacccctcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctccggcaaa
```
Signal sequence (1-57), Variable region (58-411), Constant region (412-1401)
(SEQ ID NO: 78 of Sequence Listing)

Figure 87

MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDGYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence (1-19), Variable region (20-137), Constant region (138-467)
(SEQ ID NO: 79 of Sequence Listing)

Figure 88 atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggcccccagcatcgaatggatgggctggatctatgccggcgacggcggcaccaagtacaac
cagaaattcaagggcagagtgacccctgaccgtggacaagagcaccagcaccgcctacatggaactgagcagcctgcggag
cgaggacaccgccgtgtactactgcgccaccgacggctacggcgactggttcgcctactggggccagggcaccctggtga
ccgtgagctcagcctccaccaagggcccaagcgtcttccccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccacctgcccagcacctgaactcctgggggaccctcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctccggcaaa
Signal sequence (1-57), Variable region (58-411), Constant region(412-1401)
(SEQ ID NO: 80 of Sequence Listing)

Figure 89

MKHLWFFLLLVAAPRWVLSQVQLVQSGAEVKKPGASVKVSCKASGFTFSTSYMSWVRQAPGPSIEWMGWIYAGDGGTKYN
QKFKGRVTLTVDKSTSTAYMELSSLRSEDTAVYYCATDGYGDWFAYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK
Signal sequence (1-19), Variable region (20-137), Constant region (138-467)
(SEQ ID NO: 81 of Sequence Listing)

Figure 90

```
atgaaacacctgtggttcttcctcctgctggtggcagctcccagatgggtgctgagccaggtgcagctggtgcagtctgg
cgccgaagtgaagaaacctgggggctagcgtgaaggtgtcctgcaaggccagcggcttcaccttcagcaccagctatatga
gctgggtccgccaggctccaggccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgagggctacggcgactggttcacatactggggccagggcaccctggtga
ccgtgagctcagcctccaccaagggcccaagcgtcttccccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcaccctgaactcctgggggaccctcagtcttcctcttcccccaaaacc
caaggacacccctcatgatctcccggacccctgaggtcacatgcgtggtggtggacgtgagccacgaagaccctgaggtca
agttcaactggtacgtggacggcgtggaggtgcataatgccaagacaaagcccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctcccggcaaa
```
Signal sequence (1-57), Variable region (58-411), Constant region (412-1401)

(SEQ ID NO: 82 of Sequence Listing)

Figure 91

```
MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATEGYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK
```
Signal sequence (1-19), Variable region (20-137), Constant region (138-467)

(SEQ ID NO: 83 of Sequence Listing)

Figure 92

```
atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgacgcctacggcgactggttcacatactgggccagggcacccctggtga
ccgtgagctcagcctccaccaagggcccaagcgtcttccccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctgggggacccctcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctccggcaaa
```
Signal sequence (1-57), Variable region (58-411), Constant region(412-1401)

(SEQ ID NO: 84 of Sequence Listing)

Figure 93

MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDAYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence (1-19), Variable region (20-137), Constant region(138-467)

(SEQ ID NO: 85 of Sequence Listing)

Figure 94 atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgacgagtacggcgactggttcacatacgggcagggcaccctggtga
ccgtgagctcagcctccaccaagggcccaagcgtcttccccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcaccgaactcctggggggacccctcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctcccggcaaa Signal sequence (1-57), Variable region (58-411), Constant region (412-1401)

(SEQ ID NO: 86 of Sequence Listing)

Figure 95

MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDEYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence (1-19), Variable region (20-137), Constant region (138-467)

(SEQ ID NO: 87 of Sequence Listing)

Figure 96 atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggcccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgacttctacggcgactggttcacatactggggccagggcaccctggtga
ccgtgagctcagcctccaccaagggcccaagcgtcttccccctggcacctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccacccctgcccagcacctgaactcctgggggaccctcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgccccat
cccggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctcccggcaaa Signal sequence (1-57), Variable region (58-411), Constant region (412-1401)

(SEQ ID NO: 88 of Sequence Listing)

Figure 97

MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDFYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence (1-19), Variable region (20-137), Constant region (138-467)

(SEQ ID NO: 89 of Sequence Listing)

Figure 98 atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggcccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgaccactacggcgactggttcacatactggggccagggcaccctggtga
ccgtgagctcagcctccaccaagggcccaagcgtcttccccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctgggggaccctcagtcttcctcttccccccaaaacc
caaggacaccctcatgatctcccgacccctgaggtcacatgcgtggtggtggacgtgagccacgaagacctgaggtca
agttcaactggtacgtggacggcgtggaggtgcataatgccaagacaaagccccggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccaccccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctccggcaaa Signal sequence (1-57), Variable region (58-411), Constant region (412-1401)

(SEQ ID NO: 90 of Sequence Listing)

Figure 99

MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDHYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence (1-19), Variable region (20-137), Constant region (138-467)

(SEQ ID NO: 91 of Sequence Listing)

Figure 100

```
atgaaacacctgtggttcttcctcctgctggtggcagctcccagatgggtgctgagccaggtgcagctggtgcagtctgg
cgccgaagtgaagaaacctgggggctagcgtgaaggtgtcctgcaaggccagcggcttcaccttcagcaccagctatatga
gctgggtccgccaggctccaggcccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgacatctacggcgactggttcacatactggggccagggcaccctggtga
ccgtgagctcagcctccaccaagggcccaagcgtcttccccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctggggggaccctcagtcttcctcttccccccaaaacc
caaggacacccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctcccggcaaa
```
Signal sequence (1-57), Variable region (58-411), Constant region (412-1401)

(SEQ ID NO: 92 of Sequence Listing)

Figure 101

```
MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDIYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK
```
Signal sequence (1-19), Variable region (20-137), Constant region (138-467)

(SEQ ID NO: 93 of Sequence Listing)

Figure 102 atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggcccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgacaagtacggcgactggttcacatactggggccagggcaccctggtga
ccgtgagctcagcctccaccaagggcccaagcgtcttccccctggcacctcctccaagagcacctctgcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctggggggaccctcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagcccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctcccggcaaa Signal sequence (1-57), Variable region (58-411), Constant region (412-1401)

(SEQ ID NO: 94 of Sequence Listing)

Figure 103

MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDKYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence (1-19), Variable region (20-137), Constant region (138-467)

(SEQ ID NO: 95 of Sequence Listing)

Figure 104

```
atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgacctgtacggcgactggttcacatactggggccagggcaccctggtga
ccgtgagctcagcctccaccaagggcccaagcgtcttccccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctggggggaccctcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctcccggcaaa
```
Signal sequence (1-57), Variable region (58-411), Constant region (412-1401)
(SEQ ID NO: 96 of Sequence Listing)

Figure 105

```
MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDLYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK
```
Signal sequence (1-19), Variable region (20-137), Constant region (138-467)
(SEQ ID NO: 97 of Sequence Listing)

Figure 106 atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgacatgtacggcgactggttcacatactggggccagggcaccctggtga
ccgtgagctcagcctccaccaagggcccaagcgtcttccccctggcacctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatctgt
gacaaaactcacacatgcccaccctgcccagcacctgaactcctgggggaccctcagtcttcctcttcccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccaccccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctcccggcaaa Signal sequence　(1-57), Variable region (58-411), Constant region(412-1401)

(SEQ ID NO: 98 of Sequence Listing)

Figure 107

MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDMYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence　(1-19), Variable region (20-137), Constant region (138-467)

(SEQ ID NO: 99 of Sequence Listing)

Figure 108

```
atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggcccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgaccagtacggcgactggttcacatactggggccagggcaccctggtga
ccgtgagctcagcctccaccaagggcccaagcgtcttccccctggcacctcctccaagagcacctctggcggcacagcc
gccctgggctgcctggtcaaggactacttcccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctgggggaccctcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctccggcaaa
```
Signal sequence (1-57), Variable region (58-411), Constant region (412-1401)
(SEQ ID NO: 100 of Sequence Listing)

Figure 109

```
MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDQYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK
```
Signal sequence (1-19), Variable region (20-137), Constant region (138-467)
(SEQ ID NO: 101 of Sequence Listing)

Figure 110 atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggcccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgaccggtacggcgactggttcacatactggggccagggcaccctggtga
ccgtgagctcagcctccaccaagggcccaagcgtcttccccctggcaccctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccacccgcccagcacctgaactcctgggggaccctcagtcttcctcttcccccaaaacc
caaggacacctcatgatctcccgaccccctgaggtcacatgcgtggtggtggacgtgagccacgaagaccctgaggtca
agttcaactggtacgtggacggcgtggaggtgcataatgccaagacaaagcccgggaggagcagtacaacagcacgtac
cggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctccggcaaa Signal sequence (1–57), Variable region (58–411), Constant region (412–1401)

(SEQ ID NO: 102 of Sequence Listing)

Figure 111

MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDRYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence (1–19), Variable region (20–137), Constant region (138–467)

(SEQ ID NO: 103 of Sequence Listing)

Figure 112 atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgacgtgtacggcgactggttcacatactggggccagggcaccctggtga
ccgtgagctcagcctccaccaagggcccaagcgtcttccccctggcacctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccacctgcccagcacctgaactcctgggggaccctcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagcccgggaggagcagtacaacagcacgtac
cgggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccaccccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctccggcaaa Signal sequence (1-57), Variable region (58-411), Constant region(412-1401)

(SEQ ID NO: 104 of Sequence Listing)

Figure 113

MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDVYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence (1-19), Variable region (20-137), Constant region (138-467)

(SEQ ID NO: 105 of Sequence Listing)

Figure 114 atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggcccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgactggtacgcgactggttcacatactggggccagggcaccctggtga
ccgtgagctcagcctccaccaagggcccaagcgtcttccccctggcacctcctccaagagcacctctggcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctgggggaccctcagtcttcctcttcccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagcccgggaggagcagtacaacagcacgtac
cggtggtcagcgtcctcaccgtcctgcaccaggactggctgaatggcaaggagtacaagtgcaaggtctccaacaaagc
cctcccagcccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctcccctgtctcccggcaaa Signal sequence (1-57), Variable region (58-411), Constant region (412-1401)

(SEQ ID NO: 106 of Sequence Listing)

Figure 115

MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDWYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Signal sequence (1-19), Variable region (20-137), Constant region (138-467)

(SEQ ID NO: 107 of Sequence Listing)

Figure 116

```
atgaaacacctgtggttcttcctcctgctggtggcagctcccagatgggtgctgagccaggtgcagctggtgcagtctgg
cgccgaagtgaagaaacctggggctagcgtgaaggtgtcctgcaaggccagcggcttcaccttcagcaccagctatatga
gctgggtccgccaggctccaggccccagcaccgaatggatgggctggatctatgccggcgacggcggcaccaagtacaac
cagaaattcaagggcagagtgaccctgaccgtggacaagagcaccagcaccgcctacatggaactgagcagcctgcggag
cgaggacaccgccgtgtactactgcgccaccgactactacggcgactggttcacatactggggccagggcaccctggtga
ccgtgagctcagcctccaccaagggcccaagcgtcttccccctggcacctcctccaagagcacctctgcggcacagcc
gccctgggctgcctggtcaaggactacttccccgaacccgtgaccgtgagctggaactcaggcgccctgaccagcggcgt
gcacaccttccccgctgtcctgcagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgt
gacaaaactcacacatgcccaccctgcccagcacctgaactcctgggggaccctcagtcttcctcttccccccaaaacc
caaggacaccctcatgatctcccggaccctgaggtcacatgcgtggtggtggacgtgagccacgaagaccctgaggtca
agttcaactggtacgtggacggcgtggaggtgcataatgccaagacaaagcccgggaggagcagtacaacagcacgtac
cggtggtcagcgtcctcaccgtcctgcaccaggactggctgaatggcaaggagtacaagtgcaaggtctccaacaaagc
cctcccagccccatcgagaaaaccatctccaaagccaaaggccagccccgggaaccacaggtgtacaccctgcccccat
cccgggaggagatgaccaagaaccaggtcagcctgacctgcctggtcaaaggcttctatcccagcgacatcgccgtggag
tgggagagcaatggccagcccgagaacaactacaagaccacccctcccgtgctggactccgacggctccttcttcctcta
cagcaagctcaccgtggacaagagcaggtggcagcagggcaacgtcttctcatgctccgtgatgcatgaggctctgcaca
accactacacccagaagagcctctccctgtctccggcaaa
```
Signal sequence (1-57), Variable region (58-411), Constant region (412-1401)
(SEQ ID NO: 108 of Sequence Listing)

Figure 117

```
MKHLWFFLLLVAAPRWVLSQVQLVQSGAEVKKPGASVKVSCKASGFTFSTSYMSWVRQAPGPSTEWMGWIYAGDGGTKYN
QKFKGRVTLTVDKSTSTAYMELSSLRSEDTAVYYCATDYYGDWFTYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK
```
Signal sequence (1-19), Variable region (20-137), Constant region (138-467)
(SEQ ID NO: 109 of Sequence Listing)

Figure 118

GGCAGAGTGACCCTGACCGCCGACAAGAGCACCAGCACC
(SEQ ID NO: 110 of Sequence Listing)

Figure 119

GGTGCTGGTGCTCTTGTCGGCGGTCAGGGTCACTCTGCC
(SEQ ID NO: 111 of Sequence Listing)

Figure 120

CTGTTTCAAGGTCCGAGCAATAACAAACGTGCACCGTATTGG
(SEQ ID NO: 112 of Sequence Listing)

Figure 121

CGCAAGCTTGTCGACTCAAACAACATCCAGATGATAGGTATG
(SEQ ID NO: 113 of Sequence Listing)

FIG. 122

| | Name | KD (M) | Analyte (Antigen variant) |
|---|---|---|---|
| 1 | hFR2-14_H1/L1 | 1.2E-08 | IIIb |
| 2 | hFR2-14_H2/L1 | 8.7E-09 | IIIb |
| 3 | hFR2-14_H3/L1 | 7.4E-09 | IIIb |
| 4 | hFR2-14_H4/L1 | 5.4E-09 | IIIb |
| 5 | cFR2-14 | 6.3E-08 | IIIb |
| | | | |
| 6 | hFR2-14_H1/L1 | 3.0E-09 | IIIc |
| 7 | hFR2-14_H2/L1 | 6.4E-09 | IIIc |
| 8 | hFR2-14_H3/L1 | 3.3E-09 | IIIc |
| 9 | hFR2-14_H4/L1 | 2.8E-09 | IIIc |

FIG. 123

| | Name | KD (M) | Analyte (Antigen variant) |
|---|---|---|---|
| 1 | hFR2-14_H5/L1 | 9.5E-10 | IIIc |
| 2 | hFR2-14_H6/L1 | 1.5E-09 | IIIc |
| 3 | hFR2-14_H7/L1 | 1.2E-09 | IIIc |
| 4 | hFR2-14_H8/L1 | 1.5E-09 | IIIc |
| 5 | hFR2-14_H9/L1 | 5.1E-10 | IIIc |
| 6 | hFR2-14_H10/L1 | 6.9E-10 | IIIc |
| 7 | hFR2-14_H11/L1 | 2.1E-09 | IIIc |
| 8 | hFR2-14_H12/L1 | 7.6E-10 | IIIc |
| 9 | hFR2-14_H13/L1 | 6.7E-10 | IIIc |
| 10 | hFR2-14_H14/L1 | 2.3E-09 | IIIc |
| 11 | hFR2-14_H15/L1 | 3.4E-09 | IIIc |
| 12 | hFR2-14_H16/L1 | 9.1E-10 | IIIc |
| 13 | hFR2-14_H17/L1 | 1.5E-09 | IIIc |
| 14 | hFR2-14_H18/L1 | 1.2E-09 | IIIc |
| 15 | hFR2-14_H3/L1 | 6.4E-09 | IIIc |

FIG. 125C

| Name | Tm (°C) |
|---|---|
| hFR2-14_H1/L1 | 87.6 |
| hFR2-14_H2/L1 | 87.2 |
| hFR2-14_H3/L1 | 79.5 |
| hFR2-14_H4/L1 | 81.6 |
| hFR2-14_H5/L1 | 77.2 |
| hFR2-14_H8/L1 | 81.0 |
| hFR2-14_H9/L1 | 78.8 |
| hFR2-14_H11/L1 | 80.3 |
| hFR2-14_H12/L1 | 82.2 |
| hFR2-14_H19/L1 | 82.2 |

FIG. 126

| Experiment No. | Antibody name | Antibody-producing cell | KD (M) |
|---|---|---|---|
| 1 | hFR2-14_H1/L1 | 293F | 3.4E-09 |
| | hFR2-14_H1/L1 degraded analyte | 293F | 1.5E-07 |
| | hFR2-14_H2/L1 | 293F | 3.7E-09 |
| | hFR2-14_H2/L1 degraded analyte | 293F | 4.0E-08 |
| | hFR2-14_H3/L1 | 293F | 1.2E-08 |
| | hFR2-14_H3/L1 degraded analyte | 293F | 1.7E-07 |
| | hFR2-14_H4/L1 | 293F | 1.9E-09 |
| | hFR2-14_H4/L1 degraded analyte | 293F | 8.3E-08 |
| 2 | hFR2-14_H3/L1 | 293F | 9.0E-09 |
| | hFR2-14_H3/L1 degraded analyte | 293F | 1.1E-07 |
| | hFR2-14_H5/L1 | 293F | 1.5E-09 |
| | hFR2-14_H5/L1 degraded analyte | 293F | 2.2E-09 |
| | hFR2-14_H8/L1 | 293F | 9.0E-10 |
| | hFR2-14_H8/L1 degraded analyte | 293F | 1.6E-09 |
| | hFR2-14_H9/L1 | 293F | 1.9E-09 |
| | hFR2-14_H9/L1 degraded analyte | 293F | 3.5E-08 |
| | hFR2-14_H11/L1 | 293F | 1.4E-09 |
| | hFR2-14_H11/L1 degraded analyte | 293F | 4.7E-09 |
| | hFR2-14_H12/L1 | 293F | 9.5E-10 |
| | hFR2-14_H12/L1 degraded analyte | 293F | 1.3E-09 |
| 3 | hFR2-14_H12/L1 | CHO | 5.0E-09 |
| | hFR2-14_H12/L1 degraded analyte | CHO | 6.0E-09 |
| | hFR2-14_H19/L1 | CHO | 5.5E-09 |
| | hFR2-14_H19/L1 degraded analyte | CHO | 4.7E-09 |

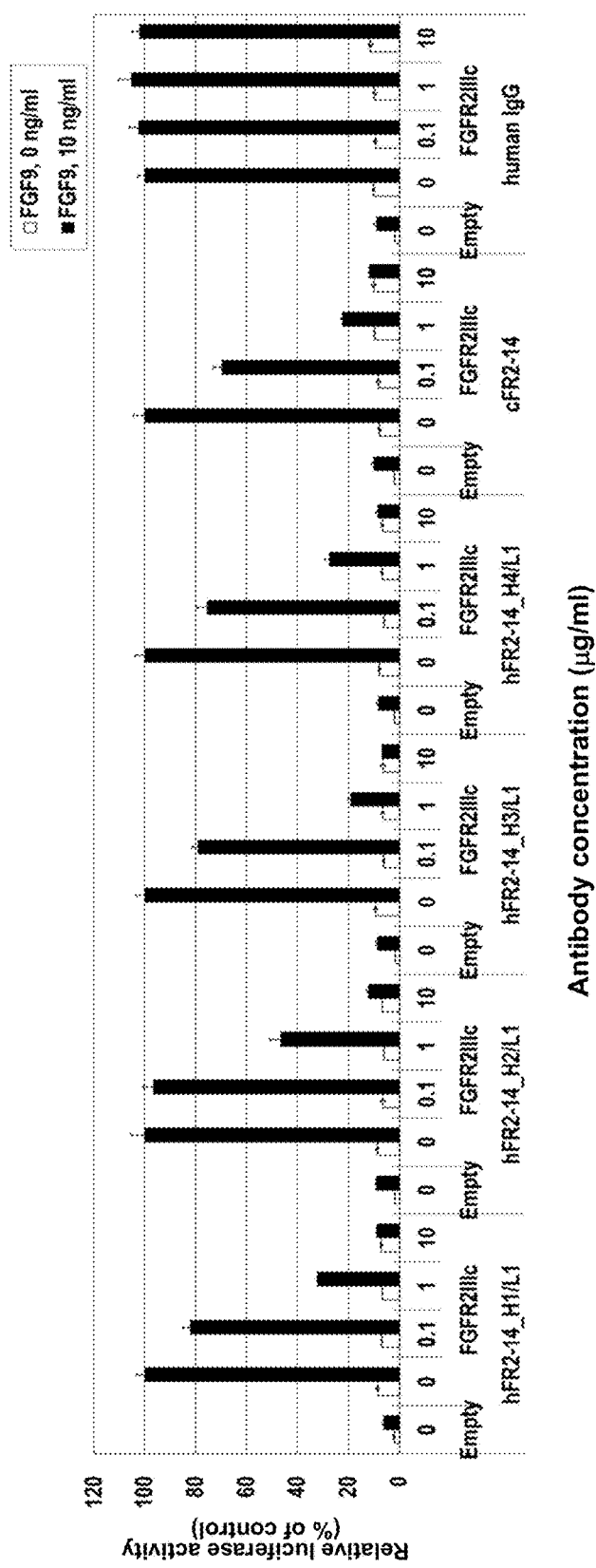

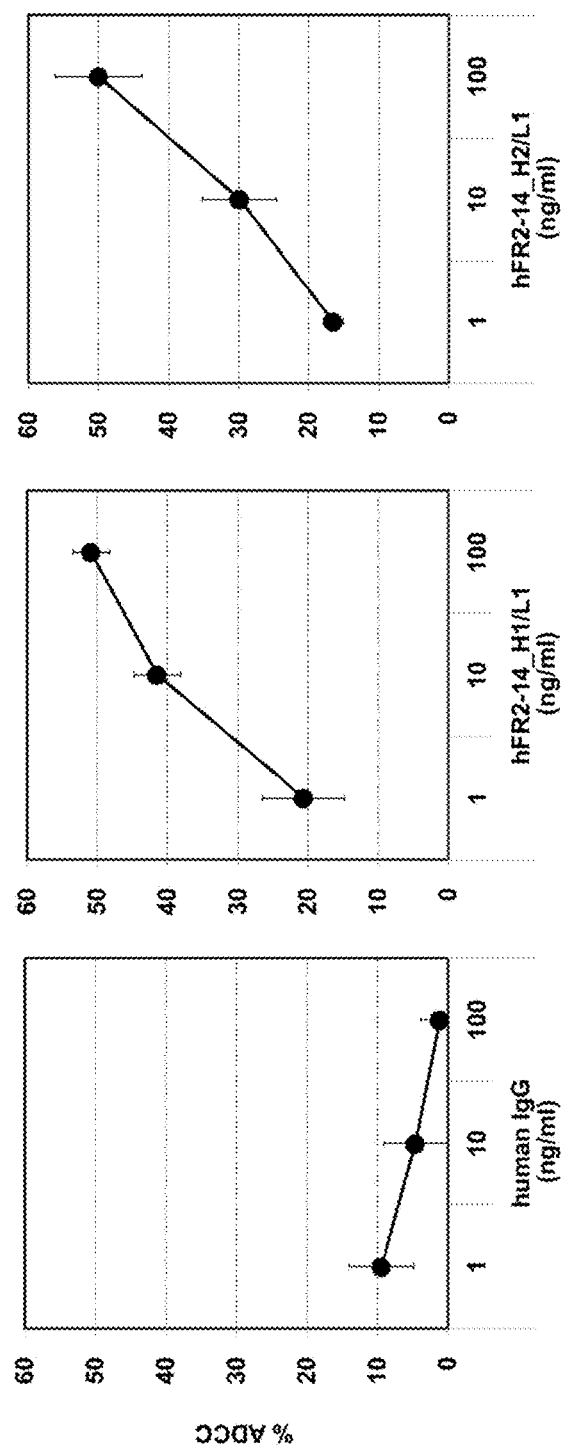

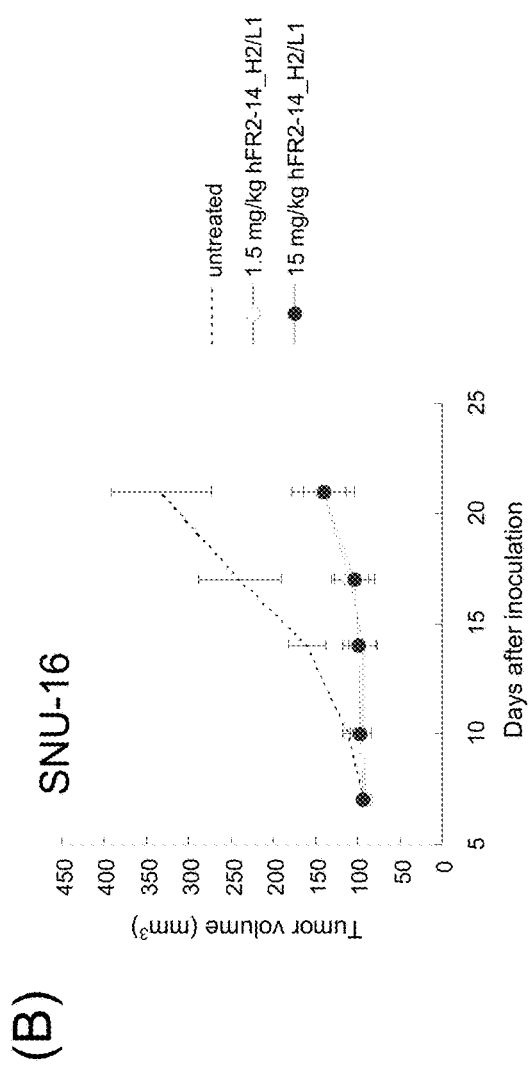

FIG. 141
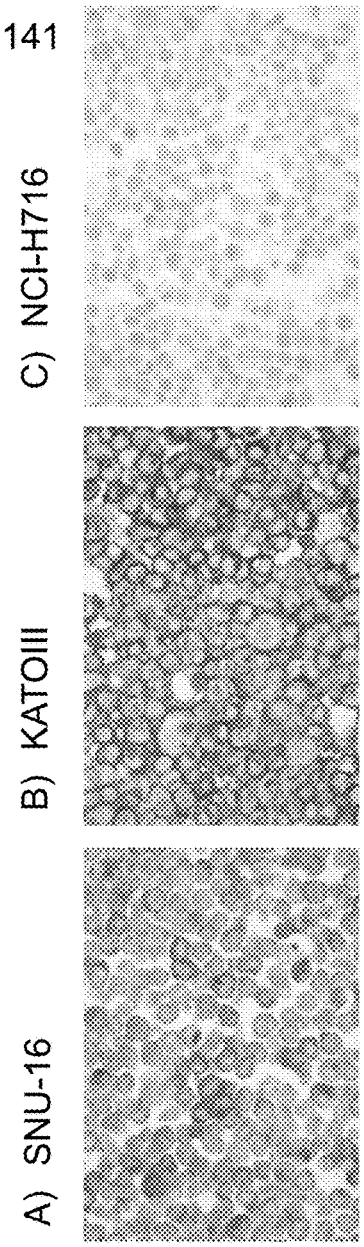
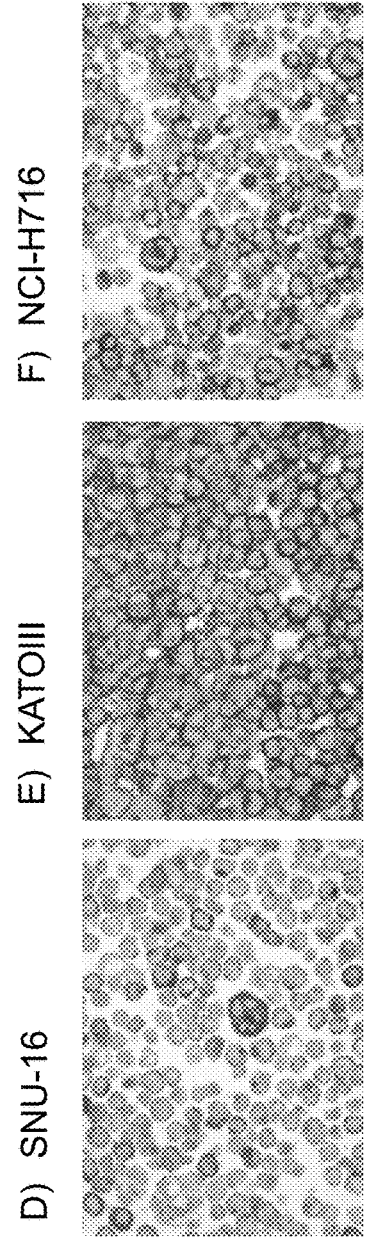

```
                          SEQUENCE LISTING

<160> NUMBER OF SEQ ID NOS: 128

<210> SEQ ID NO 1
<211> LENGTH: 12
<212> TYPE: PRT
<213> ORGANISM: Rattus norvegicus

<400> SEQUENCE: 1

Glu Val Gln Leu Val Glu Ser Gly Gly Gly Leu Val
1               5                   10

<210> SEQ ID NO 2
<211> LENGTH: 13
<212> TYPE: PRT
<213> ORGANISM: Rattus norvegicus

<400> SEQUENCE: 2

Asp Ile Gln Met Thr Gln Ser Pro Ser Ser Leu Ser Ala
1               5                   10

<210> SEQ ID NO 3
<211> LENGTH: 5
<212> TYPE: PRT
<213> ORGANISM: Rattus norvegicus

<400> SEQUENCE: 3

Gln Val Lys Leu Leu
1               5

<210> SEQ ID NO 4
<211> LENGTH: 17
<212> TYPE: PRT
<213> ORGANISM: Rattus norvegicus

<400> SEQUENCE: 4

Asp Ile Gln Met Thr Gln Ser Pro Ala Ser Leu Ser Ala Ser Leu Gly
1               5                   10                  15

Glu

<210> SEQ ID NO 5
<211> LENGTH: 5
<212> TYPE: PRT
<213> ORGANISM: Rattus norvegicus

<400> SEQUENCE: 5

Gln Val Lys Leu Leu
```

```
<210> SEQ ID NO 6
<211> LENGTH: 17
<212> TYPE: PRT
<213> ORGANISM: Rattus norvegicus

<400> SEQUENCE: 6

Asp Ile Gln Met Thr Gln Ser Pro Ala Ser Leu Ser Ala Ser Leu Gly
1               5                   10                  15

Glu

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gagttacttt tgagagcagt tccaggag                                      28

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggttctccca ctcagtaatc                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
catatgatca gtgtcctctc                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atatgatcag tgtcctctcc                                               20

<210> SEQ ID NO 11
<211> LENGTH: 366
<212> TYPE: DNA
<213> ORGANISM: Rattus norvegicus
<220> FEATURE:
<221> NAME/KEY: CDS
<222> LOCATION: (1)..(366)

<400> SEQUENCE: 11 gag gtg cag ctg gtg gag tct ggg gga ggc ctg gtg cag cct gga agg    48
```

```
Glu Val Gln Leu Val Glu Ser Gly Gly Gly Leu Val Gln Pro Gly Arg
1               5                   10                  15 tct ctg aaa cta tcc tgt gta gcc tct gga ttc aga ttc aat gac ttt       96
Ser Leu Lys Leu Ser Cys Val Ala Ser Gly Phe Arg Phe Asn Asp Phe
            20                  25                  30 tgg atg acc tgg atc cgc cag gct cca ggg aag ggg ctg gag tgg gtt      144
Trp Met Thr Trp Ile Arg Gln Ala Pro Gly Lys Gly Leu Glu Trp Val
        35                  40                  45 gca tcc att act tat act ggt gat aac act tac tat gca ggc tct gtg      192
Ala Ser Ile Thr Tyr Thr Gly Asp Asn Thr Tyr Tyr Ala Gly Ser Val
50                  55                  60 aag ggc cga atc act atc tcc aga gat aat gcg aag agc acc cta tac      240
Lys Gly Arg Ile Thr Ile Ser Arg Asp Asn Ala Lys Ser Thr Leu Tyr
65                  70                  75                  80 ctg caa atg aac agt ctg agg tct gag gac acg gcc act tat tac tgt      288
Leu Gln Met Asn Ser Leu Arg Ser Glu Asp Thr Ala Thr Tyr Tyr Cys
                85                  90                  95 aca aga gat gac tac gga gga tat agc ccc tac tat atg gat gcc tgg      336
Thr Arg Asp Asp Tyr Gly Gly Tyr Ser Pro Tyr Tyr Met Asp Ala Trp
            100                 105                 110 ggt caa gga act tca gtc act gtc tcc tca                              366
Gly Gln Gly Thr Ser Val Thr Val Ser Ser
        115                 120

<210> SEQ ID NO 12
<211> LENGTH: 122
<212> TYPE: PRT
<213> ORGANISM: Rattus norvegicus

<400> SEQUENCE: 12

Glu Val Gln Leu Val Glu Ser Gly Gly Gly Leu Val Gln Pro Gly Arg
1               5                   10                  15

Ser Leu Lys Leu Ser Cys Val Ala Ser Gly Phe Arg Phe Asn Asp Phe
            20                  25                  30

Trp Met Thr Trp Ile Arg Gln Ala Pro Gly Lys Gly Leu Glu Trp Val
        35                  40                  45

Ala Ser Ile Thr Tyr Thr Gly Asp Asn Thr Tyr Tyr Ala Gly Ser Val
50                  55                  60

Lys Gly Arg Ile Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Asp Asp Tyr Gly Gly Tyr Ser Pro Tyr Tyr Met Asp Ala Trp
            100                 105                 110

Gly Gln Gly Thr Ser Val Thr Val Ser Ser
        115                 120

<210> SEQ ID NO 13
<211> LENGTH: 354
<212> TYPE: DNA
<213> ORGANISM: Rattus norvegicus
<220> FEATURE:
<221> NAME/KEY: CDS
<222> LOCATION: (1)..(354)

<400> SEQUENCE: 13 cag gtt aag ctg ctg cag tct ggg gct gag ctg gta aaa cct ggt gct       48
Gln Val Lys Leu Leu Gln Ser Gly Ala Glu Leu Val Lys Pro Gly Ala
1               5                   10                  15 tca gtg aag ttg tcc tgc aag act tct ggt ttt acc ttc agc act agc       96
```

| | | |
|---|---|---|
| Ser Val Lys Leu Ser Cys Lys Thr Ser Gly Phe Thr Phe Ser Thr Ser<br>              20                        25                        30 | |
| tat atg agt tgg ttg aag cag gtg cct gga ccg agt att gag tgg att<br>Tyr Met Ser Trp Leu Lys Gln Val Pro Gly Pro Ser Ile Glu Trp Ile<br>        35                        40                        45 | 144 |
| gga tgg att tat gct gga gat ggt ggt act aag tat aat cag aag ttc<br>Gly Trp Ile Tyr Ala Gly Asp Gly Gly Thr Lys Tyr Asn Gln Lys Phe<br>    50                        55                        60 | 192 |
| aag ggc aag gcc aca ctg aca gta gac aaa tct tct agc aca gca tac<br>Lys Gly Lys Ala Thr Leu Thr Val Asp Lys Ser Ser Ser Thr Ala Tyr<br>65                       70                        75                        80 | 240 |
| atg gat ctc agc agc ctg aca tct gag gac gct gca gtc tat ttt tgt<br>Met Asp Leu Ser Ser Leu Thr Ser Glu Asp Ala Ala Val Tyr Phe Cys<br>                        85                        90                        95 | 288 |
| gca acg gat ggt tat ggg gat tgg ttt gct tac tgg ggc caa ggc act<br>Ala Thr Asp Gly Tyr Gly Asp Trp Phe Ala Tyr Trp Gly Gln Gly Thr<br>            100                        105                        110 | 336 |
| ctg gtc act gtc tct tca<br>Leu Val Thr Val Ser Ser<br>            115 | 354 |

<210> SEQ ID NO 14
<211> LENGTH: 118
<212> TYPE: PRT
<213> ORGANISM: Rattus norvegicus

<400> SEQUENCE: 14

Gln Val Lys Leu Leu Gln Ser Gly Ala Glu Leu Val Lys Pro Gly Ala
1               5                   10                  15

Ser Val Lys Leu Ser Cys Lys Thr Ser Gly Phe Thr Phe Ser Thr Ser
            20                  25                  30

Tyr Met Ser Trp Leu Lys Gln Val Pro Gly Pro Ser Ile Glu Trp Ile
        35                  40                  45

Gly Trp Ile Tyr Ala Gly Asp Gly Gly Thr Lys Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Ser Ser Leu Thr Ser Glu Asp Ala Ala Val Tyr Phe Cys
                85                  90                  95

Ala Thr Asp Gly Tyr Gly Asp Trp Phe Ala Tyr Trp Gly Gln Gly Thr
            100                 105                 110

Leu Val Thr Val Ser Ser
        115

<210> SEQ ID NO 15
<211> LENGTH: 354
<212> TYPE: DNA
<213> ORGANISM: Rattus norvegicus
<220> FEATURE:
<221> NAME/KEY: CDS
<222> LOCATION: (1)..(354)

<400> SEQUENCE: 15

| | |
|---|---|
| cag gtt aag ctg ctg cag tct ggg gct gag ctg gta aaa cct ggt gct<br>Gln Val Lys Leu Leu Gln Ser Gly Ala Glu Leu Val Lys Pro Gly Ala<br>1                 5                     10                       15 | 48 |
| tca gtg aag ttg tcc tgc aag act tct ggt ttt aca ttc agc act agt<br>Ser Val Lys Leu Ser Cys Lys Thr Ser Gly Phe Thr Phe Ser Thr Ser<br>            20                        25                        30 | 96 |
| tat atg agt tgg ttg aag cag gtg cct gga ccg agt act gag tgg att | 144 |

```
                    Tyr Met Ser Trp Leu Lys Gln Val Pro Gly Pro Ser Thr Glu Trp Ile
                            35                  40                  45 gga tgg att tat gct gga gat ggt ggt act aag tat aat cag aag ttc        192
Gly Trp Ile Tyr Ala Gly Asp Gly Gly Thr Lys Tyr Asn Gln Lys Phe
 50                  55                  60 aag ggc aag gcc aca ctg aca gta gac aaa ttt tct agc aca gca tac        240
Lys Gly Lys Ala Thr Leu Thr Val Asp Lys Phe Ser Ser Thr Ala Tyr
 65                  70                  75                  80 atg gat ctc agc agc ctg aca tct gag gac gct gca gtc tat ttc tgt        288
Met Asp Leu Ser Ser Leu Thr Ser Glu Asp Ala Ala Val Tyr Phe Cys
                     85                  90                  95 gca acg gat ggt tat ggg gat tgg ttt act tac tgg ggc caa ggc act        336
Ala Thr Asp Gly Tyr Gly Asp Trp Phe Thr Tyr Trp Gly Gln Gly Thr
                100                 105                 110 ctg gtc act gtc tct tca                                                354
Leu Val Thr Val Ser Ser
        115

<210> SEQ ID NO 16
<211> LENGTH: 118
<212> TYPE: PRT
<213> ORGANISM: Rattus norvegicus

<400> SEQUENCE: 16

Gln Val Lys Leu Leu Gln Ser Gly Ala Glu Leu Val Lys Pro Gly Ala
 1               5                  10                  15

Ser Val Lys Leu Ser Cys Lys Thr Ser Gly Phe Thr Phe Ser Thr Ser
                 20                  25                  30

Tyr Met Ser Trp Leu Lys Gln Val Pro Gly Pro Ser Thr Glu Trp Ile
         35                  40                  45

Gly Trp Ile Tyr Ala Gly Asp Gly Gly Thr Lys Tyr Asn Gln Lys Phe
 50                  55                  60

Lys Gly Lys Ala Thr Leu Thr Val Asp Lys Phe Ser Ser Thr Ala Tyr
 65                  70                  75                  80

Met Asp Leu Ser Ser Leu Thr Ser Glu Asp Ala Ala Val Tyr Phe Cys
                 85                  90                  95

Ala Thr Asp Gly Tyr Gly Asp Trp Phe Thr Tyr Trp Gly Gln Gly Thr
                100                 105                 110

Leu Val Thr Val Ser Ser
        115

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttcatgaggc acacgactga ggcacctcc                                         29

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
```
tccagttgct aactgttccg                                           20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagtggtatc aacgcagag                                            19

<210> SEQ ID NO 20
<211> LENGTH: 327
<212> TYPE: DNA
<213> ORGANISM: Rattus norvegicus
<220> FEATURE:
<221> NAME/KEY: CDS
<222> LOCATION: (1)..(327)

<400> SEQUENCE: 20 gac atc cag atg acc cag tct cca tct tcc ctg tct gca ttt ctg gga       48
Asp Ile Gln Met Thr Gln Ser Pro Ser Ser Leu Ser Ala Phe Leu Gly
1               5                   10                  15 gac aga gtc act att act tgc cgg gca agt caa gac att gga aat tat       96
Asp Arg Val Thr Ile Thr Cys Arg Ala Ser Gln Asp Ile Gly Asn Tyr
            20                  25                  30 tta aga tgg ttc cag cag aaa ccg ggg aaa tct cct agg ctt atg att      144
Leu Arg Trp Phe Gln Gln Lys Pro Gly Lys Ser Pro Arg Leu Met Ile
        35                  40                  45 tat ggt gca acc aac ttg gca aat ggg gtc cca tca agg ttc agt ggc      192
Tyr Gly Ala Thr Asn Leu Ala Asn Gly Val Pro Ser Arg Phe Ser Gly
    50                  55                  60 agt agg tct ggg tca gat tat tct ctg acc atc aac aac ttg gag tct      240
Ser Arg Ser Gly Ser Asp Tyr Ser Leu Thr Ile Asn Asn Leu Glu Ser
65                  70                  75                  80 gaa gac atg gct att tat tac tgt ctg aag cat aat gag tat cca ttc      288
Glu Asp Met Ala Ile Tyr Tyr Cys Leu Lys His Asn Glu Tyr Pro Phe
                85                  90                  95 acg ttc ggc tca ggg acg aag ttg gaa ata aaa cgg gct                  327
Thr Phe Gly Ser Gly Thr Lys Leu Glu Ile Lys Arg Ala
            100                 105

<210> SEQ ID NO 21
<211> LENGTH: 109
<212> TYPE: PRT
<213> ORGANISM: Rattus norvegicus

<400> SEQUENCE: 21

Asp Ile Gln Met Thr Gln Ser Pro Ser Ser Leu Ser Ala Phe Leu Gly
1               5                   10                  15

Asp Arg Val Thr Ile Thr Cys Arg Ala Ser Gln Asp Ile Gly Asn Tyr
            20                  25                  30

Leu Arg Trp Phe Gln Gln Lys Pro Gly Lys Ser Pro Arg Leu Met Ile
        35                  40                  45

Tyr Gly Ala Thr Asn Leu Ala Asn Gly Val Pro Ser Arg Phe Ser Gly
    50                  55                  60

Ser Arg Ser Gly Ser Asp Tyr Ser Leu Thr Ile Asn Asn Leu Glu Ser
65                  70                  75                  80

Glu Asp Met Ala Ile Tyr Tyr Cys Leu Lys His Asn Glu Tyr Pro Phe
                85                  90                  95

```
Thr Phe Gly Ser Gly Thr Lys Leu Glu Ile Lys Arg Ala
            100                 105

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tacgtgctgt ctttgctgtc ctgatcag                                        28

<210> SEQ ID NO 23
<211> LENGTH: 330
<212> TYPE: DNA
<213> ORGANISM: Rattus norvegicus
<220> FEATURE:
<221> NAME/KEY: CDS
<222> LOCATION: (1)..(330)

<400> SEQUENCE: 23 gac atc cag atg aca cag tct cca gct tcc ctg tct gca tct ctg gga      48
Asp Ile Gln Met Thr Gln Ser Pro Ala Ser Leu Ser Ala Ser Leu Gly
1               5                   10                  15 gaa act gtc acc atc gaa tgt cga gca agt gag gac att tac agt aat      96
Glu Thr Val Thr Ile Glu Cys Arg Ala Ser Glu Asp Ile Tyr Ser Asn
            20                  25                  30 tta gcg tgg tat cag cag aaa cca ggg aac tct cct cag ctc ctg atc     144
Leu Ala Trp Tyr Gln Gln Lys Pro Gly Asn Ser Pro Gln Leu Leu Ile
        35                  40                  45 tat gat gca aat atc ttg gca gat ggg gtc cca tca cgg ttc agt ggc     192
Tyr Asp Ala Asn Ile Leu Ala Asp Gly Val Pro Ser Arg Phe Ser Gly
    50                  55                  60 agt ggg tct ggc aca cag tat tct cta aag ata aac agc ctg caa tct     240
Ser Gly Ser Gly Thr Gln Tyr Ser Leu Lys Ile Asn Ser Leu Gln Ser
65                  70                  75                  80 gaa gat gtc gca agt tat ttc tgt caa cag tat aac aat tat cct ccg     288
Glu Asp Val Ala Ser Tyr Phe Cys Gln Gln Tyr Asn Asn Tyr Pro Pro
                85                  90                  95 ttc acg ttt gga gtt ggg acc aag ctg gaa ctg aaa cgg gct             330
Phe Thr Phe Gly Val Gly Thr Lys Leu Glu Leu Lys Arg Ala
            100                 105                 110

<210> SEQ ID NO 24
<211> LENGTH: 110
<212> TYPE: PRT
<213> ORGANISM: Rattus norvegicus

<400> SEQUENCE: 24

Asp Ile Gln Met Thr Gln Ser Pro Ala Ser Leu Ser Ala Ser Leu Gly
1               5                   10                  15

Glu Thr Val Thr Ile Glu Cys Arg Ala Ser Glu Asp Ile Tyr Ser Asn
            20                  25                  30

Leu Ala Trp Tyr Gln Gln Lys Pro Gly Asn Ser Pro Gln Leu Leu Ile
        35                  40                  45

Tyr Asp Ala Asn Ile Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80
```

```
Glu Asp Val Ala Ser Tyr Phe Cys Gln Gln Tyr Asn Asn Tyr Pro Pro
                85                  90                  95

Phe Thr Phe Gly Val Gly Thr Lys Leu Glu Leu Lys Arg Ala
            100                 105                 110

<210> SEQ ID NO 25
<211> LENGTH: 330
<212> TYPE: DNA
<213> ORGANISM: Rattus norvegicus
<220> FEATURE:
<221> NAME/KEY: CDS
<222> LOCATION: (1)..(330)

<400> SEQUENCE: 25 gac atc cag atg aca cag tct cca gct tcc ctg tct gca tct ctg gga         48
Asp Ile Gln Met Thr Gln Ser Pro Ala Ser Leu Ser Ala Ser Leu Gly
1               5                   10                  15 gaa act gtc acc atc gaa tgt cga gca agt gag gac ata tac agt aat         96
Glu Thr Val Thr Ile Glu Cys Arg Ala Ser Glu Asp Ile Tyr Ser Asn
                20                  25                  30 tta gcg tgg tat cag cag aaa cca ggg aac tct cct cag ctc ctg atc        144
Leu Ala Trp Tyr Gln Gln Lys Pro Gly Asn Ser Pro Gln Leu Leu Ile
            35                  40                  45 tat gat gca aat atc ctg gca gat ggg gtc cca tca cgg ttc agt ggc        192
Tyr Asp Ala Asn Ile Leu Ala Asp Gly Val Pro Ser Arg Phe Ser Gly
        50                  55                  60 agt ggg tct ggc aca cag tat tct cta aag ata aac agc ctg caa tct        240
Ser Gly Ser Gly Thr Gln Tyr Ser Leu Lys Ile Asn Ser Leu Gln Ser
65                  70                  75                  80 gaa gat gtc gca agt tat ttc tgt caa cag tat aac aat tat cct ccg        288
Glu Asp Val Ala Ser Tyr Phe Cys Gln Gln Tyr Asn Asn Tyr Pro Pro
                85                  90                  95 ttc acg ttt gga gct ggg acc aag ctg gaa ctg aaa cgg gct                330
Phe Thr Phe Gly Ala Gly Thr Lys Leu Glu Leu Lys Arg Ala
            100                 105                 110

<210> SEQ ID NO 26
<211> LENGTH: 110
<212> TYPE: PRT
<213> ORGANISM: Rattus norvegicus

<400> SEQUENCE: 26

Asp Ile Gln Met Thr Gln Ser Pro Ala Ser Leu Ser Ala Ser Leu Gly
1               5                   10                  15

Glu Thr Val Thr Ile Glu Cys Arg Ala Ser Glu Asp Ile Tyr Ser Asn
                20                  25                  30

Leu Ala Trp Tyr Gln Gln Lys Pro Gly Asn Ser Pro Gln Leu Leu Ile
            35                  40                  45

Tyr Asp Ala Asn Ile Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln Gln Tyr Asn Asn Tyr Pro Pro
                85                  90                  95

Phe Thr Phe Gly Ala Gly Thr Lys Leu Glu Leu Lys Arg Ala
            100                 105                 110

<210> SEQ ID NO 27
<211> LENGTH: 449
<212> TYPE: DNA
<213> ORGANISM: Homo sapiens
```

<400> SEQUENCE: 27

```
gcctccggac tctagagcca ccatggtgct gcagacccag gtgttcatct ccctgctgct    60
gtggatctcc ggcgcgtacg gcgatatcgt gatgattaaa cgtacggtgg ccgcccctc   120
cgtgttcatc ttccccccct ccgacgagca gctgaagtcc ggcaccgcct ccgtggtgtg   180
cctgctgaat aacttctacc ccagagaggc caaggtgcag tggaaggtgg acaacgccct   240
gcagtccggg aactcccagg agagcgtgac cgagcaggac agcaaggaca gcacctacag   300
cctgagcagc accctgaccc tgagcaaagc cgactacgag aagcacaagg tgtacgcctg   360
cgaggtgacc caccagggcc tgagctcccc cgtcaccaag agcttcaaca ggggggagtg   420
ttagggggccc gtttaaacgg gggaggcta                                   449
```

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 28

```
tataccgtcg acctctagct agagcttggc                                    30
```

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 29

```
gctatggcag ggcctgccgc cccgacgttg                                    30
```

<210> SEQ ID NO 30
<211> LENGTH: 1132
<212> TYPE: DNA
<213> ORGANISM: Homo sapiens

<400> SEQUENCE: 30

```
gcctccggac tctagagcca ccatgaaaca cctgtggttc ttcctcctgc tggtggcagc    60
tcccagatgg gtgctgagcc aggtgcaatt gtgcaggcgg ttagctcagc ctccaccaag   120
ggcccaagcg tcttccccct ggcaccctcc tccaagagca cctctggcgg cacagccgcc   180
ctgggctgcc tggtcaagga ctacttcccc gaacccgtga ccgtgagctg gaactcaggc   240
gccctgacca gcggcgtgca caccttcccc gctgtcctgc agtcctcagg actctactcc   300
ctcagcagcg tggtgaccgt gccctccagc agcttgggca cccagaccta catctgcaac   360
gtgaatcaca agcccagcaa caccaaggtg gacaagagag ttgagcccaa atcttgtgac   420
aaaactcaca catgcccacc ctgcccagca cctgaactcc tggggggacc ctcagtcttc   480
ctcttccccc caaaacccaa ggacaccctc atgatctccc ggacccctga ggtcacatgc   540
gtggtggtgg acgtgagcca cgaagaccct gaggtcaagt tcaactggta cgtggacggc   600
gtggaggtgc ataatgccaa gacaaagccc cgggaggagc agtacaacag cacgtaccgg   660
gtggtcagcg tcctcaccgt cctgcaccag gactggctga atggcaagga gtacaagtgc   720
aaggtctcca acaaagccct cccagcccc atcgagaaaa ccatctccaa agccaaaggc   780
```

```
cagccccggg aaccacaggt gtacaccctg cccccatccc gggaggagat gaccaagaac    840
caggtcagcc tgacctgcct ggtcaaaggc ttctatccca gcgacatcgc cgtggagtgg    900
gagagcaatg ccagcccga gaacaactac aagaccaccc ctcccgtgct ggactccgac    960
ggctccttct tcctctacag caagctcacc gtggacaaga gcaggtggca gcagggcaac    1020
gtcttctcat gctccgtgat gcatgaggct ctgcacaacc actacaccca gaagagcctc    1080
tccctgtctc cggcaaatg agatatcggg cccgtttaaa cgggggaggc ta             1132
```

<210> SEQ ID NO 31
<211> LENGTH: 702
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: CDS
<222> LOCATION: (1)..(702)

<400> SEQUENCE: 31

```
atg gtg ctg cag acc cag gtg ttc atc tcc ctg ctg ctg tgg atc tcc     48
Met Val Leu Gln Thr Gln Val Phe Ile Ser Leu Leu Leu Trp Ile Ser
1               5                   10                  15 ggc gcg tac ggc gac atc cag atg acc cag tct cca tct tcc ctg tct     96
Gly Ala Tyr Gly Asp Ile Gln Met Thr Gln Ser Pro Ser Ser Leu Ser
            20                  25                  30 gca ttt ctg gga gac aga gtc act att act tgc cgg gca agt caa gac    144
Ala Phe Leu Gly Asp Arg Val Thr Ile Thr Cys Arg Ala Ser Gln Asp
        35                  40                  45 att gga aat tat tta aga tgg ttc cag cag aaa ccg ggg aaa tct cct    192
Ile Gly Asn Tyr Leu Arg Trp Phe Gln Gln Lys Pro Gly Lys Ser Pro
    50                  55                  60 agg ctt atg att tat ggt gca acc aac ttg gca aat ggg gtc cca tca    240
Arg Leu Met Ile Tyr Gly Ala Thr Asn Leu Ala Asn Gly Val Pro Ser
65                  70                  75                  80 agg ttc agt ggc agt agg tct ggg tca gat tat tct ctg acc atc aac    288
Arg Phe Ser Gly Ser Arg Ser Gly Ser Asp Tyr Ser Leu Thr Ile Asn
                85                  90                  95 aac ttg gag tct gaa gac atg gct att tat tac tgt ctg aag cat aat    336
Asn Leu Glu Ser Glu Asp Met Ala Ile Tyr Tyr Cys Leu Lys His Asn
            100                 105                 110 gag tat cca ttc acg ttc ggc tca ggg acg aag ttg gaa ata aaa cgg    384
Glu Tyr Pro Phe Thr Phe Gly Ser Gly Thr Lys Leu Glu Ile Lys Arg
        115                 120                 125 gct gtg gcc gcc ccc tcc gtg ttc atc ttc ccc ccc tcc gac gag cag    432
Ala Val Ala Ala Pro Ser Val Phe Ile Phe Pro Pro Ser Asp Glu Gln
    130                 135                 140 ctg aag tcc ggc acc gcc tcc gtg gtg tgc ctg ctg aat aac ttc tac    480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc    528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc    576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag    624
Tyr Ser Leu Ser Ser Thr Leu Thr Leu Ser Lys Ala Asp Tyr Glu Lys
        195                 200                 205 cac aag gtg tac gcc tgc gag gtg acc cac cag ggc ctg agc tcc ccc    672
```

```
His Lys Val Tyr Ala Cys Glu Val Thr His Gln Gly Leu Ser Ser Pro
    210                 215                 220 gtc acc aag agc ttc aac agg ggg gag tgt                          702
Val Thr Lys Ser Phe Asn Arg Gly Glu Cys
225                 230
```

<210> SEQ ID NO 32
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Phe Leu Gly Asp Arg Val Thr Ile Thr Cys Arg Ala Ser Gln Asp
        35                  40                  45

Ile Gly Asn Tyr Leu Arg Trp Phe Gln Gln Lys Pro Gly Lys Ser Pro
    50                  55                  60

Arg Leu Met Ile Tyr Gly Ala Thr Asn Leu Ala Asn Gly Val Pro Ser
65                  70                  75                  80

Arg Phe Ser Gly Ser Arg Ser Gly Ser Asp Tyr Ser Leu Thr Ile Asn
                85                  90                  95

Asn Leu Glu Ser Glu Asp Met Ala Ile Tyr Tyr Cys Leu Lys His Asn
            100                 105                 110

Glu Tyr Pro Phe Thr Phe Gly Ser Gly Thr Lys Leu Glu Ile Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 33

```
atctccggcg cgtacggcga catccagatg acccagtctc catcttcc              48
```

<210> SEQ ID NO 34
<211> LENGTH: 44

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34 ggaggggggcg gccacagccc gttttatttc caacttcgtc cctg         44

<210> SEQ ID NO 35
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1413)

<400> SEQUENCE: 35
```

| | | | | | | | | | | | | | | | | |
|---|---|---|---|---|---|---|---|---|---|---|---|---|---|---|---|---|
| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtg | ctg | agc | gag | gtg | cag | ctg | gtg | gag | tct | ggg | gga | ggc | ctg | gtg | cag | 96 |
| Val | Leu | Ser | Glu | Val | Gln | Leu | Val | Glu | Ser | Gly | Gly | Gly | Leu | Val | Gln | |
| | | 20 | | | | | 25 | | | | | 30 | | | | |

| | | | | | | | | | | | | | | | | |
|---|---|---|---|---|---|---|---|---|---|---|---|---|---|---|---|---|
| cct | gga | agg | tct | ctg | aaa | cta | tcc | tgt | gta | gcc | tct | gga | ttc | aga | ttc | 144 |
| Pro | Gly | Arg | Ser | Leu | Lys | Leu | Ser | Cys | Val | Ala | Ser | Gly | Phe | Arg | Phe | |
| | | | 35 | | | | | 40 | | | | | 45 | | | |

| | | | | | | | | | | | | | | | | |
|---|---|---|---|---|---|---|---|---|---|---|---|---|---|---|---|---|
| aat | gac | ttt | tgg | atg | acc | tgg | atc | cgc | cag | gct | cca | ggg | aag | ggg | ctg | 192 |
| Asn | Asp | Phe | Trp | Met | Thr | Trp | Ile | Arg | Gln | Ala | Pro | Gly | Lys | Gly | Leu | |
| 50 | | | | | 55 | | | | | 60 | | | | | | |

| | | | | | | | | | | | | | | | | |
|---|---|---|---|---|---|---|---|---|---|---|---|---|---|---|---|---|
| gag | tgg | gtt | gca | tcc | att | act | tat | act | ggt | gat | aac | act | tac | tat | gca | 240 |
| Glu | Trp | Val | Ala | Ser | Ile | Thr | Tyr | Thr | Gly | Asp | Asn | Thr | Tyr | Tyr | Ala | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ggc | tct | gtg | aag | ggc | cga | atc | act | atc | tcc | aga | gat | aat | gcg | aag | agc | 288 |
| Gly | Ser | Val | Lys | Gly | Arg | Ile | Thr | Ile | Ser | Arg | Asp | Asn | Ala | Lys | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| acc | cta | tac | ctg | caa | atg | aac | agt | ctg | agg | tct | gag | gac | acg | gcc | act | 336 |
| Thr | Leu | Tyr | Leu | Gln | Met | Asn | Ser | Leu | Arg | Ser | Glu | Asp | Thr | Ala | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| tat | tac | tgt | aca | aga | gat | gac | tac | gga | gga | tat | agc | ccc | tac | tat | atg | 384 |
| Tyr | Tyr | Cys | Thr | Arg | Asp | Asp | Tyr | Gly | Gly | Tyr | Ser | Pro | Tyr | Tyr | Met | |
| | | 115 | | | | | 120 | | | | | 125 | | | | |

| | | | | | | | | | | | | | | | | |
|---|---|---|---|---|---|---|---|---|---|---|---|---|---|---|---|---|
| gat | gcc | tgg | ggt | caa | gga | act | tca | gtc | act | gtc | agc | tca | gcc | tcc | acc | 432 |
| Asp | Ala | Trp | Gly | Gln | Gly | Thr | Ser | Val | Thr | Val | Ser | Ser | Ala | Ser | Thr | |
| 130 | | | | | 135 | | | | | 140 | | | | | | |

| | | | | | | | | | | | | | | | | |
|---|---|---|---|---|---|---|---|---|---|---|---|---|---|---|---|---|
| aag | ggc | cca | agc | gtc | ttc | ccc | ctg | gca | ccc | tcc | tcc | aag | agc | acc | tct | 480 |
| Lys | Gly | Pro | Ser | Val | Phe | Pro | Leu | Ala | Pro | Ser | Ser | Lys | Ser | Thr | Ser | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| ggc | ggc | aca | gcc | gcc | ctg | ggc | tgc | ctg | gtc | aag | gac | tac | ttc | ccc | gaa | 528 |
| Gly | Gly | Thr | Ala | Ala | Leu | Gly | Cys | Leu | Val | Lys | Asp | Tyr | Phe | Pro | Glu | |
| | | | | 165 | | | | | 170 | | | | | 175 | | |

| | | | | | | | | | | | | | | | | |
|---|---|---|---|---|---|---|---|---|---|---|---|---|---|---|---|---|
| ccc | gtg | acc | gtg | agc | tgg | aac | tca | ggc | gcc | ctg | acc | agc | ggc | gtg | cac | 576 |
| Pro | Val | Thr | Val | Ser | Trp | Asn | Ser | Gly | Ala | Leu | Thr | Ser | Gly | Val | His | |
| | | | 180 | | | | | 185 | | | | | 190 | | | |

| | | | | | | | | | | | | | | | | |
|---|---|---|---|---|---|---|---|---|---|---|---|---|---|---|---|---|
| acc | ttc | ccc | gct | gtc | ctg | cag | tcc | tca | gga | ctc | tac | tcc | ctc | agc | agc | 624 |
| Thr | Phe | Pro | Ala | Val | Leu | Gln | Ser | Ser | Gly | Leu | Tyr | Ser | Leu | Ser | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| gtg | gtg | acc | gtg | ccc | tcc | agc | agc | ttg | ggc | acc | cag | acc | tac | atc | tgc | 672 |
| Val | Val | Thr | Val | Pro | Ser | Ser | Ser | Leu | Gly | Thr | Gln | Thr | Tyr | Ile | Cys | |
| | | 210 | | | | | 215 | | | | | 220 | | | | |

```
aac gtg aat cac aag ccc agc aac acc aag gtg gac aag aga gtt gag    720
Asn Val Asn His Lys Pro Ser Asn Thr Lys Val Asp Lys Arg Val Glu
225                 230                 235                 240 ccc aaa tct tgt gac aaa act cac aca tgc cca ccc tgc cca gca cct    768
Pro Lys Ser Cys Asp Lys Thr His Thr Cys Pro Pro Cys Pro Ala Pro
                245                 250                 255 gaa ctc ctg ggg gga ccc tca gtc ttc ctc ttc ccc cca aaa ccc aag    816
Glu Leu Leu Gly Gly Pro Ser Val Phe Leu Phe Pro Pro Lys Pro Lys
            260                 265                 270 gac acc ctc atg atc tcc cgg acc cct gag gtc aca tgc gtg gtg gtg    864
Asp Thr Leu Met Ile Ser Arg Thr Pro Glu Val Thr Cys Val Val Val
        275                 280                 285 gac gtg agc cac gaa gac cct gag gtc aag ttc aac tgg tac gtg gac    912
Asp Val Ser His Glu Asp Pro Glu Val Lys Phe Asn Trp Tyr Val Asp
    290                 295                 300 ggc gtg gag gtg cat aat gcc aag aca aag ccc cgg gag gag cag tac    960
Gly Val Glu Val His Asn Ala Lys Thr Lys Pro Arg Glu Glu Gln Tyr
305                 310                 315                 320 aac agc acg tac cgg gtg gtc agc gtc ctc acc gtc ctg cac cag gac    1008
Asn Ser Thr Tyr Arg Val Val Ser Val Leu Thr Val Leu His Gln Asp
                325                 330                 335 tgg ctg aat ggc aag gag tac aag tgc aag gtc tcc aac aaa gcc ctc    1056
Trp Leu Asn Gly Lys Glu Tyr Lys Cys Lys Val Ser Asn Lys Ala Leu
            340                 345                 350 cca gcc ccc atc gag aaa acc atc tcc aaa gcc aaa ggc cag ccc cgg    1104
Pro Ala Pro Ile Glu Lys Thr Ile Ser Lys Ala Lys Gly Gln Pro Arg
        355                 360                 365 gaa cca cag gtg tac acc ctg ccc cca tcc cgg gag gag atg acc aag    1152
Glu Pro Gln Val Tyr Thr Leu Pro Pro Ser Arg Glu Glu Met Thr Lys
    370                 375                 380 aac cag gtc agc ctg acc tgc ctg gtc aaa ggc ttc tat ccc agc gac    1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag    1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc    1296
Thr Thr Pro Pro Val Leu Asp Ser Asp Gly Ser Phe Phe Leu Tyr Ser
            420                 425                 430 aag ctc acc gtg gac aag agc agg tgg cag cag ggc aac gtc ttc tca    1344
Lys Leu Thr Val Asp Lys Ser Arg Trp Gln Gln Gly Asn Val Phe Ser
        435                 440                 445 tgc tcc gtg atg cat gag gct ctg cac aac cac tac acc cag aag agc    1392
Cys Ser Val Met His Glu Ala Leu His Asn His Tyr Thr Gln Lys Ser
    450                 455                 460 ctc tcc ctg tct ccc ggc aaa                                        1413
Leu Ser Leu Ser Pro Gly Lys
465                 470

<210> SEQ ID NO 36
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Lys His Leu Trp Phe Phe Leu Leu Leu Val Ala Ala Pro Arg Trp
1               5                   10                  15
```

-continued

Val Leu Ser Glu Val Gln Leu Val Glu Ser Gly Gly Gly Leu Val Gln
          20                  25                  30

Pro Gly Arg Ser Leu Lys Leu Ser Cys Val Ala Ser Gly Phe Arg Phe
          35                  40                  45

Asn Asp Phe Trp Met Thr Trp Ile Arg Gln Ala Pro Gly Lys Gly Leu
          50                  55                  60

Glu Trp Val Ala Ser Ile Thr Tyr Thr Gly Asp Asn Thr Tyr Tyr Ala
65                  70                  75                  80

Gly Ser Val Lys Gly Arg Ile Thr Ile Ser Arg Asp Asn Ala Lys Ser
                85                  90                  95

Thr Leu Tyr Leu Gln Met Asn Ser Leu Arg Ser Glu Asp Thr Ala Thr
            100                 105                 110

Tyr Tyr Cys Thr Arg Asp Asp Tyr Gly Gly Tyr Ser Pro Tyr Tyr Met
            115                 120                 125

Asp Ala Trp Gly Gln Gly Thr Ser Val Thr Val Ser Ser Ala Ser Thr
            130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser

```
                   435                 440                 445
Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 37
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccagatgggt gctgagcgag gtgcagctgg tggagtctgg gggaggc                    47

<210> SEQ ID NO 38
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cttggtggag gctgagctga cagtgactga agttccttga ccccaggc                   48

<210> SEQ ID NO 39
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(705)

<400> SEQUENCE: 39 atg gtg ctg cag acc cag gtg ttc atc tcc ctg ctg ctg tgg atc tcc        48
Met Val Leu Gln Thr Gln Val Phe Ile Ser Leu Leu Leu Trp Ile Ser
1               5                  10                  15 ggc gcg tac ggc gac atc cag atg aca cag tct cca gct tcc ctg tct        96
Gly Ala Tyr Gly Asp Ile Gln Met Thr Gln Ser Pro Ala Ser Leu Ser
            20                  25                  30 gca tct ctg gga gaa act gtc acc atc gaa tgt cga gca agt gag gac       144
Ala Ser Leu Gly Glu Thr Val Thr Ile Glu Cys Arg Ala Ser Glu Asp
        35                  40                  45 att tac agt aat tta gcg tgg tat cag cag aaa cca ggg aac tct cct       192
Ile Tyr Ser Asn Leu Ala Trp Tyr Gln Gln Lys Pro Gly Asn Ser Pro
    50                  55                  60 cag ctc ctg atc tat gat gca aat atc ttg gca gat ggg gtc cca tca       240
Gln Leu Leu Ile Tyr Asp Ala Asn Ile Leu Ala Asp Gly Val Pro Ser
65                  70                  75                  80 cgg ttc agt ggc agt ggg tct ggc aca cag tat tct cta aag ata aac       288
Arg Phe Ser Gly Ser Gly Ser Gly Thr Gln Tyr Ser Leu Lys Ile Asn
                85                  90                  95 agc ctg caa tct gaa gat gtc gca agt tat ttc tgt caa cag tat aac       336
Ser Leu Gln Ser Glu Asp Val Ala Ser Tyr Phe Cys Gln Gln Tyr Asn
            100                 105                 110 aat tat cct ccg ttc acg ttt gga gtt ggg acc aag ctg gaa ctg aaa       384
Asn Tyr Pro Pro Phe Thr Phe Gly Val Gly Thr Lys Leu Glu Leu Lys
        115                 120                 125
```

```
cgg gct gtg gcc gcc ccc tcc gtg ttc atc ttc ccc ccc tcc gac gag      432
Arg Ala Val Ala Ala Pro Ser Val Phe Ile Phe Pro Pro Ser Asp Glu
    130             135                 140 cag ctg aag tcc ggc acc gcc tcc gtg gtg tgc ctg ctg aat aac ttc      480
Gln Leu Lys Ser Gly Thr Ala Ser Val Val Cys Leu Leu Asn Asn Phe
145             150                 155                 160 tac ccc aga gag gcc aag gtg cag tgg aag gtg gac aac gcc ctg cag      528
Tyr Pro Arg Glu Ala Lys Val Gln Trp Lys Val Asp Asn Ala Leu Gln
                165                 170                 175 tcc ggg aac tcc cag gag agc gtg acc gag cag gac agc aag gac agc      576
Ser Gly Asn Ser Gln Glu Ser Val Thr Glu Gln Asp Ser Lys Asp Ser
            180                 185                 190 acc tac agc ctg agc agc acc ctg acc ctg agc aaa gcc gac tac gag      624
Thr Tyr Ser Leu Ser Ser Thr Leu Thr Leu Ser Lys Ala Asp Tyr Glu
        195                 200                 205 aag cac aag gtg tac gcc tgc gag gtg acc cac cag ggc ctg agc tcc      672
Lys His Lys Val Tyr Ala Cys Glu Val Thr His Gln Gly Leu Ser Ser
    210                 215                 220 ccc gtc acc aag agc ttc aac agg ggg gag tgt                          705
Pro Val Thr Lys Ser Phe Asn Arg Gly Glu Cys
225                 230                 235

<210> SEQ ID NO 40
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ala Ser Leu Ser
            20                  25                  30

Ala Ser Leu Gly Glu Thr Val Thr Ile Glu Cys Arg Ala Ser Glu Asp
        35                  40                  45

Ile Tyr Ser Asn Leu Ala Trp Tyr Gln Gln Lys Pro Gly Asn Ser Pro
    50                  55                  60

Gln Leu Leu Ile Tyr Asp Ala Asn Ile Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Val Ala Ser Tyr Phe Cys Gln Gln Tyr Asn
            100                 105                 110

Asn Tyr Pro Pro Phe Thr Phe Gly Val Gly Thr Lys Leu Glu Leu Lys
        115                 120                 125

Arg Ala Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145             150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205
```

```
Lys His Lys Val Tyr Ala Cys Glu Val Thr His Gln Gly Leu Ser Ser
    210                 215                 220
Pro Val Thr Lys Ser Phe Asn Arg Gly Glu Cys
225                 230                 235

<210> SEQ ID NO 41
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atctccggcg cgtacggcga catccagatg acacagtctc cagcttcc                48

<210> SEQ ID NO 42
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42 ggaggggggcg gccacagccc gtttcagttc cagcttggtc ccaac                  45

<210> SEQ ID NO 43
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 43
```

| atg | aaa | cac | ctg | tgg | ttc | ttc | ctc | ctg | ctg | gtg | gca | gct | ccc | aga | tgg | 48 |
|---|---|---|---|---|---|---|---|---|---|---|---|---|---|---|---|---|
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |

| gtg | ctg | agc | cag | gtt | aag | ctg | ctg | cag | tct | ggg | gct | gag | ctg | gta | aaa | 96 |
|---|---|---|---|---|---|---|---|---|---|---|---|---|---|---|---|---|
| Val | Leu | Ser | Gln | Val | Lys | Leu | Leu | Gln | Ser | Gly | Ala | Glu | Leu | Val | Lys | |
| | | | 20 | | | | | 25 | | | | | 30 | | | |

| cct | ggt | gct | tca | gtg | aag | ttg | tcc | tgc | aag | act | tct | ggt | ttt | acc | ttc | 144 |
|---|---|---|---|---|---|---|---|---|---|---|---|---|---|---|---|---|
| Pro | Gly | Ala | Ser | Val | Lys | Leu | Ser | Cys | Lys | Thr | Ser | Gly | Phe | Thr | Phe | |
| | | 35 | | | | | 40 | | | | | 45 | | | | |

| agc | act | agc | tat | atg | agt | tgg | ttg | aag | cag | gtg | cct | gga | ccg | agt | att | 192 |
|---|---|---|---|---|---|---|---|---|---|---|---|---|---|---|---|---|
| Ser | Thr | Ser | Tyr | Met | Ser | Trp | Leu | Lys | Gln | Val | Pro | Gly | Pro | Ser | Ile | |
| | 50 | | | | | 55 | | | | | 60 | | | | | |

| gag | tgg | att | gga | tgg | att | tat | gct | gga | gat | ggt | ggt | act | aag | tat | aat | 240 |
|---|---|---|---|---|---|---|---|---|---|---|---|---|---|---|---|---|
| Glu | Trp | Ile | Gly | Trp | Ile | Tyr | Ala | Gly | Asp | Gly | Gly | Thr | Lys | Tyr | Asn | |
| 65 | | | | 70 | | | | | 75 | | | | | 80 | | |

| cag | aag | ttc | aag | ggc | aag | gcc | aca | ctg | aca | gta | gac | aaa | tct | tct | agc | 288 |
|---|---|---|---|---|---|---|---|---|---|---|---|---|---|---|---|---|
| Gln | Lys | Phe | Lys | Gly | Lys | Ala | Thr | Leu | Thr | Val | Asp | Lys | Ser | Ser | Ser | |
| | | | | 85 | | | | | 90 | | | | | 95 | | |

| aca | gca | tac | atg | gat | ctc | agc | agc | ctg | aca | tct | gag | gac | gct | gca | gtc | 336 |
|---|---|---|---|---|---|---|---|---|---|---|---|---|---|---|---|---|
| Thr | Ala | Tyr | Met | Asp | Leu | Ser | Ser | Leu | Thr | Ser | Glu | Asp | Ala | Ala | Val | |
| | | | 100 | | | | | 105 | | | | | 110 | | | |

| tat | ttt | tgt | gca | acg | gat | ggt | tat | ggg | gat | tgg | ttt | gct | tac | tgg | ggc | 384 |
|---|---|---|---|---|---|---|---|---|---|---|---|---|---|---|---|---|
| Tyr | Phe | Cys | Ala | Thr | Asp | Gly | Tyr | Gly | Asp | Trp | Phe | Ala | Tyr | Trp | Gly | |
| | | | 115 | | | | | 120 | | | | | 125 | | | |

| caa | ggc | act | ctg | gtc | act | gtc | agc | tca | gcc | tcc | acc | aag | ggc | cca | agc | 432 |
|---|---|---|---|---|---|---|---|---|---|---|---|---|---|---|---|---|

```
                Gln Gly Thr Leu Val Thr Val Ser Ser Ala Ser Thr Lys Gly Pro Ser
                    130                 135                 140 gtc ttc ccc ctg gca ccc tcc tcc aag agc acc tct ggc gga aca gcc         480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg         528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct         576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg         624
Val Leu Gln Ser Ser Gly Leu Tyr Ser Leu Ser Ser Val Val Thr Val
        195                 200                 205 ccc tcc agc agc ttg ggc acc cag acc tac atc tgc aac gtg aat cac         672
Pro Ser Ser Ser Leu Gly Thr Gln Thr Tyr Ile Cys Asn Val Asn His
    210                 215                 220 aag ccc agc aac acc aag gtg gac aag aga gtt gag ccc aaa tct tgt         720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg         768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg         816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac         864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg         912
Glu Asp Pro Glu Val Lys Phe Asn Trp Tyr Val Asp Gly Val Glu Val
    290                 295                 300 cat aat gcc aag aca aag ccc cgg gag gag cag tac aac agc acg tac         960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc        1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc        1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg        1104
Glu Lys Thr Ile Ser Lys Ala Lys Gly Gln Pro Arg Glu Pro Gln Val
        355                 360                 365 tac acc ctg ccc cca tcc cgg gag gag atg acc aag aac cag gtc agc        1152
Tyr Thr Leu Pro Pro Ser Arg Glu Glu Met Thr Lys Asn Gln Val Ser
    370                 375                 380 ctg acc tgc ctg gtc aaa ggc ttc tat ccc agc gac atc gcc gtg gag        1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc        1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg        1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg        1344
Asp Lys Ser Arg Trp Gln Gln Gly Asn Val Phe Ser Cys Ser Val Met
        435                 440                 445
```

```
cat gag gct ctg cac aac cac tac acc cag aag agc ctc tcc ctg tct    1392
His Glu Ala Leu His Asn His Tyr Thr Gln Lys Ser Leu Ser Leu Ser
    450                 455                 460 ccc ggc aaa                                                        1401
Pro Gly Lys
465
```

<210> SEQ ID NO 44
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Met Lys His Leu Trp Phe Phe Leu Leu Leu Val Ala Ala Pro Arg Trp
1               5                   10                  15

Val Leu Ser Gln Val Lys Leu Leu Gln Ser Gly Ala Glu Leu Val Lys
            20                  25                  30

Pro Gly Ala Ser Val Lys Leu Ser Cys Lys Thr Ser Gly Phe Thr Phe
        35                  40                  45

Ser Thr Ser Tyr Met Ser Trp Leu Lys Gln Val Pro Gly Pro Ser Ile
    50                  55                  60

Glu Trp Ile Gly Trp Ile Tyr Ala Gly Asp Gly Thr Lys Tyr Asn
65                  70                  75                  80

Gln Lys Phe Lys Gly Lys Ala Thr Leu Thr Val Asp Lys Ser Ser Ser
                85                  90                  95

Thr Ala Tyr Met Asp Leu Ser Ser Leu Thr Ser Glu Asp Ala Ala Val
            100                 105                 110

Tyr Phe Cys Ala Thr Asp Gly Tyr Gly Asp Trp Phe Ala Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320
```

```
Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccagatgggt gctgagccag gttaagctgc tgcagtctgg ggctgag                47

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cttggtggag gctgagctga cagtgaccag agtgccttgg ccccag                 46

<210> SEQ ID NO 47
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(705)

<400> SEQUENCE: 47 atg gtg ctg cag acc cag gtg ttc atc tcc ctg ctg ctg tgg atc tcc    48
Met Val Leu Gln Thr Gln Val Phe Ile Ser Leu Leu Leu Trp Ile Ser
1               5                   10                  15 ggc gcg tac ggc gac atc cag atg aca cag tct cca gct tcc ctg tct    96
Gly Ala Tyr Gly Asp Ile Gln Met Thr Gln Ser Pro Ala Ser Leu Ser
            20                  25                  30 gca tct ctg gga gaa act gtc acc atc gaa tgt cga gca agt gag gac   144
```

```
Ala Ser Leu Gly Glu Thr Val Thr Ile Glu Cys Arg Ala Ser Glu Asp
            35                  40                  45 ata tac agt aat tta gcg tgg tat cag cag aaa cca ggg aac tct cct        192
Ile Tyr Ser Asn Leu Ala Trp Tyr Gln Gln Lys Pro Gly Asn Ser Pro
 50                  55                  60 cag ctc ctg atc tat gat gca aat atc ctg gca gat ggg gtc cca tca        240
Gln Leu Leu Ile Tyr Asp Ala Asn Ile Leu Ala Asp Gly Val Pro Ser
 65                  70                  75                  80 cgg ttc agt ggc agt ggg tct ggc aca cag tat tct cta aag ata aac        288
Arg Phe Ser Gly Ser Gly Ser Gly Thr Gln Tyr Ser Leu Lys Ile Asn
                 85                  90                  95 agc ctg caa tct gaa gat gtc gca agt tat ttc tgt caa cag tat aac        336
Ser Leu Gln Ser Glu Asp Val Ala Ser Tyr Phe Cys Gln Gln Tyr Asn
            100                 105                 110 aat tat cct ccg ttc acg ttt gga gct ggg acc aag ctg gaa ctg aaa        384
Asn Tyr Pro Pro Phe Thr Phe Gly Ala Gly Thr Lys Leu Glu Leu Lys
        115                 120                 125 cgg gct gtg gcc gcc ccc tcc gtg ttc atc ttc ccc ccc tcc gac gag        432
Arg Ala Val Ala Ala Pro Ser Val Phe Ile Phe Pro Pro Ser Asp Glu
    130                 135                 140 cag ctg aag tcc ggc acc gcc tcc gtg gtg tgc ctg ctg aat aac ttc        480
Gln Leu Lys Ser Gly Thr Ala Ser Val Val Cys Leu Leu Asn Asn Phe
145                 150                 155                 160 tac ccc aga gag gcc aag gtg cag tgg aag gtg gac aac gcc ctg cag        528
Tyr Pro Arg Glu Ala Lys Val Gln Trp Lys Val Asp Asn Ala Leu Gln
                165                 170                 175 tcc ggg aac tcc cag gag agc gtg acc gag cag gac agc aag gac agc        576
Ser Gly Asn Ser Gln Glu Ser Val Thr Glu Gln Asp Ser Lys Asp Ser
            180                 185                 190 acc tac agc ctg agc agc acc ctg acc ctg agc aaa gcc gac tac gag        624
Thr Tyr Ser Leu Ser Ser Thr Leu Thr Leu Ser Lys Ala Asp Tyr Glu
        195                 200                 205 aag cac aag gtg tac gcc tgc gag gtg acc cac cag ggc ctg agc tcc        672
Lys His Lys Val Tyr Ala Cys Glu Val Thr His Gln Gly Leu Ser Ser
    210                 215                 220 ccc gtc acc aag agc ttc aac agg ggg gag tgt                            705
Pro Val Thr Lys Ser Phe Asn Arg Gly Glu Cys
225                 230                 235

<210> SEQ ID NO 48
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Val Leu Gln Thr Gln Val Phe Ile Ser Leu Leu Leu Trp Ile Ser
 1               5                  10                  15

Gly Ala Tyr Gly Asp Ile Gln Met Thr Gln Ser Pro Ala Ser Leu Ser
            20                  25                  30

Ala Ser Leu Gly Glu Thr Val Thr Ile Glu Cys Arg Ala Ser Glu Asp
        35                  40                  45

Ile Tyr Ser Asn Leu Ala Trp Tyr Gln Gln Lys Pro Gly Asn Ser Pro
 50                  55                  60

Gln Leu Leu Ile Tyr Asp Ala Asn Ile Leu Ala Asp Gly Val Pro Ser
 65                  70                  75                  80

Arg Phe Ser Gly Ser Gly Ser Gly Thr Gln Tyr Ser Leu Lys Ile Asn
                 85                  90                  95
```

```
Ser Leu Gln Ser Glu Asp Val Ala Ser Tyr Phe Cys Gln Gln Tyr Asn
            100                 105                 110

Asn Tyr Pro Pro Phe Thr Phe Gly Ala Gly Thr Lys Leu Glu Leu Lys
        115                 120                 125

Arg Ala Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235
```

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 49 ggaggggggcg gccacagccc gtttcagttc cagcttggtc ccagc         45

<210> SEQ ID NO 50
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(1401)

<400> SEQUENCE: 50

```
atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15 gtg ctg agc cag gtt aag ctg ctg cag tct ggg gct gag ctg gta aaa    96
Val Leu Ser Gln Val Lys Leu Leu Gln Ser Gly Ala Glu Leu Val Lys
            20                  25                  30 cct ggt gct tca gtg aag ttg tcc tgc aag act tct ggt ttt aca ttc   144
Pro Gly Ala Ser Val Lys Leu Ser Cys Lys Thr Ser Gly Phe Thr Phe
        35                  40                  45 agc act agt tat atg agt tgg ttg aag cag gtg cct gga ccg agt act   192
Ser Thr Ser Tyr Met Ser Trp Leu Lys Gln Val Pro Gly Pro Ser Thr
    50                  55                  60 gag tgg att gga tgg att tat gct gga gat ggt ggt act aag tat aat   240
Glu Trp Ile Gly Trp Ile Tyr Ala Gly Asp Gly Gly Thr Lys Tyr Asn
65                  70                  75                  80 cag aag ttc aag ggc aag gcc aca ctg aca gta gac aaa ttt tct agc   288
Gln Lys Phe Lys Gly Lys Ala Thr Leu Thr Val Asp Lys Phe Ser Ser
                85                  90                  95
```

```
aca gca tac atg gat ctc agc agc ctg aca tct gag gac gct gca gtc        336
Thr Ala Tyr Met Asp Leu Ser Ser Leu Thr Ser Glu Asp Ala Ala Val
            100             105             110 tat ttc tgt gca acg gat ggt tat ggg gat tgg ttt act tac tgg ggc        384
Tyr Phe Cys Ala Thr Asp Gly Tyr Gly Asp Trp Phe Thr Tyr Trp Gly
        115             120             125 caa ggc act ctg gtc act gtc agc tca gcc tcc acc aag ggc cca agc        432
Gln Gly Thr Leu Val Thr Val Ser Ser Ala Ser Thr Lys Gly Pro Ser
    130             135             140 gtc ttc ccc ctg gca ccc tcc tcc aag agc acc tct ggc ggc aca gcc        480
Val Phe Pro Leu Ala Pro Ser Ser Lys Ser Thr Ser Gly Gly Thr Ala
145             150             155             160 gcc ctg ggc tgc ctg gtc aag gac tac ttc ccc gaa ccc gtg acc gtg        528
Ala Leu Gly Cys Leu Val Lys Asp Tyr Phe Pro Glu Pro Val Thr Val
                165             170             175 agc tgg aac tca ggc gcc ctg acc agc ggc gtg cac acc ttc ccc gct        576
Ser Trp Asn Ser Gly Ala Leu Thr Ser Gly Val His Thr Phe Pro Ala
            180             185             190 gtc ctg cag tcc tca gga ctc tac tcc ctc agc agc gtg gtg acc gtg        624
Val Leu Gln Ser Ser Gly Leu Tyr Ser Leu Ser Ser Val Val Thr Val
        195             200             205 ccc tcc agc agc ttg ggc acc cag acc tac atc tgc aac gtg aat cac        672
Pro Ser Ser Ser Leu Gly Thr Gln Thr Tyr Ile Cys Asn Val Asn His
    210             215             220 aag ccc agc aac acc aag gtg gac aag aga gtt gag ccc aaa tct tgt        720
Lys Pro Ser Asn Thr Lys Val Asp Lys Arg Val Glu Pro Lys Ser Cys
225             230             235             240 gac aaa act cac aca tgc cca ccc tgc cca gca cct gaa ctc ctg ggg        768
Asp Lys Thr His Thr Cys Pro Pro Cys Pro Ala Pro Glu Leu Leu Gly
                245             250             255 gga ccc tca gtc ttc ctc ttc ccc cca aaa ccc aag gac acc ctc atg        816
Gly Pro Ser Val Phe Leu Phe Pro Pro Lys Pro Lys Asp Thr Leu Met
            260             265             270 atc tcc cgg acc cct gag gtc aca tgc gtg gtg gtg gac gtg agc cac        864
Ile Ser Arg Thr Pro Glu Val Thr Cys Val Val Val Asp Val Ser His
        275             280             285 gaa gac cct gag gtc aag ttc aac tgg tac gtg gac ggc gtg gag gtg        912
Glu Asp Pro Glu Val Lys Phe Asn Trp Tyr Val Asp Gly Val Glu Val
    290             295             300 cat aat gcc aag aca aag ccc cgg gag gag cag tac aac agc acg tac        960
His Asn Ala Lys Thr Lys Pro Arg Glu Glu Gln Tyr Asn Ser Thr Tyr
305             310             315             320 cgg gtg gtc agc gtc ctc acc gtc ctg cac cag gac tgg ctg aat ggc       1008
Arg Val Val Ser Val Leu Thr Val Leu His Gln Asp Trp Leu Asn Gly
                325             330             335 aag gag tac aag tgc aag gtc tcc aac aaa gcc ctc cca gcc ccc atc       1056
Lys Glu Tyr Lys Cys Lys Val Ser Asn Lys Ala Leu Pro Ala Pro Ile
            340             345             350 gag aaa acc atc tcc aaa gcc aaa ggc cag ccc cgg gaa cca cag gtg       1104
Glu Lys Thr Ile Ser Lys Ala Lys Gly Gln Pro Arg Glu Pro Gln Val
        355             360             365 tac acc ctg ccc cca tcc cgg gag gag atg acc aag aac cag gtc agc       1152
Tyr Thr Leu Pro Pro Ser Arg Glu Glu Met Thr Lys Asn Gln Val Ser
    370             375             380 ctg acc tgc ctg gtc aaa ggc ttc tat ccc agc gac atc gcc gtg gag       1200
Leu Thr Cys Leu Val Lys Gly Phe Tyr Pro Ser Asp Ile Ala Val Glu
385             390             395             400 tgg gag agc aat ggc cag ccc gag aac aac tac aag acc acc cct ccc       1248
Trp Glu Ser Asn Gly Gln Pro Glu Asn Asn Tyr Lys Thr Thr Pro Pro
                405             410             415
```

```
gtg ctg gac tcc gac ggc tcc ttc ttc ctc tac agc aag ctc acc gtg      1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg      1344
Asp Lys Ser Arg Trp Gln Gln Gly Asn Val Phe Ser Cys Ser Val Met
            435                 440                 445 cat gag gct ctg cac aac cac tac acc cag aag agc ctc tcc ctg tct      1392
His Glu Ala Leu His Asn His Tyr Thr Gln Lys Ser Leu Ser Leu Ser
450                 455                 460 ccc ggc aaa                                                          1401
Pro Gly Lys
465

<210> SEQ ID NO 51
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Lys His Leu Trp Phe Phe Leu Leu Leu Val Ala Ala Pro Arg Trp
1               5                   10                  15

Val Leu Ser Gln Val Lys Leu Leu Gln Ser Gly Ala Glu Leu Val Lys
            20                  25                  30

Pro Gly Ala Ser Val Lys Leu Ser Cys Lys Thr Ser Gly Phe Thr Phe
        35                  40                  45

Ser Thr Ser Tyr Met Ser Trp Leu Lys Gln Val Pro Gly Pro Ser Thr
    50                  55                  60

Glu Trp Ile Gly Trp Ile Tyr Ala Gly Asp Gly Thr Lys Tyr Asn
65                  70                  75                  80

Gln Lys Phe Lys Gly Lys Ala Thr Leu Thr Val Asp Lys Phe Ser Ser
                85                  90                  95

Thr Ala Tyr Met Asp Leu Ser Ser Leu Thr Ser Glu Asp Ala Ala Val
            100                 105                 110

Tyr Phe Cys Ala Thr Asp Gly Tyr Gly Asp Trp Phe Thr Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270
```

```
Ile Ser Arg Thr Pro Glu Val Thr Cys Val Val Val Asp Val Ser His
            275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 52
<211> LENGTH: 5
<212> TYPE: PRT
<213> ORGANISM: Rattus norvegicus

<400> SEQUENCE: 52

Asp Phe Trp Met Thr
1               5

<210> SEQ ID NO 53
<211> LENGTH: 17
<212> TYPE: PRT
<213> ORGANISM: Rattus norvegicus

<400> SEQUENCE: 53

Ser Ile Thr Tyr Thr Gly Asp Asn Thr Tyr Tyr Ala Gly Ser Val Lys
1               5                   10                  15
Gly

<210> SEQ ID NO 54
<211> LENGTH: 13
<212> TYPE: PRT
<213> ORGANISM: Rattus norvegicus

<400> SEQUENCE: 54

Asp Asp Tyr Gly Gly Tyr Ser Pro Tyr Tyr Met Asp Ala
1               5                   10

<210> SEQ ID NO 55
<211> LENGTH: 5
<212> TYPE: PRT
<213> ORGANISM: Rattus norvegicus
```

<400> SEQUENCE: 55

Thr Ser Tyr Met Ser
1               5

<210> SEQ ID NO 56
<211> LENGTH: 17
<212> TYPE: PRT
<213> ORGANISM: Rattus norvegicus

<400> SEQUENCE: 56

Trp Ile Tyr Ala Gly Asp Gly Gly Thr Lys Tyr Asn Gln Lys Phe Lys
1               5                   10                  15

Gly

<210> SEQ ID NO 57
<211> LENGTH: 9
<212> TYPE: PRT
<213> ORGANISM: Rattus norvegicus

<400> SEQUENCE: 57

Asp Gly Tyr Gly Asp Trp Phe Ala Tyr
1               5

<210> SEQ ID NO 58
<211> LENGTH: 5
<212> TYPE: PRT
<213> ORGANISM: Rattus norvegicus

<400> SEQUENCE: 58

Thr Ser Tyr Met Ser
1               5

<210> SEQ ID NO 59
<211> LENGTH: 17
<212> TYPE: PRT
<213> ORGANISM: Rattus norvegicus

<400> SEQUENCE: 59

Trp Ile Tyr Ala Gly Asp Gly Gly Thr Lys Tyr Asn Gln Lys Phe Lys
1               5                   10                  15

Gly

<210> SEQ ID NO 60
<211> LENGTH: 9
<212> TYPE: PRT
<213> ORGANISM: Rattus norvegicus

<400> SEQUENCE: 60

Asp Gly Tyr Gly Asp Trp Phe Thr Tyr
1               5

<210> SEQ ID NO 61
<211> LENGTH: 11
<212> TYPE: PRT
<213> ORGANISM: Rattus norvegicus

<400> SEQUENCE: 61

Arg Ala Ser Gln Asp Ile Gly Asn Tyr Leu Arg
1               5                   10

<210> SEQ ID NO 62
<211> LENGTH: 7

<212> TYPE: PRT
<213> ORGANISM: Rattus norvegicus

<400> SEQUENCE: 62

Gly Ala Thr Asn Leu Ala Asn
1               5

<210> SEQ ID NO 63
<211> LENGTH: 9
<212> TYPE: PRT
<213> ORGANISM: Rattus norvegicus

<400> SEQUENCE: 63

Leu Lys His Asn Glu Tyr Pro Phe Thr
1               5

<210> SEQ ID NO 64
<211> LENGTH: 11
<212> TYPE: PRT
<213> ORGANISM: Rattus norvegicus

<400> SEQUENCE: 64

Arg Ala Ser Glu Asp Ile Tyr Ser Asn Leu Ala
1               5                   10

<210> SEQ ID NO 65
<211> LENGTH: 7
<212> TYPE: PRT
<213> ORGANISM: Rattus norvegicus

<400> SEQUENCE: 65

Asp Ala Asn Ile Leu Ala Asp
1               5

<210> SEQ ID NO 66
<211> LENGTH: 10
<212> TYPE: PRT
<213> ORGANISM: Rattus norvegicus

<400> SEQUENCE: 66

Gln Gln Tyr Asn Asn Tyr Pro Pro Phe Thr
1               5                   10

<210> SEQ ID NO 67
<211> LENGTH: 11
<212> TYPE: PRT
<213> ORGANISM: Rattus norvegicus

<400> SEQUENCE: 67

Arg Ala Ser Glu Asp Ile Tyr Ser Asn Leu Ala
1               5                   10

<210> SEQ ID NO 68
<211> LENGTH: 7
<212> TYPE: PRT
<213> ORGANISM: Rattus norvegicus

<400> SEQUENCE: 68

Asp Ala Asn Ile Leu Ala Asp
1               5

<210> SEQ ID NO 69
<211> LENGTH: 10
<212> TYPE: PRT
<213> ORGANISM: Rattus norvegicus

<400> SEQUENCE: 69

Gln Gln Tyr Asn Asn Tyr Pro Pro Phe Thr
1               5                   10

<210> SEQ ID NO 70
<211> LENGTH: 822
<212> TYPE: PRT
<213> ORGANISM: Homo sapiens

<400> SEQUENCE: 70

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
    115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
    275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

```
Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
        370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
                420                 425                 430

Ala Glu Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
        450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
                515                 520                 525

Leu Ser Asp Leu Val Ser Glu Met Glu Met Met Lys Met Ile Gly Lys
        530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
        610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
                660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
        690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765
```

```
Glu Tyr Leu Asp Leu Ser Gln Pro Leu Glu Gln Tyr Ser Pro Ser Tyr
    770             775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
            820

<210> SEQ ID NO 71
<211> LENGTH: 821
<212> TYPE: PRT
<213> ORGANISM: Homo sapiens

<400> SEQUENCE: 71

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
            115                 120                 125

Ser Ser Gly Asp Asp Glu Asp Asp Thr Asp Gly Ala Glu Asp Phe Val
            130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
            290                 295                 300

Gly Leu Pro Tyr Leu Lys Val Leu Lys Ala Ala Gly Val Asn Thr Thr
305                 310                 315                 320
```

-continued

```
Asp Lys Glu Ile Glu Val Leu Tyr Ile Arg Asn Val Thr Phe Glu Asp
            325                 330                 335
Ala Gly Glu Tyr Thr Cys Leu Ala Gly Asn Ser Ile Gly Ile Ser Phe
                340                 345                 350
His Ser Ala Trp Leu Thr Val Leu Pro Ala Pro Gly Arg Glu Lys Glu
            355                 360                 365
Ile Thr Ala Ser Pro Asp Tyr Leu Glu Ile Ala Ile Tyr Cys Ile Gly
        370                 375                 380
Val Phe Leu Ile Ala Cys Met Val Val Thr Val Ile Leu Cys Arg Met
385                 390                 395                 400
Lys Asn Thr Thr Lys Lys Pro Asp Phe Ser Ser Gln Pro Ala Val His
                405                 410                 415
Lys Leu Thr Lys Arg Ile Pro Leu Arg Arg Gln Val Thr Val Ser Ala
            420                 425                 430
Glu Ser Ser Ser Ser Met Asn Ser Asn Thr Pro Leu Val Arg Ile Thr
        435                 440                 445
Thr Arg Leu Ser Ser Thr Ala Asp Thr Pro Met Leu Ala Gly Val Ser
    450                 455                 460
Glu Tyr Glu Leu Pro Glu Asp Pro Lys Trp Glu Phe Pro Arg Asp Lys
465                 470                 475                 480
Leu Thr Leu Gly Lys Pro Leu Gly Glu Gly Cys Phe Gly Gln Val Val
                485                 490                 495
Met Ala Glu Ala Val Gly Ile Asp Lys Asp Lys Pro Lys Glu Ala Val
            500                 505                 510
Thr Val Ala Val Lys Met Leu Lys Asp Asp Ala Thr Glu Lys Asp Leu
        515                 520                 525
Ser Asp Leu Val Ser Glu Met Glu Met Met Lys Met Ile Gly Lys His
    530                 535                 540
Lys Asn Ile Ile Asn Leu Leu Gly Ala Cys Thr Gln Asp Gly Pro Leu
545                 550                 555                 560
Tyr Val Ile Val Glu Tyr Ala Ser Lys Gly Asn Leu Arg Glu Tyr Leu
                565                 570                 575
Arg Ala Arg Arg Pro Pro Gly Met Glu Tyr Ser Tyr Asp Ile Asn Arg
            580                 585                 590
Val Pro Glu Glu Gln Met Thr Phe Lys Asp Leu Val Ser Cys Thr Tyr
        595                 600                 605
Gln Leu Ala Arg Gly Met Glu Tyr Leu Ala Ser Gln Lys Cys Ile His
    610                 615                 620
Arg Asp Leu Ala Ala Arg Asn Val Leu Val Thr Glu Asn Asn Val Met
625                 630                 635                 640
Lys Ile Ala Asp Phe Gly Leu Ala Arg Asp Ile Asn Asn Ile Asp Tyr
                645                 650                 655
Tyr Lys Lys Thr Thr Asn Gly Arg Leu Pro Val Lys Trp Met Ala Pro
            660                 665                 670
Glu Ala Leu Phe Asp Arg Val Tyr Thr His Gln Ser Asp Val Trp Ser
        675                 680                 685
Phe Gly Val Leu Met Trp Glu Ile Phe Thr Leu Gly Gly Ser Pro Tyr
    690                 695                 700
Pro Gly Ile Pro Val Glu Glu Leu Phe Lys Leu Leu Lys Glu Gly His
705                 710                 715                 720
Arg Met Asp Lys Pro Ala Asn Cys Thr Asn Glu Leu Tyr Met Met Met
                725                 730                 735
```

Arg Asp Cys Trp His Ala Val Pro Ser Gln Arg Pro Thr Phe Lys Gln
                740                 745                 750

Leu Val Glu Asp Leu Asp Arg Ile Leu Thr Leu Thr Thr Asn Glu Glu
            755                 760                 765

Tyr Leu Asp Leu Ser Gln Pro Leu Glu Gln Tyr Ser Pro Ser Tyr Pro
        770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 72
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(705)

<400> SEQUENCE: 72 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc gac atc cag atg acc cag agc ccc agc agc ctg agc      96
Gly Ala Tyr Gly Asp Ile Gln Met Thr Gln Ser Pro Ser Ser Leu Ser
            20                  25                  30 gcc agc gtg ggc gac aga gtg acc atc acc tgt cgg gcc agc gag gac     144
Ala Ser Val Gly Asp Arg Val Thr Ile Thr Cys Arg Ala Ser Glu Asp
        35                  40                  45 atc tac agc aac ctg gcc tgg tat cag cag aag ccc ggc aag agc ccc     192
Ile Tyr Ser Asn Leu Ala Trp Tyr Gln Gln Lys Pro Gly Lys Ser Pro
    50                  55                  60 cag ctg ctg atc tac gac gcc aac atc ctg gcc gac ggc gtg ccc agc     240
Gln Leu Leu Ile Tyr Asp Ala Asn Ile Leu Ala Asp Gly Val Pro Ser
65                  70                  75                  80 aga ttc agc ggc agc ggc tcc ggc acc gac tac acc ctg acc atc tcc     288
Arg Phe Ser Gly Ser Gly Ser Gly Thr Asp Tyr Thr Leu Thr Ile Ser
                85                  90                  95 agc ctg cag ccc gag gac ttc gcc acc tac tac tgc cag cag tac aac     336
Ser Leu Gln Pro Glu Asp Phe Ala Thr Tyr Tyr Cys Gln Gln Tyr Asn
            100                 105                 110 aac tac ccc cca ttc acc ttc ggc cag ggc acc aag gtg gaa atc aag     384
Asn Tyr Pro Pro Phe Thr Phe Gly Gln Gly Thr Lys Val Glu Ile Lys
        115                 120                 125 cgt acg gtg gcc gcc ccc tcc gtg ttc atc ttc ccc ccc tcc gac gag     432
Arg Thr Val Ala Ala Pro Ser Val Phe Ile Phe Pro Pro Ser Asp Glu
    130                 135                 140 cag ctg aag tcc ggc acc gcc tcc gtg gtg tgc ctg ctg aat aac ttc     480
Gln Leu Lys Ser Gly Thr Ala Ser Val Val Cys Leu Leu Asn Asn Phe
145                 150                 155                 160 tac ccc aga gag gcc aag gtg cag tgg aag gtg gac aac gcc ctg cag     528
Tyr Pro Arg Glu Ala Lys Val Gln Trp Lys Val Asp Asn Ala Leu Gln
                165                 170                 175 tcc ggg aac tcc cag gag agc gtg acc gag cag gac agc aag gac agc     576
Ser Gly Asn Ser Gln Glu Ser Val Thr Glu Gln Asp Ser Lys Asp Ser
            180                 185                 190

```
acc tac agc ctg agc agc acc ctg acc ctg agc aaa gcc gac tac gag     624
Thr Tyr Ser Leu Ser Ser Thr Leu Thr Leu Ser Lys Ala Asp Tyr Glu
        195                 200                 205 aag cac aag gtg tac gcc tgc gag gtg acc cac cag ggc ctg agc tcc     672
Lys His Lys Val Tyr Ala Cys Glu Val Thr His Gln Gly Leu Ser Ser
210                 215                 220 ccc gtc acc aag agc ttc aac agg ggg gag tgt                         705
Pro Val Thr Lys Ser Phe Asn Arg Gly Glu Cys
225                 230                 235

<210> SEQ ID NO 73
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asp
        35                  40                  45

Ile Tyr Ser Asn Leu Ala Trp Tyr Gln Gln Lys Pro Gly Lys Ser Pro
    50                  55                  60

Gln Leu Leu Ile Tyr Asp Ala Asn Ile Leu Ala Asp Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln Tyr Asn
            100                 105                 110

Asn Tyr Pro Pro Phe Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 74
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
```

<222> LOCATION: (1)..(1401)

<400> SEQUENCE: 74

```
atg aaa cac ctg tgg ttc ttc ctc ctg ctg gtg gca gct ccc aga tgg        48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa        96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc       144
Pro Gly Ala Ser Val Lys Val Ser Cys Lys Ala Ser Gly Phe Thr Phe
        35                  40                  45 agc acc agc tat atg agc tgg gtc cgc cag gct cca ggc cag gga ctg       192
Ser Thr Ser Tyr Met Ser Trp Val Arg Gln Ala Pro Gly Gln Gly Leu
    50                  55                  60 gaa tgg atg ggc tgg atc tat gcc ggc gac ggc ggc acc aag tac aac       240
Glu Trp Met Gly Trp Ile Tyr Ala Gly Asp Gly Gly Thr Lys Tyr Asn
65                  70                  75                  80 cag aaa ttc aag ggc aga gtg acc ctg acc gtg gac aag agc acc agc       288
Gln Lys Phe Lys Gly Arg Val Thr Leu Thr Val Asp Lys Ser Thr Ser
                85                  90                  95 acc gcc tac atg gaa ctg agc agc ctg cgg agc gag gac acc gcc gtg       336
Thr Ala Tyr Met Glu Leu Ser Ser Leu Arg Ser Glu Asp Thr Ala Val
            100                 105                 110 tac tac tgc gcc acc gac ggc tac ggc gac tgg ttc aca tac tgg ggc       384
Tyr Tyr Cys Ala Thr Asp Gly Tyr Gly Asp Trp Phe Thr Tyr Trp Gly
        115                 120                 125 cag ggc acc ctg gtg acc gtg agc tca gcc tcc acc aag ggc cca agc       432
Gln Gly Thr Leu Val Thr Val Ser Ser Ala Ser Thr Lys Gly Pro Ser
    130                 135                 140 gtc ttc ccc ctg gca ccc tcc tcc aag agc acc tct ggc ggc aca gcc       480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg       528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct       576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg       624
Val Leu Gln Ser Ser Gly Leu Tyr Ser Leu Ser Ser Val Val Thr Val
        195                 200                 205 ccc tcc agc agc ttg ggc acc cag acc tac atc tgc aac gtg aat cac       672
Pro Ser Ser Ser Leu Gly Thr Gln Thr Tyr Ile Cys Asn Val Asn His
    210                 215                 220 aag ccc agc aac acc aag gtg gac aag aga gtt gag ccc aaa tct tgt       720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg       768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg       816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac       864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg       912
Glu Asp Pro Glu Val Lys Phe Asn Trp Tyr Val Asp Gly Val Glu Val
    290                 295                 300
```

```
cat aat gcc aag aca aag ccc cgg gag gag cag tac aac agc acg tac      960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc     1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc     1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg     1104
Glu Lys Thr Ile Ser Lys Ala Lys Gly Gln Pro Arg Glu Pro Gln Val
        355                 360                 365 tac acc ctg ccc cca tcc cgg gag gag atg acc aag aac cag gtc agc     1152
Tyr Thr Leu Pro Pro Ser Arg Glu Glu Met Thr Lys Asn Gln Val Ser
370                 375                 380 ctg acc tgc ctg gtc aaa ggc ttc tat ccc agc gac atc gcc gtg gag     1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc     1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg     1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg     1344
Asp Lys Ser Arg Trp Gln Gln Gly Asn Val Phe Ser Cys Ser Val Met
        435                 440                 445 cat gag gct ctg cac aac cac tac acc cag aag agc ctc tcc ctg tct     1392
His Glu Ala Leu His Asn His Tyr Thr Gln Lys Ser Leu Ser Leu Ser
450                 455                 460 ccc ggc aaa                                                         1401
Pro Gly Lys
465

<210> SEQ ID NO 75
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Gln Gly Leu
    50                  55                  60

Glu Trp Met Gly Trp Ile Tyr Ala Gly Asp Gly Gly Thr Lys Tyr Asn
65              70                  75                  80

Gln Lys Phe Lys Gly Arg Val Thr Leu Thr Val Asp Lys Ser Thr Ser
            85                  90                  95

Thr Ala Tyr Met Glu Leu Ser Ser Leu Arg Ser Glu Asp Thr Ala Val
        100                 105                 110

Tyr Tyr Cys Ala Thr Asp Gly Tyr Gly Asp Trp Phe Thr Tyr Trp Gly
    115                 120                 125
```

```
Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 76
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)
```

```
<400> SEQUENCE: 76 atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa    96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc    144
Pro Gly Ala Ser Val Lys Val Ser Cys Lys Ala Ser Gly Phe Thr Phe
        35                  40                  45 agc acc agc tat atg agc tgg gtc cgc cag gct cca ggc cag gga ctg    192
Ser Thr Ser Tyr Met Ser Trp Val Arg Gln Ala Pro Gly Gln Gly Leu
    50                  55                  60 gaa tgg atg ggc tgg atc tat gcc ggc gac ggc ggc acc aag tac aac    240
Glu Trp Met Gly Trp Ile Tyr Ala Gly Asp Gly Gly Thr Lys Tyr Asn
65                  70                  75                  80 cag aaa ttc aag ggc aga gtg acc ctg acc gcc gac aag agc acc agc    288
Gln Lys Phe Lys Gly Arg Val Thr Leu Thr Ala Asp Lys Ser Thr Ser
                85                  90                  95 acc gcc tac atg gaa ctg agc agc ctg cgg agc gag gac acc gcc gtg    336
Thr Ala Tyr Met Glu Leu Ser Ser Leu Arg Ser Glu Asp Thr Ala Val
            100                 105                 110 tac tac tgc gcc acc gac ggc tac ggc gac tgg ttc aca tac tgg ggc    384
Tyr Tyr Cys Ala Thr Asp Gly Tyr Gly Asp Trp Phe Thr Tyr Trp Gly
        115                 120                 125 cag ggc acc ctg gtg acc gtg agc tca gcc tcc acc aag ggc cca agc    432
Gln Gly Thr Leu Val Thr Val Ser Ser Ala Ser Thr Lys Gly Pro Ser
    130                 135                 140 gtc ttc ccc ctg gca ccc tcc tcc aag agc acc tct ggc ggc aca gcc    480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg    528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct    576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg    624
Val Leu Gln Ser Ser Gly Leu Tyr Ser Leu Ser Ser Val Val Thr Val
        195                 200                 205 ccc tcc agc agc ttg ggc acc cag acc tac atc tgc aac gtg aat cac    672
Pro Ser Ser Ser Leu Gly Thr Gln Thr Tyr Ile Cys Asn Val Asn His
    210                 215                 220 aag ccc agc aac acc aag gtg gac aag aga gtt gag ccc aaa tct tgt    720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg    768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg    816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac    864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg    912
Glu Asp Pro Glu Val Lys Phe Asn Trp Tyr Val Asp Gly Val Glu Val
    290                 295                 300 cat aat gcc aag aca aag ccc cgg gag gag cag tac aac agc acg tac    960
```

```
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc      1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc      1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg      1104
Glu Lys Thr Ile Ser Lys Ala Lys Gly Gln Pro Arg Glu Pro Gln Val
        355                 360                 365 tac acc ctg ccc cca tcc cgg gag gag atg acc aag aac cag gtc agc      1152
Tyr Thr Leu Pro Pro Ser Arg Glu Glu Met Thr Lys Asn Gln Val Ser
    370                 375                 380 ctg acc tgc ctg gtc aaa ggc ttc tat ccc agc gac atc gcc gtg gag      1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc      1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg      1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg      1344
Asp Lys Ser Arg Trp Gln Gln Gly Asn Val Phe Ser Cys Ser Val Met
        435                 440                 445 cat gag gct ctg cac aac cac tac acc cag aag agc ctc tcc ctg tct      1392
His Glu Ala Leu His Asn His Tyr Thr Gln Lys Ser Leu Ser Leu Ser
    450                 455                 460 ccc ggc aaa                                                          1401
Pro Gly Lys
465

<210> SEQ ID NO 77
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Gln Gly Leu
    50                  55                  60

Glu Trp Met Gly Trp Ile Tyr Ala Gly Asp Gly Thr Lys Tyr Asn
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Asp Gly Tyr Gly Asp Trp Phe Thr Tyr Trp Gly
        115                 120                 125

Gln Gly Thr Leu Val Thr Val Ser Ser Ala Ser Thr Lys Gly Pro Ser
```

```
                130              135              140
Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 78
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 78
```

-continued

| | |
|---|---|
| atg aaa cac ctg tgg ttc ttc ctc ctg ctg gtg gca gct ccc aga tgg<br>Met Lys His Leu Trp Phe Phe Leu Leu Leu Val Ala Ala Pro Arg Trp<br>1                            5                           10                         15 | 48 |
| gtg ctg agc cag gtg cag ctg gtg cag tct ggc gcc gaa gtg aag aaa<br>Val Leu Ser Gln Val Gln Leu Val Gln Ser Gly Ala Glu Val Lys Lys<br>                  20                           25                           30 | 96 |
| cct ggg gct agc gtg aag gtg tcc tgc aag gcc agc ggc ttc acc ttc<br>Pro Gly Ala Ser Val Lys Val Ser Cys Lys Ala Ser Gly Phe Thr Phe<br>        35                         40                         45 | 144 |
| agc acc agc tat atg agc tgg gtc cgc cag gct cca ggc ccc agc acc<br>Ser Thr Ser Tyr Met Ser Trp Val Arg Gln Ala Pro Gly Pro Ser Thr<br>    50                         55                         60 | 192 |
| gaa tgg atg ggc tgg atc tat gcc ggc gac ggc ggc acc aag tac aac<br>Glu Trp Met Gly Trp Ile Tyr Ala Gly Asp Gly Gly Thr Lys Tyr Asn<br>65                           70                         75                         80 | 240 |
| cag aaa ttc aag ggc aga gtg acc ctg acc gtg gac aag agc acc agc<br>Gln Lys Phe Lys Gly Arg Val Thr Leu Thr Val Asp Lys Ser Thr Ser<br>                  85                         90                         95 | 288 |
| acc gcc tac atg gaa ctg agc agc ctg cgg agc gag gac acc gcc gtg<br>Thr Ala Tyr Met Glu Leu Ser Ser Leu Arg Ser Glu Asp Thr Ala Val<br>            100                       105                      110 | 336 |
| tac tac tgc gcc acc gac ggc tac ggc gac tgg ttc aca tac tgg ggc<br>Tyr Tyr Cys Ala Thr Asp Gly Tyr Gly Asp Trp Phe Thr Tyr Trp Gly<br>        115                       120                      125 | 384 |
| cag ggc acc ctg gtg acc gtg agc tca gcc tcc acc aag ggc cca agc<br>Gln Gly Thr Leu Val Thr Val Ser Ser Ala Ser Thr Lys Gly Pro Ser<br>130                         135                       140 | 432 |
| gtc ttc ccc ctg gca ccc tcc tcc aag agc acc tct ggc ggc aca gcc<br>Val Phe Pro Leu Ala Pro Ser Ser Lys Ser Thr Ser Gly Gly Thr Ala<br>145                         150                       155                       160 | 480 |
| gcc ctg ggc tgc ctg gtc aag gac tac ttc ccc gaa ccc gtg acc gtg<br>Ala Leu Gly Cys Leu Val Lys Asp Tyr Phe Pro Glu Pro Val Thr Val<br>                  165                       170                      175 | 528 |
| agc tgg aac tca ggc gcc ctg acc agc ggc gtg cac acc ttc ccc gct<br>Ser Trp Asn Ser Gly Ala Leu Thr Ser Gly Val His Thr Phe Pro Ala<br>            180                       185                      190 | 576 |
| gtc ctg cag tcc tca gga ctc tac tcc ctc agc agc gtg gtg acc gtg<br>Val Leu Gln Ser Ser Gly Leu Tyr Ser Leu Ser Ser Val Val Thr Val<br>        195                       200                      205 | 624 |
| ccc tcc agc agc ttg ggc acc cag acc tac atc tgc aac gtg aat cac<br>Pro Ser Ser Ser Leu Gly Thr Gln Thr Tyr Ile Cys Asn Val Asn His<br>210                       215                       220 | 672 |
| aag ccc agc aac acc aag gtg gac aag aga gtt gag ccc aaa tct tgt<br>Lys Pro Ser Asn Thr Lys Val Asp Lys Arg Val Glu Pro Lys Ser Cys<br>225                       230                       235                    240 | 720 |
| gac aaa act cac aca tgc cca ccc tgc cca gca cct gaa ctc ctg ggg<br>Asp Lys Thr His Thr Cys Pro Pro Cys Pro Ala Pro Glu Leu Leu Gly<br>            245                       250                      255 | 768 |
| gga ccc tca gtc ttc ctc ttc ccc cca aaa ccc aag gac acc ctc atg<br>Gly Pro Ser Val Phe Leu Phe Pro Pro Lys Pro Lys Asp Thr Leu Met<br>        260                       265                      270 | 816 |
| atc tcc cgg acc cct gag gtc aca tgc gtg gtg gtg gac gtg agc cac<br>Ile Ser Arg Thr Pro Glu Val Thr Cys Val Val Val Asp Val Ser His<br>275                       280                       285 | 864 |
| gaa gac cct gag gtc aag ttc aac tgg tac gtg gac ggc gtg gag gtg<br>Glu Asp Pro Glu Val Lys Phe Asn Trp Tyr Val Asp Gly Val Glu Val<br>        290                       295                      300 | 912 |
| cat aat gcc aag aca aag ccc cgg gag gag cag tac aac agc acg tac<br>His Asn Ala Lys Thr Lys Pro Arg Glu Glu Gln Tyr Asn Ser Thr Tyr<br>305                       310                       315                    320 | 960 |

```
cgg gtg gtc agc gtc ctc acc gtc ctg cac cag gac tgg ctg aat ggc    1008
Arg Val Val Ser Val Leu Thr Val Leu His Gln Asp Trp Leu Asn Gly
            325                 330                 335 aag gag tac aag tgc aag gtc tcc aac aaa gcc ctc cca gcc ccc atc    1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg    1104
Glu Lys Thr Ile Ser Lys Ala Lys Gly Gln Pro Arg Glu Pro Gln Val
            355                 360                 365 tac acc ctg ccc cca tcc cgg gag gag atg acc aag aac cag gtc agc    1152
Tyr Thr Leu Pro Pro Ser Arg Glu Glu Met Thr Lys Asn Gln Val Ser
            370                 375                 380 ctg acc tgc ctg gtc aaa ggc ttc tat ccc agc gac atc gcc gtg gag    1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc    1248
Trp Glu Ser Asn Gly Gln Pro Glu Asn Asn Tyr Lys Thr Thr Pro Pro
            405                 410                 415 gtg ctg gac tcc gac ggc tcc ttc ttc ctc tac agc aag ctc acc gtg    1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg    1344
Asp Lys Ser Arg Trp Gln Gln Gly Asn Val Phe Ser Cys Ser Val Met
            435                 440                 445 cat gag gct ctg cac aac cac tac acc cag aag agc ctc tcc ctg tct    1392
His Glu Ala Leu His Asn His Tyr Thr Gln Lys Ser Leu Ser Leu Ser
            450                 455                 460 ccc ggc aaa                                                         1401
Pro Gly Lys
465

<210> SEQ ID NO 79
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Thr Lys Tyr Asn
65                  70                  75                  80

Gln Lys Phe Lys Gly Arg Val Thr Leu Thr Val Asp Lys Ser Thr Ser
            85                  90                  95

Thr Ala Tyr Met Glu Leu Ser Ser Leu Arg Ser Glu Asp Thr Ala Val
            100                 105                 110

Tyr Tyr Cys Ala Thr Asp Gly Tyr Gly Asp Trp Phe Thr Tyr Trp Gly
        115                 120                 125

Gln Gly Thr Leu Val Thr Val Ser Ser Ala Ser Thr Lys Gly Pro Ser
    130                 135                 140
```

```
Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 80
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 80 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
```

```
           1               5                    10                       15
     gtg ctg agc cag gtg cag ctg gtg cag tct ggc gcc gaa gtg aag aaa        96
     Val Leu Ser Gln Val Gln Leu Val Gln Ser Gly Ala Glu Val Lys Lys
                      20                  25                  30 cct ggg gct agc gtg aag gtg tcc tgc aag gcc agc ggc ttc acc ttc       144
     Pro Gly Ala Ser Val Lys Val Ser Cys Lys Ala Ser Gly Phe Thr Phe
                      35                  40                  45 agc acc agc tat atg agc tgg gtc cgc cag gct cca ggc ccc agc atc       192
     Ser Thr Ser Tyr Met Ser Trp Val Arg Gln Ala Pro Gly Pro Ser Ile
                      50                  55                  60 gaa tgg atg ggc tgg atc tat gcc ggc gac ggc ggc acc aag tac aac       240
     Glu Trp Met Gly Trp Ile Tyr Ala Gly Asp Gly Gly Thr Lys Tyr Asn
     65                   70                  75                  80 cag aaa ttc aag ggc aga gtg acc ctg acc gtg gac aag agc acc agc       288
     Gln Lys Phe Lys Gly Arg Val Thr Leu Thr Val Asp Lys Ser Thr Ser
                      85                  90                  95 acc gcc tac atg gaa ctg agc agc ctg cgg agc gag gac acc gcc gtg       336
     Thr Ala Tyr Met Glu Leu Ser Ser Leu Arg Ser Glu Asp Thr Ala Val
                      100                 105                 110 tac tac tgc gcc acc gac ggc tac ggc gac tgg ttc gcc tac tgg ggc       384
     Tyr Tyr Cys Ala Thr Asp Gly Tyr Gly Asp Trp Phe Ala Tyr Trp Gly
                      115                 120                 125 cag ggc acc ctg gtg acc gtg agc tca gcc tcc acc aag ggc cca agc       432
     Gln Gly Thr Leu Val Thr Val Ser Ser Ala Ser Thr Lys Gly Pro Ser
                      130                 135                 140 gtc ttc ccc ctg gca ccc tcc tcc aag agc acc tct ggc gga aca gcc       480
     Val Phe Pro Leu Ala Pro Ser Ser Lys Ser Thr Ser Gly Gly Thr Ala
     145                  150                 155                 160 gcc ctg ggc tgc ctg gtc aag gac tac ttc ccc gaa ccc gtg acc gtg       528
     Ala Leu Gly Cys Leu Val Lys Asp Tyr Phe Pro Glu Pro Val Thr Val
                      165                 170                 175 agc tgg aac tca ggc gcc ctg acc agc ggc gtg cac acc ttc ccc gct       576
     Ser Trp Asn Ser Gly Ala Leu Thr Ser Gly Val His Thr Phe Pro Ala
                      180                 185                 190 gtc ctg cag tcc tca gga ctc tac tcc ctc agc agc gtg gtg acc gtg       624
     Val Leu Gln Ser Ser Gly Leu Tyr Ser Leu Ser Ser Val Val Thr Val
                      195                 200                 205 ccc tcc agc agc ttg ggc acc cag acc tac atc tgc aac gtg aat cac       672
     Pro Ser Ser Ser Leu Gly Thr Gln Thr Tyr Ile Cys Asn Val Asn His
                      210                 215                 220 aag ccc agc aac acc aag gtg gac aag aga gtt gag ccc aaa tct tgt       720
     Lys Pro Ser Asn Thr Lys Val Asp Lys Arg Val Glu Pro Lys Ser Cys
     225                  230                 235                 240 gac aaa act cac aca tgc cca ccc tgc cca gca cct gaa ctc ctg ggg       768
     Asp Lys Thr His Thr Cys Pro Pro Cys Pro Ala Pro Glu Leu Leu Gly
                      245                 250                 255 gga ccc tca gtc ttc ctc ttc ccc cca aaa ccc aag gac acc ctc atg       816
     Gly Pro Ser Val Phe Leu Phe Pro Pro Lys Pro Lys Asp Thr Leu Met
                      260                 265                 270 atc tcc cgg acc cct gag gtc aca tgc gtg gtg gtg gac gtg agc cac       864
     Ile Ser Arg Thr Pro Glu Val Thr Cys Val Val Val Asp Val Ser His
                      275                 280                 285 gaa gac cct gag gtc aag ttc aac tgg tac gtg gac ggc gtg gag gtg       912
     Glu Asp Pro Glu Val Lys Phe Asn Trp Tyr Val Asp Gly Val Glu Val
                      290                 295                 300 cat aat gcc aag aca aag ccc cgg gag gag cag tac aac agc acg tac       960
     His Asn Ala Lys Thr Lys Pro Arg Glu Glu Gln Tyr Asn Ser Thr Tyr
     305                  310                 315                 320 cgg gtg gtc agc gtc ctc acc gtc ctg cac cag gac tgg ctg aat ggc      1008
```

```
                Arg Val Val Ser Val Leu Thr Val Leu His Gln Asp Trp Leu Asn Gly
                                325                 330                 335 aag gag tac aag tgc aag gtc tcc aac aaa gcc ctc cca gcc ccc atc           1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg           1104
Glu Lys Thr Ile Ser Lys Ala Lys Gly Gln Pro Arg Glu Pro Gln Val
        355                 360                 365 tac acc ctg ccc cca tcc cgg gag gag atg acc aag aac cag gtc agc           1152
Tyr Thr Leu Pro Pro Ser Arg Glu Glu Met Thr Lys Asn Gln Val Ser
370                 375                 380 ctg acc tgc ctg gtc aaa ggc ttc tat ccc agc gac atc gcc gtg gag           1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc           1248
Trp Glu Ser Asn Gly Gln Pro Glu Asn Asn Tyr Lys Thr Thr Pro Pro
            405                 410                 415 gtg ctg gac tcc gac ggc tcc ttc ttc ctc tac agc aag ctc acc gtg           1296
Val Leu Asp Ser Asp Gly Ser Phe Phe Leu Tyr Ser Lys Leu Thr Val
        420                 425                 430 gac aag agc agg tgg cag cag ggc aac gtc ttc tca tgc tcc gtg atg           1344
Asp Lys Ser Arg Trp Gln Gln Gly Asn Val Phe Ser Cys Ser Val Met
    435                 440                 445 cat gag gct ctg cac aac cac tac acc cag aag agc ctc tcc ctg tct           1392
His Glu Ala Leu His Asn His Tyr Thr Gln Lys Ser Leu Ser Leu Ser
450                 455                 460 ccc ggc aaa                                                               1401
Pro Gly Lys
465
```

<210> SEQ ID NO 81
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Ile
    50                  55                  60

Glu Trp Met Gly Trp Ile Tyr Ala Gly Asp Gly Thr Lys Tyr Asn
65                  70                  75                  80

Gln Lys Phe Lys Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Asp Gly Tyr Gly Asp Trp Phe Ala Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160
```

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
        180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 82
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 82 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15

```
gtg ctg agc cag gtg cag ctg gtg cag tct ggc gcc gaa gtg aag aaa        96
Val Leu Ser Gln Val Gln Leu Val Gln Ser Gly Ala Glu Val Lys Lys
        20                  25                  30 cct ggg gct agc gtg aag gtg tcc tgc aag gcc agc ggc ttc acc ttc       144
Pro Gly Ala Ser Val Lys Val Ser Cys Lys Ala Ser Gly Phe Thr Phe
            35                  40                  45 agc acc agc tat atg agc tgg gtc cgc cag gct cca ggc ccc agc acc       192
Ser Thr Ser Tyr Met Ser Trp Val Arg Gln Ala Pro Gly Pro Ser Thr
50                  55                  60 gaa tgg atg ggc tgg atc tat gcc ggc gac ggc ggc acc aag tac aac       240
Glu Trp Met Gly Trp Ile Tyr Ala Gly Asp Gly Gly Thr Lys Tyr Asn
65                  70                  75                  80 cag aaa ttc aag ggc aga gtg acc ctg acc gtg gac aag agc acc agc       288
Gln Lys Phe Lys Gly Arg Val Thr Leu Thr Val Asp Lys Ser Thr Ser
                85                  90                  95 acc gcc tac atg gaa ctg agc agc ctg cgg agc gag gac acc gcc gtg       336
Thr Ala Tyr Met Glu Leu Ser Ser Leu Arg Ser Glu Asp Thr Ala Val
            100                 105                 110 tac tac tgc gcc acc gag ggc tac ggc gac tgg ttc aca tac tgg ggc       384
Tyr Tyr Cys Ala Thr Glu Gly Tyr Gly Asp Trp Phe Thr Tyr Trp Gly
        115                 120                 125 cag ggc acc ctg gtg acc gtg agc tca gcc tcc acc aag ggc cca agc       432
Gln Gly Thr Leu Val Thr Val Ser Ser Ala Ser Thr Lys Gly Pro Ser
130                 135                 140 gtc ttc ccc ctg gca ccc tcc tcc aag agc acc tct ggc ggc aca gcc       480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg       528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct       576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg       624
Val Leu Gln Ser Ser Gly Leu Tyr Ser Leu Ser Ser Val Val Thr Val
        195                 200                 205 ccc tcc agc agc ttg ggc acc cag acc tac atc tgc aac gtg aat cac       672
Pro Ser Ser Ser Leu Gly Thr Gln Thr Tyr Ile Cys Asn Val Asn His
210                 215                 220 aag ccc agc aac acc aag gtg gac aag aga gtt gag ccc aaa tct tgt       720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg       768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg       816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac       864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg       912
Glu Asp Pro Glu Val Lys Phe Asn Trp Tyr Val Asp Gly Val Glu Val
290                 295                 300 cat aat gcc aag aca aag ccc cgg gag gag cag tac aac agc acg tac       960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc      1008
Arg Val Val Ser Val Leu Thr Val Leu His Gln Asp Trp Leu Asn Gly
                325                 330                 335
```

```
aag gag tac aag tgc aag gtc tcc aac aaa gcc ctc cca gcc ccc atc      1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg      1104
Glu Lys Thr Ile Ser Lys Ala Lys Gly Gln Pro Arg Glu Pro Gln Val
        355                 360                 365 tac acc ctg ccc cca tcc cgg gag gag atg acc aag aac cag gtc agc      1152
Tyr Thr Leu Pro Pro Ser Arg Glu Glu Met Thr Lys Asn Gln Val Ser
    370                 375                 380 ctg acc tgc ctg gtc aaa ggc ttc tat ccc agc gac atc gcc gtg gag      1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc      1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg      1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg      1344
Asp Lys Ser Arg Trp Gln Gln Gly Asn Val Phe Ser Cys Ser Val Met
        435                 440                 445 cat gag gct ctg cac aac cac tac acc cag aag agc ctc tcc ctg tct      1392
His Glu Ala Leu His Asn His Tyr Thr Gln Lys Ser Leu Ser Leu Ser
    450                 455                 460 ccc ggc aaa                                                          1401
Pro Gly Lys
465

<210> SEQ ID NO 83
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Lys His Leu Trp Phe Phe Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Thr Lys Tyr Asn
65                  70                  75                  80

Gln Lys Phe Lys Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Glu Gly Tyr Gly Asp Trp Phe Thr Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
```

165                 170                 175
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 84
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 84 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys

```
                  20                  25                  30
cct ggg gct agc gtg aag gtg tcc tgc aag gcc agc ggc ttc acc ttc        144
Pro Gly Ala Ser Val Lys Val Ser Cys Lys Ala Ser Gly Phe Thr Phe
         35                  40                  45 agc acc agc tat atg agc tgg gtc cgc cag gct cca ggc ccc agc acc        192
Ser Thr Ser Tyr Met Ser Trp Val Arg Gln Ala Pro Gly Pro Ser Thr
 50                  55                  60 gaa tgg atg ggc tgg atc tat gcc ggc gac ggc ggc acc aag tac aac        240
Glu Trp Met Gly Trp Ile Tyr Ala Gly Asp Gly Gly Thr Lys Tyr Asn
65                   70                  75                  80 cag aaa ttc aag ggc aga gtg acc ctg acc gtg gac aag agc acc agc        288
Gln Lys Phe Lys Gly Arg Val Thr Leu Thr Val Asp Lys Ser Thr Ser
                 85                  90                  95 acc gcc tac atg gaa ctg agc agc ctg cgg agc gag gac acc gcc gtg        336
Thr Ala Tyr Met Glu Leu Ser Ser Leu Arg Ser Glu Asp Thr Ala Val
            100                 105                 110 tac tac tgc gcc acc gac gcc tac ggc gac tgg ttc aca tac tgg ggc        384
Tyr Tyr Cys Ala Thr Asp Ala Tyr Gly Asp Trp Phe Thr Tyr Trp Gly
        115                 120                 125 cag ggc acc ctg gtg acc gtg agc tca gcc tcc acc aag ggc cca agc        432
Gln Gly Thr Leu Val Thr Val Ser Ser Ala Ser Thr Lys Gly Pro Ser
    130                 135                 140 gtc ttc ccc ctg gca ccc tcc tcc aag agc acc tct ggc gga aca gcc        480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg        528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct        576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg        624
Val Leu Gln Ser Ser Gly Leu Tyr Ser Leu Ser Ser Val Val Thr Val
        195                 200                 205 ccc tcc agc agc ttg ggc acc cag acc tac atc tgc aac gtg aat cac        672
Pro Ser Ser Ser Leu Gly Thr Gln Thr Tyr Ile Cys Asn Val Asn His
    210                 215                 220 aag ccc agc aac acc aag gtg gac aag aga gtt gag ccc aaa tct tgt        720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg        768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg        816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac        864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg        912
Glu Asp Pro Glu Val Lys Phe Asn Trp Tyr Val Asp Gly Val Glu Val
    290                 295                 300 cat aat gcc aag aca aag ccc cgg gag gag cag tac aac agc acg tac        960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc       1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc       1056
```

```
                    Lys Glu Tyr Lys Cys Lys Val Ser Asn Lys Ala Leu Pro Ala Pro Ile
                                    340                 345                 350 gag aaa acc atc tcc aaa gcc aaa ggc cag ccc cgg gaa cca cag gtg               1104
Glu Lys Thr Ile Ser Lys Ala Lys Gly Gln Pro Arg Glu Pro Gln Val
            355                 360                 365 tac acc ctg ccc cca tcc cgg gag gag atg acc aag aac cag gtc agc               1152
Tyr Thr Leu Pro Pro Ser Arg Glu Glu Met Thr Lys Asn Gln Val Ser
370                 375                 380 ctg acc tgc ctg gtc aaa ggc ttc tat ccc agc gac atc gcc gtg gag               1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc               1248
Trp Glu Ser Asn Gly Gln Pro Glu Asn Asn Tyr Lys Thr Thr Pro Pro
            405                 410                 415 gtg ctg gac tcc gac ggc tcc ttc ttc ctc tac agc aag ctc acc gtg               1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg               1344
Asp Lys Ser Arg Trp Gln Gln Gly Asn Val Phe Ser Cys Ser Val Met
            435                 440                 445 cat gag gct ctg cac aac cac tac acc cag aag agc ctc tcc ctg tct               1392
His Glu Ala Leu His Asn His Tyr Thr Gln Lys Ser Leu Ser Leu Ser
450                 455                 460 ccc ggc aaa                                                                   1401
Pro Gly Lys
465

<210> SEQ ID NO 85
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Thr Lys Tyr Asn
65                  70                  75                  80

Gln Lys Phe Lys Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Asp Ala Tyr Gly Asp Trp Phe Thr Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175
```

```
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Lys
465

<210> SEQ ID NO 86
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 86 atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa    96
Val Leu Ser Gln Val Gln Leu Val Gln Ser Gly Ala Glu Val Lys Lys
            20                  25                  30
```

```
cct ggg gct agc gtg aag gtg tcc tgc aag gcc agc ggc ttc acc ttc    144
Pro Gly Ala Ser Val Lys Val Ser Cys Lys Ala Ser Gly Phe Thr Phe
        35                  40                  45 agc acc agc tat atg agc tgg gtc cgc cag gct cca ggc ccc agc acc    192
Ser Thr Ser Tyr Met Ser Trp Val Arg Gln Ala Pro Gly Pro Ser Thr
50                  55                  60 gaa tgg atg ggc tgg atc tat gcc ggc gac ggc ggc acc aag tac aac    240
Glu Trp Met Gly Trp Ile Tyr Ala Gly Asp Gly Gly Thr Lys Tyr Asn
65                  70                  75                  80 cag aaa ttc aag ggc aga gtg acc ctg acc gtg gac aag agc acc agc    288
Gln Lys Phe Lys Gly Arg Val Thr Leu Thr Val Asp Lys Ser Thr Ser
                85                  90                  95 acc gcc tac atg gaa ctg agc agc ctg cgg agc gag gac acc gcc gtg    336
Thr Ala Tyr Met Glu Leu Ser Ser Leu Arg Ser Glu Asp Thr Ala Val
            100                 105                 110 tac tac tgc gcc acc gac gag tac ggc gac tgg ttc aca tac tgg ggc    384
Tyr Tyr Cys Ala Thr Asp Glu Tyr Gly Asp Trp Phe Thr Tyr Trp Gly
        115                 120                 125 cag ggc acc ctg gtg acc gtg agc tca gcc tcc acc aag ggc cca agc    432
Gln Gly Thr Leu Val Thr Val Ser Ser Ala Ser Thr Lys Gly Pro Ser
130                 135                 140 gtc ttc ccc ctg gca ccc tcc tcc aag agc acc tct ggc ggc aca gcc    480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg    528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct    576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg    624
Val Leu Gln Ser Ser Gly Leu Tyr Ser Leu Ser Ser Val Val Thr Val
        195                 200                 205 ccc tcc agc agc ttg ggc acc cag acc tac atc tgc aac gtg aat cac    672
Pro Ser Ser Ser Leu Gly Thr Gln Thr Tyr Ile Cys Asn Val Asn His
210                 215                 220 aag ccc agc aac acc aag gtg gac aag aga gtt gag ccc aaa tct tgt    720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg    768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg    816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac    864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg    912
Glu Asp Pro Glu Val Lys Phe Asn Trp Tyr Val Asp Gly Val Glu Val
290                 295                 300 cat aat gcc aag aca aag ccc cgg gag gag cag tac aac agc acg tac    960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc   1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc   1056
Lys Glu Tyr Lys Cys Lys Val Ser Asn Lys Ala Leu Pro Ala Pro Ile
            340                 345                 350
```

```
gag aaa acc atc tcc aaa gcc aaa ggc cag ccc cgg gaa cca cag gtg    1104
Glu Lys Thr Ile Ser Lys Ala Lys Gly Gln Pro Arg Glu Pro Gln Val
        355                 360                 365 tac acc ctg ccc cca tcc cgg gag gag atg acc aag aac cag gtc agc    1152
Tyr Thr Leu Pro Pro Ser Arg Glu Glu Met Thr Lys Asn Gln Val Ser
    370                 375                 380 ctg acc tgc ctg gtc aaa ggc ttc tat ccc agc gac atc gcc gtg gag    1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc    1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg    1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg    1344
Asp Lys Ser Arg Trp Gln Gln Gly Asn Val Phe Ser Cys Ser Val Met
        435                 440                 445 cat gag gct ctg cac aac cac tac acc cag aag agc ctc tcc ctg tct    1392
His Glu Ala Leu His Asn His Tyr Thr Gln Lys Ser Leu Ser Leu Ser
    450                 455                 460 ccc ggc aaa                                                        1401
Pro Gly Lys
465

<210> SEQ ID NO 87
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Lys His Leu Trp Phe Phe Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Thr Lys Tyr Asn
65                  70                  75                  80

Gln Lys Phe Lys Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Asp Glu Tyr Gly Asp Trp Phe Thr Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190
```

```
Val Leu Gln Ser Ser Gly Leu Tyr Ser Leu Ser Ser Val Val Thr Val
            195                 200                 205

Pro Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 88
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 88 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
                20                  25                  30 cct ggg gct agc gtg aag gtg tcc tgc aag gcc agc ggc ttc acc ttc     144
Pro Gly Ala Ser Val Lys Val Ser Cys Lys Ala Ser Gly Phe Thr Phe
```

-continued

```
                35                  40                  45
agc acc agc tat atg agc tgg gtc cgc cag gct cca ggc ccc agc acc      192
Ser Thr Ser Tyr Met Ser Trp Val Arg Gln Ala Pro Gly Pro Ser Thr
 50                  55                  60 gaa tgg atg ggc tgg atc tat gcc ggc gac ggc ggc acc aag tac aac      240
Glu Trp Met Gly Trp Ile Tyr Ala Gly Asp Gly Gly Thr Lys Tyr Asn
 65                  70                  75                  80 cag aaa ttc aag ggc aga gtg acc ctg acc gtg gac aag agc acc agc      288
Gln Lys Phe Lys Gly Arg Val Thr Leu Thr Val Asp Lys Ser Thr Ser
                     85                  90                  95 acc gcc tac atg gaa ctg agc agc ctg cgg agc gag gac acc gcc gtg      336
Thr Ala Tyr Met Glu Leu Ser Ser Leu Arg Ser Glu Asp Thr Ala Val
                    100                 105                 110 tac tac tgc gcc acc gac ttc tac ggc gac tgg ttc aca tac tgg ggc      384
Tyr Tyr Cys Ala Thr Asp Phe Tyr Gly Asp Trp Phe Thr Tyr Trp Gly
                115                 120                 125 cag ggc acc ctg gtg acc gtg agc tca gcc tcc acc aag ggc cca agc      432
Gln Gly Thr Leu Val Thr Val Ser Ser Ala Ser Thr Lys Gly Pro Ser
130                 135                 140 gtc ttc ccc ctg gca ccc tcc tcc aag agc acc tct ggc ggc aca gcc      480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg      528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct      576
Ser Trp Asn Ser Gly Ala Leu Thr Ser Gly Val His Thr Phe Pro Ala
                180                 185                 190 gtc ctg cag tcc tca gga ctc tac tcc ctc agc agc gtg gtg acc gtg      624
Val Leu Gln Ser Ser Gly Leu Tyr Ser Leu Ser Ser Val Val Thr Val
                195                 200                 205 ccc tcc agc agc ttg ggc acc cag acc tac atc tgc aac gtg aat cac      672
Pro Ser Ser Ser Leu Gly Thr Gln Thr Tyr Ile Cys Asn Val Asn His
                210                 215                 220 aag ccc agc aac acc aag gtg gac aag aga gtt gag ccc aaa tct tgt      720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg      768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg      816
Gly Pro Ser Val Phe Leu Phe Pro Pro Lys Pro Lys Asp Thr Leu Met
                260                 265                 270 atc tcc cgg acc cct gag gtc aca tgc gtg gtg gtg gac gtg agc cac      864
Ile Ser Arg Thr Pro Glu Val Thr Cys Val Val Val Asp Val Ser His
                275                 280                 285 gaa gac cct gag gtc aag ttc aac tgg tac gtg gac ggc gtg gag gtg      912
Glu Asp Pro Glu Val Lys Phe Asn Trp Tyr Val Asp Gly Val Glu Val
290                 295                 300 cat aat gcc aag aca aag ccc cgg gag gag cag tac aac agc acg tac      960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc     1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc     1056
Lys Glu Tyr Lys Cys Lys Val Ser Asn Lys Ala Leu Pro Ala Pro Ile
                340                 345                 350 gag aaa acc atc tcc aaa gcc aaa ggc cag ccc cgg gaa cca cag gtg     1104
```

```
Glu Lys Thr Ile Ser Lys Ala Lys Gly Gln Pro Arg Glu Pro Gln Val
            355                 360                 365 tac acc ctg ccc cca tcc cgg gag gag atg acc aag aac cag gtc agc    1152
Tyr Thr Leu Pro Pro Ser Arg Glu Glu Met Thr Lys Asn Gln Val Ser
370                 375                 380 ctg acc tgc ctg gtc aaa ggc ttc tat ccc agc gac atc gcc gtg gag    1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc    1248
Trp Glu Ser Asn Gly Gln Pro Glu Asn Asn Tyr Lys Thr Thr Pro Pro
            405                 410                 415 gtg ctg gac tcc gac ggc tcc ttc ttc ctc tac agc aag ctc acc gtg    1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg    1344
Asp Lys Ser Arg Trp Gln Gln Gly Asn Val Phe Ser Cys Ser Val Met
            435                 440                 445 cat gag gct ctg cac aac cac tac acc cag aag agc ctc tcc ctg tct    1392
His Glu Ala Leu His Asn His Tyr Thr Gln Lys Ser Leu Ser Leu Ser
    450                 455                 460 ccc ggc aaa                                                        1401
Pro Gly Lys
465

<210> SEQ ID NO 89
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Thr Lys Tyr Asn
65              70                  75                  80

Gln Lys Phe Lys Gly Arg Val Thr Leu Thr Val Asp Lys Ser Thr Ser
            85                  90                  95

Thr Ala Tyr Met Glu Leu Ser Ser Leu Arg Ser Glu Asp Thr Ala Val
        100                 105                 110

Tyr Tyr Cys Ala Thr Asp Phe Tyr Gly Asp Trp Phe Thr Tyr Trp Gly
    115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
```

```
                195                 200                 205
Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 90
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 90 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc     144
Pro Gly Ala Ser Val Lys Val Ser Cys Lys Ala Ser Gly Phe Thr Phe
        35                  40                  45
```

-continued

```
agc acc agc tat atg agc tgg gtc cgc cag gct cca ggc ccc agc acc      192
Ser Thr Ser Tyr Met Ser Trp Val Arg Gln Ala Pro Gly Pro Ser Thr
     50                  55                  60 gaa tgg atg ggc tgg atc tat gcc ggc gac ggc ggc acc aag tac aac      240
Glu Trp Met Gly Trp Ile Tyr Ala Gly Asp Gly Gly Thr Lys Tyr Asn
 65                  70                  75                  80 cag aaa ttc aag ggc aga gtg acc ctg acc gtg gac aag agc acc agc      288
Gln Lys Phe Lys Gly Arg Val Thr Leu Thr Val Asp Lys Ser Thr Ser
                 85                  90                  95 acc gcc tac atg gaa ctg agc agc ctg cgg agc gag gac acc gcc gtg      336
Thr Ala Tyr Met Glu Leu Ser Ser Leu Arg Ser Glu Asp Thr Ala Val
            100                 105                 110 tac tac tgc gcc acc gac cac tac ggc gac tgg ttc aca tac tgg ggc      384
Tyr Tyr Cys Ala Thr Asp His Tyr Gly Asp Trp Phe Thr Tyr Trp Gly
        115                 120                 125 cag ggc acc ctg gtg acc gtg agc tca gcc tcc acc aag ggc cca agc      432
Gln Gly Thr Leu Val Thr Val Ser Ser Ala Ser Thr Lys Gly Pro Ser
    130                 135                 140 gtc ttc ccc ctg gca ccc tcc tcc aag agc acc tct ggc ggc aca gcc      480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg      528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct      576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg      624
Val Leu Gln Ser Ser Gly Leu Tyr Ser Leu Ser Ser Val Val Thr Val
        195                 200                 205 ccc tcc agc agc ttg ggc acc cag acc tac atc tgc aac gtg aat cac      672
Pro Ser Ser Ser Leu Gly Thr Gln Thr Tyr Ile Cys Asn Val Asn His
    210                 215                 220 aag ccc agc aac acc aag gtg gac aag aga gtt gag ccc aaa tct tgt      720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg      768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg      816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac      864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg      912
Glu Asp Pro Glu Val Lys Phe Asn Trp Tyr Val Asp Gly Val Glu Val
    290                 295                 300 cat aat gcc aag aca aag ccc cgg gag gag cag tac aac agc acg tac      960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc     1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc     1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg     1104
Glu Lys Thr Ile Ser Lys Ala Lys Gly Gln Pro Arg Glu Pro Gln Val
        355                 360                 365
```

```
tac acc ctg ccc cca tcc cgg gag gag atg acc aag aac cag gtc agc    1152
Tyr Thr Leu Pro Pro Ser Arg Glu Glu Met Thr Lys Asn Gln Val Ser
    370             375                 380 ctg acc tgc ctg gtc aaa ggc ttc tat ccc agc gac atc gcc gtg gag    1200
Leu Thr Cys Leu Val Lys Gly Phe Tyr Pro Ser Asp Ile Ala Val Glu
385             390                 395                 400 tgg gag agc aat ggc cag ccc gag aac aac tac aag acc acc cct ccc    1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg    1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg    1344
Asp Lys Ser Arg Trp Gln Gln Gly Asn Val Phe Ser Cys Ser Val Met
        435                 440                 445 cat gag gct ctg cac aac cac tac acc cag aag agc ctc tcc ctg tct    1392
His Glu Ala Leu His Asn His Tyr Thr Gln Lys Ser Leu Ser Leu Ser
    450                 455                 460 ccc ggc aaa                                                        1401
Pro Gly Lys
465

<210> SEQ ID NO 91
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Thr Lys Tyr Asn
65                  70                  75                  80

Gln Lys Phe Lys Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Asp His Tyr Gly Asp Trp Phe Thr Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205
```

```
Pro Ser Ser Leu Gly Thr Gln Thr Tyr Ile Cys Asn Val Asn His
    210                 215                 220
Lys Pro Ser Asn Thr Lys Val Asp Lys Arg Val Glu Pro Lys Ser Cys
225                 230                 235                 240
Asp Lys Thr His Thr Cys Pro Pro Cys Pro Ala Pro Glu Leu Leu Gly
            245                 250                 255
Gly Pro Ser Val Phe Leu Phe Pro Pro Lys Pro Lys Asp Thr Leu Met
        260                 265                 270
Ile Ser Arg Thr Pro Glu Val Thr Cys Val Val Val Asp Val Ser His
    275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
            325                 330                 335
Lys Glu Tyr Lys Cys Lys Val Ser Asn Lys Ala Leu Pro Ala Pro Ile
        340                 345                 350
Glu Lys Thr Ile Ser Lys Ala Lys Gly Gln Pro Arg Glu Pro Gln Val
    355                 360                 365
Tyr Thr Leu Pro Pro Ser Arg Glu Glu Met Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
            405                 410                 415
Val Leu Asp Ser Asp Gly Ser Phe Phe Leu Tyr Ser Lys Leu Thr Val
        420                 425                 430
Asp Lys Ser Arg Trp Gln Gln Gly Asn Val Phe Ser Cys Ser Val Met
    435                 440                 445
His Glu Ala Leu His Asn His Tyr Thr Gln Lys Ser Leu Ser Leu Ser
450                 455                 460
Pro Gly Lys
465

<210> SEQ ID NO 92
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 92 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc     144
Pro Gly Ala Ser Val Lys Val Ser Cys Lys Ala Ser Gly Phe Thr Phe
        35                  40                  45 agc acc agc tat atg agc tgg gtc cgc cag gct cca ggc ccc agc acc     192
Ser Thr Ser Tyr Met Ser Trp Val Arg Gln Ala Pro Gly Pro Ser Thr
```

```
                  50                      55                      60
gaa tgg atg ggc tgg atc tat gcc ggc gac ggc ggc acc aag tac aac      240
Glu Trp Met Gly Trp Ile Tyr Ala Gly Asp Gly Gly Thr Lys Tyr Asn
 65                  70                      75                  80 cag aaa ttc aag ggc aga gtg acc ctg acc gtg gac aag agc acc agc      288
Gln Lys Phe Lys Gly Arg Val Thr Leu Thr Val Asp Lys Ser Thr Ser
                     85                      90                  95 acc gcc tac atg gaa ctg agc agc ctg cgg agc gag gac acc gcc gtg      336
Thr Ala Tyr Met Glu Leu Ser Ser Leu Arg Ser Glu Asp Thr Ala Val
                    100                     105                 110 tac tac tgc gcc acc gac atc tac ggc gac tgg ttc aca tac tgg ggc      384
Tyr Tyr Cys Ala Thr Asp Ile Tyr Gly Asp Trp Phe Thr Tyr Trp Gly
                115                     120                     125 cag ggc acc ctg gtg acc gtg agc tca gcc tcc acc aag ggc cca agc      432
Gln Gly Thr Leu Val Thr Val Ser Ser Ala Ser Thr Lys Gly Pro Ser
130                     135                     140 gtc ttc ccc ctg gca ccc tcc tcc aag agc acc tct ggc gga aca gcc      480
Val Phe Pro Leu Ala Pro Ser Ser Lys Ser Thr Ser Gly Gly Thr Ala
145                     150                     155                 160 gcc ctg ggc tgc ctg gtc aag gac tac ttc ccc gaa ccc gtg acc gtg      528
Ala Leu Gly Cys Leu Val Lys Asp Tyr Phe Pro Glu Pro Val Thr Val
                165                     170                     175 agc tgg aac tca ggc gcc ctg acc agc ggc gtg cac acc ttc ccc gct      576
Ser Trp Asn Ser Gly Ala Leu Thr Ser Gly Val His Thr Phe Pro Ala
            180                     185                     190 gtc ctg cag tcc tca gga ctc tac tcc ctc agc agc gtg gtg acc gtg      624
Val Leu Gln Ser Ser Gly Leu Tyr Ser Leu Ser Ser Val Val Thr Val
            195                     200                     205 ccc tcc agc agc ttg ggc acc cag acc tac atc tgc aac gtg aat cac      672
Pro Ser Ser Ser Leu Gly Thr Gln Thr Tyr Ile Cys Asn Val Asn His
210                     215                     220 aag ccc agc aac acc aag gtg gac aag aga gtt gag ccc aaa tct tgt      720
Lys Pro Ser Asn Thr Lys Val Asp Lys Arg Val Glu Pro Lys Ser Cys
225                     230                     235                 240 gac aaa act cac aca tgc cca ccc tgc cca gca cct gaa ctc ctg ggg      768
Asp Lys Thr His Thr Cys Pro Pro Cys Pro Ala Pro Glu Leu Leu Gly
                245                     250                     255 gga ccc tca gtc ttc ctc ttc ccc cca aaa ccc aag gac acc ctc atg      816
Gly Pro Ser Val Phe Leu Phe Pro Pro Lys Pro Lys Asp Thr Leu Met
            260                     265                     270 atc tcc cgg acc cct gag gtc aca tgc gtg gtg gtg gac gtg agc cac      864
Ile Ser Arg Thr Pro Glu Val Thr Cys Val Val Val Asp Val Ser His
            275                     280                     285 gaa gac cct gag gtc aag ttc aac tgg tac gtg gac ggc gtg gag gtg      912
Glu Asp Pro Glu Val Lys Phe Asn Trp Tyr Val Asp Gly Val Glu Val
        290                     295                     300 cat aat gcc aag aca aag ccc cgg gag gag cag tac aac agc acg tac      960
His Asn Ala Lys Thr Lys Pro Arg Glu Glu Gln Tyr Asn Ser Thr Tyr
305                     310                     315                 320 cgg gtg gtc agc gtc ctc acc gtc ctg cac cag gac tgg ctg aat ggc     1008
Arg Val Val Ser Val Leu Thr Val Leu His Gln Asp Trp Leu Asn Gly
                325                     330                     335 aag gag tac aag tgc aag gtc tcc aac aaa gcc ctc cca gcc ccc atc     1056
Lys Glu Tyr Lys Cys Lys Val Ser Asn Lys Ala Leu Pro Ala Pro Ile
                340                     345                     350 gag aaa acc atc tcc aaa gcc aaa ggc cag ccc cgg gaa cca cag gtg     1104
Glu Lys Thr Ile Ser Lys Ala Lys Gly Gln Pro Arg Glu Pro Gln Val
            355                     360                     365 tac acc ctg ccc cca tcc cgg gag gag atg acc aag aac cag gtc agc     1152
Tyr Thr Leu Pro Pro Ser Arg Glu Glu Met Thr Lys Asn Gln Val Ser
```

```
Tyr Thr Leu Pro Pro Ser Arg Glu Glu Met Thr Lys Asn Gln Val Ser
    370             375                 380 ctg acc tgc ctg gtc aaa ggc ttc tat ccc agc gac atc gcc gtg gag    1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc    1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg    1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg    1344
Asp Lys Ser Arg Trp Gln Gln Gly Asn Val Phe Ser Cys Ser Val Met
        435                 440                 445 cat gag gct ctg cac aac cac tac acc cag aag agc ctc tcc ctg tct    1392
His Glu Ala Leu His Asn His Tyr Thr Gln Lys Ser Leu Ser Leu Ser
    450                 455                 460 ccc ggc aaa                                                         1401
Pro Gly Lys
465

<210> SEQ ID NO 93
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Thr Lys Tyr Asn
65              70                  75                  80

Gln Lys Phe Lys Gly Arg Val Thr Leu Thr Val Asp Lys Ser Thr Ser
            85                  90                  95

Thr Ala Tyr Met Glu Leu Ser Ser Leu Arg Ser Glu Asp Thr Ala Val
            100                 105                 110

Tyr Tyr Cys Ala Thr Asp Ile Tyr Gly Asp Trp Phe Thr Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220
```

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 94
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 94 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc     144
Pro Gly Ala Ser Val Lys Val Ser Cys Lys Ala Ser Gly Phe Thr Phe
        35                  40                  45 agc acc agc tat atg agc tgg gtc cgc cag gct cca ggc ccc agc acc     192
Ser Thr Ser Tyr Met Ser Trp Val Arg Gln Ala Pro Gly Pro Ser Thr
    50                  55                  60

```
gaa tgg atg ggc tgg atc tat gcc ggc gac ggc ggc acc aag tac aac    240
Glu Trp Met Gly Trp Ile Tyr Ala Gly Asp Gly Gly Thr Lys Tyr Asn
65              70                  75                  80 cag aaa ttc aag ggc aga gtg acc ctg acc gtg gac aag agc acc agc    288
Gln Lys Phe Lys Gly Arg Val Thr Leu Thr Val Asp Lys Ser Thr Ser
            85                  90                  95 acc gcc tac atg gaa ctg agc agc ctg cgg agc gag gac acc gcc gtg    336
Thr Ala Tyr Met Glu Leu Ser Ser Leu Arg Ser Glu Asp Thr Ala Val
        100                 105                 110 tac tac tgc gcc acc gac aag tac ggc gac tgg ttc aca tac tgg ggc    384
Tyr Tyr Cys Ala Thr Asp Lys Tyr Gly Asp Trp Phe Thr Tyr Trp Gly
    115                 120                 125 cag ggc acc ctg gtg acc gtg agc tca gcc tcc acc aag ggc cca agc    432
Gln Gly Thr Leu Val Thr Val Ser Ser Ala Ser Thr Lys Gly Pro Ser
130                 135                 140 gtc ttc ccc ctg gca ccc tcc tcc aag agc acc tct ggc ggc aca gcc    480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg    528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct    576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg    624
Val Leu Gln Ser Ser Gly Leu Tyr Ser Leu Ser Ser Val Val Thr Val
        195                 200                 205 ccc tcc agc agc ttg ggc acc cag acc tac atc tgc aac gtg aat cac    672
Pro Ser Ser Ser Leu Gly Thr Gln Thr Tyr Ile Cys Asn Val Asn His
    210                 215                 220 aag ccc agc aac acc aag gtg gac aag aga gtt gag ccc aaa tct tgt    720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg    768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg    816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac    864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg    912
Glu Asp Pro Glu Val Lys Phe Asn Trp Tyr Val Asp Gly Val Glu Val
    290                 295                 300 cat aat gcc aag aca aag ccc cgg gag gag cag tac aac agc acg tac    960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc   1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc   1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg   1104
Glu Lys Thr Ile Ser Lys Ala Lys Gly Gln Pro Arg Glu Pro Gln Val
        355                 360                 365 tac acc ctg ccc cca tcc cgg gag gag atg acc aag aac cag gtc agc   1152
Tyr Thr Leu Pro Pro Ser Arg Glu Glu Met Thr Lys Asn Gln Val Ser
    370                 375                 380
```

```
ctg acc tgc ctg gtc aaa ggc ttc tat ccc agc gac atc gcc gtg gag    1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc    1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg    1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg    1344
Asp Lys Ser Arg Trp Gln Gln Gly Asn Val Phe Ser Cys Ser Val Met
        435                 440                 445 cat gag gct ctg cac aac cac tac acc cag aag agc ctc tcc ctg tct    1392
His Glu Ala Leu His Asn His Tyr Thr Gln Lys Ser Leu Ser Leu Ser
450                 455                 460 ccc ggc aaa                                                        1401
Pro Gly Lys
465

<210> SEQ ID NO 95
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Thr Lys Tyr Asn
65                  70                  75                  80

Gln Lys Phe Lys Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Asp Lys Tyr Gly Asp Trp Phe Thr Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
```

```
                225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
                260                 265                 270
Ile Ser Arg Thr Pro Glu Val Thr Cys Val Val Val Asp Val Ser His
                275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
                340                 345                 350
Glu Lys Thr Ile Ser Lys Ala Lys Gly Gln Pro Arg Glu Pro Gln Val
                355                 360                 365
Tyr Thr Leu Pro Pro Ser Arg Glu Glu Met Thr Lys Asn Gln Val Ser
                370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
                420                 425                 430
Asp Lys Ser Arg Trp Gln Gln Gly Asn Val Phe Ser Cys Ser Val Met
                435                 440                 445
His Glu Ala Leu His Asn His Tyr Thr Gln Lys Ser Leu Ser Leu Ser
                450                 455                 460
Pro Gly Lys
465

<210> SEQ ID NO 96
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 96 atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa    96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc   144
Pro Gly Ala Ser Val Lys Val Ser Cys Lys Ala Ser Gly Phe Thr Phe
        35                  40                  45 agc acc agc tat atg agc tgg gtc cgc cag gct cca ggc ccc agc acc   192
Ser Thr Ser Tyr Met Ser Trp Val Arg Gln Ala Pro Gly Pro Ser Thr
    50                  55                  60 gaa tgg atg ggc tgg atc tat gcc ggc gac ggc ggc acc aag tac aac   240
Glu Trp Met Gly Trp Ile Tyr Ala Gly Asp Gly Gly Thr Lys Tyr Asn
```

-continued

```
                65                  70                  75                  80
cag aaa ttc aag ggc aga gtg acc ctg acc gtg gac aag agc acc agc         288
Gln Lys Phe Lys Gly Arg Val Thr Leu Thr Val Asp Lys Ser Thr Ser
                    85                  90                  95 acc gcc tac atg gaa ctg agc agc ctg cgg agc gag gac acc gcc gtg         336
Thr Ala Tyr Met Glu Leu Ser Ser Leu Arg Ser Glu Asp Thr Ala Val
                100                 105                 110 tac tac tgc gcc acc gac ctg tac ggc gac tgg ttc aca tac tgg ggc         384
Tyr Tyr Cys Ala Thr Asp Leu Tyr Gly Asp Trp Phe Thr Tyr Trp Gly
            115                 120                 125 cag ggc acc ctg gtg acc gtg agc tca gcc tcc acc aag ggc cca agc         432
Gln Gly Thr Leu Val Thr Val Ser Ser Ala Ser Thr Lys Gly Pro Ser
        130                 135                 140 gtc ttc ccc ctg gca ccc tcc tcc aag agc acc tct ggc ggc aca gcc         480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg         528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct         576
Ser Trp Asn Ser Gly Ala Leu Thr Ser Gly Val His Thr Phe Pro Ala
                180                 185                 190 gtc ctg cag tcc tca gga ctc tac tcc ctc agc agc gtg gtg acc gtg         624
Val Leu Gln Ser Ser Gly Leu Tyr Ser Leu Ser Ser Val Val Thr Val
            195                 200                 205 ccc tcc agc agc ttg ggc acc cag acc tac atc tgc aac gtg aat cac         672
Pro Ser Ser Ser Leu Gly Thr Gln Thr Tyr Ile Cys Asn Val Asn His
        210                 215                 220 aag ccc agc aac acc aag gtg gac aag aga gtt gag ccc aaa tct tgt         720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg         768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg         816
Gly Pro Ser Val Phe Leu Phe Pro Pro Lys Pro Lys Asp Thr Leu Met
                260                 265                 270 atc tcc cgg acc cct gag gtc aca tgc gtg gtg gtg gac gtg agc cac         864
Ile Ser Arg Thr Pro Glu Val Thr Cys Val Val Val Asp Val Ser His
            275                 280                 285 gaa gac cct gag gtc aag ttc aac tgg tac gtg gac ggc gtg gag gtg         912
Glu Asp Pro Glu Val Lys Phe Asn Trp Tyr Val Asp Gly Val Glu Val
        290                 295                 300 cat aat gcc aag aca aag ccc cgg gag gag cag tac aac agc acg tac         960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc        1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc        1056
Lys Glu Tyr Lys Cys Lys Val Ser Asn Lys Ala Leu Pro Ala Pro Ile
                340                 345                 350 gag aaa acc atc tcc aaa gcc aaa ggc cag ccc cgg gaa cca cag gtg        1104
Glu Lys Thr Ile Ser Lys Ala Lys Gly Gln Pro Arg Glu Pro Gln Val
            355                 360                 365 tac acc ctg ccc cca tcc cgg gag gag atg acc aag aac cag gtc agc        1152
Tyr Thr Leu Pro Pro Ser Arg Glu Glu Met Thr Lys Asn Gln Val Ser
        370                 375                 380 ctg acc tgc ctg gtc aaa ggc ttc tat ccc agc gac atc gcc gtg gag        1200
Leu Thr Cys Leu Val Lys Gly Phe Tyr Pro Ser Asp Ile Ala Val Glu
```

```
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc      1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg      1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg      1344
Asp Lys Ser Arg Trp Gln Gln Gly Asn Val Phe Ser Cys Ser Val Met
        435                 440                 445 cat gag gct ctg cac aac cac tac acc cag aag agc ctc tcc ctg tct      1392
His Glu Ala Leu His Asn His Tyr Thr Gln Lys Ser Leu Ser Leu Ser
    450                 455                 460 ccc ggc aaa                                                          1401
Pro Gly Lys
465

<210> SEQ ID NO 97
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Thr Lys Tyr Asn
65              70                  75                  80

Gln Lys Phe Lys Gly Arg Val Thr Leu Thr Val Asp Lys Ser Thr Ser
            85                  90                  95

Thr Ala Tyr Met Glu Leu Ser Ser Leu Arg Ser Glu Asp Thr Ala Val
            100                 105                 110

Tyr Tyr Cys Ala Thr Asp Leu Tyr Gly Asp Trp Phe Thr Tyr Trp Gly
        115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
        180                 185                 190

Val Leu Gln Ser Ser Gly Leu Tyr Ser Leu Ser Ser Val Val Thr Val
    195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240
```

```
Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 98
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 98 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc     144
Pro Gly Ala Ser Val Lys Val Ser Cys Lys Ala Ser Gly Phe Thr Phe
        35                  40                  45 agc acc agc tat atg agc tgg gtc cgc cag gct cca ggc ccc agc acc     192
Ser Thr Ser Tyr Met Ser Trp Val Arg Gln Ala Pro Gly Pro Ser Thr
    50                  55                  60 gaa tgg atg ggc tgg atc tat gcc ggc gac ggc ggc acc aag tac aac     240
Glu Trp Met Gly Trp Ile Tyr Ala Gly Asp Gly Gly Thr Lys Tyr Asn
65                  70                  75                  80
```

| | | |
|---|---|---|
| cag aaa ttc aag ggc aga gtg acc ctg acc gtg gac aag agc acc agc<br>Gln Lys Phe Lys Gly Arg Val Thr Leu Thr Val Asp Lys Ser Thr Ser<br>                85                      90                    95 | | 288 |
| acc gcc tac atg gaa ctg agc agc ctg cgg agc gag gac acc gcc gtg<br>Thr Ala Tyr Met Glu Leu Ser Ser Leu Arg Ser Glu Asp Thr Ala Val<br>                100                    105                 110 | | 336 |
| tac tac tgc gcc acc gac atg tac ggc gac tgg ttc aca tac tgg ggc<br>Tyr Tyr Cys Ala Thr Asp Met Tyr Gly Asp Trp Phe Thr Tyr Trp Gly<br>                115                    120                 125 | | 384 |
| cag ggc acc ctg gtg acc gtg agc tca gcc tcc acc aag ggc cca agc<br>Gln Gly Thr Leu Val Thr Val Ser Ser Ala Ser Thr Lys Gly Pro Ser<br>            130                    135                 140 | | 432 |
| gtc ttc ccc ctg gca ccc tcc tcc aag agc acc tct ggc ggc aca gcc<br>Val Phe Pro Leu Ala Pro Ser Ser Lys Ser Thr Ser Gly Gly Thr Ala<br>145                  150                    155                 160 | | 480 |
| gcc ctg ggc tgc ctg gtc aag gac tac ttc ccc gaa ccc gtg acc gtg<br>Ala Leu Gly Cys Leu Val Lys Asp Tyr Phe Pro Glu Pro Val Thr Val<br>                  165                    170                 175 | | 528 |
| agc tgg aac tca ggc gcc ctg acc agc ggc gtg cac acc ttc ccc gct<br>Ser Trp Asn Ser Gly Ala Leu Thr Ser Gly Val His Thr Phe Pro Ala<br>                180                    185                 190 | | 576 |
| gtc ctg cag tcc tca gga ctc tac tcc ctc agc agc gtg gtg acc gtg<br>Val Leu Gln Ser Ser Gly Leu Tyr Ser Leu Ser Ser Val Val Thr Val<br>            195                    200                 205 | | 624 |
| ccc tcc agc agc ttg ggc acc cag acc tac atc tgc aac gtg aat cac<br>Pro Ser Ser Ser Leu Gly Thr Gln Thr Tyr Ile Cys Asn Val Asn His<br>            210                    215                 220 | | 672 |
| aag ccc agc aac acc aag gtg gac aag aga gtt gag ccc aaa tct tgt<br>Lys Pro Ser Asn Thr Lys Val Asp Lys Arg Val Glu Pro Lys Ser Cys<br>225                  230                    235               240 | | 720 |
| gac aaa act cac aca tgc cca ccc tgc cca gca cct gaa ctc ctg ggg<br>Asp Lys Thr His Thr Cys Pro Pro Cys Pro Ala Pro Glu Leu Leu Gly<br>                245                    250               255 | | 768 |
| gga ccc tca gtc ttc ctc ttc ccc cca aaa ccc aag gac acc ctc atg<br>Gly Pro Ser Val Phe Leu Phe Pro Pro Lys Pro Lys Asp Thr Leu Met<br>            260                    265                 270 | | 816 |
| atc tcc cgg acc cct gag gtc aca tgc gtg gtg gtg gac gtg agc cac<br>Ile Ser Arg Thr Pro Glu Val Thr Cys Val Val Val Asp Val Ser His<br>                275                    280                 285 | | 864 |
| gaa gac cct gag gtc aag ttc aac tgg tac gtg gac ggc gtg gag gtg<br>Glu Asp Pro Glu Val Lys Phe Asn Trp Tyr Val Asp Gly Val Glu Val<br>            290                    295                 300 | | 912 |
| cat aat gcc aag aca aag ccc cgg gag gag cag tac aac agc acg tac<br>His Asn Ala Lys Thr Lys Pro Arg Glu Glu Gln Tyr Asn Ser Thr Tyr<br>305                  310                    315               320 | | 960 |
| cgg gtg gtc agc gtc ctc acc gtc ctg cac cag gac tgg ctg aat ggc<br>Arg Val Val Ser Val Leu Thr Val Leu His Gln Asp Trp Leu Asn Gly<br>                325                    330               335 | | 1008 |
| aag gag tac aag tgc aag gtc tcc aac aaa gcc ctc cca gcc ccc atc<br>Lys Glu Tyr Lys Cys Lys Val Ser Asn Lys Ala Leu Pro Ala Pro Ile<br>            340                    345                 350 | | 1056 |
| gag aaa acc atc tcc aaa gcc aaa ggc cag ccc cgg gaa cca cag gtg<br>Glu Lys Thr Ile Ser Lys Ala Lys Gly Gln Pro Arg Glu Pro Gln Val<br>                355                    360               365 | | 1104 |
| tac acc ctg ccc cca tcc cgg gag gag atg acc aag aac cag gtc agc<br>Tyr Thr Leu Pro Pro Ser Arg Glu Glu Met Thr Lys Asn Gln Val Ser<br>            370                    375                 380 | | 1152 |
| ctg acc tgc ctg gtc aaa ggc ttc tat ccc agc gac atc gcc gtg gag<br>Leu Thr Cys Leu Val Lys Gly Phe Tyr Pro Ser Asp Ile Ala Val Glu<br>385                  390                    395               400 | | 1200 |

```
tgg gag agc aat ggc cag ccc gag aac aac tac aag acc acc cct ccc     1248
Trp Glu Ser Asn Gly Gln Pro Glu Asn Asn Tyr Lys Thr Thr Pro Pro
            405                 410                 415 gtg ctg gac tcc gac ggc tcc ttc ttc ctc tac agc aag ctc acc gtg     1296
Val Leu Asp Ser Asp Gly Ser Phe Phe Leu Tyr Ser Lys Leu Thr Val
        420                 425                 430 gac aag agc agg tgg cag cag ggc aac gtc ttc tca tgc tcc gtg atg     1344
Asp Lys Ser Arg Trp Gln Gln Gly Asn Val Phe Ser Cys Ser Val Met
    435                 440                 445 cat gag gct ctg cac aac cac tac acc cag aag agc ctc tcc ctg tct     1392
His Glu Ala Leu His Asn His Tyr Thr Gln Lys Ser Leu Ser Leu Ser
450                 455                 460 ccc ggc aaa                                                          1401
Pro Gly Lys
465

<210> SEQ ID NO 99
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Gly Thr Lys Tyr Asn
65                  70                  75                  80

Gln Lys Phe Lys Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Asp Met Tyr Gly Asp Trp Phe Phe Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255
```

```
Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
355                 360                 365

Tyr Thr Leu Pro Pro Ser Arg Glu Glu Met Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
            450                 455                 460

Pro Gly Lys
465

<210> SEQ ID NO 100
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 100 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc     144
Pro Gly Ala Ser Val Lys Val Ser Cys Lys Ala Ser Gly Phe Thr Phe
        35                  40                  45 agc acc agc tat atg agc tgg gtc cgc cag gct cca ggc ccc agc acc     192
Ser Thr Ser Tyr Met Ser Trp Val Arg Gln Ala Pro Gly Pro Ser Thr
    50                  55                  60 gaa tgg atg ggc tgg atc tat gcc ggc gac ggc ggc acc aag tac aac     240
Glu Trp Met Gly Trp Ile Tyr Ala Gly Asp Gly Gly Thr Lys Tyr Asn
65                  70                  75                  80 cag aaa ttc aag ggc aga gtg acc ctg acc gtg gac aag agc acc agc     288
Gln Lys Phe Lys Gly Arg Val Thr Leu Thr Val Asp Lys Ser Thr Ser
```

```
                        85                  90                  95
acc gcc tac atg gaa ctg agc agc ctg cgg agc gag gac acc gcc gtg      336
Thr Ala Tyr Met Glu Leu Ser Ser Leu Arg Ser Glu Asp Thr Ala Val
            100                 105                 110 tac tac tgc gcc acc gac cag tac ggc gac tgg ttc aca tac tgg ggc      384
Tyr Tyr Cys Ala Thr Asp Gln Tyr Gly Asp Trp Phe Thr Tyr Trp Gly
            115                 120                 125 cag ggc acc ctg gtg acc gtg agc tca gcc tcc acc aag ggc cca agc      432
Gln Gly Thr Leu Val Thr Val Ser Ser Ala Ser Thr Lys Gly Pro Ser
130                 135                 140 gtc ttc ccc ctg gca ccc tcc tcc aag agc acc tct ggc ggc aca gcc      480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg      528
Ala Leu Gly Cys Leu Val Lys Asp Tyr Phe Pro Glu Pro Val Thr Val
            165                 170                 175 agc tgg aac tca ggc gcc ctg acc agc ggc gtg cac acc ttc ccc gct      576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg      624
Val Leu Gln Ser Ser Gly Leu Tyr Ser Leu Ser Ser Val Val Thr Val
            195                 200                 205 ccc tcc agc agc ttg ggc acc cag acc tac atc tgc aac gtg aat cac      672
Pro Ser Ser Ser Leu Gly Thr Gln Thr Tyr Ile Cys Asn Val Asn His
210                 215                 220 aag ccc agc aac acc aag gtg gac aag aga gtt gag ccc aaa tct tgt      720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg      768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg      816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac      864
Ile Ser Arg Thr Pro Glu Val Thr Cys Val Val Val Asp Val Ser His
            275                 280                 285 gaa gac cct gag gtc aag ttc aac tgg tac gtg gac ggc gtg gag gtg      912
Glu Asp Pro Glu Val Lys Phe Asn Trp Tyr Val Asp Gly Val Glu Val
290                 295                 300 cat aat gcc aag aca aag ccc cgg gag gag cag tac aac agc acg tac      960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc      1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc      1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg      1104
Glu Lys Thr Ile Ser Lys Ala Lys Gly Gln Pro Arg Glu Pro Gln Val
            355                 360                 365 tac acc ctg ccc cca tcc cgg gag gag atg acc aag aac cag gtc agc      1152
Tyr Thr Leu Pro Pro Ser Arg Glu Glu Met Thr Lys Asn Gln Val Ser
370                 375                 380 ctg acc tgc ctg gtc aaa ggc ttc tat ccc agc gac atc gcc gtg gag      1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc      1248
Trp Glu Ser Asn Gly Gln Pro Glu Asn Asn Tyr Lys Thr Thr Pro Pro
```

-continued

```
Trp Glu Ser Asn Gly Gln Pro Glu Asn Asn Tyr Lys Thr Thr Pro Pro
            405                 410                 415 gtg ctg gac tcc gac ggc tcc ttc ttc ctc tac agc aag ctc acc gtg    1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg    1344
Asp Lys Ser Arg Trp Gln Gln Gly Asn Val Phe Ser Cys Ser Val Met
            435                 440                 445 cat gag gct ctg cac aac cac tac acc cag aag agc ctc tcc ctg tct    1392
His Glu Ala Leu His Asn His Tyr Thr Gln Lys Ser Leu Ser Leu Ser
    450                 455                 460 ccc ggc aaa                                                         1401
Pro Gly Lys
465

<210> SEQ ID NO 101
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Gly Thr Lys Tyr Asn
65                  70                  75                  80

Gln Lys Phe Lys Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Asp Gln Tyr Gly Asp Trp Phe Thr Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
```

```
              260                 265                 270
Ile Ser Arg Thr Pro Glu Val Thr Cys Val Val Asp Val Ser His
            275                 280                 285

Glu Asp Pro Glu Val Lys Phe Asn Trp Tyr Val Asp Gly Val Glu Val
        290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 102
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 102 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc     144
Pro Gly Ala Ser Val Lys Val Ser Cys Lys Ala Ser Gly Phe Thr Phe
        35                  40                  45 agc acc agc tat atg agc tgg gtc cgc cag gct cca ggc ccc agc acc     192
Ser Thr Ser Tyr Met Ser Trp Val Arg Gln Ala Pro Gly Pro Ser Thr
    50                  55                  60 gaa tgg atg ggc tgg atc tat gcc ggc gac ggc ggc acc aag tac aac     240
Glu Trp Met Gly Trp Ile Tyr Ala Gly Asp Gly Gly Thr Lys Tyr Asn
65                  70                  75                  80 cag aaa ttc aag ggc aga gtg acc ctg acc gtg gac aag agc acc agc     288
Gln Lys Phe Lys Gly Arg Val Thr Leu Thr Val Asp Lys Ser Thr Ser
                85                  90                  95
```

```
acc gcc tac atg gaa ctg agc agc ctg cgg agc gag gac acc gcc gtg          336
Thr Ala Tyr Met Glu Leu Ser Ser Leu Arg Ser Glu Asp Thr Ala Val
            100                 105                 110 tac tac tgc gcc acc gac cgg tac ggc gac tgg ttc aca tac tgg ggc          384
Tyr Tyr Cys Ala Thr Asp Arg Tyr Gly Asp Trp Phe Thr Tyr Trp Gly
        115                 120                 125 cag ggc acc ctg gtg acc gtg agc tca gcc tcc acc aag ggc cca agc          432
Gln Gly Thr Leu Val Thr Val Ser Ser Ala Ser Thr Lys Gly Pro Ser
130                 135                 140 gtc ttc ccc ctg gca ccc tcc tcc aag agc acc tct ggc ggc aca gcc          480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg          528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct          576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg          624
Val Leu Gln Ser Ser Gly Leu Tyr Ser Leu Ser Ser Val Val Thr Val
        195                 200                 205 ccc tcc agc agc ttg ggc acc cag acc tac atc tgc aac gtg aat cac          672
Pro Ser Ser Ser Leu Gly Thr Gln Thr Tyr Ile Cys Asn Val Asn His
210                 215                 220 aag ccc agc aac acc aag gtg gac aag aga gtt gag ccc aaa tct tgt          720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg          768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg          816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac          864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg          912
Glu Asp Pro Glu Val Lys Phe Asn Trp Tyr Val Asp Gly Val Glu Val
290                 295                 300 cat aat gcc aag aca aag ccc cgg gag gag cag tac aac agc acg tac          960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc         1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc         1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg         1104
Glu Lys Thr Ile Ser Lys Ala Lys Gly Gln Pro Arg Glu Pro Gln Val
        355                 360                 365 tac acc ctg ccc cca tcc cgg gag gag atg acc aag aac cag gtc agc         1152
Tyr Thr Leu Pro Pro Ser Arg Glu Glu Met Thr Lys Asn Gln Val Ser
370                 375                 380 ctg acc tgc ctg gtc aaa ggc ttc tat ccc agc gac atc gcc gtg gag         1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc         1248
Trp Glu Ser Asn Gly Gln Pro Glu Asn Asn Tyr Lys Thr Thr Pro Pro
                405                 410                 415
```

```
gtg ctg gac tcc gac ggc tcc ttc ttc ctc tac agc aag ctc acc gtg       1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg       1344
Asp Lys Ser Arg Trp Gln Gln Gly Asn Val Phe Ser Cys Ser Val Met
        435                 440                 445 cat gag gct ctg cac aac cac tac acc cag aag agc ctc tcc ctg tct       1392
His Glu Ala Leu His Asn His Tyr Thr Gln Lys Ser Leu Ser Leu Ser
    450                 455                 460 ccc ggc aaa                                                           1401
Pro Gly Lys
465

<210> SEQ ID NO 103
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Gly Thr Lys Tyr Asn
65                  70                  75                  80

Gln Lys Phe Lys Gly Arg Val Thr Leu Thr Val Asp Lys Ser Thr Ser
            85                  90                  95

Thr Ala Tyr Met Glu Leu Ser Ser Leu Arg Ser Glu Asp Thr Ala Val
            100                 105                 110

Tyr Tyr Cys Ala Thr Asp Arg Tyr Gly Asp Trp Phe Tyr Trp Gly
            115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270
```

```
Ile Ser Arg Thr Pro Glu Val Thr Cys Val Val Val Asp Val Ser His
            275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
            355                 360                 365
Tyr Thr Leu Pro Pro Ser Arg Glu Glu Met Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
            435                 440                 445
His Glu Ala Leu His Asn His Tyr Thr Gln Lys Ser Leu Ser Leu Ser
450                 455                 460
Pro Gly Lys
465

<210> SEQ ID NO 104
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 104 atg aaa cac ctg tgg ttc ttc ctc ctg ctg gtg gca gct ccc aga tgg     48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa     96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc    144
Pro Gly Ala Ser Val Lys Val Ser Cys Lys Ala Ser Gly Phe Thr Phe
        35                  40                  45 agc acc agc tat atg agc tgg gtc cgc cag gct cca ggc ccc agc acc    192
Ser Thr Ser Tyr Met Ser Trp Val Arg Gln Ala Pro Gly Pro Ser Thr
    50                  55                  60 gaa tgg atg ggc tgg atc tat gcc ggc gac ggc ggc acc aag tac aac    240
Glu Trp Met Gly Trp Ile Tyr Ala Gly Asp Gly Gly Thr Lys Tyr Asn
65                  70                  75                  80 cag aaa ttc aag ggc aga gtg acc ctg acc gtg gac aag agc acc agc    288
Gln Lys Phe Lys Gly Arg Val Thr Leu Thr Val Asp Lys Ser Thr Ser
                85                  90                  95 acc gcc tac atg gaa ctg agc agc ctg cgg agc gag gac acc gcc gtg    336
Thr Ala Tyr Met Glu Leu Ser Ser Leu Arg Ser Glu Asp Thr Ala Val
```

```
                  100                 105                 110
tac tac tgc gcc acc gac gtg tac ggc gac tgg ttc aca tac tgg ggc    384
Tyr Tyr Cys Ala Thr Asp Val Tyr Gly Asp Trp Phe Thr Tyr Trp Gly
        115                 120                 125 cag ggc acc ctg gtg acc gtg agc tca gcc tcc acc aag ggc cca agc    432
Gln Gly Thr Leu Val Thr Val Ser Ser Ala Ser Thr Lys Gly Pro Ser
130                 135                 140 gtc ttc ccc ctg gca ccc tcc tcc aag agc acc tct ggc ggc aca gcc    480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg    528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct    576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg    624
Val Leu Gln Ser Ser Gly Leu Tyr Ser Leu Ser Ser Val Val Thr Val
        195                 200                 205 ccc tcc agc agc ttg ggc acc cag acc tac atc tgc aac gtg aat cac    672
Pro Ser Ser Ser Leu Gly Thr Gln Thr Tyr Ile Cys Asn Val Asn His
    210                 215                 220 aag ccc agc aac acc aag gtg gac aag aga gtt gag ccc aaa tct tgt    720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg    768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg    816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac    864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg    912
Glu Asp Pro Glu Val Lys Phe Asn Trp Tyr Val Asp Gly Val Glu Val
    290                 295                 300 cat aat gcc aag aca aag ccc cgg gag gag cag tac aac agc acg tac    960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc   1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc   1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg   1104
Glu Lys Thr Ile Ser Lys Ala Lys Gly Gln Pro Arg Glu Pro Gln Val
        355                 360                 365 tac acc ctg ccc cca tcc cgg gag gag atg acc aag aac cag gtc agc   1152
Tyr Thr Leu Pro Pro Ser Arg Glu Glu Met Thr Lys Asn Gln Val Ser
    370                 375                 380 ctg acc tgc ctg gtc aaa ggc ttc tat ccc agc gac atc gcc gtg gag   1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc   1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg   1296
Val Leu Asp Ser Asp Gly Ser Phe Phe Leu Tyr Ser Lys Leu Thr Val
```

```
Val Leu Asp Ser Asp Gly Ser Phe Phe Leu Tyr Ser Lys Leu Thr Val
                420                 425                 430 gac aag agc agg tgg cag cag ggc aac gtc ttc tca tgc tcc gtg atg      1344
Asp Lys Ser Arg Trp Gln Gln Gly Asn Val Phe Ser Cys Ser Val Met
                435                 440                 445 cat gag gct ctg cac aac cac tac acc cag aag agc ctc tcc ctg tct      1392
His Glu Ala Leu His Asn His Tyr Thr Gln Lys Ser Leu Ser Leu Ser
    450                 455                 460 ccc ggc aaa                                                          1401
Pro Gly Lys
465

<210> SEQ ID NO 105
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ala Ser Val Lys Val Ser Cys Lys Ala Ser Gly Phe Thr Phe
            35                  40                  45

Ser Thr Ser Tyr Met Ser Trp Val Arg Gln Ala Pro Gly Pro Ser Thr
        50                  55                  60

Glu Trp Met Gly Trp Ile Tyr Ala Gly Asp Gly Thr Lys Tyr Asn
65              70                  75                  80

Gln Lys Phe Lys Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Asp Val Tyr Gly Asp Trp Phe Thr Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

```
Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 106
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 106 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc     144
Pro Gly Ala Ser Val Lys Val Ser Cys Lys Ala Ser Gly Phe Thr Phe
        35                  40                  45 agc acc agc tat atg agc tgg gtc cgc cag gct cca ggc ccc agc acc     192
Ser Thr Ser Tyr Met Ser Trp Val Arg Gln Ala Pro Gly Pro Ser Thr
    50                  55                  60 gaa tgg atg ggc tgg atc tat gcc ggc gac ggc ggc acc aag tac aac     240
Glu Trp Met Gly Trp Ile Tyr Ala Gly Asp Gly Gly Thr Lys Tyr Asn
65                  70                  75                  80 cag aaa ttc aag ggc aga gtg acc ctg acc gtg gac aag agc acc agc     288
Gln Lys Phe Lys Gly Arg Val Thr Leu Thr Val Asp Lys Ser Thr Ser
                85                  90                  95 acc gcc tac atg gaa ctg agc agc ctg cgg agc gag gac acc gcc gtg     336
Thr Ala Tyr Met Glu Leu Ser Ser Leu Arg Ser Glu Asp Thr Ala Val
            100                 105                 110
```

| | | | | | | | | | | | | | | | | |
|---|---|---|---|---|---|---|---|---|---|---|---|---|---|---|---|---|
| tac | tac | tgc | gcc | acc | gac | tgg | tac | ggc | gac | tgg | ttc | aca | tac | tgg | ggc | 384 |
| Tyr | Tyr | Cys | Ala | Thr | Asp | Trp | Tyr | Gly | Asp | Trp | Phe | Thr | Tyr | Trp | Gly | |
| | | 115 | | | | 120 | | | | 125 | | | | | | |

| | | | | | | | | | | | | | | | | |
|---|---|---|---|---|---|---|---|---|---|---|---|---|---|---|---|---|
| cag | ggc | acc | ctg | gtg | acc | gtg | agc | tca | gcc | tcc | acc | aag | ggc | cca | agc | 432 |
| Gln | Gly | Thr | Leu | Val | Thr | Val | Ser | Ser | Ala | Ser | Thr | Lys | Gly | Pro | Ser | |
| 130 | | | | | 135 | | | | | 140 | | | | | | |

| | | | | | | | | | | | | | | | | |
|---|---|---|---|---|---|---|---|---|---|---|---|---|---|---|---|---|
| gtc | ttc | ccc | ctg | gca | ccc | tcc | tcc | aag | agc | acc | tct | ggc | ggc | aca | gcc | 480 |
| Val | Phe | Pro | Leu | Ala | Pro | Ser | Ser | Lys | Ser | Thr | Ser | Gly | Gly | Thr | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gcc | ctg | ggc | tgc | ctg | gtc | aag | gac | tac | ttc | ccc | gaa | ccc | gtg | acc | gtg | 528 |
| Ala | Leu | Gly | Cys | Leu | Val | Lys | Asp | Tyr | Phe | Pro | Glu | Pro | Val | Thr | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| agc | tgg | aac | tca | ggc | gcc | ctg | acc | agc | ggc | gtg | cac | acc | ttc | ccc | gct | 576 |
| Ser | Trp | Asn | Ser | Gly | Ala | Leu | Thr | Ser | Gly | Val | His | Thr | Phe | Pro | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| gtc | ctg | cag | tcc | tca | gga | ctc | tac | tcc | ctc | agc | agc | gtg | gtg | acc | gtg | 624 |
| Val | Leu | Gln | Ser | Ser | Gly | Leu | Tyr | Ser | Leu | Ser | Ser | Val | Val | Thr | Val | |
| | | | 195 | | | | | 200 | | | | | 205 | | | |

| | | | | | | | | | | | | | | | | |
|---|---|---|---|---|---|---|---|---|---|---|---|---|---|---|---|---|
| ccc | tcc | agc | agc | ttg | ggc | acc | cag | acc | tac | atc | tgc | aac | gtg | aat | cac | 672 |
| Pro | Ser | Ser | Ser | Leu | Gly | Thr | Gln | Thr | Tyr | Ile | Cys | Asn | Val | Asn | His | |
| | 210 | | | | | 215 | | | | | 220 | | | | | |

| | | | | | | | | | | | | | | | | |
|---|---|---|---|---|---|---|---|---|---|---|---|---|---|---|---|---|
| aag | ccc | agc | aac | acc | aag | gtg | gac | aag | aga | gtt | gag | ccc | aaa | tct | tgt | 720 |
| Lys | Pro | Ser | Asn | Thr | Lys | Val | Asp | Lys | Arg | Val | Glu | Pro | Lys | Ser | Cys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gac | aaa | act | cac | aca | tgc | cca | ccc | tgc | cca | gca | cct | gaa | ctc | ctg | ggg | 768 |
| Asp | Lys | Thr | His | Thr | Cys | Pro | Pro | Cys | Pro | Ala | Pro | Glu | Leu | Leu | Gly | |
| | | | | 245 | | | | | 250 | | | | | 255 | | |

| | | | | | | | | | | | | | | | | |
|---|---|---|---|---|---|---|---|---|---|---|---|---|---|---|---|---|
| gga | ccc | tca | gtc | ttc | ctc | ttc | ccc | cca | aaa | ccc | aag | gac | acc | ctc | atg | 816 |
| Gly | Pro | Ser | Val | Phe | Leu | Phe | Pro | Pro | Lys | Pro | Lys | Asp | Thr | Leu | Met | |
| | | | 260 | | | | | 265 | | | | | 270 | | | |

| | | | | | | | | | | | | | | | | |
|---|---|---|---|---|---|---|---|---|---|---|---|---|---|---|---|---|
| atc | tcc | cgg | acc | cct | gag | gtc | aca | tgc | gtg | gtg | gtg | gac | gtg | agc | cac | 864 |
| Ile | Ser | Arg | Thr | Pro | Glu | Val | Thr | Cys | Val | Val | Val | Asp | Val | Ser | His | |
| | | | 275 | | | | | 280 | | | | | 285 | | | |

| | | | | | | | | | | | | | | | | |
|---|---|---|---|---|---|---|---|---|---|---|---|---|---|---|---|---|
| gaa | gac | cct | gag | gtc | aag | ttc | aac | tgg | tac | gtg | gac | ggc | gtg | gag | gtg | 912 |
| Glu | Asp | Pro | Glu | Val | Lys | Phe | Asn | Trp | Tyr | Val | Asp | Gly | Val | Glu | Val | |
| | 290 | | | | | 295 | | | | | 300 | | | | | |

| | | | | | | | | | | | | | | | | |
|---|---|---|---|---|---|---|---|---|---|---|---|---|---|---|---|---|
| cat | aat | gcc | aag | aca | aag | ccc | cgg | gag | gag | cag | tac | aac | agc | acg | tac | 960 |
| His | Asn | Ala | Lys | Thr | Lys | Pro | Arg | Glu | Glu | Gln | Tyr | Asn | Ser | Thr | Tyr | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| cgg | gtg | gtc | agc | gtc | ctc | acc | gtc | ctg | cac | cag | gac | tgg | ctg | aat | ggc | 1008 |
| Arg | Val | Val | Ser | Val | Leu | Thr | Val | Leu | His | Gln | Asp | Trp | Leu | Asn | Gly | |
| | | | | 325 | | | | | 330 | | | | | 335 | | |

| | | | | | | | | | | | | | | | | |
|---|---|---|---|---|---|---|---|---|---|---|---|---|---|---|---|---|
| aag | gag | tac | aag | tgc | aag | gtc | tcc | aac | aaa | gcc | ctc | cca | gcc | ccc | atc | 1056 |
| Lys | Glu | Tyr | Lys | Cys | Lys | Val | Ser | Asn | Lys | Ala | Leu | Pro | Ala | Pro | Ile | |
| | | | 340 | | | | | 345 | | | | | 350 | | | |

| | | | | | | | | | | | | | | | | |
|---|---|---|---|---|---|---|---|---|---|---|---|---|---|---|---|---|
| gag | aaa | acc | atc | tcc | aaa | gcc | aaa | ggc | cag | ccc | cgg | gaa | cca | cag | gtg | 1104 |
| Glu | Lys | Thr | Ile | Ser | Lys | Ala | Lys | Gly | Gln | Pro | Arg | Glu | Pro | Gln | Val | |
| | | | 355 | | | | | 360 | | | | | 365 | | | |

| | | | | | | | | | | | | | | | | |
|---|---|---|---|---|---|---|---|---|---|---|---|---|---|---|---|---|
| tac | acc | ctg | ccc | cca | tcc | cgg | gag | gag | atg | acc | aag | aac | cag | gtc | agc | 1152 |
| Tyr | Thr | Leu | Pro | Pro | Ser | Arg | Glu | Glu | Met | Thr | Lys | Asn | Gln | Val | Ser | |
| | 370 | | | | | 375 | | | | | 380 | | | | | |

| | | | | | | | | | | | | | | | | |
|---|---|---|---|---|---|---|---|---|---|---|---|---|---|---|---|---|
| ctg | acc | tgc | ctg | gtc | aaa | ggc | ttc | tat | ccc | agc | gac | atc | gcc | gtg | gag | 1200 |
| Leu | Thr | Cys | Leu | Val | Lys | Gly | Phe | Tyr | Pro | Ser | Asp | Ile | Ala | Val | Glu | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| tgg | gag | agc | aat | ggc | cag | ccc | gag | aac | aac | tac | aag | acc | acc | cct | ccc | 1248 |
| Trp | Glu | Ser | Asn | Gly | Gln | Pro | Glu | Asn | Asn | Tyr | Lys | Thr | Thr | Pro | Pro | |
| | | | | 405 | | | | | 410 | | | | | 415 | | |

| | | | | | | | | | | | | | | | | |
|---|---|---|---|---|---|---|---|---|---|---|---|---|---|---|---|---|
| gtg | ctg | gac | tcc | gac | ggc | tcc | ttc | ttc | ctc | tac | agc | aag | ctc | acc | gtg | 1296 |
| Val | Leu | Asp | Ser | Asp | Gly | Ser | Phe | Phe | Leu | Tyr | Ser | Lys | Leu | Thr | Val | |
| | | | 420 | | | | | 425 | | | | | 430 | | | |

```
gac aag agc agg tgg cag cag ggc aac gtc ttc tca tgc tcc gtg atg    1344
Asp Lys Ser Arg Trp Gln Gln Gly Asn Val Phe Ser Cys Ser Val Met
        435                 440                 445 cat gag gct ctg cac aac cac tac acc cag aag agc ctc tcc ctg tct    1392
His Glu Ala Leu His Asn His Tyr Thr Gln Lys Ser Leu Ser Leu Ser
    450                 455                 460 ccc ggc aaa                                                        1401
Pro Gly Lys
465
```

<210> SEQ ID NO 107
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Thr Ser Tyr Met Ser Trp Val Arg Gln Ala Pro Gly Pro Ser Thr
    50                  55                  60

Glu Trp Met Gly Trp Ile Tyr Ala Gly Asp Gly Thr Lys Tyr Asn
65              70                  75                  80

Gln Lys Phe Lys Gly Arg Val Thr Leu Thr Val Asp Lys Ser Thr Ser
            85                  90                  95

Thr Ala Tyr Met Glu Leu Ser Ser Leu Arg Ser Glu Asp Thr Ala Val
            100                 105                 110

Tyr Tyr Cys Ala Thr Asp Trp Tyr Gly Asp Trp Phe Thr Tyr Trp Gly
            115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
```

```
                        290                 295                 300
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465

<210> SEQ ID NO 108
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 108 atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa    96
Val Leu Ser Gln Val Gln Leu Val Gln Ser Gly Ala Glu Val Lys Lys
            20                  25                  30 cct ggg gct agc gtg aag gtg tcc tgc aag gcc agc ggc ttc acc ttc   144
Pro Gly Ala Ser Val Lys Val Ser Cys Lys Ala Ser Gly Phe Thr Phe
        35                  40                  45 agc acc agc tat atg agc tgg gtc cgc cag gct cca ggc ccc agc acc   192
Ser Thr Ser Tyr Met Ser Trp Val Arg Gln Ala Pro Gly Pro Ser Thr
    50                  55                  60 gaa tgg atg ggc tgg atc tat gcc ggc gac ggc ggc acc aag tac aac   240
Glu Trp Met Gly Trp Ile Tyr Ala Gly Asp Gly Gly Thr Lys Tyr Asn
65                  70                  75                  80 cag aaa ttc aag ggc aga gtg acc ctg acc gtg gac aag agc acc agc   288
Gln Lys Phe Lys Gly Arg Val Thr Leu Thr Val Asp Lys Ser Thr Ser
                85                  90                  95 acc gcc tac atg gaa ctg agc agc ctg cgg agc gag gac acc gcc gtg   336
Thr Ala Tyr Met Glu Leu Ser Ser Leu Arg Ser Glu Asp Thr Ala Val
            100                 105                 110 tac tac tgt gcc acc gac tac tac ggc gac tgg ttc aca tac tgg ggc   384
Tyr Tyr Cys Ala Thr Asp Tyr Tyr Gly Asp Trp Phe Thr Tyr Trp Gly
```

-continued

```
                 115                 120                 125
cag ggc acc ctg gtg acc gtg agc tca gcc tcc acc aag ggc cca agc      432
Gln Gly Thr Leu Val Thr Val Ser Ser Ala Ser Thr Lys Gly Pro Ser
    130                 135                 140 gtc ttc ccc ctg gca ccc tcc tcc aag agc acc tct ggc ggc aca gcc      480
Val Phe Pro Leu Ala Pro Ser Ser Lys Ser Thr Ser Gly Gly Thr Ala
145                 150                 155                 160 gcc ctg ggc tgc ctg gtc aag gac tac ttc ccc gaa ccc gtg acc gtg      528
Ala Leu Gly Cys Leu Val Lys Asp Tyr Phe Pro Glu Pro Val Thr Val
                165                 170                 175 agc tgg aac tca ggc gcc ctg acc agc ggc gtg cac acc ttc ccc gct      576
Ser Trp Asn Ser Gly Ala Leu Thr Ser Gly Val His Thr Phe Pro Ala
            180                 185                 190 gtc ctg cag tcc tca gga ctc tac tcc ctc agc agc gtg gtg acc gtg      624
Val Leu Gln Ser Ser Gly Leu Tyr Ser Leu Ser Ser Val Val Thr Val
        195                 200                 205 ccc tcc agc agc ttg ggc acc cag acc tac atc tgc aac gta aat cac      672
Pro Ser Ser Ser Leu Gly Thr Gln Thr Tyr Ile Cys Asn Val Asn His
    210                 215                 220 aag ccc agc aac acc aag gtg gac aag aga gtt gag ccc aaa tct tgt      720
Lys Pro Ser Asn Thr Lys Val Asp Lys Arg Val Glu Pro Lys Ser Cys
225                 230                 235                 240 gac aaa act cac aca tgc cca ccc tgc cca gca cct gaa ctc ctg ggg      768
Asp Lys Thr His Thr Cys Pro Pro Cys Pro Ala Pro Glu Leu Leu Gly
                245                 250                 255 gga ccc tca gtc ttc ctc ttc ccc cca aaa ccc aag gac acc ctc atg      816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac      864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg      912
Glu Asp Pro Glu Val Lys Phe Asn Trp Tyr Val Asp Gly Val Glu Val
    290                 295                 300 cat aat gcc aag aca aag ccc cgg gag gag cag tac aac agc acg tac      960
His Asn Ala Lys Thr Lys Pro Arg Glu Glu Gln Tyr Asn Ser Thr Tyr
305                 310                 315                 320 cgg gtg gtc agc gtc ctc acc gtc ctg cac cag gac tgg ctg aat ggc     1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc     1056
Lys Glu Tyr Lys Cys Lys Val Ser Asn Lys Ala Leu Pro Ala Pro Ile
            340                 345                 350 gag aaa acc atc tcc aaa gcc aaa ggc cag ccc cgg gaa cca cag gtg     1104
Glu Lys Thr Ile Ser Lys Ala Lys Gly Gln Pro Arg Glu Pro Gln Val
        355                 360                 365 tac acc ctg ccc cca tcc cgg gag gag atg acc aag aac cag gtc agc     1152
Tyr Thr Leu Pro Pro Ser Arg Glu Glu Met Thr Lys Asn Gln Val Ser
    370                 375                 380 ctg acc tgc ctg gtc aaa ggc ttc tat ccc agc gac atc gcc gtg gag     1200
Leu Thr Cys Leu Val Lys Gly Phe Tyr Pro Ser Asp Ile Ala Val Glu
385                 390                 395                 400 tgg gag agc aat ggc cag ccc gag aac aac tac aag acc acc cct ccc     1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg     1296
Val Leu Asp Ser Asp Gly Ser Phe Phe Leu Tyr Ser Lys Leu Thr Val
            420                 425                 430 gac aag agc agg tgg cag cag ggc aac gtc ttc tca tgc tcc gtg atg     1344
```

```
Asp Lys Ser Arg Trp Gln Gln Gly Asn Val Phe Ser Cys Ser Val Met
        435                 440                 445 cat gag gct ctg cac aac cac tac acc cag aag agc ctc tcc ctg tct    1392
His Glu Ala Leu His Asn His Tyr Thr Gln Lys Ser Leu Ser Leu Ser
        450                 455                 460 ccc ggc aaa                                                        1401
Pro Gly Lys
465

<210> SEQ ID NO 109
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ala Ser Val Lys Val Ser Cys Lys Ala Ser Gly Phe Thr Phe
            35                  40                  45

Ser Thr Ser Tyr Met Ser Trp Val Arg Gln Ala Pro Gly Pro Ser Thr
        50                  55                  60

Glu Trp Met Gly Trp Ile Tyr Ala Gly Asp Gly Thr Lys Tyr Asn
65              70                  75                  80

Gln Lys Phe Lys Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Asp Tyr Tyr Gly Asp Trp Phe Thr Tyr Trp Gly
        115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300
```

```
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 110
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
ggcagagtga ccctgaccgc cgacaagagc accagcacc                          39

<210> SEQ ID NO 111
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ggtgctggtg ctcttgtcgg cggtcagggt cactctgcc                          39

<210> SEQ ID NO 112
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ctgtttcaag gtccgagcaa taacaaacgt gcaccgtatt gg                      42

<210> SEQ ID NO 113
<211> LENGTH: 42
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 113
cgcaagcttg tcgactcaaa caacatccag atgataggta tg                42

<210> SEQ ID NO 114
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gagggctacg gcgactggtt cacatac                                 27

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ggtggcgcag tagtacacgg cggt                                    24

<210> SEQ ID NO 116
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gacgcctacg gcgactggtt cacatac                                 27

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gacgagtacg gcgactggtt cacatac                                 27

<210> SEQ ID NO 118
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gacttctacg gcgactggtt cacatac                                 27

<210> SEQ ID NO 119
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gaccactacg gcgactggtt cacatac         27

<210> SEQ ID NO 120
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gacatctacg gcgactggtt cacatac         27

<210> SEQ ID NO 121
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gacaagtacg gcgactggtt cacatac         27

<210> SEQ ID NO 122
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gacctgtacg gcgactggtt cacatac         27

<210> SEQ ID NO 123
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gacatgtacg gcgactggtt cacatac         27

<210> SEQ ID NO 124
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gaccagtacg gcgactggtt cacatac         27

<210> SEQ ID NO 125
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 125
gaccggtacg gcgactggtt cacatac                                              27

<210> SEQ ID NO 126
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gacgtgtacg gcgactggtt cacatac                                              27

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gactggtacg gcgactggtt cacatac                                              27

<210> SEQ ID NO 128
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gactactacg gcgactggtt cacatac                                              27
```

ANTI-FGFR2 ANTIBODIES AND METHODS OF USE THEREOF FOR TREATING CANCER

CROSS-REFERENCE TO RELATED APPLICATIONS

This application is a National Stage application of PCT/JP2013/061340, filed Apr. 9, 2013, which claims priority from Japanese application JP2012-088299, filed Apr. 9, 2012.

The instant application contains a Sequence Listing which has been submitted electronically in ASCII format and is hereby incorporated by reference in its entirety. Said ASCII copy, created on Dec. 16, 2014, is named 098065-0127_SL.txt and is 305,599 bytes in size.

TECHNICAL FIELD

The present invention relates to a novel antibody, a nucleotide comprising a nucleotide sequence encoding the amino acid sequence of the antibody, a vector having an insert of the nucleotide, a cell comprising the nucleotide or the vector, a method for producing the antibody, comprising the step of culturing the cell, a pharmaceutical composition comprising the antibody, a composition for diagnosis comprising the antibody, a functional fragment of the antibody, a modified form of the antibody, etc.

BACKGROUND ART

Fibroblast growth factors (FGFs) are known to play an important role in embryogenesis, tissue homeostasis, and metabolism via FGF receptor (FGFR) signals (Non Patent Literature 1). In humans, 22 FGFs (FGF1 to FGF14 and FGF16 to FGF23) and 4 FGF receptors (FGFR1 to FGFR4; hereinafter, collectively referred to as "FGFRs") having a tyrosine kinase domain are found. These FGFRs are each constituted by an extracellular region comprising a ligand binding site composed of 2 or 3 immunoglobulin-like domains (IgD1 to IgD3), a single-pass transmembrane region, and an intracellular region comprising the tyrosine kinase domain. FGFR1, FGFR2, and FGFR3 each have two splicing variants called IIIb and IIIc. These isoforms differ in the sequence of approximately 50 amino acids in the latter half of IgD3 and exhibit distinctive tissue distribution and ligand specificity. It is generally known that the IIIb isoform is expressed in epithelial cells, while the IIIc isoform is expressed in mesenchymal cells. Upon binding of FGFs to FGFRs, these FGFRs are dimerized and phosphorylated at their particular tyrosine residues. This phenomenon promotes the recruiting of important adaptor proteins such as FGFR substrate 2α (FRS2α) and induces the activation of many signaling pathways including MAPK and PI3K/Akt pathways. As a result, FGFs and their corresponding receptors control a wide range of cell functions including growth, differentiation, migration, and survival.

The abnormal activation of FGFRs is known to participate in particular types of malignant tumor development in humans (Non Patent Literature 1 and 2). Particularly, findings such as the overexpression of FGFR2 and its ligand, receptor mutations or gene amplification, and isoform switching, have been made as to the association of FGFR2 signal abnormality with cancer. Specifically, a single nucleotide polymorphism (SNP) in intron 2 of the FGFR2 gene reportedly correlates with the risk of breast cancer progression caused by the high expression of FGFR2 (Non Patent Literature 3 and 4). Missense mutations that constitutively activate FGFR2 have been reported in endometrial cancer, ovary cancer, breast cancer, lung cancer, and stomach cancer (Non Patent Literature 2, 3, and 5). Also, the amplification or overexpression of the FGFR2 gene has been reported in stomach cancer and breast cancer (Non Patent Literature 2, 3, and 5). In addition, class switch from FGFR2 IIIb to FGFR2 IIIc is also known to occur during the progression of prostate cancer or kidney cancer and correlate with poor prognosis (Non Patent Literature 6 and 7).

As mentioned above, the association of FGFR2 overexpression or mutations or switching from IIIb to IIIc, with many cancer types suggests the possibility of FGFR2 as an excellent therapeutic target for cancer. In fact, monoclonal antibodies against FGFR2 have been obtained and are under evaluation for their antitumor effects in preclinical trials in order to reveal the role of FGFR2 in oncogenesis and determine the possibility of FGFR2 as a therapeutic target for cancer (Non Patent Literature 8 and 9). All of these antibodies have been shown to have a neutralizing effect that inhibits signaling derived from a ligand for FGFR2 IIIb. Unfortunately, there has been no report on a functional antibody having effector effects such as ADCC or a neutralizing effect on IIIc.

CITATION LIST

Non Patent Literature

Non Patent Literature 1: Eswarakumar, V. P., et al., J. Cytokine Growth Factor Rev., April 2005, Vol. 16 (No. 2), p. 139-149, published online on Feb. 1, 2005, Review Non Patent Literature 2: Turner, N. and Grose, R., Nat. Rev. Cancer, February 2010, Vol. 10 (No. 2), p. 116-129, Review Non Patent Literature 3: Easton, D. F., et al., Nature, Jun. 28, 2007, Vol. 447 (No. 7148), p. 1087-1093

Non Patent Literature 4: Hunter D J, et al., Nat. Genet., July 2007, Vol. 39 (No. 7), p. 870-874, published online on May 27, 2007

Non Patent Literature 5: Katoh, Y. and Katoh, M., Int. J. Mol. Med., March 2009, Vol. 23 (No. 3), p. 307-311, Review Non Patent Literature 6: Chaffer, C. L., et al., Differentiation, November 2007, Vol. 75 (No. 9), p. 831-842, published online on Aug. 14, 2007, Review Non Patent Literature 7: Carstens, R. P., et al., Oncogene, Dec. 18, 1997, Vol. 15 (No. 25), p. 3059-3065

Non Patent Literature 8: Zhao, W. M., et al., Clin. Cancer Res., Dec. 1, 2010, Vol. 16 (No. 23), p. 5750-5758, published online on Jul. 29, 2010

Non Patent Literature 9: Bai, A., et al., Cancer Res., Oct. 1, 2010, Vol. 70 (No. 19), p. 7630-7639, published online on Aug. 13, 2010

SUMMARY OF INVENTION

Technical Problem

An object of the present invention is to provide an antibody against FGFR2.

Another object of the present invention is to provide a pharmaceutical composition, etc. comprising an anti-FGFR2 antibody having an anticancer effect.

An alternative object of the present invention includes a nucleotide encoding the amino acid sequence of the antibody, a vector having an insert of the nucleotide, a cell comprising the nucleotide or the vector, a method for producing the antibody, comprising the step of culturing the cell, etc.

A further alternative object of the present invention is to provide a method for treating cancer using the antibody.

Solution to Problem

The present inventors have conducted diligent studies to attain the objects and consequently completed the present invention by developing a novel anti-FGFR2 antibody and have found that the antibody has an anticancer effect.

The present invention relates to:
(1) An antibody or a functional fragment thereof, which has antibody dependent cellular cytotoxic activity and binds to a fibroblast growth factor receptor (FGFR);
(2) The antibody or functional fragment thereof according to (1), wherein the fibroblast growth factor receptor (FGFR) is human FGFR;
(3) The antibody or functional fragment thereof according to (1) or (2), wherein the fibroblast growth factor receptor (FGFR) is FGFR2;
(4) The antibody or functional fragment thereof according to any one of (1) to (3), wherein the antibody or functional fragment thereof binds to human fibroblast growth factor receptor 2 (human FGFR2) IIIb and/or human fibroblast growth factor receptor 2 (human FGFR2) IIIc;
(5) The antibody or functional fragment thereof according to any one of (1) to (4), wherein the antibody or functional fragment thereof binds to human fibroblast growth factor receptor 2 (human FGFR2) IIIb and human fibroblast growth factor receptor (human FGFR2) IIIc;
(6) The antibody or functional fragment thereof according to any one of (1) to (5), wherein the antibody or functional fragment thereof binds to one or two or more immunoglobulin-like domains of the human fibroblast growth factor receptor 2;
(7) The antibody or functional fragment thereof according to any one of (1) to (6), wherein the antibody or functional fragment thereof binds to immunoglobulin-like domain 2 of the human fibroblast growth factor receptor 2;
(8) The antibody or functional fragment thereof according to any one of (1) to (4) and (6), wherein the antibody or functional fragment thereof binds to immunoglobulin-like domain 3 of the human fibroblast growth factor receptor 2;
(9) The antibody or functional fragment thereof according to any one of (1) to (8), wherein the antibody or functional fragment thereof has neutralizing activity against the human fibroblast growth factor receptor 2 (human FGFR2) IIIb and/or the human fibroblast growth factor receptor 2 (human FGFR2) IIIc;
(10) The antibody or functional fragment thereof according to any one of (1) to (9), wherein the antibody or functional fragment thereof has neutralizing activity against the human fibroblast growth factor receptor 2 (human FGFR2) IIIb and the human fibroblast growth factor receptor 2 (human FGFR2) IIIc;
(11) The antibody or functional fragment thereof according to any one of (1) to (10), wherein the antibody or functional fragment thereof has antitumor activity;
(12) The antibody or functional fragment thereof according to (11), wherein the antibody or functional fragment thereof exhibits antitumor activity in vivo;
(13) The antibody or functional fragment thereof according to any one of (1) to (4), (6), (8), (9), (11) and (12), wherein the antibody consists of a heavy chain comprising CDRH1 consisting of the amino acid sequence represented by SEQ ID NO: 52 (FIG. 60) of the Sequence Listing or an amino acid sequence derived from the amino acid sequence by the substitution of one or two amino acids, CDRH2 consisting of the amino acid sequence represented by SEQ ID NO: 53 (FIG. 61) of the Sequence Listing or an amino acid sequence derived from the amino acid sequence by the substitution of one or two amino acids, and CDRH3 consisting of the amino acid sequence represented by SEQ ID NO: 54 (FIG. 62) of the Sequence Listing or an amino acid sequence derived from the amino acid sequence by the substitution of one or two amino acids, and a light chain comprising CDRL1 consisting of the amino acid sequence represented by SEQ ID NO: 61 (FIG. 69) of the Sequence Listing or an amino acid sequence derived from the amino acid sequence by the substitution of one or two amino acids, CDRL2 consisting of the amino acid sequence represented by SEQ ID NO: 62 (FIG. 70) of the Sequence Listing or an amino acid sequence derived from the amino acid sequence by the substitution of one or two amino acids, and CDRL3 consisting of the amino acid sequence represented by SEQ ID NO: 63 (FIG. 71) of the Sequence Listing or an amino acid sequence derived from the amino acid sequence by the substitution of one or two amino acids, and binds to human FGFR2;
(14) The antibody or functional fragment thereof according to any one of (1) to (7) and (9) to (12), wherein the antibody consists of a heavy chain comprising CDRH1 consisting of the amino acid sequence represented by SEQ ID NO: 55 (FIG. 63) of the Sequence Listing or an amino acid sequence derived from the amino acid sequence by the substitution of one or two amino acids, CDRH2 consisting of the amino acid sequence represented by SEQ ID NO: 56 (FIG. 64) of the Sequence Listing or an amino acid sequence derived from the amino acid sequence by the substitution of one or two amino acids, and CDRH3 consisting of the amino acid sequence represented by SEQ ID NO: 57 (FIG. 65) of the Sequence Listing or an amino acid sequence derived from the amino acid sequence by the substitution of one or two amino acids, and a light chain comprising CDRL1 consisting of the amino acid sequence represented by SEQ ID NO: 64 (FIG. 72) of the Sequence Listing or an amino acid sequence derived from the amino acid sequence by the substitution of one or two amino acids, CDRL2 consisting of the amino acid sequence represented by SEQ ID NO: 65 (FIG. 73) of the Sequence Listing or an amino acid sequence derived from the amino acid sequence by the substitution of one or two amino acids, and CDRL3 consisting of the amino acid sequence represented by SEQ ID NO: 66 (FIG. 74) of the Sequence Listing or an amino acid sequence derived from the amino acid sequence by the substitution of one or two amino acids, and binds to human FGFR2;
(15) The antibody or functional fragment thereof according to any one of (1) to (7) and (9) to (12), wherein the antibody consists of a heavy chain comprising CDRH1 consisting of the amino acid sequence represented by SEQ ID NO: 58 (FIG. 66) of the Sequence Listing or an amino acid sequence derived from the amino acid sequence by the substitution of one or two amino acids, CDRH2 consisting of the amino acid sequence represented by SEQ ID NO: 59 (FIG. 67) of the Sequence Listing or an amino acid sequence derived from the amino acid sequence by the substitution of one or two amino acids, and CDRH3 consisting of the amino acid sequence represented by SEQ ID NO: 60 (FIG. 68) of the Sequence Listing or an amino acid sequence derived from the amino acid sequence by the substitution of one or two amino acids, and a light chain comprising CDRL1 consisting of the amino acid sequence represented by SEQ ID NO: 67 (FIG. 75) of the Sequence Listing or an amino acid sequence derived from the amino acid sequence by the substitution of one or two amino acids, CDRL2 consisting of the amino acid sequence represented by SEQ ID NO: 68 (FIG. 76) of the Sequence Listing or an amino acid sequence derived from the amino acid sequence by the substitution of one or two amino acids, and CDRL3 consisting of the amino acid sequence represented by SEQ ID NO: 69 (FIG. 77) of the Sequence Listing or an amino acid sequence derived from the amino acid sequence by the substitution of one or two amino acids, and binds to human FGFR2;

(16) The antibody or functional fragment thereof according to (15), wherein the CDRH3 consists of an amino acid sequence derived from the amino acid sequence represented by SEQ ID NO: 60 (FIG. 68) of the Sequence Listing by the substitution of one or two amino acids;

(17) The antibody or functional fragment thereof according to any one of (1) to (16), wherein the antibody is a monoclonal antibody;

(18) The antibody or functional fragment thereof according to any one of (1) to (17), wherein the antibody is a chimeric antibody;

(19) The antibody or functional fragment thereof according to any one of (1) to (18), wherein the antibody is a humanized antibody;

(20) The antibody or functional fragment thereof according to (19), wherein the antibody is selected from the following (i) to (xix):

(i) a humanized antibody (hFR2-14_H19/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 97 (FIG. 105);

(ii) a humanized antibody (hFR2-14_H12/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 97 (FIG. 105);

(iii) a humanized antibody (hFR2-14_H8/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 89 (FIG. 97);

(iv) a humanized antibody (hFR2-14_H11/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 95 (FIG. 103);

(v) a humanized antibody (hFR2-14_H5/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 83 (FIG. 91);

(vi) a humanized antibody (hFR2-14_H1/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 75 (FIG. 83);

(vii) a humanized antibody (hFR2-14_H2/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 77 (FIG. 85);

(viii) a humanized antibody (hFR2-14_H3/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 79 (FIG. 87);

(ix) a humanized antibody (hFR2-14_H4/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 81 (FIG. 89);

(x) a humanized antibody (hFR2-14_H6/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 85 (FIG. 93);

(xi) a humanized antibody (hFR2-14_H7/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 87 (FIG. 95);

(xii) a humanized antibody (hFR2-14_H9/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 91 (FIG. 99);

(xiii) a humanized antibody (hFR2-14_H10/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 93 (FIG. 101);

(xiv) a humanized antibody (hFR2-14_H13/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 99 (FIG. 107);

(xv) a humanized antibody (hFR2-14_H14/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 101 (FIG. 109);

(xvi) a humanized antibody (hFR2-14_H15/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 103 (FIG. 111);

(xvii) a humanized antibody (hFR2-14_H16/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 105 (FIG. 113);

(xviii) a humanized antibody (hFR2-14_H17/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 107 (FIG. 115); and (xix) a humanized antibody (hFR2-14_H18/L1) comprising a light chain comprising amino acid positions 21 to 235 of the amino acid sequence represented by SEQ ID NO: 73 (FIG. 81), and a heavy chain comprising amino acid positions 20 to 467 of the amino acid sequence represented by SEQ ID NO: 109 (FIG. 117);

(21) The antibody or functional fragment thereof according to any one of (1) to (12), wherein the antibody comprises heavy and light chains comprising amino acid sequences having 95% or higher identity to the amino acid sequences of the heavy and light chains, respectively, of an antibody according to (20), and binds to human FGFR2;

(22) The antibody or functional fragment thereof according to any one of (1) to (12), wherein the antibody or functional fragment thereof binds to a site on an antigen recognized by an antibody according to any one of (13) to (16) and (20);

(23) The antibody or functional fragment thereof according to any one of (1) to (12), wherein the antibody or functional fragment thereof competes with an antibody according to any one of (13) to (16) and (20) for binding to human FGFR2;

(24) The antibody or functional fragment thereof according to any one of (1) to (12), wherein the antibody or functional fragment thereof binds to an epitope on human FGFR2, the epitope being constituted by tyrosine (Tyr) at residue 155, threonine (Thr) at residue 157, lysine (Lys) at residue 176, alanine (Ala) at residue 181, glycine (Gly) at residue 182, glycine (Gly) at residue 183, asparagine (Asn) at residue 184, proline (Pro) at residue 185, methionine (Met) at residue 186, threonine (Thr) at residue 188, glutamine (Gln) at residue 200, glutamic acid (Glu) at residue 201, glycine (Gly) at residue 205, glycine (Gly) at residue 206, lysine (Lys) at residue 208, valine (Val) at residue 209, arginine (Arg) at residue 210, asparagine (Asn) at residue 211, glutamine (Gin) at residue 212, histidine (His) at residue 213, tryptophan (Trp) at residue 214, and isoleucine (Ile) at residue 217 in the amino acid sequence represented by SEQ ID NO: 70 (FIG. 78) or SEQ ID NO: 71 (FIG. 79);

(25) The antibody or functional fragment thereof according to any one of (1) to (12), wherein the antibody or functional fragment thereof has an interaction distance with each of tyrosine (Tyr) at residue 155, threonine (Thr) at residue 157, lysine (Lys) at residue 176, alanine (Ala) at residue 181, glycine (Gly) at residue 182, glycine (Gly) at residue 183, asparagine (Asn) at residue 184, proline (Pro) at residue 185, methionine (Met) at residue 186, threonine (Thr) at residue 188, glutamine (Gin) at residue 200, glutamic acid (Glu) at residue 201, glycine (Gly) at residue 205, glycine (Gly) at residue 206, lysine (Lys) at residue 208, valine (Val) at residue 209, arginine (Arg) at residue 210, asparagine (Asn) at residue 211, glutamine (Gin) at residue 212, histidine (His) at residue 213, tryptophan (Trp) at residue 214, and isoleucine (Ile) at residue 217 in the amino acid sequence represented by SEQ ID NO: 70 (FIG. 78) or SEQ ID NO: 71 (FIG. 79);

(26) The antibody or functional fragment thereof according to (25), wherein the interaction distance is 6 angstroms or shorter;

(27) The antibody or functional fragment thereof according to (25) or (26), wherein the interaction distance is 4 angstroms or shorter;

(28) The antibody or functional fragment thereof according to any one of (1) to (12) and (21) to (27), wherein the antibody is a human antibody;

(29) The antibody or functional fragment thereof according to any one of (1) to (28), wherein the antibody or functional fragment thereof inhibits the binding of FGF to human FGFR2;

(30) The antibody or functional fragment thereof according to any one of (1) to (29), wherein the antibody or functional fragment thereof has antibody dependent cellular cytotoxic activity and/or antibody dependent cell phagocytosis activity;

(31) A nucleotide of any one of the following (i) to (iii):
(i) a nucleotide comprising a nucleotide sequence encoding a partial or whole amino acid sequence of the heavy or light chain of an antibody according to any one of (1) to (30);
(ii) a nucleotide consisting of a nucleotide sequence comprising the nucleotide sequence encoding a partial or whole amino acid sequence of the heavy or light chain of an antibody according to any one of (1) to (30); and
(iii) a nucleotide consisting of the nucleotide sequence encoding a partial or whole amino acid sequence of the heavy or light chain of an antibody according to any one of (1) to (30);

(32) A recombinant vector having an insert of a nucleotide according to (31);

(33) A recombinant cell comprising a nucleotide according to (31) or a recombinant vector according to (32);

(34) A cell producing an antibody or a functional fragment thereof according to any one of (1) to (30);

(35) A method for producing an antibody or a functional fragment thereof according to any one of (1) to (30), comprising the following steps (i) and (ii):
(i) culturing a cell according to (33) or (34); and
(ii) recovering the antibody or functional fragment thereof according to any one of (1) to (30) from the cultures obtained in the step (i);

(36) The antibody or functional fragment thereof according to any one of (1) to (12) which is obtained by a method according to (35);

(37) The antibody or functional fragment thereof according to any one of (1) to (30) and (36), wherein 1 to 5 amino acids are deleted from the amino terminus or carboxyl terminus of the heavy or light chain;

(38) A modified form of an antibody or a functional fragment thereof according to any one of (1) to (30), (36), and (37);

(39) The modified form according to (38), wherein a sugar chain modification is regulated;

(40) The modified form according to (39), wherein the antibody is selected from antibodies (i) to (xix) of (20);

(41) A pharmaceutical composition comprising an antibody or a functional fragment thereof according to any one of (1) to (30), (36), and (37), or a modified form according to any one of (38) to (40) as an active ingredient;

(42) The pharmaceutical composition according to (41), wherein the pharmaceutical composition is an anticancer agent;

(43) The pharmaceutical composition according to (42), wherein the cancer is FGFR2-positive;

(44) A composition for testing or diagnosis of cancer comprising an antibody or a functional fragment thereof according to any one of (1) to (30), (36), and (37), or a modified form according to any one of (38) to (40);
(45) A composition comprising an antibody or a functional fragment thereof which has human FGFR2 IIIb selectivity or a modified form of the antibody or the functional fragment;
(46) The composition according to (45), wherein the antibody comprises a heavy chain comprising CDRH1 to CDRH3 and a light chain comprising CDRL1 to CDRL3 according to (13);
(47) The composition according to (46), wherein the antibody comprises a heavy chain variable region having the amino acid sequence represented by SEQ ID NO: 12 (FIG. 20) and a light chain variable region having the amino acid sequence represented by SEQ ID NO: 21 (FIG. 29);
(48) The composition according to (46) or (47), wherein the antibody is a chimeric antibody or a rat antibody;
(49) The composition according to any one of (45) to (48), wherein the composition is for detection or assay of human FGFR2 IIIb;
(50) A method for detecting or assaying human FGFR2 IIIb, comprising the step of contacting a test sample with a composition according to any one of (45) to (48);
(51) A method for detecting or assaying human FGFR2 IIIc, comprising the following steps (i) to (iii):
(i) contacting a test sample with a composition comprising an antibody or a functional fragment thereof which selectively binds to human FGFR2 IIIb and human FGFR2 IIIc, or a modified form of the antibody or the functional fragment to detect or assay human FGFR2 IIIb and human FGFR2 IIIc in the test sample;
(ii) contacting the test sample with a composition according to any one of (45) to (49) to detect or assay the human FGFR2 IIIb in the test sample; and
(iii) comparing the results of detection or assay in the step (i) with the results of detection or assay in the step (ii) or subtracting the results of detection or assay in the step (ii) from the results of detection or assay in the step (i) to obtain detection or assay results or a value of the human FGFR2 IIIc in the test sample;
(52) The composition according to any one of (44) to (49) or the method according to (50) or (51), wherein the composition or the method is for diagnosis or testing of a human FGFR2-positive cancer;
(53) A method for identifying a recipient individual for a pharmaceutical composition according to any one of (41) to (43), comprising the following steps (i) and (ii):
(i) contacting an individual-derived sample with a composition according to any one of (44) to (49); and
(ii) determining the individual to be positive when human FGFR2 is detected in the sample;
(54) The method according to (53), wherein the human FGFR2 is human FGFR2 IIIb;
(55) The method according to (53), wherein the human FGFR2 is human FGFR2 IIIc and human FGFR2 IIIb;
(56) The composition according to any one of (44) to (49), wherein the composition is used in a method according to any one of (53) to (55);
(57) The method according to any one of (53) to (55) or the composition according to (56), wherein the individual has cancer or is at risk thereof;
(58) The pharmaceutical composition according to any one of (41) to (43), wherein the pharmaceutical composition is administered to an individual identified to be positive by a method according to any one of (53) to (55);
(59) A reagent comprising an antibody or a functional fragment thereof according to any one of (1) to (30), (36), and (37), or a modified form according to any one of (38) to (40);
(60) A method for identifying a substance having antitumor activity, comprising the following steps (i) to (iii):
(i) contacting a test substance with a protein comprising tyrosine (Tyr) at amino acid position 155 to isoleucine (Ile) at amino acid position 217 in the amino acid sequence represented by SEQ ID NO: 70 (FIG. 78) or SEQ ID NO: 71 (FIG. 79);
(ii) measuring or determining the distance between the substance and each of tyrosine (Tyr) at residue 155, threonine (Thr) at residue 157, lysine (Lys) at residue 176, alanine (Ala) at residue 181, glycine (Gly) at residue 182, glycine (Gly) at residue 183, asparagine (Asn) at residue 184, proline (Pro) at residue 185, methionine (Met) at residue 186, threonine (Thr) at residue 188, glutamine (Gln) at residue 200, glutamic acid (Glu) at residue 201, glycine (Gly) at residue 205, glycine (Gly) at residue 206, lysine (Lys) at residue 208, valine (Val) at residue 209, arginine (Arg) at residue 210, asparagine (Asn) at residue 211, glutamine (Gln) at residue 212, histidine (His) at residue 213, tryptophan (Trp) at residue 214, and isoleucine (Ile) at residue 217 in the amino acid sequence represented by SEQ ID NO: 70 in the protein; and
(iii) determining the substance to be positive when the substance has an interaction distance with each of the residues;
(61) The method according to (60), further comprising the following step (iv):
(iv) assaying the antitumor activity of the substance;
(62) The method according to (60) or (61), wherein the substance is an antibody or a functional fragment thereof, or a modified form of the antibody or the functional fragment, or a peptide;
(63) A method for producing a substance determined to be positive in step (iii) according to (60) or (61), comprising preparing the substance by a step including gene recombination, peptide synthesis, or in vitro translation;
(64) The pharmaceutical composition according to any one of (41) to (43) and (58), further comprising an additional drug;
(65) The antibody or functional fragment thereof according to any one of (1) to (30), (36), and (37), or the modified form according to any one of (38) to (40), wherein the antibody, the functional fragment, or the modified form is conjugated with an additional compound; and
(66) The pharmaceutical composition according to any one of (41) to (43), (58), and (64), wherein the pharmaceutical composition comprises an antibody, a functional fragment, or a modified form according to (65), etc.

Advantageous Effects of Invention

Use of the antibody provided by the present invention enables treatment or prevention of various cancers and testing or diagnosis of various cancers.

BRIEF DESCRIPTION OF DRAWINGS

FIG. 6A is a diagram showing the signal-neutralizing activity of the human chimeric anti-FGFR2 antibodies (cFR2-10, cFR2-13, and cFR2-14) against human FGFR2 IIIb by Elk1 trans-reporter assay.

FIG. 7 is a diagram showing the ADCC activity of the human chimeric anti-FGFR2 antibodies (cFR2-10, cFR2-13, and cFR2-14). 293T-lacZ cells expressing human FGFR2 IIIb were used as target cells, and human PBMC was used as effector cells.

FIG. 8A) shows the results for the cFR2-10 antibody. FIG. 8B) shows the results for the cFR2-13 antibody. FIG. 8C) shows the results for the cFR2-14 antibody.

FIG. 9 shows the N-terminal amino acid sequence of a band corresponding to the heavy chain of the rat anti-FGFR2 antibody FR2-10 (SEQ ID NO: 1 of the Sequence Listing).

FIG. 10 shows the N-terminal amino acid sequence of a band corresponding to the light chain of the rat anti-FGFR2 antibody FR2-10 (SEQ ID NO: 2 of the Sequence Listing).

FIG. 11 shows the N-terminal amino acid sequence of a band corresponding to the heavy chain of the rat anti-FGFR2 antibody FR2-13 (SEQ ID NO: 3 of the Sequence Listing).

FIG. 12 shows the N-terminal amino acid sequence of a band corresponding to the light chain of the rat anti-FGFR2 antibody FR2-13 (SEQ ID NO: 4 of the Sequence Listing).

FIG. 13 shows the N-terminal amino acid sequence of a band corresponding to the heavy chain of the rat anti-FGFR2 antibody FR2-14 (SEQ ID NO: 5 of the Sequence Listing).

FIG. 14 shows the N-terminal amino acid sequence of a band corresponding to the light chain of the rat anti-FGFR2 antibody FR2-14 (SEQ ID NO: 6 of the Sequence Listing).

FIG. 15 shows a primer for gene amplification of a rat heavy chain (SEQ ID NO: 7 of the Sequence Listing).

FIG. 16 shows a sequencing primer for the heavy chain of FR2-10 (SEQ ID NO: 8 of the Sequence Listing).

FIG. 17 shows a sequencing primer for the heavy chain of FR2-13 (SEQ ID NO: 9 of the Sequence Listing).

FIG. 18 shows a sequencing primer for the heavy chain of FR2-14 (SEQ ID NO: 10 of the Sequence Listing).

FIG. 19 shows the nucleotide sequence of a cDNA encoding the heavy chain variable region of the rat anti-FGFR2 antibody FR2-10 (SEQ ID NO: 11 of the Sequence Listing).

FIG. 20 shows the amino acid sequence of the heavy chain variable region of the rat anti-FGFR2 antibody FR2-10 (SEQ ID NO: 12 of the Sequence Listing).

FIG. 21 shows the nucleotide sequence of a cDNA encoding the heavy chain variable region of the rat anti-FGFR2 antibody FR2-13 (SEQ ID NO: 13 of the Sequence Listing).

FIG. 22 shows the amino acid sequence of the heavy chain variable region of the rat anti-FGFR2 antibody FR2-13 (SEQ ID NO: 14 of the Sequence Listing).

FIG. 23 shows the nucleotide sequence of a cDNA encoding the heavy chain variable region of the rat anti-FGFR2 antibody FR2-14 (SEQ ID NO: 15 of the Sequence Listing).

FIG. 24 shows the amino acid sequence of the heavy chain variable region of the rat anti-FGFR2 antibody FR2-14 (SEQ ID NO: 16 of the Sequence Listing).

FIG. 25 shows a primer for gene amplification of a rat light chain (SEQ ID NO: 17 of the Sequence Listing).

FIG. 26 shows a sequencing primer for a rat light chain (SEQ ID NO: 18 of the Sequence Listing).

FIG. 27 shows a sequencing primer for the light chain of FR2-10 (SEQ ID NO: 19 of the Sequence Listing).

FIG. 28 shows the nucleotide sequence of a cDNA encoding the light chain variable region of the rat anti-FGFR2 antibody FR2-10 (SEQ ID NO: 20 of the Sequence Listing).

FIG. 29 shows the amino acid sequence of the light chain variable region of the rat anti-FGFR2 antibody FR2-10 (SEQ ID NO: 21 of the Sequence Listing).

FIG. 30 shows a primer for gene amplification of the rat FR2-13 or FR2-14 light chain (SEQ ID NO: 22 of the Sequence Listing).

FIG. 31 shows the nucleotide sequence of a cDNA encoding the light chain variable region of the rat anti-FGFR2 antibody FR2-13 (SEQ ID NO: 23 of the Sequence Listing).

FIG. 32 shows the amino acid sequence of the light chain variable region of the rat anti-FGFR2 antibody FR2-13 (SEQ ID NO: 24 of the Sequence Listing).

FIG. 33 shows the nucleotide sequence of a cDNA encoding the light chain variable region of the rat anti-FGFR2 antibody FR2-14 (SEQ ID NO: 25 of the Sequence Listing).

FIG. 34 shows the amino acid sequence of the light chain variable region of the rat anti-FGFR2 antibody FR2-14 (SEQ ID NO: 26 of the Sequence Listing).

FIG. 35 shows a DNA fragment comprising a DNA sequence encoding the amino acids of a human κ chain secretory signal sequence and a human κ chain constant region (SEQ ID NO: 27 of the Sequence Listing).

FIG. 36 shows a primer F for a light chain expression vector (SEQ ID NO: 28 of the Sequence Listing).

FIG. 37 shows a primer R for a light chain expression vector (SEQ ID NO: 29 of the Sequence Listing).

FIG. 38 shows a DNA fragment comprising a DNA sequence encoding the amino acids of a human heavy chain signal sequence and a human IgG1 constant region (SEQ ID NO: 30 of the Sequence Listing).

FIG. 39 shows the nucleotide sequence of the light chain of human chimeric FR2-10 (cFR2-10) (SEQ ID NO: 31 of the Sequence Listing). In this sequence, nucleotide positions 1 to 60 represent a signal sequence, which is usually not contained in the nucleotide sequences of most of mature cFR2-10 light chains.

FIG. 40 shows the amino acid sequence of the light chain of human chimeric FR2-10 (cFR2-10) (SEQ ID NO: 32 of the Sequence Listing). In this sequence, amino acid positions 1 to 20 represent a signal sequence, which is usually not contained in the amino acid sequences of most of mature cFR2-10 light chains.

FIG. 41 shows a primer set F for the light chain of human chimeric FR2-10 (SEQ ID NO: 33 of the Sequence Listing).

FIG. 42 shows a primer set R for the light chain of human chimeric FR2-10 (SEQ ID NO: 34 of the Sequence Listing).

FIG. 43 shows the nucleotide sequence of the heavy chain of human chimeric FR2-10 (cFR2-10) (SEQ ID NO: 35 of the Sequence Listing). In this sequence, nucleotide positions 1 to 57 represent a signal sequence, which is usually not contained in the nucleotide sequences of most of mature cFR2-10 heavy chains.

FIG. 44 shows the amino acid sequence of the heavy chain of human chimeric FR2-10 (cFR2-10) (SEQ ID NO: 36 of the Sequence Listing). In this sequence, amino acid positions 1 to 19 represent a signal sequence, which is usually not included in the amino acid sequence of most of mature cFR2-10 heavy chains.

FIG. 45 shows a primer set F for the heavy chain of human chimeric FR2-10 (SEQ ID NO: 37 of the Sequence Listing).

FIG. 46 shows a primer set R for the heavy chain of human chimeric FR2-10 (SEQ ID NO: 38 of the Sequence Listing).

FIG. 47 shows the nucleotide sequence of the light chain of human chimeric FR2-13 (cFR2-13) (SEQ ID NO: 39 of the Sequence Listing). In this sequence, nucleotide positions 1 to 60 represent a signal sequence, which is usually not contained in the nucleotide sequences of most of mature cFR2-13 light chains.

FIG. 48 shows the amino acid sequence of the light chain of human chimeric FR2-13 (cFR2-13) (SEQ ID NO: 40 of the Sequence Listing). In this sequence, amino acid positions 1 to 20 represent a signal sequence, which is usually not contained in the amino acid sequences of most of mature cFR2-13 light chains.

FIG. 49 shows a primer F for the light chain of human chimeric FR2-13 (SEQ ID NO: 41 of the Sequence Listing).

FIG. 50 shows a primer R for the light chain of human chimeric FR2-13 (SEQ ID NO: 42 of the Sequence Listing).

FIG. 51 shows the nucleotide sequence of the heavy chain of human chimeric FR2-13 (cFR2-13) (SEQ ID NO: 43 of the Sequence Listing). In this sequence, nucleotide positions 1 to 57 represent a signal sequence, which is usually not contained in the nucleotide sequences of most of mature cFR2-13 heavy chains.

FIG. 52 shows the amino acid sequence of the heavy chain of human chimeric FR2-13 (cFR2-13) (SEQ ID NO: 44 of the Sequence Listing). In this sequence, amino acid positions 1 to 19 represent a signal sequence, which is usually not contained in the amino acid sequences of most of mature cFR2-13 heavy chains.

FIG. 53 shows a primer F for the heavy chain of human chimeric FR2-13 (SEQ ID NO: 45 of the Sequence Listing).

FIG. 54 shows a primer R for the heavy chain of human chimeric FR2-13 (SEQ ID NO: 46 of the Sequence Listing).

FIG. 55 shows the nucleotide sequence of the light chain of human chimeric FR2-14 (cFR2-14) (SEQ ID NO: 47 of the Sequence Listing). In this sequence, nucleotide positions 1 to 60 represent a signal sequence, which is usually not contained in the nucleotide sequences of most of mature cFR2-14 light chains.

FIG. 56 shows the amino acid sequence of the light chain of human chimeric FR2-14 (cFR2-14) (SEQ ID NO: 48 of the Sequence Listing). In this sequence, amino acid positions 1 to 20 represent a signal sequence, which is usually not contained in the amino acid sequences of most of mature cFR2-14 light chains.

FIG. 57 shows a primer for the light chain of human chimeric FR2-14 (SEQ ID NO: 49 of the Sequence Listing).

FIG. 58 shows the nucleotide sequence of the heavy chain of human chimeric FR2-14 (cFR2-14) (SEQ ID NO: 50 of the Sequence Listing). In this sequence, nucleotide positions 1 to 57 represent a signal sequence, which is usually not contained in the nucleotide sequences of most of mature cFR2-14 heavy chains.

FIG. 59 shows the amino acid sequence of the heavy chain of human chimeric FR2-14 (cFR2-14) (SEQ ID NO: 51 of the Sequence Listing). In this sequence, amino acid positions 1 to 19 represent a signal sequence, which is usually not contained in the amino acid sequences of most of mature cFR2-14 heavy chains.

FIG. 60 shows the amino acid sequence of the heavy chain CDR1 of the rat anti-FGFR2 antibody FR2-10 (SEQ ID NO: 52 of the Sequence Listing).

FIG. 61 shows the amino acid sequence of the heavy chain CDR2 of the rat anti-FGFR2 antibody FR2-10 (SEQ ID NO: 53 of the Sequence Listing).

FIG. 62 shows the amino acid sequence of the heavy chain CDR3 of the rat anti-FGFR2 antibody FR2-10 (SEQ ID NO: 54 of the Sequence Listing).

FIG. 63 shows the amino acid sequence of the heavy chain CDR1 of the rat anti-FGFR2 antibody FR2-13 (SEQ ID NO: 55 of the Sequence Listing).

FIG. 64 shows the amino acid sequence of the heavy chain CDR2 of the rat anti-FGFR2 antibody FR2-13 (SEQ ID NO: 56 of the Sequence Listing).

FIG. 65 shows the amino acid sequence of the heavy chain CDR3 of the rat anti-FGFR2 antibody FR2-13 (SEQ ID NO: 57 of the Sequence Listing).

FIG. 66 shows the amino acid sequence of the heavy chain CDR1 of the rat anti-FGFR2 antibody FR2-14 (SEQ ID NO: 58 of the Sequence Listing).

FIG. 67 shows the amino acid sequence of the heavy chain CDR2 of the rat anti-FGFR2 antibody FR2-14 (SEQ ID NO: 59 of the Sequence Listing).

FIG. 68 shows the amino acid sequence of the heavy chain CDR3 of the rat anti-FGFR2 antibody FR2-14 (SEQ ID NO: 60 of the Sequence Listing).

FIG. 69 shows the amino acid sequence of the light chain CDR1 of the rat anti-FGFR2 antibody FR2-10 (SEQ ID NO: 61 of the Sequence Listing).

FIG. 70 shows the amino acid sequence of the light chain CDR2 of the rat anti-FGFR2 antibody FR2-10 (SEQ ID NO: 62 of the Sequence Listing).

FIG. 71 shows the amino acid sequence of the light chain CDR3 of the rat anti-FGFR2 antibody FR2-10 (SEQ ID NO: 63 of the Sequence Listing).

FIG. 72 shows the amino acid sequence of the light chain CDR1 of the rat anti-FGFR2 antibody FR2-13 (SEQ ID NO: 64 of the Sequence Listing).

FIG. 73 shows the amino acid sequence of the light chain CDR2 of the rat anti-FGFR2 antibody FR2-13 (SEQ ID NO: 65 of the Sequence Listing).

FIG. 74 shows the amino acid sequence of the light chain CDR3 of the rat anti-FGFR2 antibody FR2-13 (SEQ ID NO: 66 of the Sequence Listing).

FIG. 75 shows the amino acid sequence of the light chain CDR1 of the rat anti-FGFR2 antibody FR2-14 (SEQ ID NO: 67 of the Sequence Listing).

FIG. 76 shows the amino acid sequence of the light chain CDR2 of the rat anti-FGFR2 antibody FR2-14 (SEQ ID NO: 68 of the Sequence Listing).

FIG. 77 shows the amino acid sequence of the light chain CDR3 of the rat anti-FGFR2 antibody FR2-14 (SEQ ID NO: 69 of the Sequence Listing).

FIG. 78 shows the amino acid sequence of human FGFR2 IIIb (SEQ ID NO: 70 of the Sequence Listing).

FIG. 79 shows the amino acid sequence of human FGFR2 IIIc (SEQ ID NO: 71 of the Sequence Listing).

FIG. 80 shows the nucleotide sequence of hFR2-14_L1 (SEQ ID NO: 72 of the Sequence Listing). In this sequence, nucleotide positions 1 to 60 represent a signal sequence, which is usually not included in the nucleotide sequence of most of mature light chains hFR2-14_L1.

FIG. 81 shows the amino acid sequence of hFR2-14_L1 (SEQ ID NO: 73 of the Sequence Listing). In this sequence, amino acid positions 1 to 20 represent a signal sequence, which is usually not included in the amino acid sequence of most of mature light chains hFR2-14_L1.

FIG. 82 shows the nucleotide sequence of hFR2-14_H1 (SEQ ID NO: 74 of the Sequence Listing). In this sequence, nucleotide positions 1 to 57 represent a signal sequence, which is usually not included in the nucleotide sequence of most of mature heavy chains hFR2-14_H1.

FIG. 83 shows the amino acid sequence of hFR2-14_H1 (SEQ ID NO: 75 of the Sequence Listing). In this sequence, amino acid positions 1 to 19 represent a signal sequence, which is usually not included in the amino acid sequence of most of mature heavy chains hFR2-14_H1.

FIG. 84 shows the nucleotide sequence of hFR2-14_H2 (SEQ ID NO: 76 of the Sequence Listing). In this sequence, nucleotide positions 1 to 57 represent a signal sequence, which is usually not included in the nucleotide sequence of most of mature heavy chains hFR2-14_H2.

FIG. 85 shows the amino acid sequence of hFR2-14_H2 (SEQ ID NO: 77 of the Sequence Listing). In this sequence, amino acid positions 1 to 19 represent a signal sequence, which is usually not included in the amino acid sequence of most of mature heavy chains hFR2-14_H2.

FIG. 86 shows the nucleotide sequence of hFR2-14_H3 (SEQ ID NO: 78 of the Sequence Listing). In this sequence, nucleotide positions 1 to 57 represent a signal sequence, which is usually not included in the nucleotide sequence of most of mature heavy chains hFR2-14_H3.

FIG. 87 shows the amino acid sequence of hFR2-14_H3 (SEQ ID NO: 79 of the Sequence Listing). In this sequence, amino acid positions 1 to 19 represent a signal sequence, which is usually not included in the amino acid sequence of most of mature heavy chains hFR2-14_H3.

FIG. 88 shows the nucleotide sequence of hFR2-14_H4 (SEQ ID NO: 80 of the Sequence Listing). In this sequence, nucleotide positions 1 to 57 represent a signal sequence, which is usually not included in the nucleotide sequence of most of mature heavy chains hFR2-14_H4.

FIG. 89 shows the amino acid sequence of hFR2-14_H4 (SEQ ID NO: 81 of the Sequence Listing). In this sequence, amino acid positions 1 to 19 represent a signal sequence, which is usually not included in the amino acid sequence of most of mature heavy chains hFR2-14_H4.

FIG. 90 shows the nucleotide sequence of hFR2-14_H5 (SEQ ID NO: 82 of the Sequence Listing). In this sequence, nucleotide positions 1 to 57 represent a signal sequence, which is usually not included in the nucleotide sequence of most of mature heavy chains hFR2-14_H5.

FIG. 91 shows the amino acid sequence of hFR2-14_H5 (SEQ ID NO: 83 of the Sequence Listing). In this sequence, amino acid positions 1 to 19 represent a signal sequence, which is usually not included in the amino acid sequence of most of mature heavy chains hFR2-14_H5.

FIG. 92 shows the nucleotide sequence of hFR2-14_H6 (SEQ ID NO: 84 of the Sequence Listing). In this sequence, nucleotide positions 1 to 57 represent a signal sequence, which is usually not included in the nucleotide sequence of most of mature heavy chains hFR2-14_H6.

FIG. 93 shows the amino acid sequence of hFR2-14_H6 (SEQ ID NO: 85 of the Sequence Listing). In this sequence, amino acid positions 1 to 19 represent a signal sequence, which is usually not included in the amino acid sequence of most of mature heavy chains hFR2-14_H6.

FIG. 94 shows the nucleotide sequence of hFR2-14_H7 (SEQ ID NO: 86 of the Sequence Listing). In this sequence, nucleotide positions 1 to 57 represent a signal sequence, which is usually not included in the nucleotide sequence of most of mature heavy chains hFR2-14_H7.

FIG. 95 shows the amino acid sequence of hFR2-14_H7 (SEQ ID NO: 87 of the Sequence Listing). In this sequence, amino acid positions 1 to 19 represent a signal sequence, which is usually not included in the amino acid sequence of most of mature heavy chains hFR2-14_H7.

FIG. 96 shows the nucleotide sequence of hFR2-14_H8 (SEQ ID NO: 88 of the Sequence Listing). In this sequence, nucleotide positions 1 to 57 represent a signal sequence, which is usually not included in the nucleotide sequence of most of mature heavy chains hFR2-14_H8.

FIG. 97 shows the amino acid sequence of hFR2-14_H8 (SEQ ID NO: 89 of the Sequence Listing). In this sequence, amino acid positions 1 to 19 represent a signal sequence, which is usually not included in the amino acid sequence of most of mature heavy chains hFR2-14_H8.

FIG. 98 shows the nucleotide sequence of hFR2-14_H9 (SEQ ID NO: 90 of the Sequence Listing). In this sequence, nucleotide positions 1 to 57 represent a signal sequence, which is usually not included in the nucleotide sequence of most of mature heavy chains hFR2-14_H9.

FIG. 99 shows the amino acid sequence of hFR2-14_H9 (SEQ ID NO: 91 of the Sequence Listing). In this sequence, amino acid positions 1 to 19 represent a signal sequence, which is usually not included in the amino acid sequence of most of mature heavy chains hFR2-14_H9.

FIG. 100 shows the nucleotide sequence of hFR2-14_H10 (SEQ ID NO: 92 of the Sequence Listing). In this sequence, nucleotide positions 1 to 57 represent a signal sequence, which is usually not included in the nucleotide sequence of most of mature heavy chains hFR2-14_H10.

FIG. 101 shows the amino acid sequence of hFR2-14_H10 (SEQ ID NO: 93 of the Sequence Listing). In this sequence, amino acid positions 1 to 19 represent a signal sequence, which is usually not included in the amino acid sequence of most of mature heavy chains hFR2-14_H10.

FIG. 102 shows the nucleotide sequence of hFR2-14_H11 (SEQ ID NO: 94 of the Sequence Listing). In this sequence, nucleotide positions 1 to 57 represent a signal sequence, which is usually not included in the nucleotide sequence of most of mature heavy chains hFR2-14_H11.

FIG. 103 shows the amino acid sequence of hFR2-14_H11 (SEQ ID NO: 95 of the Sequence Listing). In this sequence, amino acid positions 1 to 19 represent a signal sequence, which is usually not included in the amino acid sequence of most of mature heavy chains hFR2-14_H11.

FIG. 104 shows the nucleotide sequence of hFR2-14_H12 or hFR2-14_H19 (SEQ ID NO: 96 of the Sequence Listing). In this sequence, nucleotide positions 1 to 57 represent a signal sequence, which is usually not included in the nucleotide sequence of most of mature heavy chains hFR2-14_H12 or hFR2-14_H19.

FIG. 105 shows the amino acid sequence of hFR2-14_H12 or hFR2-14_H19 (SEQ ID NO: 97 of the Sequence Listing). In this sequence, amino acid positions 1 to 19 represent a signal sequence, which is usually not included in the amino acid sequence of most of mature heavy chains hFR2-14_H12 or hFR2-14_H19.

FIG. 106 shows the nucleotide sequence of hFR2-14_H13 (SEQ ID NO: 98 of the Sequence Listing). In this sequence, nucleotide positions 1 to 57 represent a signal sequence, which is usually not included in the nucleotide sequence of most of mature heavy chains hFR2-14_H13.

FIG. 107 shows the amino acid sequence of hFR2-14_H13 (SEQ ID NO: 99 of the Sequence Listing). In this sequence, amino acid positions 1 to 19 represent a signal sequence, which is usually not included in the amino acid sequence of most of mature heavy chains hFR2-14_H13.

FIG. 108 shows the nucleotide sequence of hFR2-14_H14 (SEQ ID NO: 100 of the Sequence Listing). In this sequence, nucleotide positions 1 to 57 represent a signal sequence, which is usually not included in the nucleotide sequence of most of mature heavy chains hFR2-14_H14.

FIG. 109 shows the amino acid sequence of hFR2-14_H14 (SEQ ID NO: 101 of the Sequence Listing). In this sequence, amino acid positions 1 to 19 represent a signal sequence, which is usually not included in the amino acid sequence of most of mature heavy chains hFR2-14_H14.

FIG. 110 shows the nucleotide sequence of hFR2-14_H15 (SEQ ID NO: 102 of the Sequence Listing). In this sequence, nucleotide positions 1 to 57 represent a signal sequence, which is usually not included in the nucleotide sequence of most of mature heavy chains hFR2-14_H15.

FIG. 111 shows the amino acid sequence of hFR2-14_H15 (SEQ ID NO: 103 of the Sequence Listing). In this sequence, amino acid positions 1 to 19 represent a signal sequence, which is usually not included in the amino acid sequence of most of mature heavy chains hFR2-14_H15.

FIG. 112 shows the nucleotide sequence of hFR2-14_H16 (SEQ ID NO: 104 of the Sequence Listing). In this sequence, nucleotide positions 1 to 57 represent a signal sequence, which is usually not included in the nucleotide sequence of most of mature heavy chains hFR2-14_H16.

FIG. 113 shows the amino acid sequence of hFR2-14_H16 (SEQ ID NO: 105 of the Sequence Listing). In this sequence, amino acid positions 1 to 19 represent a signal sequence, which is usually not included in the amino acid sequence of most of mature heavy chains hFR2-14_H16.

FIG. 114 shows the nucleotide sequence of hFR2-14_H17 (SEQ ID NO: 106 of the Sequence Listing). In this sequence, nucleotide positions 1 to 57 represent a signal sequence, which is usually not included in the nucleotide sequence of most of mature heavy chains hFR2-14_H17.

FIG. 115 shows the amino acid sequence of hFR2-14_H17 (SEQ ID NO: 107 of the Sequence Listing). In this sequence, amino acid positions 1 to 19 represent a signal sequence, which is usually not included in the amino acid sequence of most of mature heavy chains hFR2-14_H17.

FIG. 116 shows the nucleotide sequence of hFR2-14_H18 (SEQ ID NO: 108 of the Sequence Listing). In this sequence, nucleotide positions 1 to 57 represent a signal sequence, which is usually not included in the nucleotide sequence of most of mature heavy chains hFR2-14_H18.

FIG. 117 shows the amino acid sequence of hFR2-14_H18 (SEQ ID NO: 109 of the Sequence Listing). In this sequence, amino acid positions 1 to 19 represent a signal sequence, which is usually not included in the amino acid sequence of most of mature heavy chains hFR2-14_H18.

FIG. 118 shows a primer VH3A-F for an hFR2-14_H2 type heavy chain (SEQ ID NO: 110 of the Sequence Listing).

FIG. 119 shows a primer VH3A-R for an hFR2-14_H2 type heavy chain (SEQ ID NO: 111 of the Sequence Listing).

FIG. 120 shows a primer D23fw for gene amplification of D2 (SEQ ID NO: 112 of the Sequence Listing).

FIG. 121 shows a primer D23rv for gene amplification of D2 (SEQ ID NO: 113 of the Sequence Listing).

FIG. 122 is a diagram showing results of assaying the binding activity of 4 types of humanized anti-FGFR2 antibodies (hFR2-14_H1/L1 to hFR2-14_H4/L1) and the human chimeric anti-FGFR2 antibody (cFR2-14) against each human FGFR2 variant protein using Biacore. Each antibody was expressed in 293F cells and purified for use in the assay.

FIG. 123 is a diagram showing results of assaying the binding activity of 15 types of humanized anti-FGFR2 antibodies (hFR2-14_H3/L1 and hFR2-14_H5/L1 to hFR2-14_H18/L1) against a human FGFR2 IIIc variant protein using Biacore. Each antibody was expressed in 293F cells, and its culture supernatant was used in the assay.

FIG. 124 is a diagram showing results of testing the human FGFR2-selective binding activity of 3 types of humanized anti-FGFR2 antibodies (hFR2-14_H3/L1, hFR2-14_H8/L1, and hFR2-14_H12/L1) by Cell-ELISA.

FIG. 125A is a diagram showing the thermograms of 5 types of humanized anti-FGFR2 antibodies.

FIG. 125B is a diagram showing the thermograms of 5 types of humanized anti-FGFR2 antibodies.

FIG. 125C is a diagram showing the Tm values of 10 types of humanized anti-FGFR2 antibodies.

FIG. 126 is a diagram showing the KD values of hFR2-14_H1/L1, hFR2-14_H2/L1, hFR2-14_H3/L1, hFR2-14_H4/L1, hFR2-14_H5/L1, hFR2-14_H8/L1, hFR2-14_H9/L1, hFR2-14_H11/L1, hFR2-14_H12/L1, and hFR2-14_H19/L1 antibody analytes for an antigen before and after degradation.

FIG. 127A is a diagram showing the signal-neutralizing activity of the humanized anti-FGFR2 antibodies (hFR2-14_H1/L1, hFR2-14_H2/L1, hFR2-14_H3/L1, and hFR2-14_H4/L1) and the human chimeric anti-FGFR2 antibody (cFR2-14) against human FGFR2 IIIb by Elk1 trans-reporter assay.

FIG. 127B is a diagram showing the signal-neutralizing activity of the humanized anti-FGFR2 antibodies (hFR2-14_H1/L1, hFR2-14_H2/L1, hFR2-14_H3/L1, and hFR2-14_H4/L1) and the human chimeric anti-FGFR2 antibody (cFR2-14) against human FGFR2 IIIc by Elk1 trans-reporter assay.

Figure 128A:
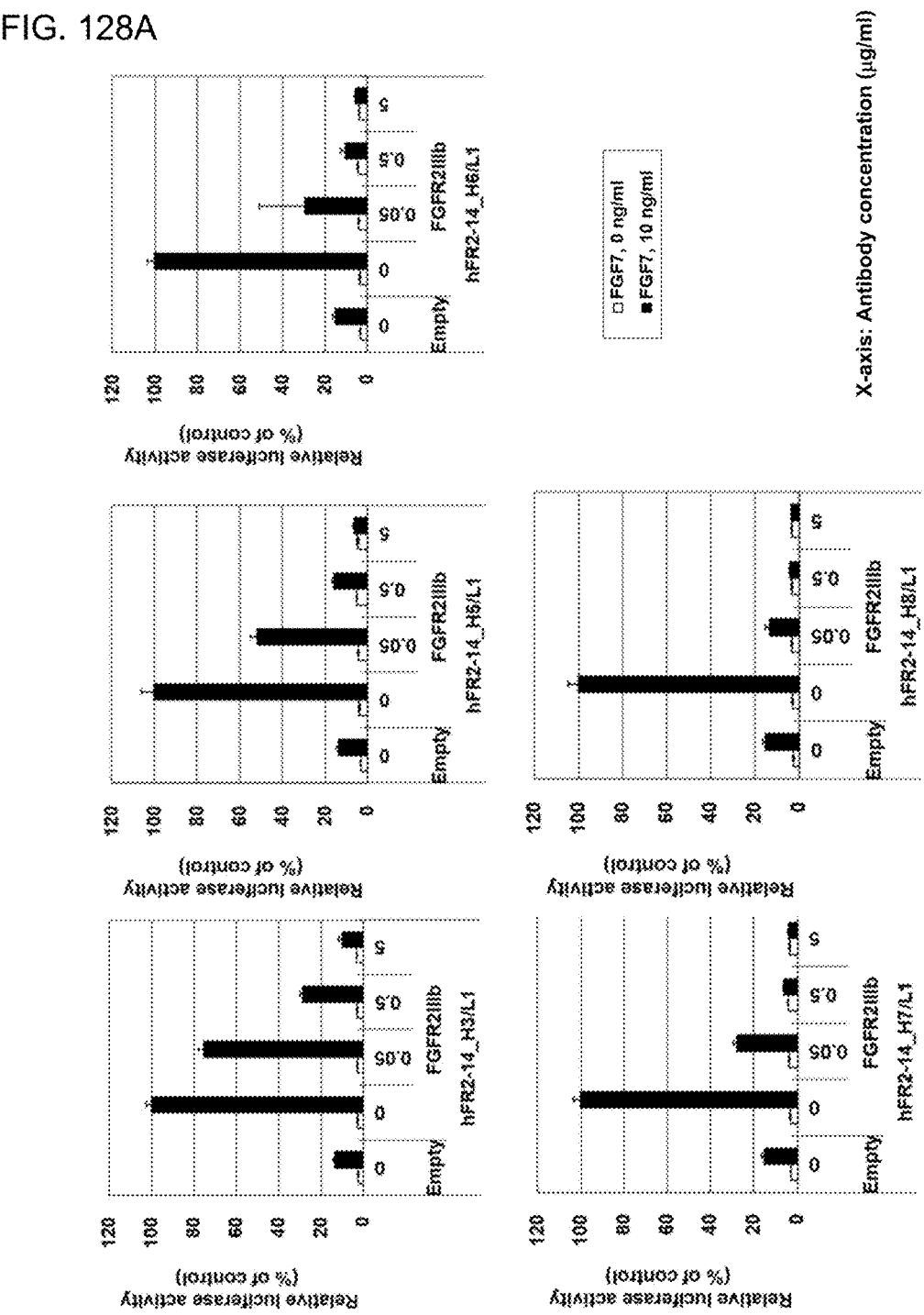

FIG. 128A is a diagram showing the signal-neutralizing activity of the humanized anti-FGFR2 antibodies (hFR2-14_H3/L1, hFR2-14_H5/L1, hFR2-14_H6/L1, hFR2-14_H7/L1, and hFR2-14_H8/L1) against human FGFR2 IIIb by Elk1 trans-reporter assay.

Figure 128B:
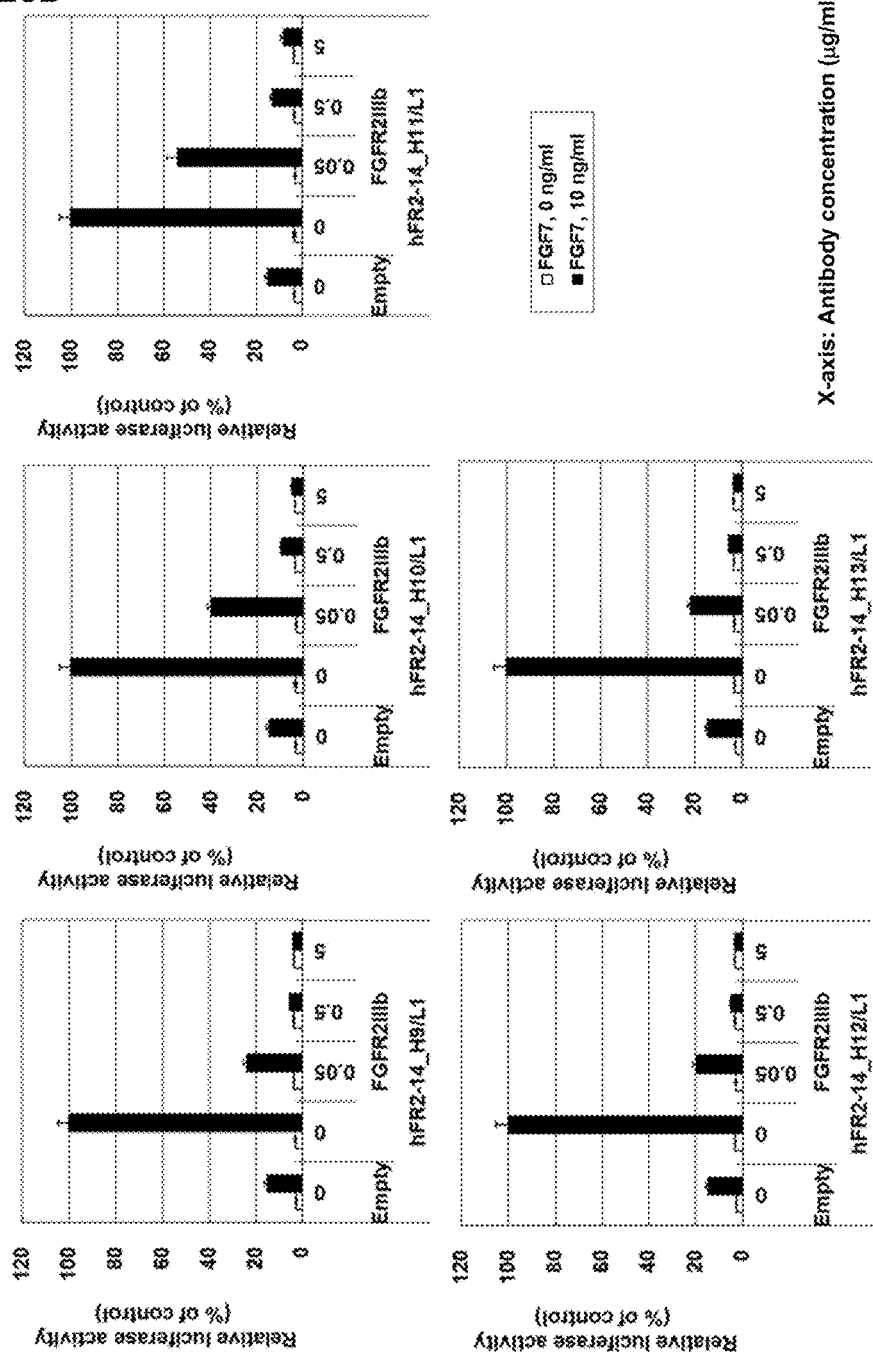

FIG. 128B is a diagram showing the signal-neutralizing activity of the humanized anti-FGFR2 antibodies (hFR2-14_H9/L1, hFR2-14_H10/L1, hFR2-14_H11/L1, hFR2-

14_H12/L1, and hFR2-14_H13/L1) against human FGFR2 IIIb by Elk1 trans-reporter assay.

Figure 128C:
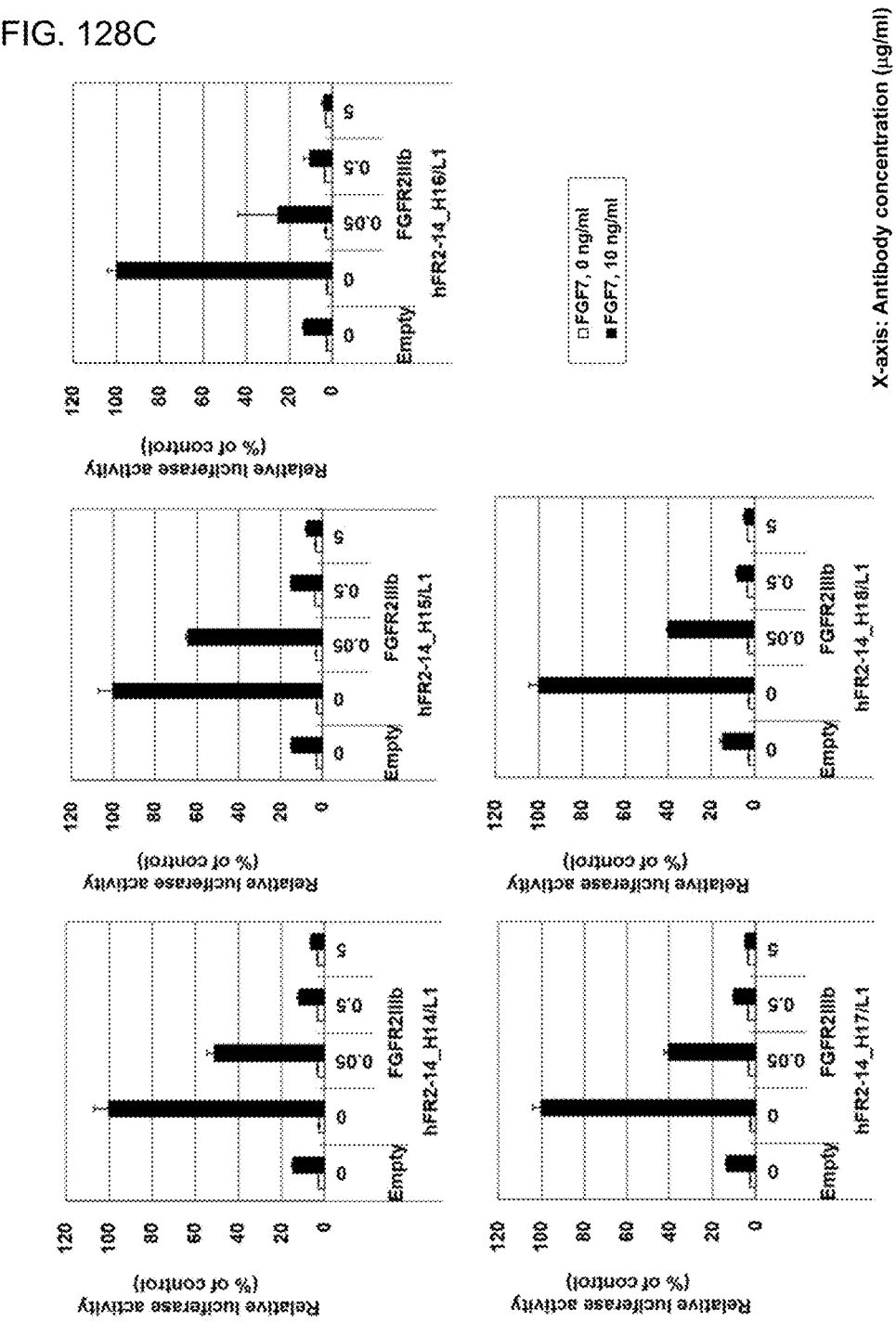

FIG. 128C is a diagram showing the signal-neutralizing activity of the humanized anti-FGFR2 antibodies (hFR2-14_H14/L1, hFR2-14_H15/L1, hFR2-14_H16/L1, hFR2-14_H17/L1, and hFR2-14_H18/L1) against human FGFR2 IIIb by Elk1 trans-reporter assay.

Figure 129A:
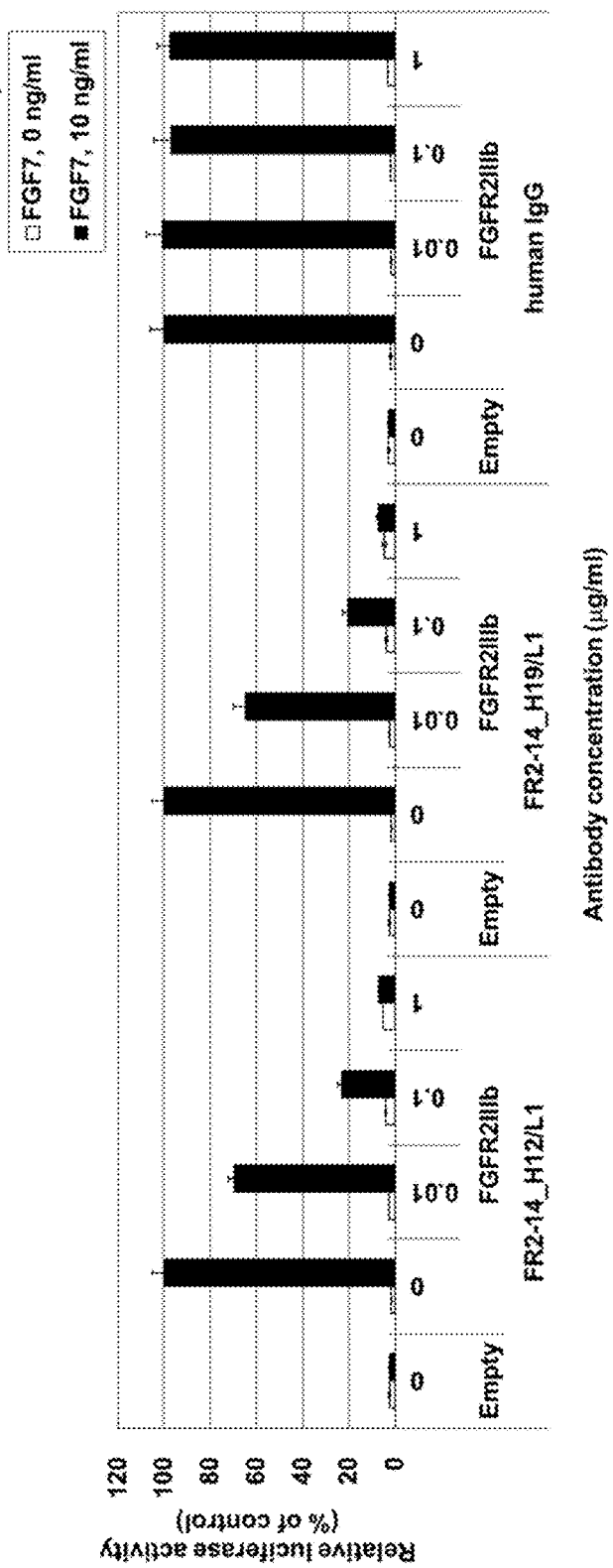

FIG. 129A is a diagram showing the signal-neutralizing activity of the humanized anti-FGFR2 antibodies (hFR2-14_H12/L1 and hFR2-14_H19/L1) against human FGFR2 IIIb by Elk1 trans-reporter assay.

Figure 129B:
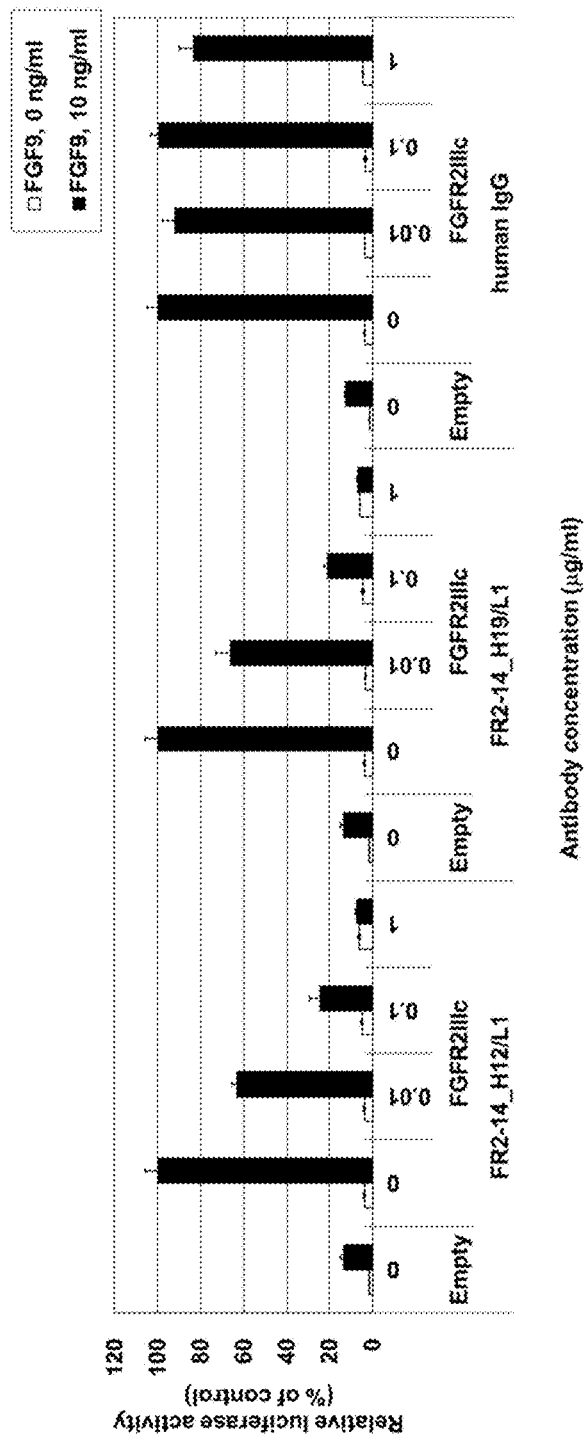

FIG. 129B is a diagram showing the signal-neutralizing activity of the humanized anti-FGFR2 antibodies (hFR2-14_H12/L1 and hFR2-14_H19/L1) against human FGFR2 IIIc by Elk1 trans-reporter assay.

FIG. 130A is a diagram showing the ADCC activity of the humanized anti-FGFR2 antibodies (hFR2-14_H1/L1 and hFR2-14_H2/L1). 293T-lacZ cells expressing human FGFR2 IIIb were used as target cells, and human PBMC was used as effector cells.

Figure 130B:
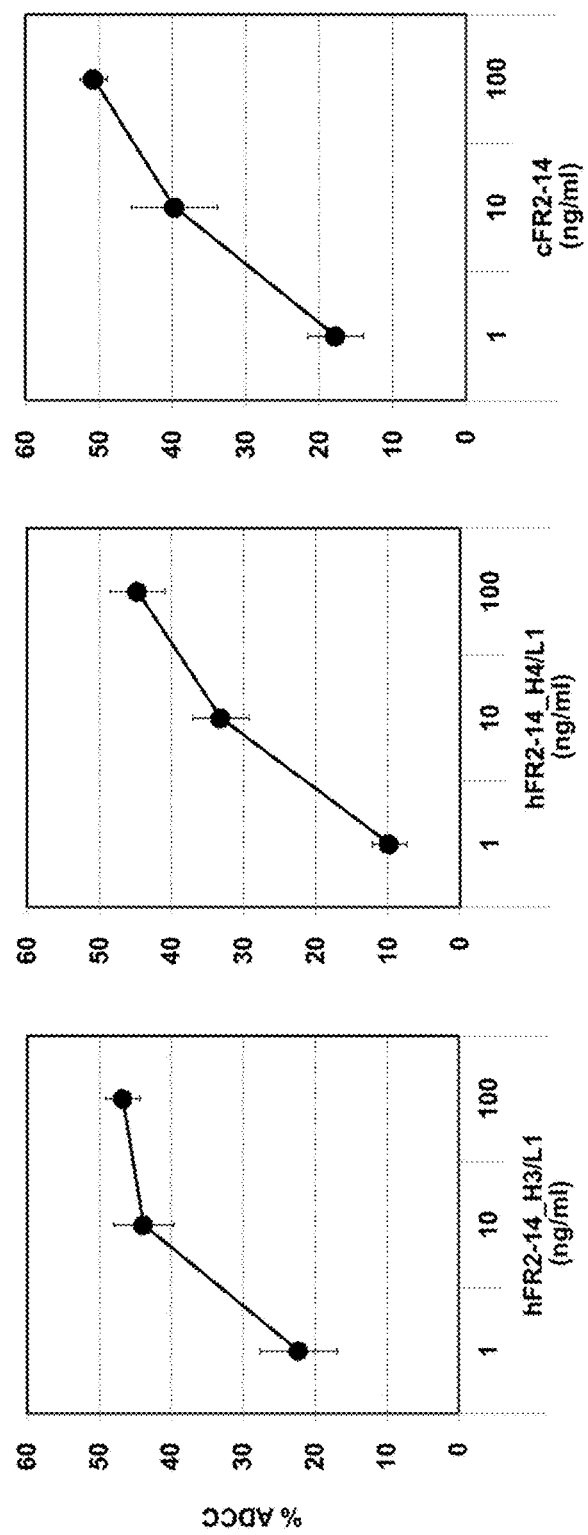

FIG. 130B is a diagram showing the ADCC activity of the humanized anti-FGFR2 antibodies (hFR2-14_H3/L1 and hFR2-14_H4/L1) and the human chimeric anti-FGFR2 antibody (cFR2-14). 293T-lacZ cells expressing human FGFR2 IIIb were used as target cells, and human PBMC was used as effector cells.

Figure 131:
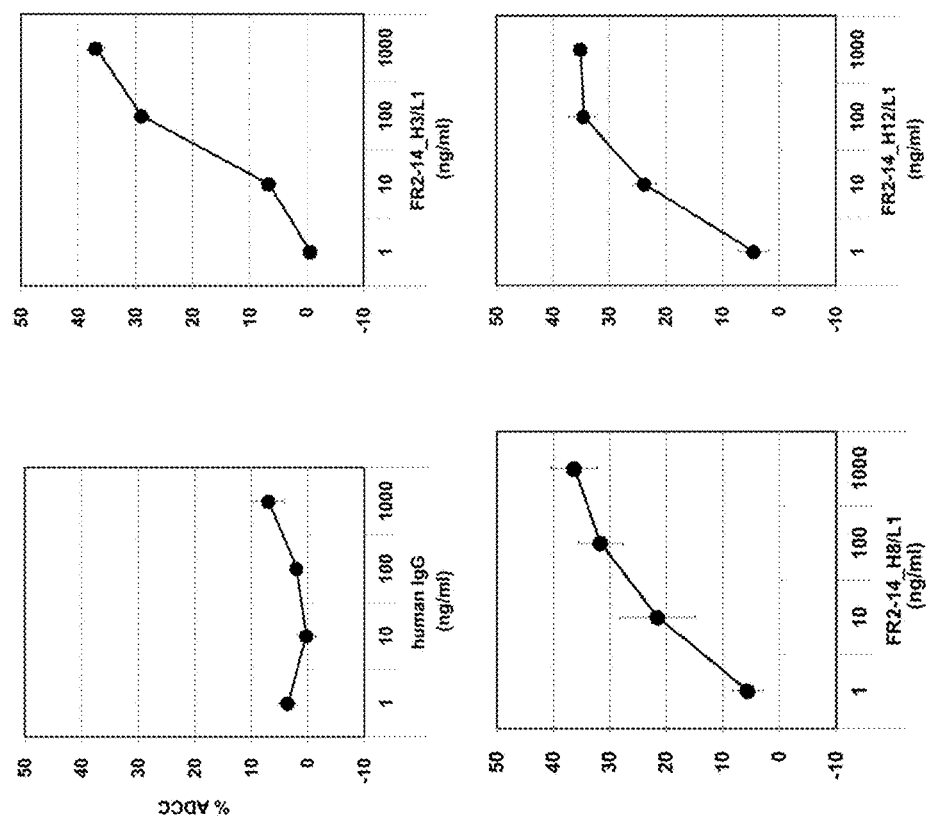

FIG. 131 is a diagram showing the ADCC activity of the humanized anti-FGFR2 antibodies (hFR2-14_H3/L1, hFR2-14_H8/L1, and hFR2-14_H12/L1). NCI-H716 cells expressing human FGFR2 were used as target cells, and human PBMC was used as effector cells.

Figure 132:
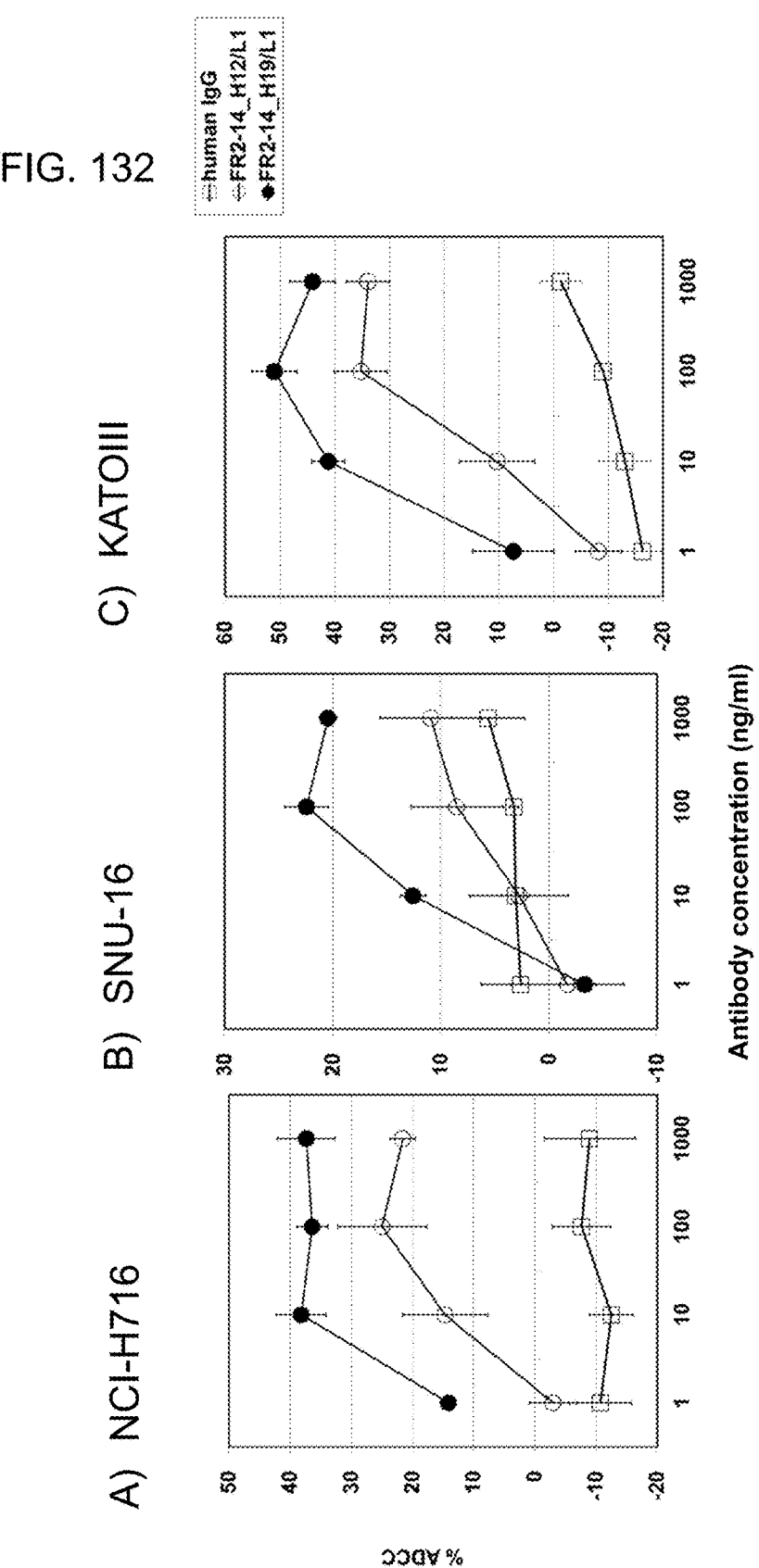

FIG. 132 is a diagram showing the ADCC activity of the humanized anti-FGFR2 antibodies (hFR2-14_H12/L1 and hFR2-14_H19/L1). NCI-H716 cells (FIG. 132A)), SNU-16 cells (FIG. 132B)), or KATO III cells (FIG. 132C)) expressing human FGFR2 were used as target cells, and human PBMC was used as effector cells.

Figure 133:
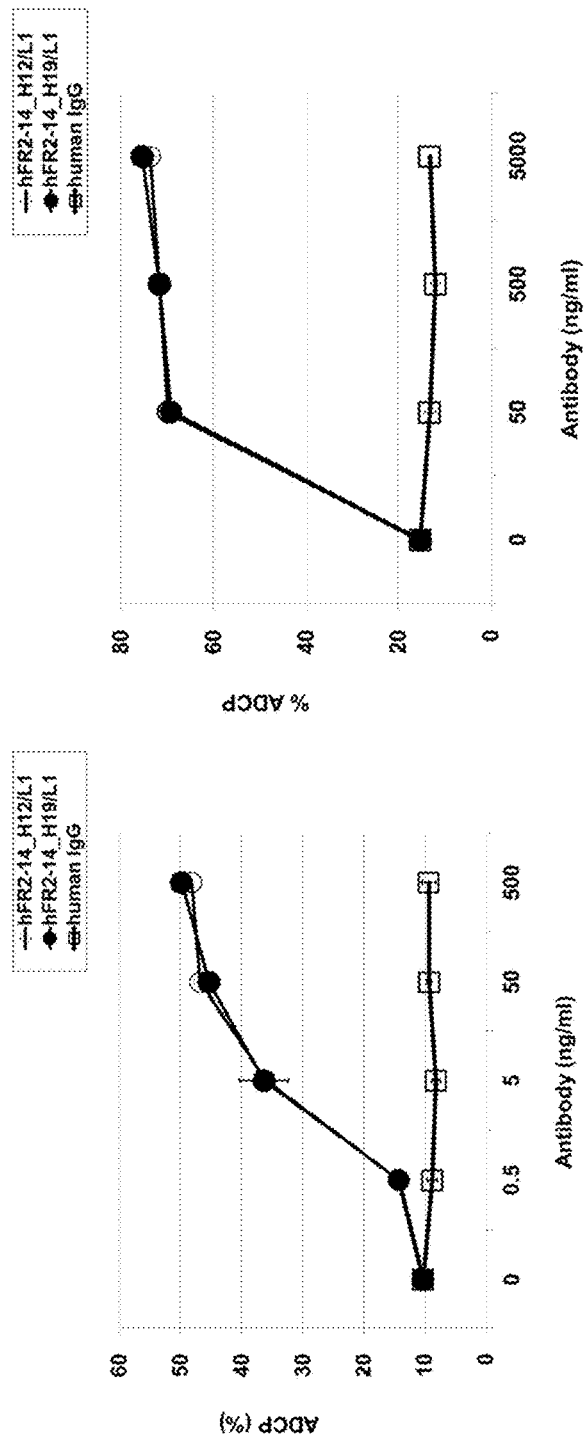

FIG. 133 is a diagram showing the ADCP activity of the humanized anti-FGFR2 antibodies (hFR2-14_H12/L1 and hFR2-14_H19/L1). NCI-H716 cells (FIG. 133A)) or KATO III cells (FIG. 133B)) expressing human FGFR2 were used as target cells, and macrophage-like cells differentiated from human PBMC were used as effector cells.

Figure 134A:
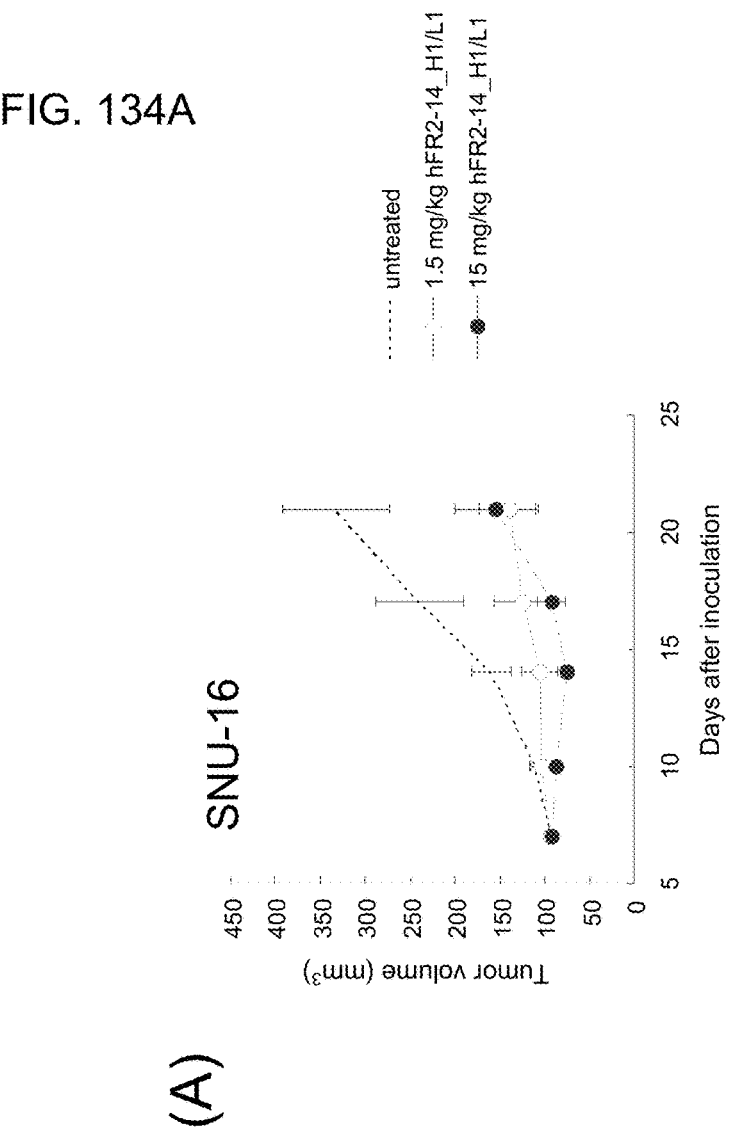

FIG. 134A is a diagram showing the in vivo antitumor activity of the humanized anti-FGFR2 antibody hFR2-14_H1/L1 against human stomach cancer cell line SNU-16-transplanted nude mice.

FIG. 134B is a diagram showing the in vivo antitumor activity of the humanized anti-FGFR2 antibody hFR2-14_H2/L1 against human stomach cancer cell line SNU-16-transplanted nude mice.

Figure 134C:
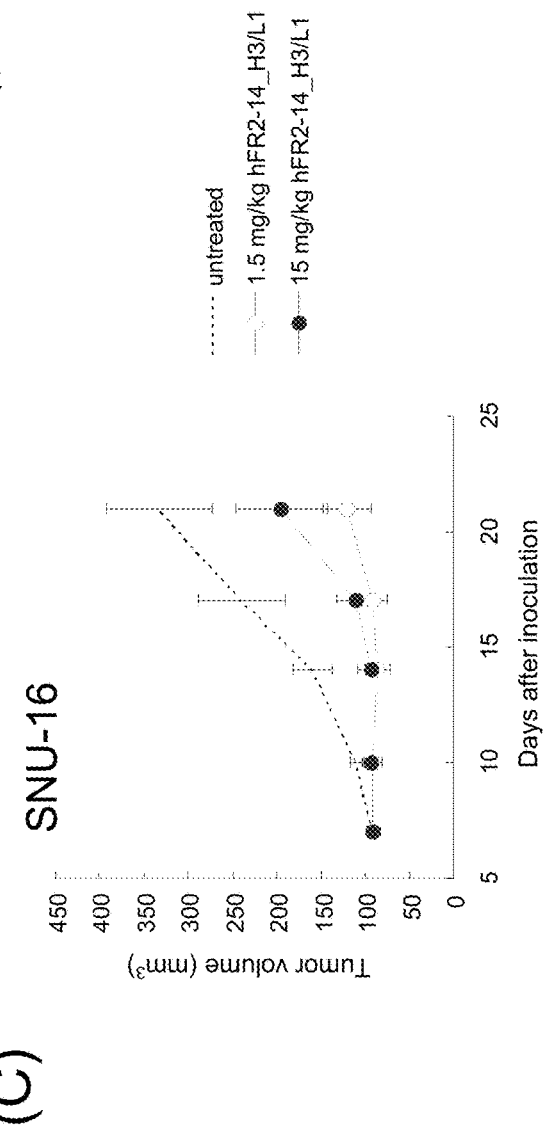

FIG. 134C is a diagram showing the in vivo antitumor activity of the humanized anti-FGFR2 antibody hFR2-14_H3/L1 against human stomach cancer cell line SNU-16-transplanted nude mice.

Figure 134D:
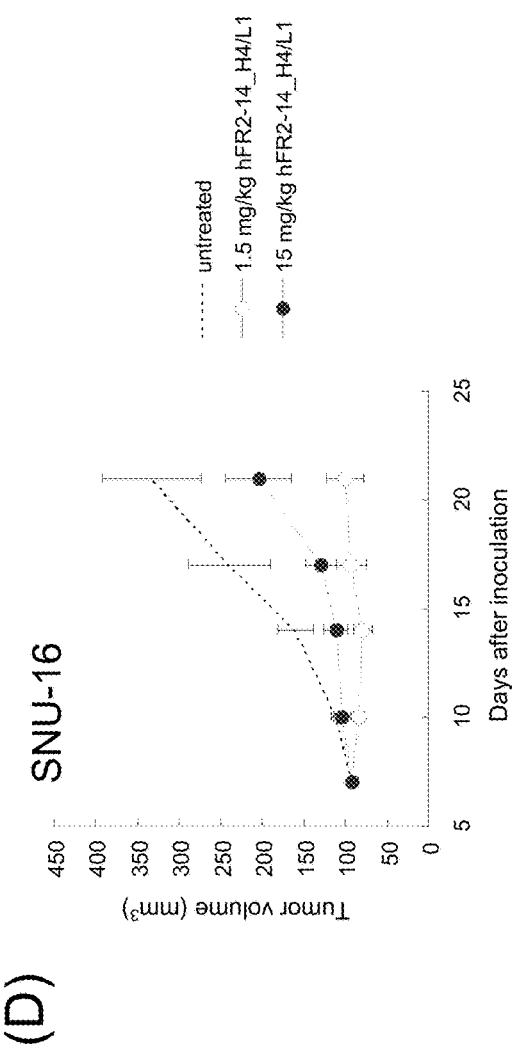

FIG. 134D is a diagram showing the in vivo antitumor activity of the humanized anti-FGFR2 antibody hFR2-14_H4/L1 against human stomach cancer cell line SNU-16-transplanted nude mice.

Figure 135A:
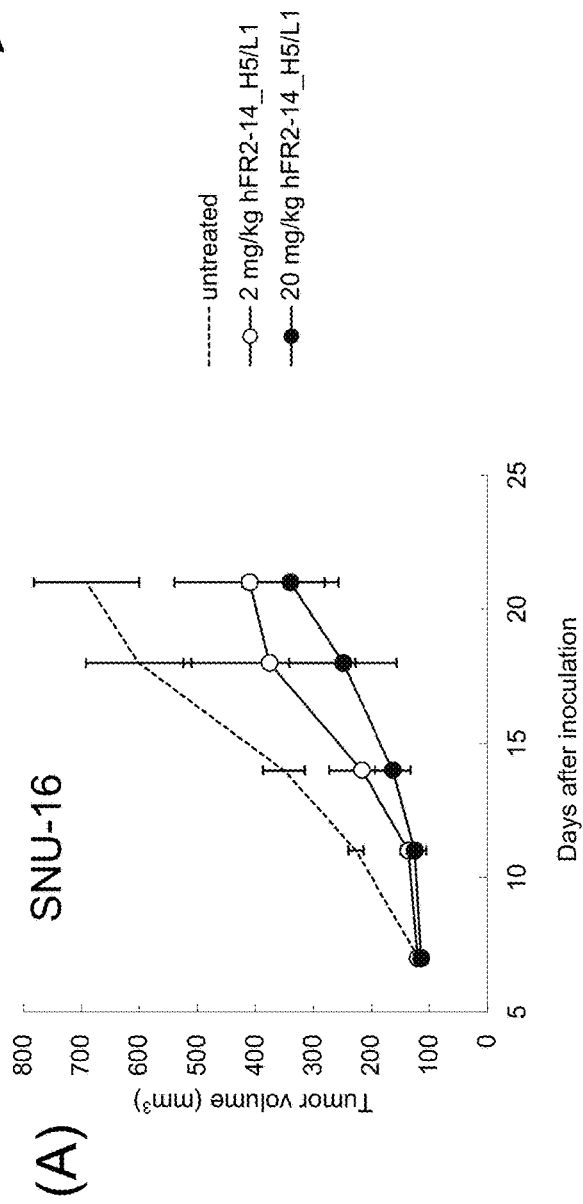

FIG. 135A is a diagram showing the in vivo antitumor activity of the humanized anti-FGFR2 antibody hFR2-14_H5/L1 against human stomach cancer cell line SNU-16-subcutaneously transplanted models.

Figure 135B:
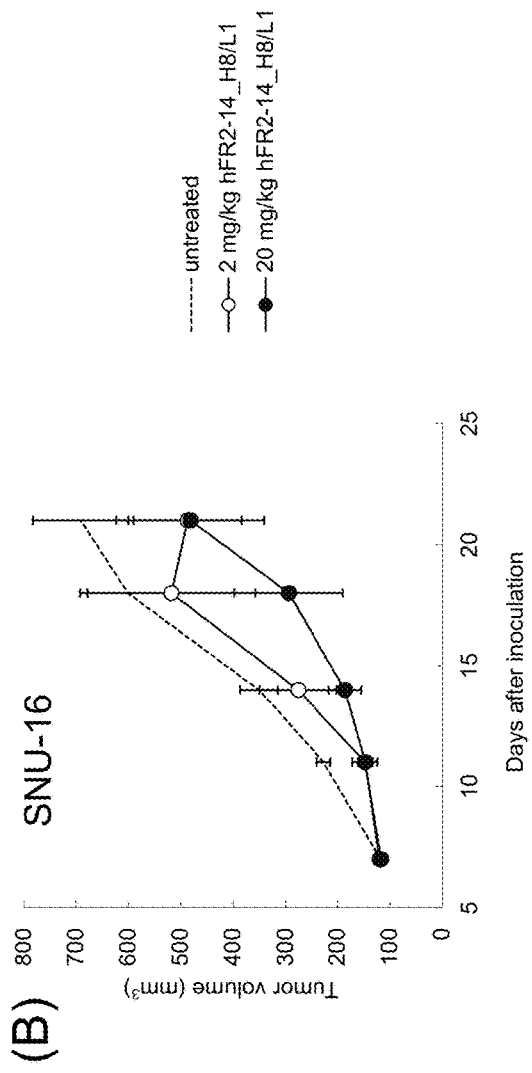

FIG. 135B is a diagram showing the in vivo antitumor activity of the humanized anti-FGFR2 antibody hFR2-14_H8/L1 against human stomach cancer cell line SNU-16-subcutaneously transplanted models.

Figure 135C:
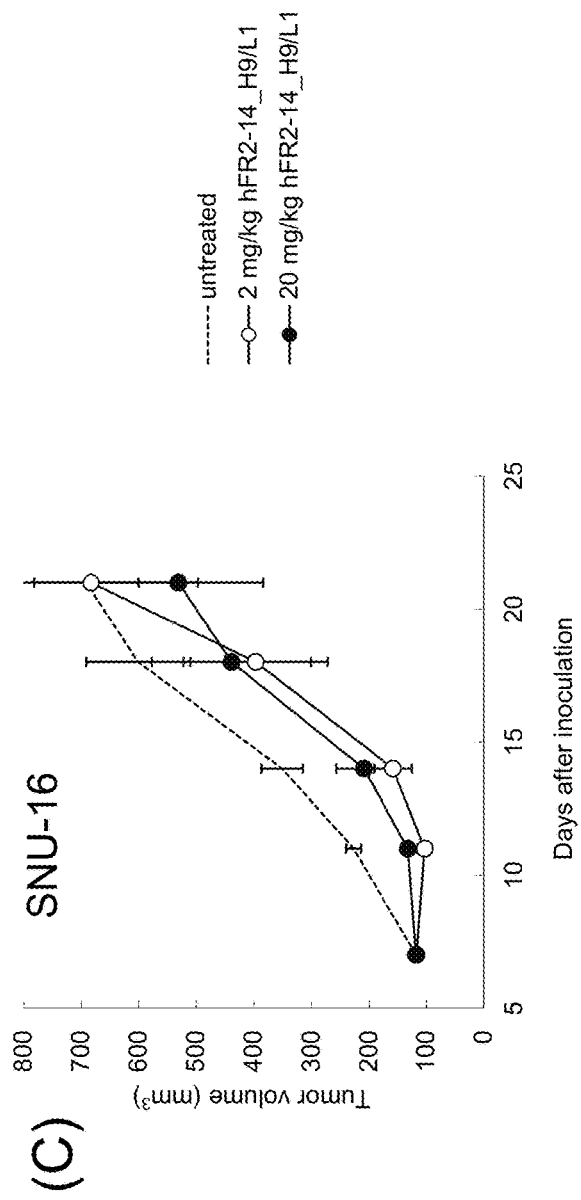

FIG. 135C is a diagram showing the in vivo antitumor activity of the humanized anti-FGFR2 antibody hFR2-14_H9/L1 against human stomach cancer cell line SNU-16-subcutaneously transplanted models.

Figure 135D:
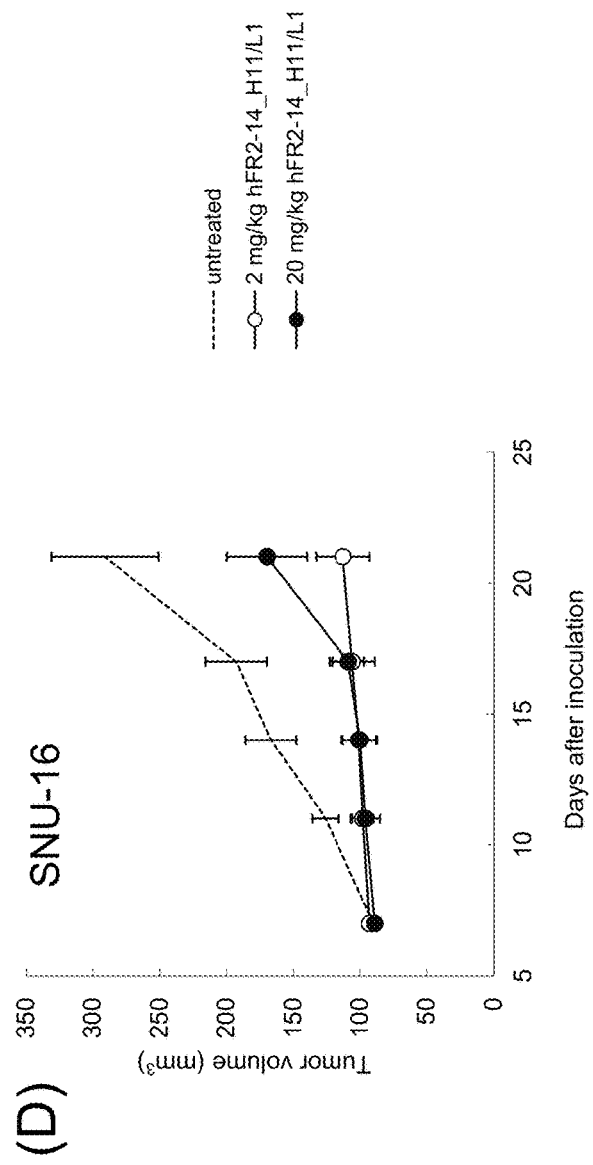

FIG. 135D is a diagram showing the in vivo antitumor activity of the humanized anti-FGFR2 antibody hFR2-14_H11/L1 against human stomach cancer cell line SNU-16-subcutaneously transplanted models.

Figure 135E:
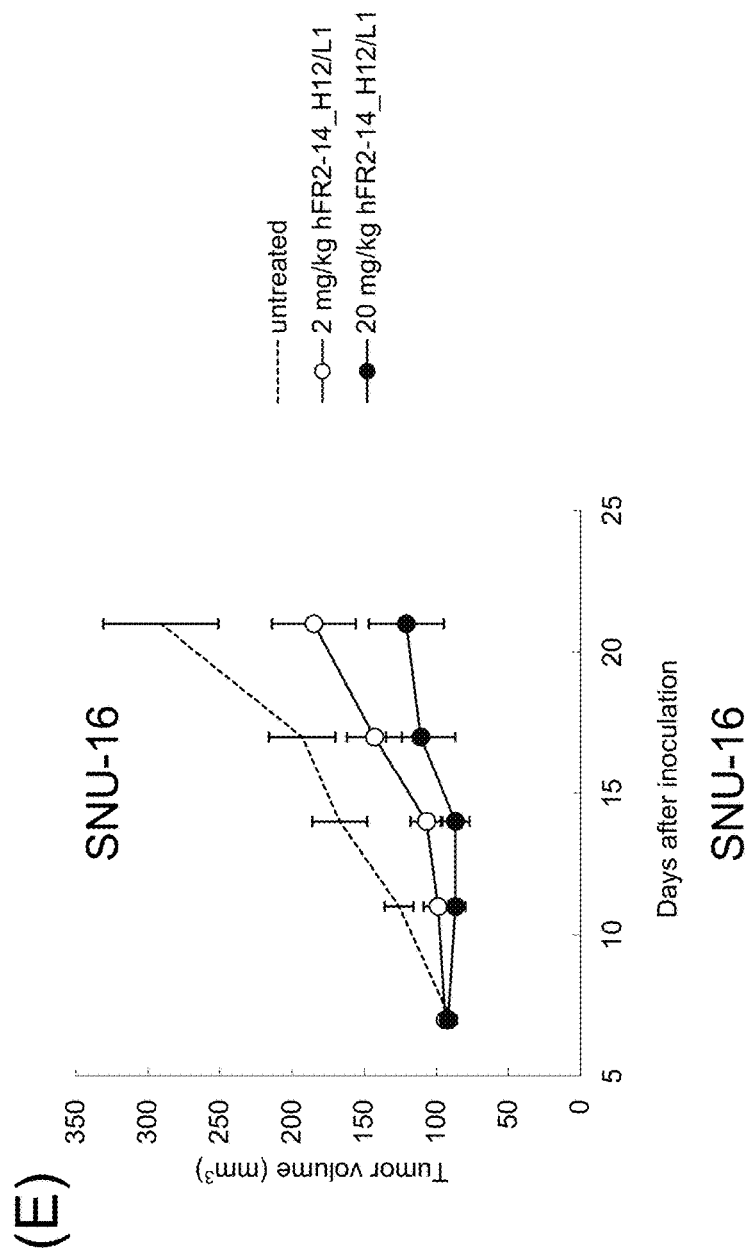

FIG. 135E is a diagram showing the in vivo antitumor activity of the humanized anti-FGFR2 antibody hFR2-14_H12/L1 against human stomach cancer cell line SNU-16-subcutaneously transplanted models.

Figure 135F:
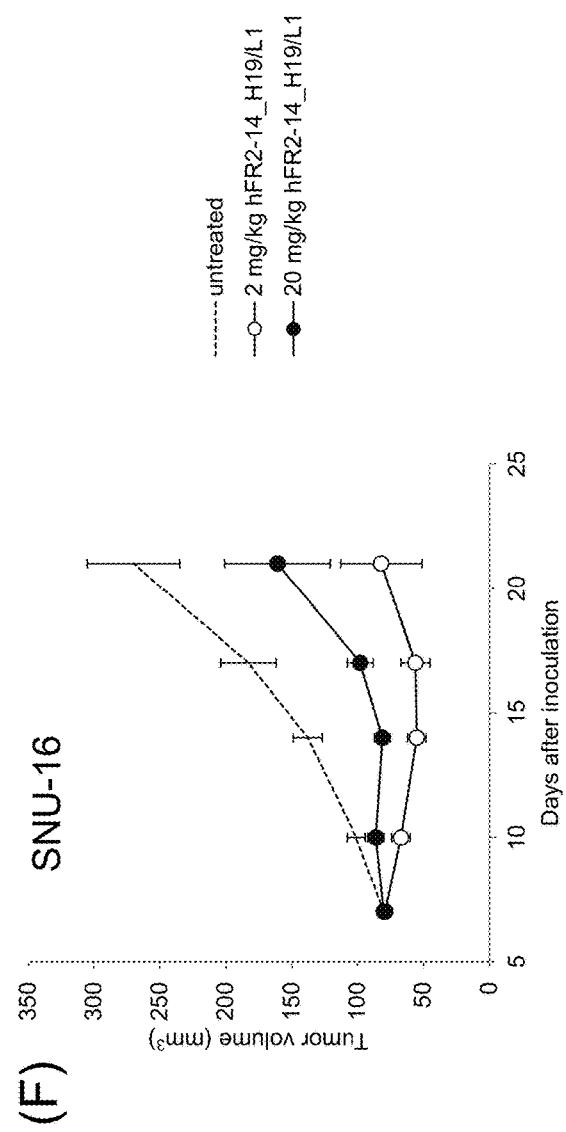

FIG. 135F is a diagram showing the in vivo antitumor activity of the humanized anti-FGFR2 antibody hFR2-14_H19/L1 against human stomach cancer cell line SNU-16-subcutaneously transplanted models.

Figure 136:
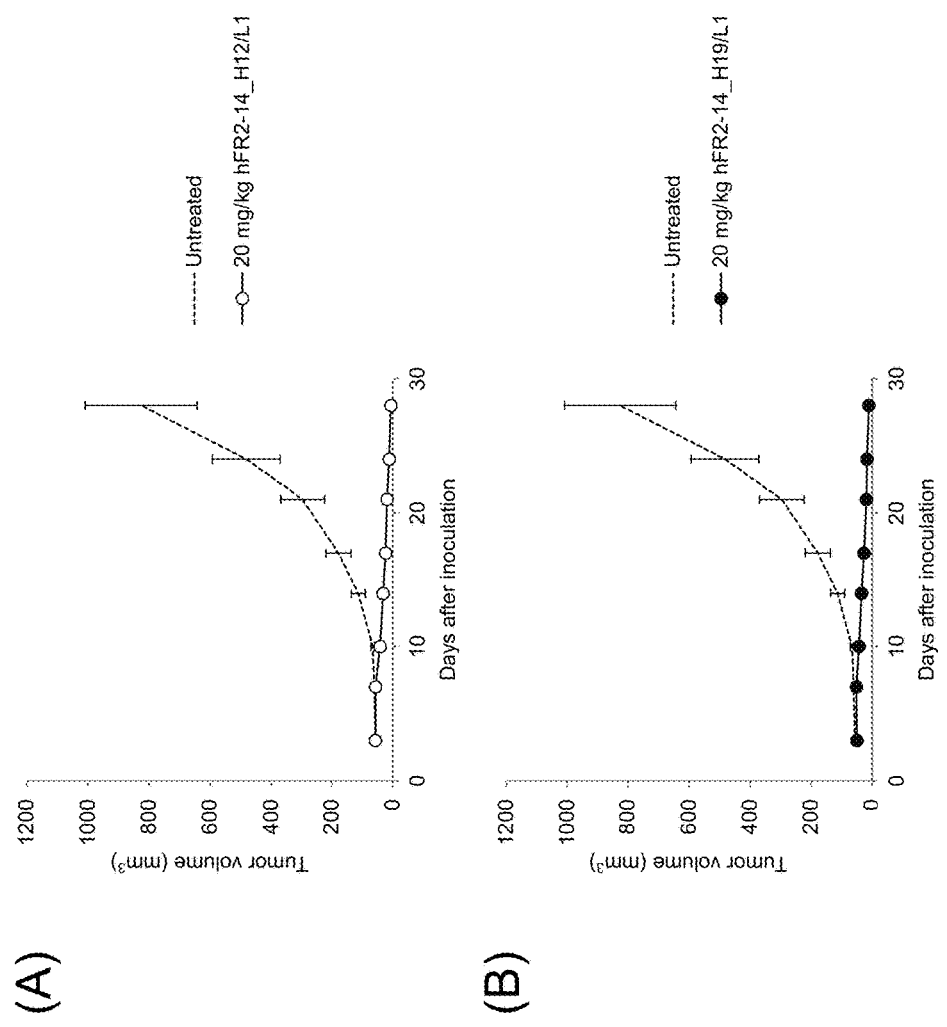

FIG. 136 is a diagram showing the in vivo antitumor activity of the humanized anti-FGFR2 antibodies (hFR2-14_H12/L1 and hFR2-14_H19/L1) against human colorectal cancer cell line NCI-H716 tumor block models. FIG. 136(A) shows the results for hFR2-14_H12/L1. FIG. 136(B) shows the results for hFR2-14_H19/L1.

Figure 137:
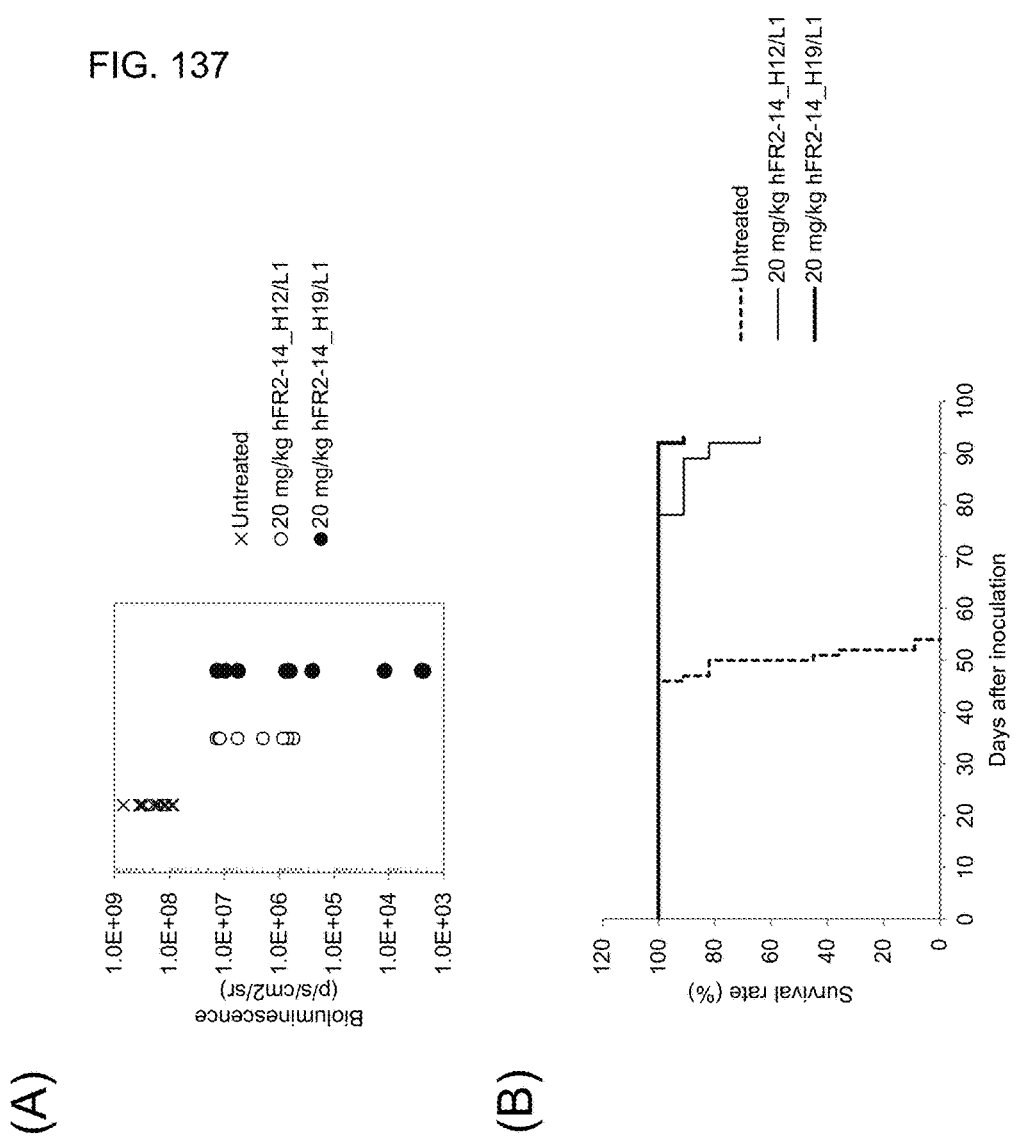

FIG. 137 is a diagram showing the in vivo antitumor activity of the humanized anti-FGFR2 antibodies (hFR2-14_H12/L1 and hFR2-14_H19/L1) against human colorectal cancer cell line NCI-H716-luc-peritoneally disseminated models. FIG. 137(A) shows the results showing luciferase activity. FIG. 137(B) shows the results showing survival rates.

Figure 138:
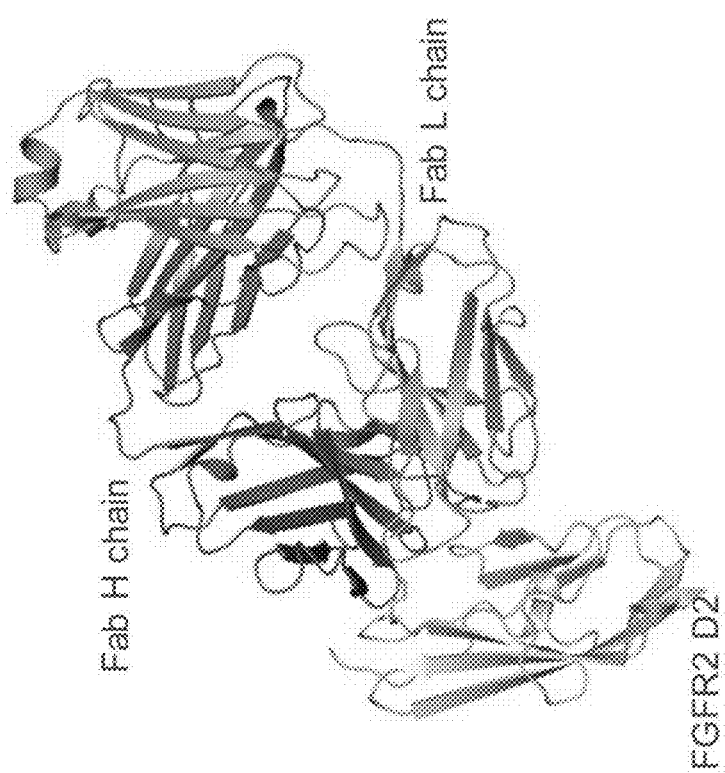

FIG. 138 is a diagram showing a ribbon model of an FGFR2D2/H3L1Fab complex. FGFR2D2 is shown at the lower left. The H chain (dark gray) of H3L1Fab is shown from the center to the upper right. The L chain of H3L1Fab is shown at the right thereof.

Figure 139:
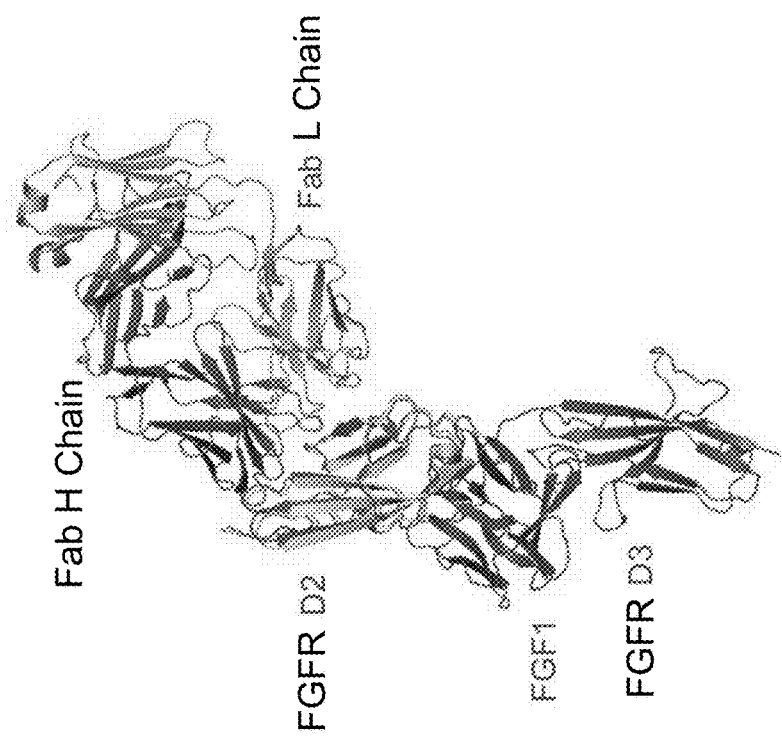

FIG. 139 is a diagram showing the superposition of FGFR2/FGF1 and FGFR2D2/H3L1Fab. FGFRD3 (IgD3) is shown at the lower center. FGF1 (dark gray) is shown above FGFRD3. FGFRD2 is shown above FGF1. The H chain (dark gray) and L chain of H3L1Fab are each shown at the upper right of FGFRD2.

Figure 140:
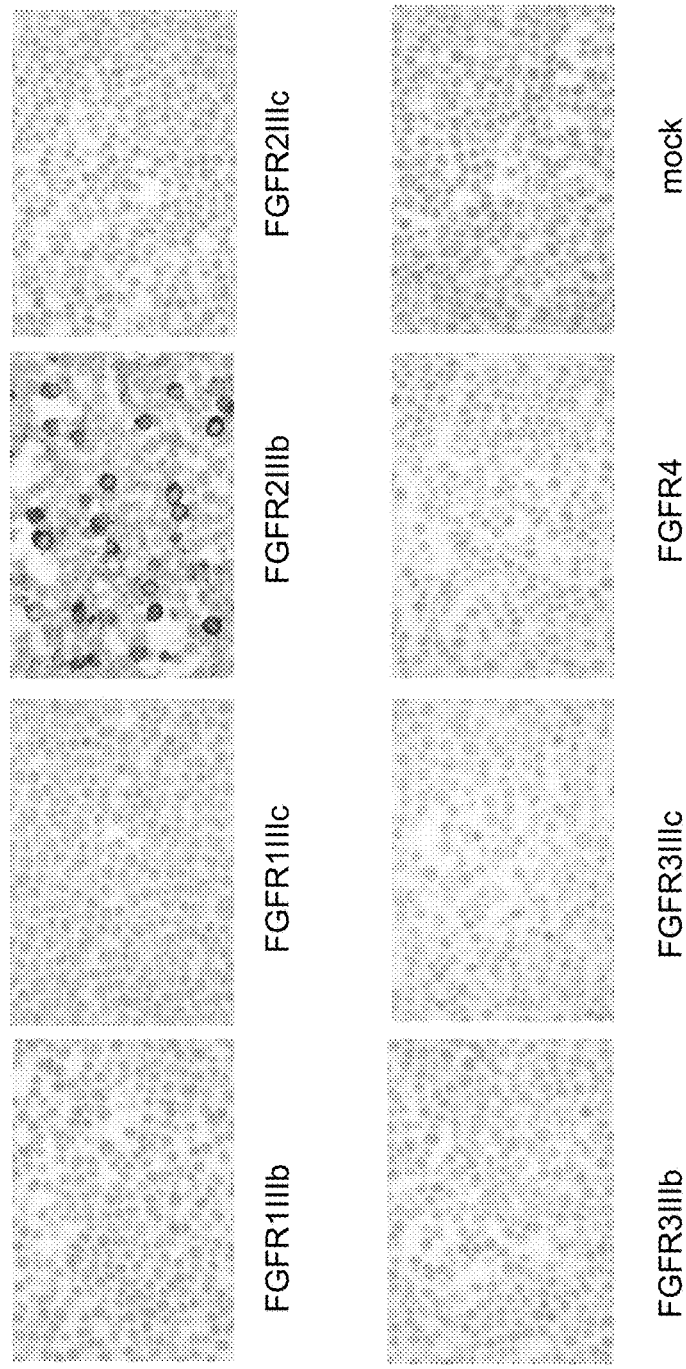

FIG. 140 is a diagram showing results of immunostainingblocks of 293α cells forced to express each molecule of the FGFR family, using the rat antibody FR2-10.

FIG. 141 is a diagram showing results of immunostaining blocks of SNU-16 cells (FIGS. 141A and 141D), KATO III cells (FIGS. 141B and 141E), and NCI-H716 cells (FIGS. 141C and 141F). FIGS. 141A to 141C show the results obtained using the rat antibody FR2-10. FIGS. 141D to 141F show the results obtained using a commercially available antibody.

Figure 142:
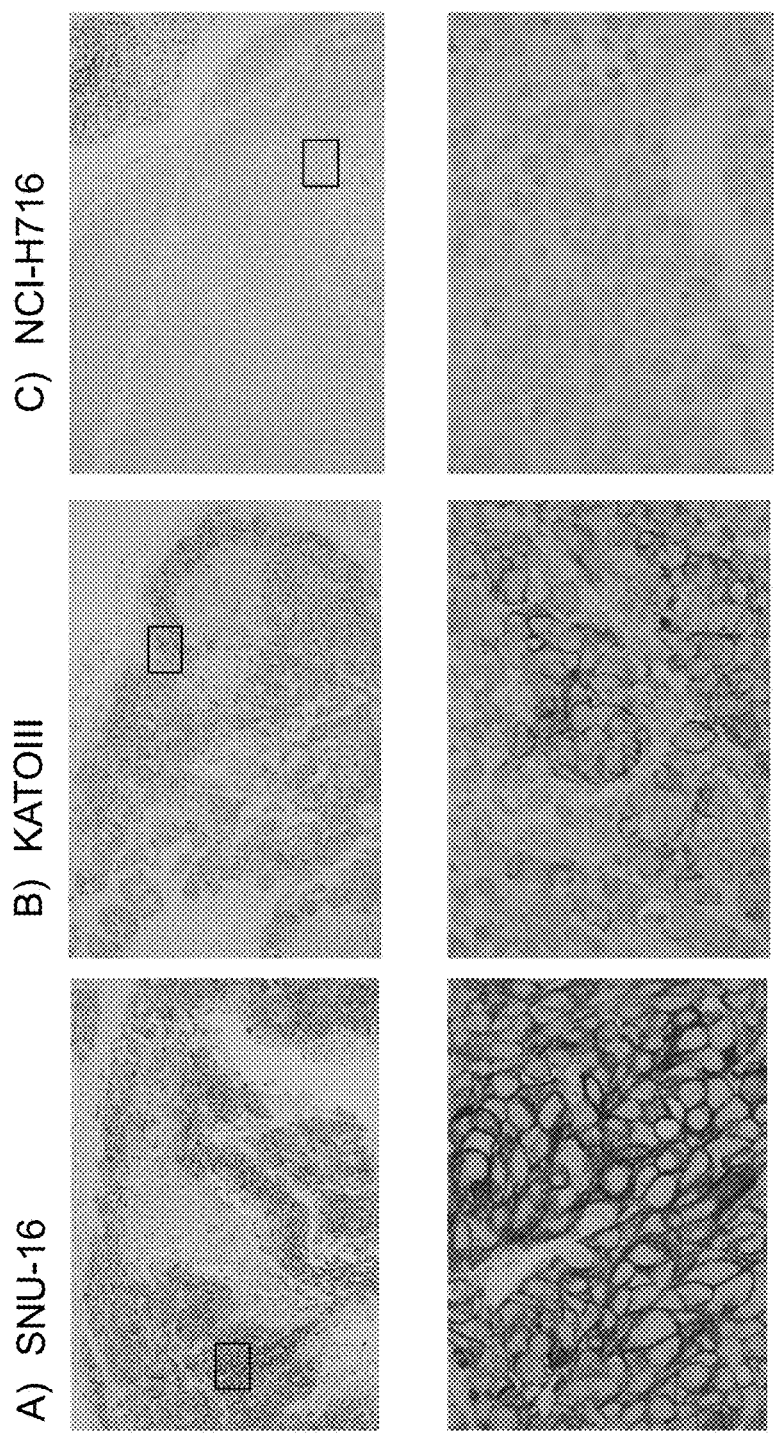

FIG. 142 is a diagram showing results of immunostaining xenograft tumor samples of SNU-16 cells (FIG. 142A), KATO III cells (FIG. 142B), and NCI-H716 cells (FIG. 142C) using the rat antibody FR2-10.

Figure 143:
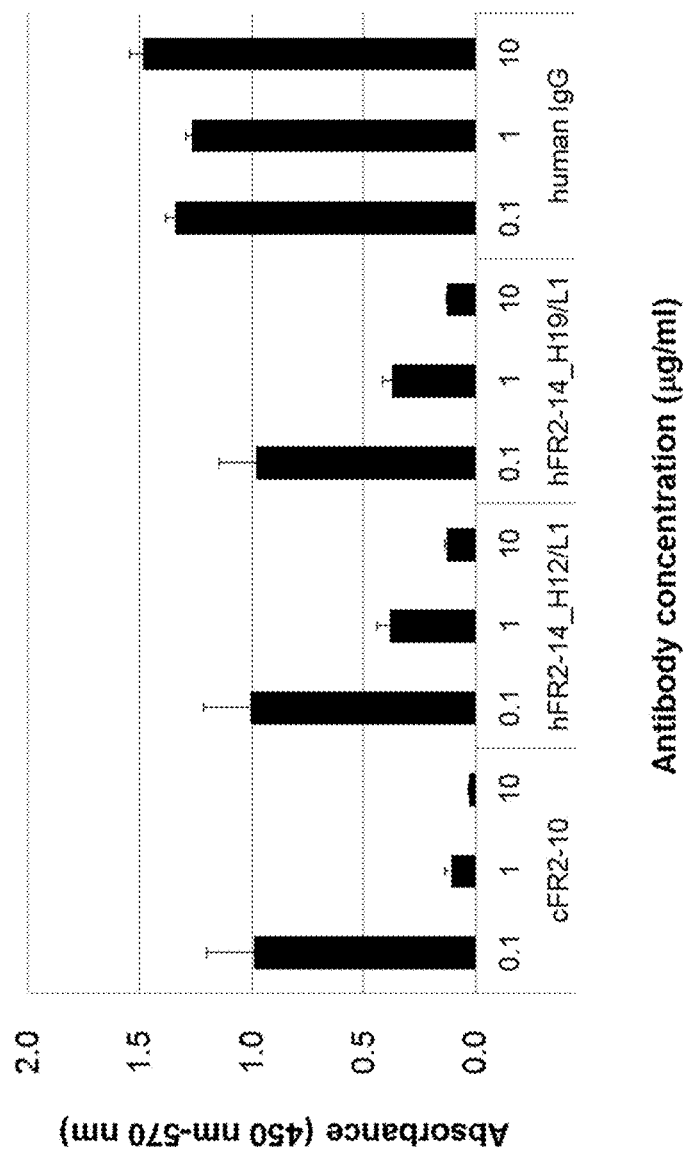

FIG. 143 is a diagram showing the activity of inhibiting the binding of a ligand FGF7 to its receptor FGFR2 by the cFR2-10, hFR2-14_H12/L1, and hFR2-14_H19/L1 antibodies.

DESCRIPTION OF EMBODIMENTS

1. Definitions

In the present invention, the term "gene" means a nucleotide comprising a nucleotide sequence encoding the amino acids of a protein, or its complementary strand. The "gene" is meant to include, for example, a polynucleotide, an oligonucleotide, DNA, mRNA, cDNA, and cRNA as the nucleotide comprising a nucleotide sequence encoding the amino acids of a protein, or its complementary strand. Such a gene is a single-stranded, double-stranded, or triple or more stranded nucleotide. The "gene" is also meant to include an association of DNA and RNA strands, a mixture of ribonucleotides (RNAs) and deoxyribonucleotides (DNAs) on one nucleotide strand, and a double-stranded or triple or more stranded nucleotide comprising such a nucleotide strand. Examples of the "FGFR2 gene" of the present invention can include DNA, mRNA, cDNA, and cRNA comprising a nucleotide sequence encoding the amino acid sequence of the FGFR2 protein.

In the present invention, the term "nucleotide" has the same meaning as a "nucleic acid" and is also meant to include, for example, DNA, RNA, a probe, an oligonucleotide, a polynucleotide, and a primer. Such a nucleotide is a single-stranded, double-stranded, or triple or more stranded nucleotide. The "nucleotide" is also meant to include an association of DNA and RNA strands, a mixture of ribonucleotides (RNAs) and deoxyribonucleotides (DNAs) on one nucleotide strand, and an associate of two strands or three or more strands comprising such a nucleotide strand.

In the present invention, the terms "polypeptide", "peptide", and "protein" have the same meaning.

In the present invention, the term "antigen" has the same meaning as "immunogen".

In the present invention, the term "cell" also includes, for example, various cells derived from individual animals, subcultured cells, primary cultured cells, cell lines, recombinant cells, and microbial cells.

In the present invention, antibodies recognizing FGFR2, FGFR2 IIIb, FGFR2 IIIc, FGFR3, FGFRs, and the like are also referred to as an "anti-FGFR2 antibody", an "anti-FGFR2 IIIb antibody", an "anti-FGFR2 IIIc antibody", an "anti-FGFR3 antibody", and an "anti-FGFRs antibody", respectively. These antibodies include chimeric antibodies, humanized antibodies, human antibodies, and the like.

In the present invention, the term "functional fragment of the antibody" means an antibody fragment that exerts at least a portion of functions exerted by the original antibody. Examples of the "functional fragment of the antibody" can include, but are not limited to, Fab, F(ab')2, scFv, Fab', and single chain immunoglobulin. Such a functional fragment of the antibody may be obtained by treating a full-length molecule of the antibody protein with an enzyme such as papain or pepsin or may be a recombinant protein produced in an appropriate host cell using a recombinant gene.

In the present invention, the "site" to which an antibody binds, i.e., the "site" recognized by an antibody, means a partial peptide or partial conformation on an antigen bound or recognized by the antibody. In the present invention, such a site is also referred to as an epitope or an antibody binding site. Examples of the site on the FGFR2 protein bound or recognized by the anti-FGFR2 antibody of the present invention can include a partial peptide or partial conformation on the FGFR2 protein.

The heavy and light chains of an antibody molecule are known to each have three complementarity determining regions (CDRs). The complementarity determining regions are also called hypervariable domains. These regions are located in the variable regions of the antibody heavy and light chains. These sites have a particularly highly variable primary structure and are usually separated at three positions on the respective primary structures of heavy and light chain polypeptide strands. In the present invention, the complementarity determining regions of the antibody are referred to as CDRH1, CDRH2, and CDRH3 from the amino terminus of the heavy chain amino acid sequence for the complementarity determining regions of the heavy chain and as CDRL1, CDRL2, and CDRL3 from the amino terminus of the light chain amino acid sequence for the complementarity determining regions of the light chain. These sites are proximal to each other on the three-dimensional structure and determine specificity for the antigen to be bound.

In the present invention, the term "antibody mutant" means a polypeptide that has an amino acid sequence derived from the amino acid sequence of the original antibody by the substitution, deletion, addition, and/or insertion (hereinafter, collectively referred to as a "mutation") of amino acid(s) and binds to the FGFR2 protein of the present invention. The number of mutated amino acids in such an antibody mutant is 1 to 2, 1 to 3, 1 to 4, 1 to 5, 1 to 6, 1 to 7, 1 to 8, 1 to 9, 1 to 10, 1 to 12, 1 to 15, 1 to 20, 1 to 25, 1 to 30, 1 to 40, or 1 to 50. Such an antibody mutant is also encompassed by the "antibody" of the present invention.

In the present invention, the term "several" in "1 to several" refers to 3 to 10.

Examples of activities or properties exerted by the antibody of the present invention can include biological activities or physicochemical properties and can specifically include various biological activities, binding activity against an antigen or an epitope, stability during production or storage, and thermal stability.

In the present invention, the phrase "hybridizing under stringent conditions" means hybridization under conditions involving hybridization at 65° C. in a solution containing 5×SSC, followed by washing at 65° C. for 20 minutes in an aqueous solution containing 2×SSC-0.1% SDS, at 65° C. for 20 minutes in an aqueous solution containing 0.5×SSC-0.1% SDS, and at 65° C. for 20 minutes in an aqueous solution containing 0.2×SSC-0.1% SDS, or hybridization under conditions equivalent thereto. SSC means an aqueous solution of 150 mM NaCl-15 mM sodium citrate, and n×SSC means SSC with an n-fold concentration.

In the present invention, the term "cytotoxicity" refers to some pathological change brought about to cells and means not only direct trauma but every structural or functional damage to cells, including DNA cleavage, formation of base dimers, chromosomal break, damage on mitotic apparatus, and reduction in the activities of various enzymes.

In the present invention, the term "cytotoxic activity" means activity that causes the cytotoxicity mentioned above.

In the present invention, the term "antibody dependent cellular cytotoxic activity", also called "ADCC activity", means the effect or activity of damaging target cells such as tumor cells by NK cells via antibodies.

In the present invention, the term "antibody dependent cell phagocytosis activity", also called "ADCP activity", means the effect or activity of englobing target cells such as tumor cells by monocyte or macrophage cells via antibodies. This activity is also referred to as "antibody dependent phagocytic effect or activity".

In the present invention, the term "complement dependent cytotoxic activity", also called "CDC activity", means the effect or activity of damaging target cells such as tumor cells by complement via antibodies.

In the present invention, the term "cancer" has the same meaning as "tumor".

In the present invention, the term "immunohistochemistry (IHC)" means a histological (histochemical) approach of detecting an antigen in a tissue preparation. The immunohistochemistry is synonymous with an "immune antibody method" and has the same meaning as "immunostaining".

2. Antigenic Protein

(2-1) Properties

FGFRs are receptor proteins that bind to fibroblast growth factors (FGFs). In the present invention, FGFRs are derived from vertebrates, preferably mammals, more preferably humans. Human FGFs and FGFRs are classified into 22 FGFs (FGF1 to FGF14 and FGF16 to FGF23) and 4 FGFRs (FGFR1 to FGFR4) having a tyrosine kinase domain, respectively. These FGFRs are each composed of an extracellular region comprising a ligand binding site composed of 2 or 3 immunoglobulin-like domains (IgD1 to IgD3), a single-pass transmembrane region, and an intracellular region comprising the tyrosine kinase domain. Of them, FGFR1, FGFR2, and FGFR3 each have two splicing variants called IIIb and IIIc. These isoforms differ in the sequence of approximately 50 amino acids in the latter half of IgD3 and exhibit distinctive tissue distribution and ligand specificity. FGFRs have the following activities: (1) binding to FGFs; (2) this binding dimerizes the FGFRs; (3) this dimerization phosphorylates the FGFRs at their particular tyrosine residues; (4) this phosphorylation promotes the recruitment of adaptor proteins such as FGFR substrate 2a (FRS2α); and (5) this transduces signals generated by FGF stimulation to cells or tissues expressing the FGFRs or activates signal transduction.

The FGFR2 protein according to the present invention has the following properties:

(i) Binding to FGF.

The FGFR2 IIIb protein typically binds to one or two or more FGFs selected from the group consisting of FGF1, FGF3, FGF7 (KGF), FGF10, FGF22, and FGF23. The FGFR2 IIIb protein may bind to other FGFs and may not bind to mutated forms of the FGFs included in the above group.

The FGFR2 IIIc protein typically binds to one or two or more FGFs selected from the group consisting of FGF1, FGF2, FGF4, FGF6, FGF9, FGF17, FGF18, FGF21, and FGF23. The FGFR2 IIIc protein may bind to other FGFs and may not bind to mutated forms of the FGFs included in the above group.

(ii) Transducing signals generated by FGF stimulation into FGFR2-expressing cells or tissues Examples of the transduction of signals generated by FGF stimulation can include, but are not particularly limited to, FGFR2 autophosphorylation, recruitment of FGFR substrates and promotion thereof, and activation of signaling pathways such as MAPK, PI3K, Akt, and extracellular signal-regulated kinase (ERK) pathways via these events. Examples of the FGFR substrates can include FGFR substrate 2α (FRS2α).

Testing methods for evaluating the activation of this signal transduction and the inhibition thereof are not particularly limited and can be arbitrarily selected from methods known in the art. Examples thereof can include evaluation systems for ERK signal transduction, and Elk1 luciferase reporter assay described later.

(iii) The FGFR2 IIIb protein according to the present invention comprises an amino acid sequence described in any one of the following (a) to (d) (hereinafter, referred to as an "FGFR2 IIIb amino acid sequence"), consists of an amino acid sequence comprising the FGFR2 IIIb amino acid sequence, or consists of the FGFR2 IIIb amino acid sequence:

(a) the amino acid sequence represented by SEQ ID NO: 70 (FIG. 78) of the Sequence Listing;
(b) an amino acid sequence that exhibits 80% or higher, 82% or higher, 84% or higher, 86% or higher, 88% or higher, 90% or higher, 92% or higher, 94% or higher, 96% or higher, 98% or higher, or 99% or higher, sequence identity to the amino acid sequence represented by SEQ ID NO: 70 (FIG. 78) of the Sequence Listing and is carried by a polypeptide having FGF binding activity;
(c) an amino acid sequence that is derived from the amino acid sequence represented by SEQ ID NO: 70 (FIG. 78) of the Sequence Listing by the substitution, deletion, addition, or insertion of 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and is carried by a polypeptide having FGF binding activity; and
(d) an amino acid sequence that is encoded by the nucleotide sequence of a nucleotide hybridizing under stringent conditions to a nucleotide having a nucleotide sequence complementary to a nucleotide sequence encoding the amino acid sequence represented by SEQ ID NO: 70 (FIG. 78) of the Sequence Listing and is carried by a polypeptide having FGF binding activity.

The polypeptide described in any one of (b) to (d) may have FGFR2 activities other than the FGF binding activity.

The FGFR2 IIIc protein according to the present invention comprises an amino acid sequence described in any one of the following (a) to (d) (hereinafter, referred to as an "FGFR2 IIIc amino acid sequence"), consists of an amino acid sequence comprising the FGFR2 IIIc amino acid sequence, or consists of the FGFR2 IIIc amino acid sequence:

(a) an amino acid sequence represented by SEQ ID NO: 71 (FIG. 79) of the Sequence Listing;
(b) an amino acid sequence that exhibits 80% or higher, 82% or higher, 84% or higher, 86% or higher, 88% or higher, 90% or higher, 92% or higher, 94% or higher, 96% or higher, 98% or higher, or 99% or higher, sequence identity to the amino acid sequence represented by SEQ ID NO: 71 (FIG. 79) of the Sequence Listing and is carried by a polypeptide having FGF binding activity;
(c) an amino acid sequence that is derived from the amino acid sequence represented by SEQ ID NO: 71 (FIG. 79) of the Sequence Listing by the substitution, deletion, addition, or insertion of 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and is carried by a polypeptide having FGF binding activity; and
(d) an amino acid sequence that is encoded by the nucleotide sequence of a nucleotide hybridizing under stringent conditions to a nucleotide having a nucleotide sequence complementary to a nucleotide sequence encoding the amino acid sequence represented by SEQ ID NO: 71 (FIG. 79) of the Sequence Listing and is carried by a polypeptide having FGF binding activity.

The polypeptide described in any one of (b) to (d) may have FGFR2 activities other than the FGF binding activity.

Examples of the amino acid sequences of human FGFR2 IIIb and human FGFR2 IIIc can include the amino acids (a) to (d) as well as the amino acids published under NP_075259 and NP_000132, respectively.

(iv) The FGFR2 protein of the present invention can be obtained from FGFR2-expressing cells, tissues, or cancer tissues, cells derived from the tissues, cultures of the cells, and the like, of a vertebrate, preferably of a mammal, more preferably of a rodent such as a mouse or a rat and a human, even more preferably of a human, a rat, or a mouse.

Examples of the normal tissues highly expressing FGFR2 can include the brain, the large intestine, thyroid glands, the uterine, the gallbladder, and the skin. Gene amplification is found in some cancers highly expressing FGFR2, such as stomach cancer and breast cancer, while overexpression is found in some cancers highly expressing FGFR2, such as pancreatic cancer and ovarian cancer. Examples of the cultured cell lines highly expressing FGFR2 IIIb can include stomach cancer cell lines and breast cancer cell lines. Examples of the cultured cell lines highly expressing FGFR2 IIIb can include colorectal (cecal) cancer cell lines. Examples of cancer tissues expressing FGFR2 IIIc can include tissues with uterine cervix cancer and non-small cell lung cancer. Of these cancers, uterine cervix cancer highly expresses FGFR2 IIIc.

The FGFR2 protein of the present invention may be a native (non-recombinant) or recombinant protein. The FGFR2 protein is also meant to include fusion products with another peptide or protein such as a carrier or a tag. The FGFR2 protein is further meant to include forms provided with chemical modification including the addition of a polymer such as PEG and/or with biological modification including sugar chain modification. Moreover, the FGFR2 protein of the present invention is meant to include an FGFR2 protein fragment. An FGFR2 protein fragment possessing the properties described above in (i) and/or (ii) is referred to as a functional fragment of the FGFR2 protein.

(2-2) Antigen Gene

The FGFR2 IIIb gene according to the present invention comprises a nucleotide sequence described in any one of the following (a) to (c) (hereinafter, referred to as an "FGFR2 gene sequence"), consists of a nucleotide sequence comprising the FGFR2 gene sequence, or consists of the FGFR2 gene sequence:

(a) a nucleotide sequence encoding the amino acid sequence represented by SEQ ID NO: 70 (FIG. 78) of the Sequence Listing;
(b) a nucleotide sequence that hybridizes under stringent conditions to a nucleotide consisting of a nucleotide sequence complementary to the nucleotide sequence encoding the amino acid sequence represented by SEQ ID NO: 70 (FIG. 78) of the Sequence Listing and encodes the amino acid sequence of a polypeptide having FGF binding activity; and
(c) a nucleotide sequence that encodes an amino acid sequence derived from the amino acid sequence represented by SEQ ID NO: 70 (FIG. 78) of the Sequence Listing by the substitution, deletion, addition, or insertion of 1 to 50, 1 to 45, 1 to 40, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and encodes the amino acid sequence of a polypeptide having FGF binding activity.

The polypeptide having the amino acid sequence encoded by the nucleotide sequence (b) or (c) may have FGFR2 activities other than the FGF binding activity.

The FGFR2 IIIc gene according to the present invention comprises a nucleotide sequence described in any one of the following (a) to (c) (hereinafter, referred to as an "FGFR2 gene sequence"), consists of a nucleotide sequence comprising the FGFR2 gene sequence, or consists of the FGFR2 gene sequence:

(a) a nucleotide sequence encoding the amino acid sequence represented by SEQ ID NO: 71 (FIG. 79) of the Sequence Listing;
(b) a nucleotide sequence that hybridizes under stringent conditions to a nucleotide consisting of a nucleotide sequence complementary to the nucleotide sequence encoding the amino acid sequence represented by SEQ ID NO: 71 (FIG. 79) of the Sequence Listing and encodes the amino acid sequence of a polypeptide having FGF binding activity; and
(c) a nucleotide sequence that encodes an amino acid sequence derived from the amino acid sequence represented by SEQ ID NO: 71 (FIG. 79) of the Sequence Listing by the substitution, deletion, addition, or insertion of 1 to 50, 1 to 45, 1 to 40, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and encodes the amino acid sequence of a polypeptide having FGF binding activity.

The polypeptide having the amino acid sequence encoded by the nucleotide sequence (b) or (c) may have FGFR2 activities other than the FGF binding activity.

The expression and expression level of the FGFR2 gene may be assayed with either an FGFR2 gene transcript or the FGFR2 protein as an index. The former index can be determined by RT-PCR, Northern blot hybridization, or the like, while the latter index can be determined by, for example, immunoassay such as enzyme-linked immunosorbent assay (hereinafter, referred to as "ELISA"), Western blotting, or immunohistological staining.

(2-3) Preparation of Antigenic Protein

The FGFR2 protein of the present invention can be prepared by purification or isolation from animal tissues (including body fluids), cells derived from the tissues, or cultures of the cells, gene recombination, in vitro translation, chemical synthesis, etc.

(2-3-1) Purification or Isolation of Non-Recombinant FGFR2

The non-recombinant FGFR2protein can he purified or isolated from FGFR2-expressing cells, normal tissues, or cancer tissues, or cells derived therefrom. Examples of the FGFR2-expressing normal tissues, cancer tissues, or cancer cells can include those described in (iv) of paragraph (2-1), though the origin of the non-recombinant FGFR2protein is not limited thereto.

The purification or isolation from such tissues, cells, cell cultures, or the like, can be performed by the combination of approaches well known by those skilled in the art, such as fractionation and chromatography. Such approaches include, but are not limited to, salting out, gel filtration, ion-exchange chromatography, affinity chromatography, hydrophobic chromatography, normal-phase or reverse-phase chromatography, and the like. A column for affinity chromatography can be prepared by packing the column with an affinity gel cross-linked with an anti-FGFR2 monoclonal antibody. A crude or partially purified fraction containing the FGFR2 protein is applied to this column. Subsequently, non-specifically adsorbed substances are removed with sterilized phosphate-buffered saline (PBS), and a buffer solution for elution can then be applied thereto to thereby selectively recover the FGFR2 protein. The solution containing the FGFR2 protein can be subjected to gel filtration or to buffer replacement and/or concentration using a concentrator such as Centriprep.

(2-3-2) Preparation of Recombinant FGFR2 Protein

The FGFR2 protein of the present invention can also be prepared in a recombinant form. Specifically, host cells are transfected with a gene encoding the amino acid sequence of the FGFR2 protein or an FGFR2 protein fragment, and the FGFR2 protein can be recovered from cultures of the cells. For example, the FGFR2 gene or its fragment is inserted into an expression vector. Subsequently, prokaryotic or eukaryotic host cells are transfected with the resulting recombinant vector, and the obtained recombinant cells can be incubated to thereby express the FGFR2 protein. An expression pattern known in the art, such as secretion expression, intracellular expression of soluble forms, or expression in inclusion body forms can be used. Also, the FGFR2 protein can be expressed not only as a molecule having the same amino terminus (N terminus) and/or carboxy terminus (C terminus) as native ones, but also as a fusion protein with a secretory signal, an intracellular localization signal, a tag for affinity purification, or a partner peptide. The FGFR2 protein can be purified or isolated from such recombinant cell cultures by an appropriate combination of methods such as fractionation and chromatography described in (2-3-1)
Purification or Isolation of Non-Recombinant FGFR2 Protein.

The FGFR2 gene or its fragment can be prepared by a method well known by those skilled in the art.

Examples thereof can include: polymerase chain reaction (hereinafter, referred to as "PCR"; Saiki, R. K., et al., Science (1988) 239, p. 487-489) with a cDNA library prepared from FGFR2-expressing cells, tissues, or the like as a template using one set of primers capable of specifically amplifying the sequence; reverse transcription PCR (hereinafter, referred to as "RT-PCR") with an mRNA fraction prepared from FGFR2-expressing cells, tissues, or the like as a template using a primer capable of reverse-transcribing the sequence and one set of primers capable of specifically amplifying the sequence; expression cloning using immunoassay; and cDNA cloning using the partial amino acid sequence of purified FGFR2 protein.

(2-3-3) In Vitro Translation

The FGFR2 protein of the present invention can also be prepared by in vitro translation. Such a translation method is not particularly limited as long as the method employs a cell-free translation system involving enzymes necessary for transcription and translation, substrates, and energy substances. Examples thereof can include a method using Rapid Translation System (RTS) manufactured by Roche Diagnostics K.K.

(2-3-4) Chemical Synthesis

The FGFR2 protein of the present invention can also be prepared by chemical synthesis. Examples of the chemical synthesis method can include solid-phase peptide synthesis methods such as Fmoc and Boc synthesis methods.

3. Antibody (3-1) Classification of Antibody

The antibodies of the present invention may be either monoclonal or polyclonal antibodies. Examples of the monoclonal antibody of the present invention can include non-human animal-derived antibodies (non-human animal antibodies), human-derived antibodies (human antibodies), chimeric antibodies, and humanized antibodies.

Examples of the non-human animal antibody can include antibodies derived from vertebrates such as mammals and birds. Examples of the mammal-derived antibody can include rodent-derived antibodies such as mouse antibodies and rat antibodies. Examples of the bird-derived antibody can include chicken antibodies. Examples of the anti-human FGFR2 rat monoclonal antibody can include FR2-10, FR2-13, and FR2-14.

Examples of the chimeric antibody can include, but are not limited to, an antibody comprising non-human animal antibody-derived variable regions bound with human antibody (human immunoglobulin) constant regions. Examples of the chimeric antibody comprising non-human animal antibody-derived variable regions bound with human antibody constant regions can include cFR2-10, cFR2-13, and cFR2-14 having heavy and light chain variable regions derived from the rat monoclonal antibody FR2-10, FR2-13, or FR2-14 mentioned above, and human heavy and light chain constant regions.

Examples of the humanized antibody can include, but are not limited to, a human antibody (human immunoglobulin variable regions) grafted with CDRs in the variable regions of a non-human animal antibody, a human antibody grafted with the CDRs as well as with partial sequences of framework regions of a non-human animal antibody, and an antibody having human antibody amino acid(s) substituted for one or two or more non-human animal antibody-derived amino acid(s) in any of these humanized antibodies. Examples of the CDRs in the variable regions of a non-human animal antibody can include CDRH1 to CDRH3 in the heavy chain variable region and CDRL1 to CDRL3 in the light chain variable region derived from FR2-10, FR2-13, or FR2-14 mentioned above.

The human antibody is not particularly limited as long as the antibody recognizes the antigen of the present invention. Examples thereof can include a human antibody binding to the same site, as in the case of an antibody having the CDRs of the antibody of the present invention, and a human antibody binding to the same site on FGFR2 as in the case of FR2-10, FR2-13, or FR2-14 mentioned above.

The antibody according to the present invention may be comprised of portions derived from a plurality of different antibodies as long as the antibody has FGFR2 binding activity. Examples of such an antibody can include an antibody comprising heavy and/or light chains exchanged among a plurality of different antibodies, an antibody comprising full-length heavy and/or light chains exchanged thereamong, an antibody comprising variable or constant regions exchanged thereamong, and an antibody comprising all or some CDRs exchanged thereamong. The heavy and light chain variable regions of the chimeric antibody may be derived from different antibodies of the present invention. CDRH1 to CDRH3 and CDRL1 to CDRL3 in the heavy and light chain variable regions of the humanized antibody may be derived from two or more different antibodies of the present invention. CDRH1 to CDRH3 and CDRL1 to CDRL3 in the heavy and light chain variable regions of the human antibody may be a combination of CDRs carried by two or more different antibodies of the present invention. Such an antibody comprised of portions derived from a plurality of different antibodies may have one or two or more of the activities described in paragraphs (3-3) to (3-6).

Examples of the isotype of the monoclonal antibody of the present invention can include, but are not particularly limited to, IgG such as IgG1, IgG2, IgG3, and IgG4, IgM, IgA such as IgA1 and IgA2, IgD, and IgE and can preferably include IgG and IgM. The isotype and subclass of the monoclonal antibody can be determined by, for example, an Ouchterlony test, ELISA, or radio immunoassay (hereinafter, referred to as "RIA"). A commercially available kit for identification (e.g., Mouse Typer Kit; Bio-Rad Laboratories, Inc., and RAT MONOCLONAL ANTIBODY ISOTYPING TEST KIT: AbD Serotec) may be used.

(3-2) Binding Specificity of Antibody

The antibody of the present invention recognizes the FGFR2 protein. In other words, the antibody of the present invention binds to the FGFR2 protein. Such an antibody is referred to as an "anti-FGFR2 antibody". Preferably, the antibody of the present invention specifically recognizes the FGFR2 protein. In other words, preferably, the antibody of the present invention specifically binds to the FGFR2 protein. More preferably, the antibody of the present invention specifically binds to the FGFR2 IIIb protein and/or the FGFR2 IIIc protein. Even more preferably, the antibody of the present invention specifically binds to the immunoglobulin-like domain (hereinafter, referred to as "Ig-like domain")

of the FGFR2 IIIb protein and/or the FGFR2 IIIc protein. Examples of such an Ig-like domain can include Ig-like domain 2 and Ig-like domain 3.

In the present invention, the "specific recognition", i.e., "specific binding", means binding which is not non-specific adsorption. Examples of criteria for determination of whether binding is specific or not can include a dissociation constant (hereinafter, referred to as "KD"). Preferably, the antibody of the present invention has a KD value of $1\times10^{-5}$ or lower, $5\times10^{-6}$ or lower, $2\times10^{-6}$ or lower, or $1\times10^{-6}$ or lower, more preferably $5\times10^{-7}$ or lower, $2\times10^{-7}$ or lower, or $1\times10^{-7}$ or lower, even more preferably $5\times10^{-8}$ or lower, $2\times10^{-8}$ or lower, or $1\times10^{-8}$ or lower, further more preferably $5\times10^{-9}$ or lower, $2\times10^{-9}$ or lower, or $1\times10^{-9}$ or lower, most preferably $5\times10^{-10}$ or lower, $2\times10^{-10}$ or lower, or $1\times10^{-10}$ or lower for the FGFR2 protein.

In the present invention, the binding of the antibody to the antigen can be assayed or determined by ELISA, RIA, surface plasmon resonance (hereinafter, referred to as "SPR") analysis, or the like. Examples of equipment used in the SPR analysis can include BIAcore™ (manufactured by GE Healthcare Bio-Sciences Corp.), ProteOn™ (manufactured by Bio-Rad Laboratories, Inc.), SPR-Navi™ (manufactured by BioNavis Oy Ltd.), Spreeta™ (manufactured by Texas Instruments Inc.), SPRi-Plex II™ (manufactured by Horiba, Ltd.), and Autolab SPR™ (manufactured by Metrohm Japan Ltd.). The binding of the antibody to the antigen expressed on cell surface can be assayed by flow cytometry, Cell-ELISA, or the like.

(3-3) Antitumor Activity of Antibody

The antibody of the present invention has antitumor activity. Preferably, the antibody of the present invention has antitumor activity in vivo. In the present invention, the "antitumor activity" has the same meaning as "anti-cancer activity".

In the present invention, the antitumor activity means the activity of inhibiting the growth, malignant transformation, invasion, or metastasis of tumor tissues and/or tumor cells, increase in tumor size or weight, etc.

The antitumor activity can be evaluated according to a standard method. The in vivo antitumor activity can be evaluated as an effect on human tumor, for example, by use of human cancer tissue- or cancer cell-transplanted non-human animal models (xenografts). Examples of the non-human animal used for the xenografts can include mice such as nude mice, and rats.

Alternatively, the antitumor activity may be evaluated as suppressive or inhibitory activity against the growth of cancer cells.

(3-4) Cytotoxic Activity of Antibody

The anti-FGFR2 antibody of the present invention may have antibody dependent cellular cytotoxic (ADCC) activity and/or complement dependent cytotoxic (CDC) activity and/or antibody dependent cell phagocytosis (ADCP) activity. Preferably, the antibody of the present invention has ADCC activity. More preferably, the antibody of the present invention has ADCC activity against FGFR2-expressing cells. The ADCC activity, the CDC activity, and the ADCP activity can be assayed by a method known in the art.

Cells expressing the antigen of interest (target cells) and effector cells capable of killing the target cells are used in the ADCC activity assay. The effector cells recognize the Fc regions of antibodies bound with the target cells via Fcγ receptors. The effector cells kill the target cells by signals transduced from the Fcγ receptors. In the case of assaying the ADCC activity of an antibody having a human-derived Fc region, human NK cells are used as the effector cells. The human NK cells can be prepared from human peripheral blood mononuclear cells (PBMCs) by a method known in the art. Alternatively, PBMCs may be used directly as the effector cells.

Cells expressing the antigen of interest (target cells) and effector cells (e.g., monocytes or macrophages) capable of englobing the target cells are used in the ADCP activity assay. These effector cells can be prepared by inducing, by a method known in the art, differentiation from monocyte fractions to macrophages, wherein said monocyte fractions have been separated from human peripheral blood mononuclear cells (PBMCs) by a method known in the art.

(3-5) Effect of Antibody on Signal Transduction

The biological activities and properties of the anti-FGFR2 antibody of the present invention can also be evaluated through FGFR2-mediated FGF signals. Examples of the FGFR2-mediated signal transduction by FGF stimulation can include, but are not particularly limited to, FGFR2 autophosphorylation, recruitment of FGFR substrates and promotion thereof, and activation of signaling pathways such as MAPK, PI3K, Akt, and extracellular signal-regulated kinase (ERK) pathways via these events. Examples of the FGFR substrates can include FGFR substrate 2α (FRS2α). Testing methods for evaluating the activation of this signal transduction and the inhibition thereof are not particularly limited and can be arbitrarily selected from methods known in the art. Examples thereof can include evaluation systems for ERK signal transduction, and Elk1 luciferase reporter assay described later.

Preferably, the antibody of the present invention also has neutralizing activity against FGFR2. More preferably, the antibody of the present invention has neutralizing activity against FGFR2 IIIb and/or FGFR2 IIIc. The neutralizing activity means the activity of inhibiting or suppressing the activation of FGFR2 by an FGFR2 ligand. For example, an antibody inhibiting FGF dependent FGFR2-mediated signals, signal transduction, or the like can be confirmed to have such neutralizing activity. Exemplary assay of the neutralizing activity is shown in 2)-3 of Example 2 and Example 11.

(3-6) Activity of Inhibiting Receptor-Ligand Binding by Antibody

Preferably, the antibody of the present invention inhibits the binding of FGFR2 to its ligand. More preferably, the antibody of the present invention inhibits the binding of FGFR2 IIIb and/or FGFR2 IIIc to FGF. This inhibition of receptor-ligand binding may be any of competitive inhibition and noncompetitive inhibition. Examples of the ligands of FGFR2 IIIb and FGFR2 IIIc can include FGF1, FGF3, FGF7, FGF10, FGF22, and FGF23, and FGF1, FGF2, FGF4, FGF6, FGF9, FGF17, FGF18, FGF21, and FGF23, respectively.

(3-7) Monoclonal Antibody

The present invention provides a monoclonal antibody. The monoclonal antibody includes, for example, non-human animal-derived monoclonal antibodies such as rat, mouse, rabbit, chicken, and fish antibodies, chimeric antibodies, humanized antibodies, human antibodies, functional fragments thereof, and modified forms of these antibodies or functional fragments. Of them, examples of the rat monoclonal antibody can include the FR2-10, FR2-13, and FR2-14 antibodies.

FR2-10 is an anti-human FGFR2 rat monoclonal antibody obtained by the method described in Example 1. The nucleotide sequence of the heavy chain variable region of FR2-10 is described in SEQ ID NO: 11 (FIG. 19) of the Sequence Listing, and its amino acid sequence is described in SEQ ID NO: 12 (FIG. 20). The nucleotide sequence of the light chain variable region of FR2-10 is described in SEQ ID NO: 20 (FIG. 28) of the Sequence Listing, and its amino acid sequence is described in SEQ ID NO: 21 (FIG. 29). The amino acid sequence of CDRH1 of FR2-10 is described in SEQ ID NO: 52 (FIG. 60). The amino acid sequence of CDRH2 thereof is described in SEQ ID NO: 53 (FIG. 61). The amino acid sequence of CDRH3 thereof is described in SEQ ID NO: 54 (FIG. 62). The amino acid sequence of CDRL1 thereof is described in SEQ ID NO: 61 (FIG. 69). The amino acid sequence of CDRL2 thereof is described in SEQ ID NO: 62 (FIG. 70). The amino acid sequence of CDRL3 thereof is described in SEQ ID NO: 63 (FIG. 71).

FR2-13 is an anti-human FGFR2 rat monoclonal antibody obtained by the method described in Example 1. The nucleotide sequence of the heavy chain variable region of FR2-13 is described in SEQ ID NO: 13 (FIG. 21) of the Sequence Listing, and its amino acid sequence is described in SEQ ID NO: 14 (FIG. 22). The nucleotide sequence of the light chain variable region of FR2-13 is described in SEQ ID NO: 23 (FIG. 31) of the Sequence Listing, and its amino acid sequence is described in SEQ ID NO: 24 (FIG. 32). The amino acid sequence of CDRH1 of FR2-13 is described in SEQ ID NO: 55 (FIG. 63). The amino acid sequence of CDRH2 thereof is described in SEQ ID NO: 56 (FIG. 64). The amino acid sequence of CDRH3 thereof is described in SEQ ID NO: 57 (FIG. 65). The amino acid sequence of CDRL1 thereof is described in SEQ ID NO: 64 (FIG. 72). The amino acid sequence of CDRL2 thereof is described in SEQ ID NO: 65 (FIG. 73). The amino acid sequence of CDRL3 thereof is described in SEQ ID NO: 66 (FIG. 74).

FR2-14 is an anti-human FGFR2 rat monoclonal antibody obtained by the method described in Example 1. The nucleotide sequence of the heavy chain variable region of FR2-14 is described in SEQ ID NO: 15 (FIG. 23) of the Sequence Listing, and its amino acid sequence is described in SEQ ID NO: 16 (FIG. 24). The nucleotide sequence of the light chain variable region of FR2-14 is described in SEQ ID NO: 25 (FIG. 33) of the Sequence Listing, and its amino acid sequence is described in SEQ ID NO: 26 (FIG. 34). The amino acid sequence of CDRH1 of FR2-14 is described in SEQ ID NO: 58 (FIG. 66). The amino acid sequence of CDRH2 thereof is described in SEQ ID NO: 59 (FIG. 67). The amino acid sequence of CDRH3 thereof is described in SEQ ID NO: 60 (FIG. 68). The amino acid sequence of CDRL1 thereof is described in SEQ ID NO: 67 (FIG. 75). The amino acid sequence of CDRL2 thereof is described in SEQ ID NO: 68 (FIG. 76). The amino acid sequence of CDRL3 thereof is described in SEQ ID NO: 69 (FIG. 77).

The antibody mutant of the present invention preferably exhibits, for example, reduced sensitivity to protein degradation or oxidation, an improved biological activity, an improved ability to bind to the antigen, or physicochemical or functional properties imparted thereto. Examples of such an antibody mutant can include an antibody having an amino acid sequence derived from the amino acid sequence of the original antibody by conservative amino acid substitution. The conservative amino acid substitution is a substitution that occurs in an amino acid group related to amino acid side chains.

Preferred amino acid groups are as follows: an acidic group including aspartic acid and glutamic acid; a basic group including lysine, arginine, and histidine; a nonpolar group including alanine, valine, leucine, isoleucine, proline, phenylalanine, methionine, and tryptophan; and an uncharged polar family including glycine, asparagine, glutamine, cysteine, serine, threonine, and tyrosine. Other preferred amino acid groups are as follows: an aliphatic hydroxy group including serine and threonine; an amide-containing group including asparagine and glutamine; an aliphatic group including alanine, valine, leucine, and isoleucine; and an aromatic group including phenylalanine, tryptophan, and tyrosine. Such amino acid substitution in the antibody mutant is preferably performed without reducing the antigen binding activity of the original antibody.

Aspartic acid contained in a protein is easily converted to isoaspartic acid by isomerization when an amino acid linked thereto on the C terminal side has a small side chain. On the other hand, asparagine is easily converted to aspartic acid by deamidation and may be further converted to isoaspartic acid by isomerization. The progression of such isomerization or deamidation may influence the stability of the protein. Accordingly, aspartic acid or asparagine in the protein or, for example, an amino acid adjacent thereto, can be substituted by a different amino acid in order to circumvent such isomerization or deamidation. Preferably, an antibody mutant having such amino acid substitution maintains the antigen binding activity of the original antibody.

The present invention also encompasses, for example: an antibody mutant having an amino acid sequence derived from the amino acid sequence of FR2-10, FR2-13, or FR2-14 of the present invention by conservative amino acid substitution; and a mouse antibody, a rat antibody, a chimeric antibody, a humanized antibody, or a human antibody comprising a CDR having an amino acid sequence in which a conservative amino acid mutation occurs in the amino acid sequence of any of CDRH1 to CDRH3 and CDRL1 to CDRL3 derived from FR2-10, FR2-13, or FR2-14.

The mutant of the antibody of the present invention encompasses a human FGFR2-binding antibody mutant comprising CDRH1 to CDRH3 and CDRL1 to CDRL3 having amino acid sequences derived from the amino acid sequences of any one or two or more of CDRH1 to CDRH3 and CDRL1 to CDRL3 derived from FR2-10, FR2-13, or FR2-14 of the present invention by the substitution of 1 to several, preferably 1 to 3, more preferably 1 or 2, most preferably 1 amino acid(s) by different amino acid(s).

Preferred examples of the mutant of FR2-14 can include an antibody comprising CDRH3 having an amino acid sequence derived from the CDRH3 amino acid sequence by the substitution of amino acid(s) by different amino acid(s).

Preferred examples of the mutant of FR2-14 in which amino acid(s) of heavy chain CDRH3 is substituted can include: a mutant with the first amino acid aspartic acid (amino acid at position 118 of SEQ ID NO: 51 (FIG. 59)) substituted by glutamic acid; a mutant with the second amino acid glycine (amino acid at position 119 of SEQ ID NO: 51 (FIG. 59)) substituted by tyrosine, alanine, tryptophan, valine, arginine, asparagine, methionine, leucine, lysine, isoleucine, histidine, phenylalanine, or glutamic acid; and a mutant with the 8th amino acid threonine substituted by alanine.

The antibody mutant also includes an antibody having CDRH1 to CDRH3 and CDRL1 to CDRL3 derived from a plurality of antibodies. Examples of such a mutant can include an antibody mutant comprising CDRH3 derived from a certain antibody and CDRH1, CDRH2, and CDRL1 to CDRL3 derived from another antibody.

The "antibody" according to the present invention also encompasses these antibody mutants.

The constant regions of the antibody of the present invention are not particularly limited. Preferably, constant regions derived from a human antibody are used in the antibody of the present invention for the treatment or prevention of a disease in a human. Examples of the heavy chain constant region of the human antibody can include Cγ1, Cγ2, Cγ3, Cγ4, Cμ, Cδ, Cα1, Cα2, and Cε. Examples of the light chain constant region of the human antibody can include Cκ and Cλ.

(3-8) Chimeric Antibody

The anti-FGFR2 chimeric antibody of the present invention or a functional fragment thereof has antitumor activity. Preferably, the anti-FGFR2 chimeric antibody of the present invention or the functional fragment thereof has antitumor activity in vivo. Also preferably, such a chimeric antibody or a functional fragment thereof specifically binds to the FGFR2 IIIb protein and/or the FGFR2 IIIc protein. More preferably, the chimeric antibody or functional fragment thereof binds to the Ig-like domains of these proteins. Preferably, such a chimeric antibody further has ADCC activity and/or ADCP activity. The chimeric antibody of the present invention or the functional fragment thereof also has neutralizing activity against FGFR2. Preferably, the chimeric antibody of the present invention or the functional fragment thereof has neutralizing activity against FGFR2 IIIb and/or FGFR2 IIIc. More preferably, the chimeric antibody of the present invention or the functional fragment thereof has neutralizing activity against FGFR2 IIIb and FGFR2 IIIc. Preferably, the chimeric antibody of the present invention or the functional fragment thereof further inhibits the binding of FGFR2 to its ligand.

The nucleotide sequence and amino acid sequence of the light chain of cFR2-10 exemplified as the rat-human chimeric antibody of the present invention and the nucleotide sequence and amino acid sequence of the heavy chain thereof are shown in SEQ ID NOs: 31, 32, 35, and 36 (FIGS. 39, 40, 43, and 44), respectively, of the Sequence Listing. Likewise, the nucleotide sequence and amino acid sequence of the light chain of cFR2-13 and the nucleotide sequence and amino acid sequence of the heavy chain thereof are shown in SEQ ID NOs: 39, 40, 43, and 44 (FIGS. 47, 48, 51, and 52), respectively, of the Sequence Listing. The nucleotide sequence and amino acid sequence of the light chain of cFR2-14 and the nucleotide sequence and amino acid sequence of the heavy chain thereof are shown in SEQ ID NOs: 47, 48, 50, and 51 (FIGS. 55, 56, 58, and 59), respectively, of the Sequence Listing. Nucleotide positions 1 to 60 in the nucleotide sequences of the light chains and amino acid positions 1 to 20 in the amino acid sequences of the light chains represent a signal sequence, which is usually not contained in the nucleotide sequences and amino acid sequences of most of mature light chains, respectively. Likewise, nucleotide positions 1 to 57 in the nucleotide sequences of the heavy chains and amino acid positions 1 to 19 in the amino acid sequences of the heavy chains represent a signal sequence, which is usually not contained in the nucleotide sequences and amino acid sequences of most of mature heavy chains, respectively.

(3-9) Functional Fragment of Antibody

According to one aspect, the present invention provides a functional fragment of the anti-FGFR2 antibody of the present invention. The functional fragment of the antibody means a fragment that maintains at least a portion of the functions of the antibody. Examples of such functions of the antibody can generally include antigen binding activity, antigen activity-regulating activity, antibody dependent cellular cytotoxic (ADCC) activity, and antibody dependent cell phagocytosis (ADCP) activity. Examples of the functions of the anti-FGFR2 antibody of the present invention can include FGFR2 protein binding activity, ADCC activity, ADCP activity, neutralizing activity against FGFR2, in vivo antitumor activity, and the activity of inhibiting the binding of FGFR2 to its ligand.

The functional fragment of the antibody is not particularly limited as long as the fragment of the antibody maintains at least a portion of the activities of the antibody. Examples thereof can include, but are not limited to, Fab, F(ab')2, Fv, single chain Fv (scFv) comprising heavy and light chain Fvs linked via an appropriate linker, diabodies, linear antibodies, multispecific antibodies formed from antibody fragments, and Fab', which is a monovalent fragment of antibody variable regions obtained by the treatment of F(ab')2 under reducing conditions. The functional fragment of the antibody of the present invention is also meant to include a molecule comprising the fragment of the antibody of the present invention as well as other portions, such as scFv retaining a linker portion.

A molecule that is derived from the antibody protein by the deletion of 1 to several or more amino acid(s) at its amino terminus and/or carboxy terminus and maintains at least a portion of the functions of the antibody is also encompassed in the meaning of the functional fragment of the antibody. For example, the heavy chain of an antibody produced by cultured mammalian cells is known to lack a lysine residue at the carboxy terminus (Journal of Chromatography A, 705: 129-134 (1995)). Also, the heavy chain of such an antibody is known to lack two amino acid residues (glycine and lysine) at the carboxy terminus and instead have an amidated proline residue at the carboxy terminus (Analytical Biochemistry, 360: 75-83 (2007)). The deletion and the modification in these heavy chain sequences, however, do not influence the ability of the antibody to bind to the antigen or its effector functions (complement activation, antibody dependent cytotoxic effects, etc.). Such a modified form of the functional fragment of the antibody is also encompassed by the antibody of the present invention or the functional fragment thereof, or a modified form (described later) of the antibody or functional fragment.

The antibody of the present invention or the functional fragment thereof may be a multispecific antibody having specificity for at least 2 types of different antigens. The multispecific antibody is not limited to a bispecific antibody, which binds to 2 types of different antigens, and an antibody having specificity for 3 or more types of different antigens is also encompassed in the meaning of the "multispecific antibody" of the present invention.

The multispecific antibody of the present invention may be a full-length antibody or a functional fragment thereof (e.g., bispecific F(ab')2 antibody). The bispecific antibody can also be prepared by linking the heavy and light chains (HL pairs) of two types of antibodies. Alternatively, the bispecific antibody may be obtained by fusing two or more types of monoclonal antibody-producing hybridomas to prepare bispecific antibody-producing fusion cells (Millstein et al., Nature (1983) 305, p. 537-539). The multispecific antibody can also be prepared in the same way as above.

According to one aspect, the antibody of the present invention is a single chain antibody (single chain Fv; hereinafter, referred to as "scFv"). The scFv is obtained by linking the heavy and light chain V regions of the antibody via a polypeptide linker (Pluckthun, The Pharmacology of Monoclonal Antibodies, 113, Rosenburg and Moore, ed., Springer Verlag, New York, p. 269-315 (1994); and Nature Biotechnology (2005), 23, p. 1126-1136). Also, bi-scFv comprising two scFvs linked via a polypeptide linker can be used as a bispecific antibody. Alternatively, multi-scFv comprising three or more scFvs may be used as a multispecific antibody.

The present invention includes a single chain immunoglobulin comprising full-length heavy and light chain sequences of the antibody linked via an appropriate linker (Lee, H-S, et al., Molecular Immunology (1999), 36, p. 61-71; and Shirrmann, T. et al., mAbs (2010), 2 (1) p. 1-4). Such a single chain immunoglobulin can be dimerized to thereby maintain a structure and activities similar to those of the antibody, which is originally a tetramer. Also, the antibody of the present invention may be an antibody that has a single heavy chain variable region and has no light chain sequence. Such an antibody, called a single domain antibody (sdAb) or a nanobody, has been reported to maintain the ability to bind to an antigen (Muyldemans S. et al., Protein Eng. (1994), 7 (9), 1129-35; and Hamers-Casterman C. et al., Nature (1993), 363 (6428), 446-8). These antibodies are also encompassed in the meaning of the functional fragment of the antibody according to the present invention.

(3-10) Humanized Antibody and Human Antibody

According to one aspect, the present invention provides a humanized antibody or a functional fragment thereof.

The anti-FGFR2 humanized antibody of the present invention or a functional fragment thereof has antitumor activity. Preferably, the anti-FGFR2 humanized antibody of the present invention or the functional fragment thereof has antitumor activity in vivo. Also preferably, such a humanized antibody or a functional fragment thereof specifically binds to the FGFR2 IIIb protein and/or the FGFR2 IIIc protein. More preferably, the humanized antibody or functional fragment thereof binds to the Ig-like domains of these proteins. Preferably, such a humanized antibody or a functional fragment thereof further has ADCC activity and/or ADCP activity. The humanized antibody of the present invention or the functional fragment thereof also has neutralizing activity against FGFR2. Preferably, the humanized antibody of the present invention or the functional fragment thereof has neutralizing activity against FGFR2 IIIb and/or FGFR2 IIIc. More preferably, the humanized antibody of the present invention or the functional fragment thereof has neutralizing activity against FGFR2 IIIb and FGFR2 IIIc. Preferably, the humanized antibody of the present invention or the functional fragment thereof further inhibits the binding of FGFR2 to its ligand.

Preferred examples of the humanized antibody of the present invention can include humanized antibodies having the heavy chain CDRH1 to CDRH3 and light chain CDRL1 to CDRL3 of the rat FR2-10 antibody, the rat FR2-13 antibody, or the rat FR2-14 antibody as described below in A to C.

(A. Humanized Antibody Having Heavy Chain CDRH1 to CDRH3 and Light Chain CDRL1 to CDRL3 of Rat FR2-10 Antibody)

Examples of the anti-FGFR2 humanized antibody of the present invention or a functional fragment thereof can include a humanized antibody that consists of a heavy chain having a variable region comprising CDRH1 consisting of the amino acid sequence represented by SEQ ID NO: 52 (FIG. 60) of the Sequence Listing, CDRH2 consisting of the amino acid sequence represented by SEQ ID NO: 53 (FIG. 61) of the Sequence Listing, and CDRH3 consisting of the amino acid sequence represented by SEQ ID NO: 54 (FIG. 62) of the Sequence Listing, and a light chain having a variable region comprising CDRL1 consisting of the amino acid sequence represented by SEQ ID NO: 61 (FIG. 69) of the Sequence Listing, CDRL2 consisting of the amino acid sequence represented by SEQ ID NO: 62 (FIG. 70) of the Sequence Listing, and CDRL3 consisting of the amino acid sequence represented by SEQ ID NO: 63 (FIG. 71) of the Sequence Listing, and that recognizes the FGFR2 protein of the present invention, and a fragment of the antibody that maintains the FGFR2 protein binding activity of the antibody, and mutants of the antibody or the fragment.

(B. Humanized Antibody Having Heavy Chain CDRH1 to CDRH3 and Light Chain CDRL1 to CDRL3 of Rat FR2-13 Antibody)

Alternative examples of the anti-FGFR2 humanized antibody or a functional fragment thereof can include a humanized antibody that consists of a heavy chain having a variable region comprising CDRH1 consisting of the amino acid sequence represented by SEQ ID NO: 55 (FIG. 63) of the Sequence Listing, CDRH2 consisting of the amino acid sequence represented by SEQ ID NO: 56 (FIG. 64) of the Sequence Listing, and CDRH3 consisting of the amino acid sequence represented by SEQ ID NO: 57 (FIG. 65) of the Sequence Listing, and a light chain having a variable region comprising CDRL1 consisting of the amino acid sequence represented by SEQ ID NO: 64 (FIG. 72) of the Sequence Listing, CDRL2 consisting of the amino acid sequence represented by SEQ ID NO: 65 (FIG. 73) of the Sequence Listing, and CDRL3 consisting of the amino acid sequence represented by SEQ ID NO: 66 (FIG. 74) of the Sequence Listing, and that recognizes the FGFR2 protein of the present invention, and a fragment of the antibody that maintains the FGFR2 protein binding activity of the antibody, and mutants thereof.

(C. Humanized Antibody Having Heavy Chain CDRH1 to CDRH3 and Light Chain CDRL1 to CDRL3 of Rat FR2-14 Antibody)

Alternative examples of the anti-FGFR2 humanized antibody or a functional fragment thereof can include a humanized antibody that consists of a heavy chain having a variable region comprising CDRH1 consisting of the amino acid sequence represented by SEQ ID NO: 58 (FIG. 66) of the Sequence Listing, CDRH2 consisting of the amino acid sequence represented by SEQ ID NO: 59 (FIG. 67) of the Sequence Listing, and CDRH3 consisting of the amino acid sequence represented by SEQ ID NO: 60 (FIG. 68) of the Sequence Listing, and a light chain having a variable region comprising CDRL1 consisting of the amino acid sequence represented by SEQ ID NO: 67 (FIG. 75) of the Sequence Listing, CDRL2 consisting of the amino acid sequence represented by SEQ ID NO: 68 (FIG. 76) of the Sequence Listing, and CDRL3 consisting of the amino acid sequence represented by SEQ ID NO: 69 (FIG. 77) of the Sequence Listing, and that recognizes the FGFR2 protein of the present invention, and a fragment of the antibody that maintains the FGFR2 protein binding activity of the antibody, and mutants thereof.

The preferred humanized antibody of the present invention is not limited to those described above in A to C. The humanized antibody is more preferably a humanized FR2-14 antibody and its mutants. Examples thereof include, but are not limited to, hFR2-14_H1/L1 to hFR2-14_H19/L1. The more preferred humanized antibody of the present invention also includes, for example, an antibody comprising a heavy chain comprising the heavy chain variable region of any one of the humanized antibodies hFR2-14_H1/L1 to hFR2-14_H19/L1, and a light chain comprising the light chain variable region of any one of the humanized antibodies hFR2-14_H1/L1 to hFR2-14_H19/L1.

hFR2-14_H1/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 74 (FIG. 82), and its amino acid sequence comprises amino acid positions 20 to 467 of SEQ ID NO: 75 (FIG. 83). The antibody was excellent in conformational stability because of its high Tm value and had high binding activity against FGFR2, FGFR2 ligand dependent FGFR2 signal-neutralizing activity, ADCC activity, and in vivo antitumor activity (see Examples).

hFR2-14_H2/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 76 (FIG. 84), and its amino acid sequence comprises amino acid positions 20 to 467 of SEQ ID NO: 77 (FIG. 85). The antibody was excellent in conformational stability because of its high Tm value and had high binding activity against FGFR2, FGFR2 ligand dependent FGFR2 signal-neutralizing activity, ADCC activity, and in vivo antitumor activity (see Examples).

hFR2-14_H3/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 78 (FIG. 86), and its amino acid sequence comprises amino acid positions 20 to 467 of SEQ ID NO: 79 (FIG. 87). The antibody was excellent in conformational stability because of its high Tm value and had high binding activity against FGFR2, FGFR2 ligand dependent FGFR2 signal-neutralizing activity, ADCC activity, and in vivo antitumor activity (see Examples).

hFR2-14_H4/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 80 (FIG. 88), and its amino acid sequence comprises amino acid positions 20 to 467 of SEQ ID NO: 81 (FIG. 89). The antibody was excellent in conformational stability because of its high Tm value and had high binding activity against FGFR2, FGFR2 ligand dependent FGFR2 signal-neutralizing activity, ADCC activity, and in vivo antitumor activity (see Examples).

hFR2-14_H5/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 82 (FIG. 90), and its amino acid sequence comprises amino acid positions 20 to 467 of SEQ ID NO: 83 (FIG. 91). The antibody was excellent in conformational stability because of its high Tm value, had high binding activity against FGFR2, excellent thermal stability, FGFR2 ligand dependent FGFR2 signal-neutralizing activity, and in vivo antitumor activity, and maintained its high antigen binding activity even when exposed to severe conditions (see Examples).

hFR2-14_H6/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 84 (FIG. 92), and its amino acid sequence comprises amino acid positions 20 to 467 of SEQ ID NO: 85 (FIG. 93). The antibody was excellent in conformational stability because of its high Tm value and had high binding activity against FGFR2 and FGFR2 ligand dependent FGFR2 signal-neutralizing activity (see Examples).

hFR2-14_H7/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 86 (FIG. 94), and its amino acid sequence comprises amino acid positions 20 to 467 of SEQ ID NO: 87 (FIG. 95). The antibody was excellent in conformational stability because of its high Tm value and had high binding activity against FGFR2 and FGFR2 ligand dependent FGFR2 signal-neutralizing activity (see Examples).

hFR2-14_H8/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 88 (FIG. 96), and its amino acid sequence comprises amino acid positions 20 to 467 of SEQ ID NO: 89 (FIG. 97). The antibody was excellent in conformational stability because of its high Tm value, had high binding activity against FGFR2, excellent thermal stability, FGFR2 ligand dependent FGFR2 signal-neutralizing activity, ADCC activity, and in vivo antitumor activity, and maintained its high antigen binding activity even when exposed to severe conditions (see Examples).

hFR2-14_H9/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 90 (FIG. 98), and its amino acid sequence comprises amino acid positions 20 to 467 of SEQ ID NO: 91 (FIG. 99). The antibody was excellent in conformational stability because of its high Tm value and had high binding activity against FGFR2, excellent thermal stability, FGFR2 ligand dependent FGFR2 signal-neutralizing activity, and in vivo antitumor activity (see Examples).

hFR2-14_H10/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 92 (FIG. 100), and its amino acid sequence comprises amino acid positions 20 to 467 of SEQ ID NO: 93 (FIG. 101). The antibody was excellent in conformational stability because of its high Tm value and had high binding activity against FGFR2 and FGFR2 ligand dependent FGFR2 signal-neutralizing activity (see Examples).

hFR2-14_H11/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 94 (FIG. 102), and its amino acid sequence comprises amino acid positions 20 to 467 of SEQ ID NO: 95 (FIG. 103). The antibody was excellent in conformational stability because of its high Tm value, had high binding activity against FGFR2, excellent thermal stability, FGFR2 ligand dependent FGFR2 signal-neutralizing activity, ADCC activity, and in vivo antitumor activity, and maintained its high antigen binding activity even when exposed to severe conditions (see Examples).

hFR2-14_H12/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 96 (FIG. 104), and its amino acid sequence comprises amino acid positions 20 to 467 of SEQ ID NO: 97 (FIG. 105). The antibody was excellent in conformational stability because of its high Tm value, had high binding activity against FGFR2, excellent thermal stability, FGFR2 ligand dependent FGFR2 signal-neutralizing activity, ADCC activity, ADCP activity, the activity of inhibiting the binding of an FGFR2 ligand to FGFR2, and in vivo antitumor activity, and maintained its high antigen binding activity even when exposed to severe conditions (see Examples).

hFR2-14_H13/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 98 (FIG. 106), and its amino acid sequence comprises amino acid positions 20 to 467 of SEQ ID NO: 99 (FIG. 107). The antibody was excellent in conformational stability because of its high Tm value and had high binding activity against FGFR2 and FGFR2 ligand dependent FGFR2 signal-neutralizing activity (see Examples).

hFR2-14_H14/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 100 (FIG. 108), and its amino acid sequence comprises amino acid positions 20 to 467 of SEQ ID NO: 101 (FIG. 109). The antibody was excellent in conformational stability because of its high Tm value and had high binding activity against FGFR2 and FGFR2 ligand dependent FGFR2 signal-neutralizing activity (see Examples).

hFR2-14_H15/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 102 (FIG. 110), and its amino acid sequence comprises amino acid positions 20 to 467 of SEQ ID NO: 103 (FIG. 111). The antibody was excellent in conformational stability because of its high Tm value and had high binding activity against FGFR2 and FGFR2 ligand dependent FGFR2 signal-neutralizing activity (see Examples).

hFR2-14_H16/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 104 (FIG. 112), and its amino acid sequence comprises amino acid positions 20 to 467 of SEQ ID NO: 105 (FIG. 113). The antibody was excellent in conformational stability because of its high Tm value and had high binding activity against FGFR2 and FGFR2 ligand dependent FGFR2 signal-neutralizing activity (see Examples).

hFR2-14_H17/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 106 (FIG. 114), and its amino acid sequence comprises amino acid positions 20 to 467 of SEQ ID NO: 107 (FIG. 115). The antibody was excellent in conformational stability because of its high Tm value and had high binding activity against FGFR2 and FGFR2 ligand dependent FGFR2 signal-neutralizing activity (see Examples).

hFR2-14_H18/L1 is a humanized antibody obtained in Example 8. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 108 (FIG. 116), and its amino acid sequence comprises amino acid positions 20 to 467 of SEQ ID NO: 109 (FIG. 117). The antibody was excellent in conformational stability because of its high Tm value and had high binding activity against FGFR2, FGFR2 ligand dependent FGFR2 signal-neutralizing activity, ADCC activity, and in vivo antitumor activity (see Examples).

hFR2-14_H19/L1 is a humanized antibody with regulated sugar chain modification obtained in Example 9. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 96 (FIG. 104), and its amino acid sequence comprises amino acid positions 20 to 467 of SEQ ID NO: 97 (FIG. 105). The antibody was excellent in conformational stability because of its high Tm value, had high binding activity against FGFR2, excellent thermal stability, FGFR2 ligand dependent FGFR2 signal-neutralizing activity, ADCC activity, ADCP activity, the activity of inhibiting the binding of an FGFR2 ligand to FGFR2, and in vivo antitumor activity, and maintained its high antigen binding activity even when exposed to severe conditions (see Examples).

These humanized FR2-14 antibodies were not found to cause weight loss or other significant toxic events, when administered to mice. The hFR2-14_H12/L1 antibody and the hFR2-14_H19/L1 antibody were administered at a single dose of approximately 150 mg/kg to each cynomolgus monkey and observed 14 days later. As a result, significant clinical findings, hematological change, weight loss, or other significant toxic events were not observed. Thus, the humanized antibody of the present invention possesses excellent safety as a pharmaceutical composition for treatment or prevention of a disease.

Among the more preferred humanized antibodies hFR2-14_H1/L1 to hFR2-14_H19/L1 of the present invention, the antibody is even more preferably hFR2-14_H5/L1, hFR2-14_H11/L1, hFR2-14_H8/L1, hFR2-14_H12/L1, or hFR2-14_H19/L1, further more preferably hFR2-14_H12/L1 or hFR2-14_H19/L1.

The present invention also encompasses an antibody that comprises a heavy or light chain comprising an amino acid sequence having 80% or higher, 82% or higher, 84% or higher, 86% or higher, 88% or higher, 90% or higher, 92% or higher, 94% or higher, 96% or higher, 98% or higher, or 99% or higher identity to the amino acid sequence of the heavy or light chain of any one of the rat FR2-10, FR-10FR, and FR2-14 antibodies, the chimeric cFR2-10, cFR2-13, and cFR2-14 antibodies, and the humanized hFR2-14_H1/L1 to hFR2-14_H19/L1 antibodies of the present invention and binds to FGFR2, or a functional fragment thereof. Such sequence identity is preferably 94% or higher, more preferably 96% or higher, even more preferably 98% or higher, most preferably 99% or higher. Preferably, these antibodies have one or more of the activities described in paragraphs (3-3) to (3-6).

The identity or homology between two types of amino acid sequences can be determined using the default parameter of Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm is also available, for example, by Internet access at last.ncbi.nlm.nih.gov.

The present invention also encompasses an antibody that comprises a heavy or light chain comprising an amino acid sequence derived from the amino acid sequence of the heavy or light chain of any one of the rat FR2-10, FR-10FR, and FR2-14 antibodies, the chimeric cFR2-10, cFR2-13, and cFR2-14 antibodies, and the humanized hFR2-14_H1/L1 to hFR2-14_H19/L1 antibodies of the present invention by the substitution, deletion, addition, or insertion of 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and binds to the FGFR2 protein, or a functional fragment thereof. Such an amino acid mutation is preferably substitution. The number of mutated amino acids is preferably 1 to 5, more preferably 1 to 4, even more preferably 1 to 3, further more preferably 1 or 2, most preferably 1. Preferably, these antibodies have one or more of the activities described in paragraphs (3-3) to (3-6).

The present invention also encompasses an antibody that comprises a heavy or light chain comprising an amino acid sequence encoded by the nucleotide sequence of a nucleotide hybridizing under stringent conditions to a nucleotide having a nucleotide sequence complementary to a nucleotide sequence encoding the amino acid sequence of the heavy or light chain of any one of the rat FR2-10, FR-10FR, and FR2-14 antibodies, the chimeric cFR2-10, cFR2-13, and cFR2-14 antibodies, and the humanized hFR2-14_H1/L1 to hFR2-14_H19/L1 antibodies of the present invention and binds to the FGFR2 protein, or a functional fragment thereof. Preferably, these antibodies have one or more of the activities described in paragraphs (3-3) to (3-6).

According to an alternative aspect, the present invention provides a human antibody or a functional fragment thereof. The human antibody of the present invention is not particularly limited as long as the antibody is derived from a human and binds to FGFR2. The human antibody of the present invention or a functional fragment thereof has antitumor activity, preferably in vivo antitumor activity. Also preferably, such a human antibody or a functional fragment thereof specifically binds to the FGFR2 IIIb protein and/or the FGFR2 IIIc protein. More preferably, the human antibody or functional fragment thereof binds to the Ig-like domains of these proteins. Preferably, such a human antibody or a functional fragment thereof further has ADCC activity and/or ADCP activity. The human antibody of the present invention or the functional fragment thereof also has neutralizing activity against FGFR2. Preferably, the human antibody of the present invention or the functional fragment thereof has neutralizing activity against FGFR2 IIIb and/or FGFR2 IIIc. More preferably, the human antibody of the present invention or the functional fragment thereof has neutralizing activity against FGFR2 IIIb and FGFR2 IIIc. Preferably, the human antibody of the present invention or the functional fragment thereof further inhibits the binding of FGFR2 to its ligand.

(3-11) Antibody Binding to Epitope

An "antibody binding to the same site" as in the case of the antibody provided by the present invention is also included in the antibody of the present invention. The "antibody binding to the same site" as in the case of a certain antibody means another antibody that binds to a site on an antigen molecule recognized by the antibody. If a second antibody binds to a partial peptide or a partial three-dimensional structure on an antigen molecule bound by a first antibody, the first and second antibodies are determined as binding to the same site. Alternatively, the first and second antibodies are determined as binding to the same site by confirming that the second antibody competes with the first antibody for binding to the antigen, i.e., the second antibody interferes with the binding of the first antibody to the antigen, even if the peptide sequence or three-dimensional structure of the specific binding site is not determined. When the first and second antibodies bind to the same site and the first antibody has an effect characteristic of one aspect of the antibody of the present invention, such as an antitumor activity, the second antibody also has an exceedingly high probability of having the same activity thereas. Thus, if a second anti-FGFR2 antibody binds to a site bound by a first anti-FGFR2 antibody, the first and second antibodies are determined as binding to the same site on the FGFR2 protein. Alternatively, the first and second anti-FGFR2 antibodies are determined as binding to the same site on the FGFR2 protein by confirming that the second anti-FGFR2 antibody competes with the first anti-FGFR2 antibody for binding to the FGFR2 protein.

The present invention also encompasses an antibody binding to a site on the FGFR2 protein recognized by the monoclonal antibody FR2-10, FR2-13, or FR2-14 of the present invention.

The antibody binding site can be determined by a method well known by those skilled in the art, such as immunoassay. For example, a series of peptides are prepared by appropriately sequentially cleaving the amino acid sequence of the antigen from its C terminus or N terminus, and the reactivity of the antibody thereto is studied to roughly determine a recognition site. Then, shorter peptides are synthesized, and the reactivity of the antibody to these peptides can be studied to thereby determine the binding site. The antigen fragment peptides can be prepared using a technique such as gene recombination or peptide synthesis.

When the antibody binds to or recognizes the partial conformation of the antigen, the binding site for the antibody can be determined by identifying amino acid residues on the antigen adjacent to the antibody using X-ray structural analysis. For example, the antibody or its fragment and the antigen or its fragment can be bound to each other and crystallized, followed by structural analysis to identify each amino acid residue on the antigen having an interaction distance with the antibody. The interaction distance is 8 angstroms or shorter, preferably 6 angstroms or shorter, more preferably 4 angstroms or shorter. One or more such amino acid residues having an interaction distance with the antibody can constitute a site (epitope) on the antigen to which the antibody binds. Two or more such amino acid residues may not be adjacent to each other on the primary sequence.

The Fab fragment of the rat, chimeric, or humanized FR2-14 antibody and the D2 fragment (peptide consisting of amino acid positions 128 to 249 of SEQ ID NO: 70 (FIG. 78)) of human FGFR2 IIIb are bound to each other and crystallized under conditions involving 1.1 to 2.1 M ammonium sulfate-0.15 M Tris-HCl buffer solution (pH 6.5 to 8.5) to obtain crystals in the tetragonal system with a space group of P41212 and unit cells of a=b=60.57 angstroms and c=331.2 angstroms. A molecular replacement method can be performed using the three-dimensional structure coordinates thereof to determine a phase (see Example 15).

The rat, chimeric, or humanized FR2-14 antibody recognizes partial conformation on human FGFR2 IIIb. The epitope for this antibody is constituted by tyrosine (Tyr) at residue 155, threonine (Thr) at residue 157, lysine (Lys) at residue 176, alanine (Ala) at residue 181, glycine (Gly) at residue 182, glycine (Gly) at residue 183, asparagine (Asn) at residue 184, proline (Pro) at residue 185, methionine (Met) at residue 186, threonine (Thr) at residue 188, glutamine (Gln) at residue 200, glutamic acid (Glu) at residue 201, glycine (Gly) at residue 205, glycine (Gly) at residue 206, lysine (Lys) at residue 208, valine (Val) at residue 209, arginine (Arg) at residue 210, asparagine (Asn) at residue 211, glutamine (Gln) at residue 212, histidine (His) at residue 213, tryptophan (Trp) at residue 214, and isoleucine (Ile) at residue 217 in the amino acid sequence (SEQ ID NO: 70; FIG. 78) of human FGFR2 IIIb or the amino acid sequence (SEQ ID NO: 71; FIG. 79) of human FGFR2 IIIc. In other words, this antibody has an interaction distance with each of tyrosine (Tyr) at residue 155, threonine (Thr) at residue 157, lysine (Lys) at residue 176, alanine (Ala) at residue 181, glycine (Gly) at residue 182, glycine (Gly) at residue 183, asparagine (Asn) at residue 184, proline (Pro) at residue 185, methionine (Met) at residue 186, threonine (Thr) at residue 188, glutamine (Gln) at residue 200, glutamic acid (Glu) at residue 201, glycine (Gly) at residue 205, glycine (Gly) at residue 206, lysine (Lys) at residue 208, valine (Val) at residue 209, arginine (Arg) at residue 210, asparagine (Asn) at residue 211, glutamine (Gin) at residue 212, histidine (His) at residue 213, tryptophan (Trp) at residue 214, and isoleucine (Ile) at residue 217 in the amino acid sequence (SEQ ID NO: 70; FIG. 78) of human FGFR IIIb or the amino acid sequence (SEQ ID NO: 71; FIG. 79) of human FGFR2 IIIc. The epitope site for this antibody is also found in the amino acid sequence of human FGFR2 IIIc. The antibody of the present invention or the functional fragment thereof, or a modified form of the antibody or functional fragment also encompasses an antibody binding to this epitope or having an interaction distance with these amino acid residues, a functional fragment thereof, or a modified form of the antibody or functional fragment.

(3-12) Modified Form of Antibody

The present invention provides a modified form of the antibody or functional fragment thereof. The modified form of the antibody of the present invention or the functional fragment thereof means an antibody of the present invention or a functional fragment thereof provided with chemical or biological modification. The chemically modified form includes, for example, a form having an amino acid skeleton conjugated with a chemical moiety, and a form having a chemically modified N-linked or O-linked carbohydrate chain. The biologically modified form includes, for example, a form that has undergone post-translational modification (e.g., N-linked or O-linked glycosylation, N-terminal or C-terminal processing, deamidation, isomerization of aspartic acid, or oxidation of methionine), and a form containing a methionine residue added to the N-terminus by expression using prokaryotic host cells. Such a modified form is also meant to include a form labeled to permit detection or isolation of the antibody or the antigen of the present invention, for example, an enzyme-labeled form, a fluorescently labeled form, or an affinity-labeled form. Such a modified form of the antibody of the present invention or the functional fragment thereof is useful for improvement of the stability or blood retention of the original antibody of the present invention or the original functional fragment thereof, reduction in antigenicity, detection or isolation of the antibody or the antigen, etc.

Examples of the chemical moiety contained in the chemically modified form can include water-soluble polymers such as polyethylene glycol, ethylene glycol/propylene glycol copolymers, carboxymethylcellulose, dextran, and polyvinyl alcohol.

Examples of the biologically modified form can include a form modified by enzymatic treatment, cell treatment, or the like, a form fused with another peptide, such as a tag, added by gene recombination, and a form prepared from host cells expressing an endogenous or exogenous sugar chain-modifying enzyme.

The antibody dependent cellular cytotoxic activity of the antibody of the present invention or the functional fragment thereof may be enhanced by regulating the modification (glycosylation, defucosylation, etc.) of the sugar chain bound with the antibody or functional fragment. For example, methods described in WO99/54342, WO00/61739, and WO02/31140 are known as such a technique of regulating the sugar chain modification of the antibody, though this technique is not limited thereto. The modified form of the antibody of the present invention also includes an antibody that has undergone the sugar chain modification thus regulated.

Such a modification may be made at an arbitrary position or a desired position in the antibody or functional fragment thereof. Alternatively, the same or two or more different modifications may be made at one or two or more positions therein.

In the present invention, the "modified form of the antibody fragment" is also meant to include even a "fragment of the modified form of the antibody".

In the present invention, the modified form of the antibody or the modified form of the functional fragment thereof is also simply referred to as an "antibody" or a "functional fragment of the antibody".

hFR2-14_H19/L1 is a humanized antibody with regulated sugar chain modification obtained in Example 9. The nucleotide sequence of the light chain of this antibody comprises nucleotide positions 61 to 705 of SEQ ID NO: 72 (FIG. 80), and its amino acid sequence comprises amino acid positions 21 to 235 of SEQ ID NO: 73 (FIG. 81). The nucleotide sequence of the heavy chain of this antibody comprises nucleotide positions 58 to 1401 of SEQ ID NO: 96 (FIG. 104), and its amino acid sequence comprises amino acid positions 20 to 467 of SEQ ID NO: 97 (FIG. 105). Such a humanized antibody is also encompassed by the antibody of the present invention or the modified form of the antibody of the present invention.

4. Method for Producing Antibody (4-1) Method Using Hybridoma

In order to prepare the anti-FGFR2 antibody of the present invention, anti-FGFR2 antibody-producing cells are isolated from the spleens of animals immunized with the FGFR2 protein or its soluble form according to the method of Kohler and Milstein (Kohler and Milstein, Nature (1975), 256, p. 495-497; and Kennet, R. ed., Monoclonal Antibodies, p. 365-367, Plenum Press, N.Y. (1980)). The cells are fused with myeloma cells to thereby establish hybridomas. Monoclonal antibodies can be obtained from cultures of these hybridomas.

(4-1-1) Preparation of Antigen

The antigen for the preparation of the anti-FGFR2 antibody can be obtained according to, for example, the method for preparing a native or recombinant FGFR2 protein described in other paragraphs of the present specification. Examples of the antigen that may be thus prepared can include the FGFR2 protein and an FGFR2 protein fragment comprising a partial sequence with at least 6 consecutive amino acids of the FGFR2 protein, and their derivatives further comprising an arbitrary amino acid sequence or carrier added thereto (hereinafter, collectively referred to as an "FGFR2 antigen").

The recombinant FGFR2 antigen can be prepared by transfecting host cells with a gene comprising a nucleotide sequence encoding the amino acid sequence of the FGFR2 antigen, and recovering the antigen from cultures of the cells. Such a recombinant antigen may be a fusion protein with another protein such as an immunoglobulin Fc region. An FGFR2 antigen obtained in a cell-free in vitro translation system from a gene comprising a nucleotide sequence encoding the amino acid sequence of the FGFR2 antigen is also included in the recombinant FGFR2antigen. The non-recombinant FGFR2 antigen can be purified or isolated from FGFR2- expressing normal tissues, cancer tissues, or cancer cells, cultures of the cancer cells, or the like described in (iv) of paragraph (2-1).

(4-1-2) Production of Anti-FGFR2 Monoclonal Antibody

The monoclonal antibody is typically produced through the following steps:

(a) preparing an antigen,
(b) preparing antibody-producing cells,
(c) preparing myeloma cells (hereinafter, referred to as "myelomas"),
(d) fusing the antibody-producing cells with the myelomas,
(e) screening for a hybridoma group producing the antibody of interest, and
(f) obtaining single cell clones (cloning).

This production method further involves (g) a step of culturing the hybridomas, a step of raising hybridoma-transplanted animals, etc., and (h) a step of assaying or determining the biological activity of the monoclonal antibody, etc., if necessary.

Hereinafter, the method for preparing the monoclonal antibody will be described in detail with reference to these steps. However, the method for preparing the antibody is not limited to those steps, and, for example, antibody-producing cells other than spleen cells and myelomas may be used.

(a) Purification of Antigen

This step is performed according to the method for preparing the FGFR2 protein described above in (2-3).

(b) Step of Preparing Antibody-Producing Cell

The antigen obtained in step (a) is mixed with an adjuvant such as a complete or incomplete Freund's adjuvant or potassium aluminum sulfate, and laboratory animals are immunized with the resulting immunogen. Any laboratory animal used in a hybridoma preparation method known in the art can be used without limitations. Specifically, for example, mice, rats, goats, sheep, cattle, or horses can be used. From the viewpoint of readily available myeloma cells to be fused with isolated antibody-producing cells, etc., the animals to be immunized are preferably mice or rats.

The strain of mice or rats actually used is not particularly limited. In the case of mice, for example, A, AKR, BALB/c, BALB/cAnNCrj, BDP, BA, CE, C3H, 57BL, C57BL, C57L, DBA, FL, HTH, HT1, LP, NZB, NZW, RF, R III, SJL, SWR, WB, or 129 can be used. In the case of rats, for example, Wistar, Low, Lewis, Sprague-Dawley, ACI, BN, or Fischer can be used.

These mice and rats are available from laboratory animal breeders or distributors, for example, CLEA Japan, Inc. or Charles River Laboratories Japan Inc.

Of those mice and rats, a BALB/c mouse strain or Wistar and Low rat strains are particularly preferred as animals to be immunized in consideration of fusion compatibility with the myeloma cells described later.

Also, in consideration of the homology between human and mouse antigens, mice whose biological mechanism to remove autoantibodies has been reduced, i.e., autoimmune disease mice, are also preferably used.

In this context, these mice or rats are preferably 5 to 12 weeks old, more preferably 6 to 8 weeks old, at the time of immunization.

The animals can be immunized with the FGFR2 protein using, for example, the method of Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Spigfield, Ill. (1964).

Examples of methods for determining antibody titers can include, but are not limited to, immunoassay such as RIA and ELISA.

Antibody-producing cells derived from spleen cells or lymphocytes separated from the immunized animals, can be prepared according to a method known in the art, for example, Kohler et al., Nature (1975) 256, p. 495; Kohler et al., Eur. J. Immnol. (1977) 6, p. 511; Milstein et al., Nature (1977), 266, p. 550; Walsh, Nature, (1977) 266, p. 495.

In the case of spleen cells, a general method can be adopted, which involves chopping the spleens, filtering cells through a stainless mesh, and then floating the resulting cells in an Eagle's minimum essential medium (MEM) or the like, to separate antibody-producing cells.

(c) Step of Preparing Myeloma

The myeloma cells used in cell fusion are not particularly limited and can be selected appropriately for use from cell lines known in the art. For example, a hypoxanthine-guanine phosphoribosyl transferase (HGPRT)-deficient line, i.e., mouse-derived X63-Ag8 (X63), NS1-ANS/1 (NS1), P3X63-Ag8.U1 (P3U1), X63-Ag8.653 (X63.653), SP2/0-Ag14 (SP2/0), MPC11-45.6TG1.7 (45.6TG), FO, S149/5XXO, or BU.1, rat-derived 210.RSY3.Ag.1.2.3 (Y3), or human-derived U266AR (SKO-007), GM1500-GTG-A12 (GM1500), UC729-6, LICR-LOW-HMy2 (HMy2), or 8226AR/NIP4-1 (NP41), whose screening procedures have already been established, is preferably used in consideration of convenience in the selection of hybridomas from fusion cells. These HGPRT-deficient lines are available from, for example, American Type Culture Collection (ATCC).

These cell lines are subcultured in an appropriate medium, for example, an 8-azaguanine medium [RPMI-1640 medium supplemented with glutamine, 2-mercaptoethanol, gentamicin, and fetal bovine serum (hereinafter, referred to as "FBS") and further supplemented with 8-azaguanine], an Iscove's modified Dulbecco's medium (hereinafter, referred to as "IMDM"), or a Dulbecco's modified Eagle medium (hereinafter, referred to as "DMEM") and subcultured in a normal medium [e.g., ASF104 medium (manufactured by Ajinomoto Co., Inc.) containing 10% FBS] 3 to 4 days before cell fusion to secure that the number of cells is equal to or greater than $2 \times 10^7$ cells on the day of cell fusion.

(d) Step of Fusing Antibody-Producing Cell with Myeloma Cell

The antibody-producing cells can be fused with the myeloma cells under conditions that prevent cell viability from being exceedingly reduced, according to any method known in the art (e.g., Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Spigfield, Ill. (1964)). For example, a chemical method which involves mixing antibody-producing cells with myeloma cells in a high-concentration solution of a polymer such as polyethylene glycol, or a physical method using electric stimulation can be used.

(e) Step of Screening for Hybridoma Group Producing Antibody of Interest

A method for selection from the hybridomas obtained by cell fusion is not particularly limited, and a hypoxanthine-aminopterin-thymidine (HAT) selection method (Kohler et al., Nature (1975) 256, p. 495; Milstein et al., Nature (1977) 266, p. 550) is typically used. This method is effective for obtaining hybridomas using an HGPRT-deficient myeloma cell line, which cannot survive in the presence of aminopterin. Specifically, unfused cells and hybridomas can be cultured in a HAT medium to thereby allow only hybridomas resistant to aminopterin to selectively live and grow.

(f) Step of Obtaining Single Cell Clone (Cloning)

The hybridomas can be cloned using any method known in the art, for example, a methylcellulose, soft agarose, or limiting dilution method (see e.g., Barbara, B. M. and Stanley, M. S.: Selected Methods in Cellular Immunology, W.H. Freeman and Company, San Francisco (1980)). The limiting dilution method is preferred.

(g) Step of Culturing Hybridoma and Step of Raising Hybridoma-Transplanted Animal The selected hybridomas can be cultured to thereby produce monoclonal antibodies. Preferably, the desired hybridomas are cloned and then subjected to antibody production.

The monoclonal antibody produced by such a hybridoma can be recovered from cultures of the hybridoma. Also, a recombinant antibody can be recovered from cultures of cells transfected with the monoclonal antibody gene. Alternatively, the hybridoma may be injected intraperitoneally to mice of the same strain (e.g., BALB/cAnNCrj described above) or Nu/Nu mice and allowed to grow. Then, the monoclonal antibody can be recovered from their ascites.

(h) Step of Assaying or Determining Biological Activity of Monoclonal Antibody

Various biological tests can be selected and applied thereto according to the purpose.

(4-2) Cell Immunization Method

Cells expressing the native FGFR2 protein, cells expressing the recombinant FGFR2 protein or its fragment, or the like, can be used as immunogens to thereby prepare an anti-FGFR2 antibody by the hybridoma method described above.

Examples of the cells expressing the native FGFR2 protein can include FGFR2-expressing cells, cell lines derived from FGFR2-expressing tissues or cancer, and cell lines derived from cancer tissues in which switching from FGFR2 IIIb to FGFR2 IIIc expression is seen. Cancer highly expressing FGFR2 includes: cancers found to have gene amplification, such as stomach cancer and breast cancer; and cancers found to have overexpression, such as pancreatic cancer and ovary cancer. Examples of cultured cell lines highly expressing FGFR2 IIIb can include stomach cancer cell lines and breast cancer cell lines. Examples of cultured cell lines highly expressing FGFR2 IIIc can include colorectal (cecal) cancer cell lines. Examples of the cancer tissues in which switching from FGFR2 IIIb to FGFR2 IIIc expression is seen can include tissues of prostate cancer, urinary bladder cancer, and breast cancer. Examples of the cancer tissues expressing FGFR2 IIIc can include tissues of uterine cervix cancer and non-small cell lung cancer. Of these cancers, uterine cervix cancer highly expresses FGFR2 IIIc. Examples of the normal tissues highly expressing FGFR2 can include the brain, the large intestine, thyroid glands, the uterine, the gallbladder, and the skin.

These FGFR2-expressing cells are used in an amount of $1 \times 10^5$ to $1 \times 10^9$ cells, preferably $1 \times 10^6$ to $1 \times 10^8$ cells, more preferably 0.5 to $2 \times 10^7$ cells, even more preferably $1 \times 10^7$ cells, per immunization shot. The number of cells used for immunization can be changed according to the expression level of the FGFR2 protein. The immunogens are generally administered intraperitoneally and may be administered through an intradermal route or the like. The hybridomas can be prepared by the application of the method described in paragraph (4-1-2).

(4-3) Gene Recombination

In order to prepare the antibody of the present invention, a nucleotide (heavy chain nucleotide) comprising a nucleotide sequence encoding the amino acid sequence of its heavy chain and a nucleotide (light chain nucleotide) comprising a nucleotide sequence encoding the amino acid sequence of its light chain, or a vector having an insert of the heavy chain nucleotide and a vector having an insert of the light chain nucleotide are introduced into host cells, and then the cells are cultured, and the antibody can be recovered from the cultures. The heavy chain nucleotide and the light chain nucleotide may be inserted in one vector.

Prokaryotic or eukaryotic cells can be used as the host cells. In the case of using host eukaryotic cells, animal cells, plant cells, or eukaryotic microbes can be used.

Examples of the animal cells can include mammal-derived cells, i.e., monkey-derived COS cells (Gluzman, Y. Cell (1981), 23, p. 175-182, ATCC CRL-1650), mouse fibroblast NIH3T3 (ATCC No. CRL-1658), a mouse NS0 cell line (ECACC), Chinese hamster ovary cells (CHO cells, ATCC CCL-61), dihydrofolate reductase-deficient lines thereof (CHO$^{dhfr-}$; Urlaub, G. and Chasin, L. A. Proc. Natl. Acad. Sci. U.S.A. (1980), 77, p. 4126-4220), CHOK1SV (Lonza Biologics), cells derived from birds such as chickens, and cells derived from insects.

Also, cells modified to regulate the sugar chain modification of proteins such as antibodies can be used as the hosts. For example, CHO cells modified such that sugar chains with fucose bound to N-acetylglucosamine at their reducing ends are reduced or removed among complex-type N-glycoside-linked sugar chains binding to the Fc region of the antibody, may be used in antibody expression to thereby prepare a defucosylated antibody (also referred to as a modified form of the antibody) (WO00/61739, WO02/31140, etc.).

Examples of the eukaryotic microbes can include yeasts.

Examples of the prokaryotic cells can include *E. coli* and *Bacillus subtilis*.

A signal peptide for the secretion of the antibody of the present invention (monoclonal antibody derived from each animal, rat antibody, mouse antibody, chimeric antibody, humanized antibody, human antibody, etc.) is not limited to the secretory signal of an antibody of the same species, the same type, and the same subtype as the antibody of the present invention or to the antibody of the present invention's own secretory signal. Any secretory signal of an antibody of different type or subtype therefrom or any secretory signal of a protein derived from a different eukaryotic species therefrom or a prokaryotic species can be selected and used.

(4-4) Methods for Designing and Preparing Humanized Antibody

Examples of the humanized antibody can include, but are not limited to, a human-derived antibody having CDRs replaced with the CDRs of a non-human animal antibody (see Nature (1986), 321, p. 522-525), a human antibody grafted with the CDR sequences and with some amino acid residues of framework regions by CDR grafting (see WO90/07861 and U.S. Pat. No. 6,972,323), and an antibody having human antibody amino acid(s) replaced for one or two or more non-human animal antibody-derived amino acid(s) in any of these humanized antibodies.

(4-5) Method for Preparing Human Antibody

Further examples of the antibody of the present invention can include a human antibody. The anti-FGFR2 human antibody means an anti-FGFR2 antibody consisting of the amino acid sequence of a human-derived antibody. The anti-FGFR2 human antibody can be obtained by a method using human antibody-producing mice carrying human genomic DNA fragments comprising human antibody heavy and light chain genes (see e.g., Tomizuka, K. et al., Nature Genetics (1997) 16, p. 133-143; Kuroiwa, Y. et. al., Nuc. Acids Res. (1998) 26, p. 3447-3448; Yoshida, H. et. al., Animal Cell Technology: Basic and Applied Aspects vol. 10, p. 69-73 (Kitagawa, Y., Matuda, T. and Iijima, S. eds.), Kluwer Academic Publishers, 1999; Tomizuka, K. et. al., Proc. Natl. Acad. Sci. USA (2000) 97, p. 722-727).

Specifically, such human antibody-producing animals may be any of recombinant animals that are obtained by disrupting the endogenous immunoglobulin heavy and light chain gene loci of non-human mammals and instead introducing thereto human immunoglobulin heavy and light chain gene loci via yeast artificial chromosome (YAC) vectors or the like, and recombinant animals that are created by crossing these animals.

Alternatively, eukaryotic cells may be transfected with cDNAs encoding the heavy and light chains, respectively, of such a human antibody, preferably with vectors comprising the cDNAs, by a gene recombination technique. The transfected cells producing a recombinant human monoclonal antibody can be cultured. This antibody can be obtained from the culture supernatant.

In this context, for example, eukaryotic cells, preferably mammalian cells such as CHO cells, lymphocytes, or myelomas, can be used as the hosts.

Also, a method for obtaining a phage display-derived human antibody selected from a human antibody library (see e.g., Wormstone, I. M. et. al, Investigative Ophthalmology & Visual Science. (2002) 43 (7), p. 2301-2308; Carmen, S. et. al., Briefings in Functional Genomics and Proteomics (2002), 1 (2), p. 189-203; Siriwardena, D. et. al., Opthalmology (2002) 109 (3), p. 427-431) is known.

For example, a phage display method (Nature Biotechnology (2005), 23, (9), p. 1105-1116) can be used, which involves allowing the variable regions of a human antibody to be expressed as a single chain antibody (scFv) on phage surface and selecting a phage binding to the antigen.

The phage selected on the basis of its ability to bind to the antigen can be subjected to gene analysis to thereby determine DNA sequences encoding the variable regions of the human antibody binding to the antigen.

If the DNA sequence of scFv binding to the antigen is determined, an expression vector having this sequence can be prepared and introduced to appropriate hosts to allow them to express the human antibody (WO92/01047, WO92/20791, WO93/06213, WO93/11236, WO93/19172, WO95/01438, WO95/15388, Annu. Rev. Immunol (1994) 12, p. 433-455, Nature Biotechnology (2005) 23 (9), p. 1105-1116).

(4-6) Method for Preparing Functional Fragment of Antibody

The method for preparing a single chain antibody is well known in the art (see e.g., U.S. Pat. Nos. 4,946,778, 5,260,203, 5,091,513, and 5,455,030). In this scFv, a heavy chain variable region and a light chain variable region are linked via a linker that prevents them from forming a conjugate, preferably a polypeptide linker (Huston, J. S. et al., Proc. Natl. Acad. Sci. U.S.A. (1988), 85, p. 5879-5883). The heavy chain variable region and the light chain variable region in scFv may be derived from the same antibody or may be derived from different antibodies.

For example, an arbitrary single chain peptide consisting of 12 to 19 residues is used as the polypeptide linker that links these variable regions.

In order to obtain scFv-encoding DNA, of the sequences of DNA encoding the heavy chain or heavy chain variable region of the antibody and DNA encoding the light chain or light chain variable region thereof, each DNA portion encoding the whole or desired amino acid sequence is used as a template and amplified by PCR using a primer pair flanking both ends of the template. Subsequently, DNA encoding the polypeptide linker moiety is further amplified in combination with a primer pair flanking both ends of the DNA so that the obtained fragment can be linked at its ends to the heavy and light chain DNAs, respectively.

The scFv-encoding DNA can be used to thereby prepare, according to a routine method, an expression vector containing the DNA and host cells transformed with the expression vector. In addition, the host cells can be cultured, and the scFv can be recovered from the cultures according to a routine method.

Also in order to obtain any other functional fragment of the antibody, a gene encoding the functional fragment is obtained according to the method described above and introduced into cells. The functional fragment of interest can be recovered from cultures of the cells.

The antibody of the present invention may be multimerized to thereby enhance its affinity for the antigen. In this case, antibodies of the same type may be multimerized, or a plurality of antibodies recognizing a plurality of epitopes, respectively, of the same antigen may be multimerized. Examples of methods for multimerizing these antibodies can include the binding of two scFvs to an IgG CH3 domain, the binding thereof to streptavidin, and the introduction of a helix-turn-helix motif.

The antibody of the present invention may be a mixture of plural types of anti-FGFR2 antibodies differing in amino acid sequence, i.e., a polyclonal antibody. Examples of the polyclonal antibody can include a mixture of plural types of antibodies differing in a portion or the whole of CDRs. Such a polyclonal antibody can be recovered from cultures of mixed-cultured different antibody-producing cells (WO2004/061104). Alternatively, separately prepared antibodies may be mixed. Antiserum, which is one aspect of the polyclonal antibody, can be prepared by immunizing animals with the desired antigen and recovering serum from the animals according to a standard method.

Antibodies conjugated with various molecules such as polyethylene glycol (PEG) can also be used as modified forms of the antibody.

The antibody of the present invention may further be any of conjugates formed by these antibodies with other drugs (immunoconjugates). Examples of such an antibody can include the antibody conjugated with a radioactive material or a compound having a pharmacological action (Nature Biotechnology (2005), 23, p. 1137-1146).

(4-7) Purification of Antibody

The obtained antibody can be purified until homogeneous. Usual protein separation and purification methods can be used for the separation and purification of the antibody.

The antibody can be separated and purified by appropriately selected or combined approach(es), for example, chromatography columns, filters, ultrafiltration, salting out, dialysis, preparative polyacrylamide gel electrophoresis, and/or isoelectric focusing (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)) though the separation and purification method is not limited thereto.

Examples of chromatography include affinity chromatography, ion-exchange chromatography, hydrophobic chromatography, gel filtration, reverse-phase chromatography, and adsorption chromatography.

These chromatography approaches can be performed using liquid-phase chromatography such as HPLC or FPLC.

Examples of columns used in affinity chromatography can include protein A, protein G, and antigen columns.

Examples of the protein A columns include Protein A Ceramic HyperD (manufactured by Pall Corp.), POROS (manufactured by Applied Biosystems, Inc.), and Sepharose F. F. (manufactured by GE Healthcare Bio-Sciences Corp.).

Also, the antibody may be purified using its binding activity against the antigen using an antigen-immobilized carrier.

(4-8) Nucleotides Encoding Antibody, Recombinant Vector, and Recombinant Cell

The present invention provides a nucleotide(s) encoding the antibody of the present invention or the functional fragment thereof, or the modified form of the antibody or functional fragment (hereinafter, this nucleotide is referred to as an "antibody gene"), a recombinant vector having an insert of the gene, a cell comprising the gene or the vector (hereinafter, this cell is referred to as an "antibody gene-transfected cell"), and a cell producing the antibody of the present invention or the functional fragment thereof, or the modified form of the antibody or functional fragment (hereinafter, this cell is referred to as an "antibody-producing cell").

Preferably, the antibody gene of the present invention comprises a nucleotide sequence described in any one of the following (a) to (e) (hereinafter, referred to as an "antibody gene sequence"), consists of a nucleotide sequence comprising the antibody gene sequence, or consists of the antibody gene sequence:

(a) a combination of a nucleotide sequence encoding the heavy chain amino acid sequence of any one of the rat FR2-10, FR2-13, and FR2-14, chimeric cFR2-10, cFR2-13, and cFR2-14, and humanized hFR2-14_H1/L1 to hFR2-14_H19/L1 antibodies and a nucleotide sequence encoding the light chain amino acid sequence of any one thereof;

(b) a combination of a nucleotide sequence encoding the amino acid sequence of a heavy chain comprising CDRH1 to CDRH3 of any one of the rat FR2-10, FR2-13, and FR2-14, chimeric cFR2-10, cFR2-13, and cFR2-14, and humanized hFR2-14_H1/L1 to hFR2-14_H19/L1 antibodies and a nucleotide sequence encoding the amino acid sequence of a light chain comprising CDRL1 to CDRL3 of any one thereof;

(c) a combination of a nucleotide sequence encoding a heavy chain amino acid sequence comprising the amino acid sequence of the heavy chain variable region of any one of the rat FR2-10, FR2-13, and FR2-14, chimeric cFR2-10, cFR2-13, and cFR2-14, and humanized hFR2-14_H1/L1 to hFR2-14_H19/L1 antibodies and a nucleotide sequence encoding a light chain amino acid sequence comprising the amino acid sequence of the light chain variable region of any one thereof;

(d) a nucleotide sequence that hybridizes under stringent conditions to a nucleotide consisting of a nucleotide sequence complementary to any one of the nucleotide sequences (a) to (c) and encodes the amino acid sequence of an antibody binding to FGFR2; and (e) a nucleotide sequence that encodes an amino acid sequence derived from any one of the amino acid sequences (a) to (c) by the substitution, deletion, addition, or insertion of 1 to 50, 1 to 45, 1 to 40, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and encodes the amino acid sequence of an antibody binding to FGFR2.

The antibody having the amino acid sequence encoded by the nucleotide sequence (d) or (e) may have one or two or more of the activities described in paragraphs (3-3) to (3-6), in addition to FGFR2 binding activity.

However, the antibody gene of the present invention is not limited to those described in (a) to (e).

The present invention provides, as described in paragraph (4-3), a method for producing the antibody of the present invention or the functional fragment thereof, or the modified form of the antibody or functional fragment, comprising the steps of: culturing the antibody gene-transfected cell of the present invention and recovering the antibody, the functional fragment, or the modified form from the cultures. The antibody or functional fragment thereof, or the modified form of the antibody or functional fragment obtained by this production method is also included in the present invention.

5. Pharmaceutical Composition

The present invention provides a pharmaceutical composition comprising the anti-FGFR2 antibody or functional fragment thereof, or the modified form of the antibody or functional fragment.

The pharmaceutical composition of the present invention is useful in the treatment or prevention of various diseases that are initiated or exacerbated by abnormal or increased FGFR2 signals due to overexpression of FGFR2 or its ligand or FGFR2 mutations or gene amplification, or by isoform switching of FGFR2 (hereinafter, these diseases are referred to as "FGFR2-related diseases"), particularly, various cancers.

Examples of causes of the initiation or exacerbation of such cancers to be treated or prevented can include single nucleotide polymorphism (SNP) in an intron of the FGFR2 gene, high expression of FGFR2, missense mutations that constitutively activate FGFR2, amplification or overexpression of the FGFR2 gene, and switching from FGFR2 IIIb to FGFR2 IIIc.

Examples of such cancer types can include breast cancer, endometrial cancer, ovary cancer, lung cancer (e.g., non-small cell lung cancer), stomach cancer, prostate cancer, kidney cancer, liver cancer, pancreatic cancer, colorectal cancer, esophageal cancer, urinary bladder cancer, uterine cervix cancer, blood cancer, lymphoma, and malignant melanoma. Preferred examples thereof can include these cancers expressing the FGFR2 protein.

In the present invention, the treatment or prevention of a disease includes, but is not limited to, the prevention of the onset of the disease, preferably the disease in an individual expressing the FGFR2 protein, the suppression or inhibition of exacerbation or progression thereof, the alleviation of one or two or more symptoms exhibited by an individual affected with the disease, the suppression or remission of exacerbation or progression thereof, the treatment or prevention of a secondary disease, etc.

The pharmaceutical composition of the present invention can comprise a therapeutically or prophylactically effective amount of the anti-FGFR2 antibody or the functional fragment of the antibody and a pharmaceutically acceptable diluent, vehicle, solubilizer, emulsifier, preservative, and/or additive.

The "therapeutically or prophylactically effective amount" means an amount that exerts therapeutic or prophylactic effects on a particular disease by means of a particular dosage form and administration route and has the same meaning as a "pharmacologically effective amount".

The pharmaceutical composition of the present invention may comprise materials for changing, maintaining, or retaining pH, osmotic pressure, viscosity, transparency, color, tonicity, sterility, or the stability, solubility, sustained release, absorbability, permeability, dosage form, strength, properties, shape, etc., of the composition or the antibody comprised therein (hereinafter, referred to as "pharmaceutical materials"). The pharmaceutical materials are not particularly limited as long as the materials are pharmacologically acceptable. For example, no or low toxicity is a property preferably possessed by these pharmaceutical materials.

Examples of the pharmaceutical materials can include, but are not limited to, the following: amino acids such as glycine, alanine, glutamine, asparagine, histidine, arginine, and lysine; antimicrobial agents; antioxidants such as ascorbic acid, sodium sulfate, and sodium bisulfite; buffers such as phosphate, citrate, or borate buffers, sodium bicarbonate, and Tris-HCl solutions; fillers such as mannitol and glycine; chelating agents such as ethylenediaminetetraacetic acid (EDTA); complexing agents such as caffeine, polyvinylpyrrolidine, β-cyclodextrin, and hydroxypropyl-β-cyclodextrin; bulking agents such as glucose, mannose, and dextrin; other hydrocarbons such as monosaccharides, disaccharides, glucose, mannose, and dextrin; coloring agents; corrigents; diluents; emulsifiers; hydrophilic polymers such as polyvinylpyrrolidine; low-molecular-weight polypeptides; salt-forming counterions; antiseptics such as benzalkonium chloride, benzoic acid, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; suspending agents; surfactants such as PEG, sorbitan ester, polysorbates such as polysorbate 20 and polysorbate 80, triton, tromethamine, lecithin, and cholesterol; stability enhancers such as sucrose and sorbitol; elasticity enhancers such as sodium chloride, potassium chloride, mannitol, and sorbitol; transport agents; diluents; excipients; and/or pharmaceutical additives.

The amount of these pharmaceutical materials added is 0.001 to 1000 times, preferably 0.01 to 100 times, more preferably 0.1 to 10 times the weight of the anti-FGFR2 antibody or functional fragment thereof, or the modified form of the antibody or functional fragment.

An immunoliposome comprising the anti-FGFR2 antibody or functional fragment thereof, or the modified form of the antibody or functional fragment encapsulated in a liposome, or a modified antibody form comprising the antibody conjugated with a liposome (U.S. Pat. No. 6,214,388, etc.) is also included in the pharmaceutical composition of the present invention.

The excipients or vehicles are not particularly limited as long as they are liquid or solid materials usually used in injectable water, saline, artificial cerebrospinal fluids, and other preparations for oral or parenteral administration. Examples of saline can include neutral saline and serum albumin-containing saline.

Examples of buffers can include a Tris buffer adjusted to bring the final pH of the pharmaceutical composition to 7.0 to 8.5, an acetate buffer adjusted to bring the final pH thereof to 4.0 to 5.5, a citrate buffer adjusted to bring the final pH thereof to 5.0 to 8.0, and a histidine buffer adjusted to bring the final pH thereof to 5.0 to 8.0.

The pharmaceutical composition of the present invention is a solid, a liquid, a suspension, or the like. Another example of the pharmaceutical composition of the present invention can include freeze-dried preparations. The freeze-dried preparations can be formed using an excipient such as sucrose.

The administration route of the pharmaceutical composition of the present invention may be any of enteral administration, local administration, and parenteral administration. Examples thereof can include intravenous administration, intraarterial administration, intramuscular administration, intradermal administration, hypodermic administration, intraperitoneal administration, transdermal administration, intraosseous administration, intraarticular administration, and the like.

The composition of a pharmaceutical composition can be determined according to the administration method, the binding affinity of the antibody for the FGFR2 protein, etc. The anti-FGFR2 antibody of the present invention or the functional fragment thereof, or the modified form of the antibody or functional fragment having higher affinity (lower KD value) for the FGFR2 protein can exert its pharmaceutical efficacy at a lower dose.

The dose of the anti-FGFR2 antibody of the present invention is not limited as long as the dose is a pharmacologically effective amount. The dose can be appropriately determined according to the species of an individual, the type of disease, symptoms, sex, age, pre-existing conditions, the binding affinity of the antibody for the FGFR2 protein or its biological activity, and other factors. A dose of usually 0.01 to 1000 mg/kg, preferably 0.1 to 100 mg/kg, can be administered once every day to every 180 days or twice or three or more times a day.

Examples of the form of the pharmaceutical composition can include injections (including freeze-dried preparations and drops), suppositories, transnasal absorption preparations, transdermal absorption preparations, sublingual formulations, capsules, tablets, ointments, granules, aerosols, pills, powders, suspensions, emulsions, eye drops, and biological implant formulations.

The pharmaceutical composition comprising the anti-FGFR2 antibody or functional fragment thereof, or the modified form of the antibody or functional fragment as an active ingredient can be administered concurrently with or separately from an additional drug. For example, the pharmaceutical composition comprising the anti-FGFR2 antibody or functional fragment thereof as an active ingredient may be administered after administration of the additional drug, or the additional drug may be administered after administration of the pharmaceutical composition. Alternatively, the pharmaceutical composition and the additional drug may be administered concurrently. Examples of the additional drug can include various anticancer agents such as chemotherapeutics and radiation therapy. These use approaches are collectively referred to as "combined use of the additional drug" with the antibody of the present invention. The present invention also encompasses a pharmaceutical composition comprising the antibody of the present invention or the functional fragment thereof, or the modified form of the antibody or functional fragment and further comprising an additional drug.

The present invention provides a method for treating or preventing FGFR-related diseases such as cancer, use of the antibody of the present invention for preparing a pharmaceutical composition for treatment or prevention of the diseases, and use of the antibody of the present invention for treating or preventing the diseases. The present invention also encompasses a kit for treatment or prevention comprising the antibody of the present invention.

6. Composition for Diagnosis

The present invention provides a composition for testing or diagnosis (hereinafter, referred to as a "composition for diagnosis") comprising the anti-FGFR2 antibody of the present invention or the functional fragment thereof, or the modified form of the antibody or functional fragment.

The composition for diagnosis of the present invention is useful in the testing or diagnosis of FGFR2-related diseases such as cancer or of FGFR2 expression. In the present invention, the testing or the diagnosis includes, for example, the determination or measurement of a risk of developing a disease, the determination of the presence or absence of a disease, the measurement of the degree of progression or exacerbation of a disease, the measurement or determination of the effect of drug therapy using the pharmaceutical composition comprising the anti-FGFR2 antibody or the like, the measurement or determination of the effect of therapy other than drug therapy, the measurement of a risk of recurrence of a disease, and the determination of the presence or absence of recurrence of a disease. However, the testing or the diagnosis according to the present invention is not limited to these, and any approach can be used.

The composition for diagnosis of the present invention is useful in the identification of a recipient individual for the antibody of the present invention or the functional fragment thereof, or the modified form of the antibody or functional fragment, a composition comprising the same, or a pharmaceutical composition comprising the same.

The composition for diagnosis can comprise a pH buffer, an osmoregulator, salts, a stabilizer, an antiseptic, a color developer, a sensitizer, an aggregation inhibitor, and the like.

The present invention provides a method for testing or diagnosing FGFR2-related diseases such as cancer, use of the antibody of the present invention for preparing a composition for diagnosis of the diseases, and use of the antibody of the present invention for testing or diagnosing the diseases. The present invention also encompasses a kit for testing or diagnosis comprising the antibody of the present invention.

The desirable testing or diagnosis method involving the antibody of the present invention is sandwich ELISA. Any usual detection method using antibodies, such as ELISA, RIA, enzyme-linked immunospot (ELISPOT) assay, dot blotting, Ouchterlony test, or counterimmunoelectrophoresis (CIE), may be used. The antibodies can be labeled by a method using biotin or by any other labeling method that can be carried out in biochemical analysis using a labeling material such as HRP, alkaline phosphatase, or FITC. A chromogenic substrate such as TMB (3,3',5,5'-tetramethylbenzidine), BCIP (5-bromo-4-chloro-3-indolyl phosphate), ρ-NPP (ρ-nitrophenyl phosphate), OPD (o-Phenylenediamine), ABTS (3-Ethylbenzothiazoline-6-sulfonic acid), and SuperSignal ELISA Pico Chemiluminescent Substrate (Thermo Fisher Scientific Inc.), a fluorescent substrate QuantaBlu™ Fluorogenic Peroxidase Substrate (Thermo Fisher Scientific Inc.), and a chemiluminescent substrate can be used in detection using enzymatic labeling. Samples derived from humans or non-human animals as well as artificially treated samples such as recombinant proteins can be subjected to this assay. Examples of test samples derived from individual organisms can include, but are not limited to, blood, synovial fluids, ascites, lymph, cerebrospinal fluids, tissue homogenate supernatants, and tissue sections.

The sandwich ELISA kit for testing or diagnosis comprising the antibody of the present invention may comprise a solution of FGFR2 protein standards, a coloring reagent, a buffer solution for dilution, an antibody for solid phase, an antibody for detection, and a washing solution, and the like. Preferably, the amount of the antibody bound to the antigen can be measured by the application of a method such as an absorbance, fluorescence, luminescence, or radioisotope (RI) method. Preferably, an absorbance plate reader, a fluorescence plate reader, a luminescence plate reader, an RI liquid scintillation counter, or the like is used in the measurement.

The present invention provides an antibody useful for immunohistochemistry (IHC) analysis or a functional fragment thereof, and a modified form of the antibody or functional fragment, and a composition comprising the same. Such a composition is also encompassed by the "composition for diagnosis" of the present invention.

The immunohistochemistry is not particularly limited as long as this approach involves reacting a tissue section with an antigen-binding antibody (primary antibody) and detecting the primary antibody bound with the antigen.

Preferably, the tissue section is treated with paraffin. The paraffin-treated tissue section is deparaffinized, followed by antigen retrieval treatment and nonspecific reaction inhibition treatment. Examples of methods for the antigen retrieval treatment can include heat treatment and enzymatic treatment using trypsin or the like. Heat treatment is preferred. The heat treatment is usually performed under preferred conditions involving a temperature of 90 to 110° C., pH 8 to 10, and a treatment time ranging from 20 to 60 minutes. A Tris-EDTA buffer solution (e.g., a 10 mM Tris buffer solution containing 1 mM EDTA) or the like can be used in pH adjustment. A method for inactivating an endogenous enzyme having the same or similar catalytic activity as an enzyme used in color development is usually used as the nonspecific reaction inhibition treatment. For color development through peroxidase reaction, endogenous peroxidase present in tissues is preferably inhibited in advance using $H_2O_2$ or the like. A solvent such as water or methanol can be used for $H_2O_2$. The concentration of $H_2O_2$ is 0.1 to 3%, preferably 0.3 to 3%. The $H_2O_2$ solution can be supplemented with sodium azide. Also, a blocking method using serum or casein can be used as the nonspecific reaction inhibition treatment. Tissues can be treated with serum or casein before the primary antibody reaction. Alternatively, serum or casein may be contained in a solvent for diluting the primary antibody.

The reaction conditions for the primary antibody are not particularly limited and involve a temperature of 20 to 50° C., preferably 25 to 42° C., more preferably 37° C. The reaction time is 5 minutes to all night and all day, preferably 10 minutes to 6 hours, more preferably 30 minutes to 2 hours.

Preferably, an antibody (secondary antibody) capable of being visualized and binding to the primary antibody can be used in the detection of the primary antibody. Preferably, the secondary antibody can be visualized by use of a method involving binding an enzyme such as peroxidase or alkaline phosphatase to the secondary antibody or adding biotin or the like to the secondary antibody and binding thereto streptavidin or the like conjugated with the enzyme, followed by reaction with a chromogenic substrate compatible with the enzyme. Examples of the method involving binding an enzyme to the secondary antibody can include a method using a reagent comprising a dextrin polymer or an amino acid polymer to which multiple molecules of the enzyme and the secondary antibody are attached (polymer method). A chromogenic substrate such as DAB can be used in the method involving reacting a biotinylated secondary antibody with peroxidase-labeled streptavidin (LSAB method).

The immunohistochemistry procedure can be performed automatically using an immunological apparatus programmed with a reaction solution, reaction conditions, the number of washing runs, etc.

The antibody or functional fragment thereof, or the modified form of the antibody or functional fragment comprised in the composition for diagnosis of the present invention is preferably an antibody binding to FGFR2, i.e., an antibody having FGFR2 selectivity or a functional fragment thereof, or a modified form of the antibody or functional fragment, more preferably an antibody having human FGFR2 IIIb selectivity or functional fragment thereof or a modified form of the antibody or functional fragment. More preferably, according to another aspect, the antibody or functional fragment thereof, or the modified form of the antibody or functional fragment contained in the composition for diagnosis of the present invention more has selectivity for both human FGFR2 IIIb and human FGFR2 IIIc.

Examples of the antibody having human FGFR2 IIIb selectivity can include an antibody comprising a heavy chain comprising the heavy chain CDRH1 to CDRH3 of the rat FR2-10 antibody and a light chain comprising the light chain CDRL1 to CDRL3 thereof, an antibody comprising the heavy and light chain variable regions of the rat FR2-10 antibody, and an antibody comprising the heavy and light chains of the rat FR2-10 antibody. Examples of such antibodies can include, but are not limited to, the rat FR2-10 antibody, the chimeric cFR2-10 antibody, and the humanized FR2-10 antibodies.

Examples of the antibody having selectivity for both human FGFR2 IIIb and human FGFR2 IIIc can include an antibody comprising a heavy chain comprising the heavy chain CDRH1 to CDRH3 of the rat FR2-13 antibody and a light chain comprising the light chain CDRL1 to CDRL3 thereof, an antibody comprising a heavy chain comprising the heavy chain CDRH1 to CDRH3 of the rat FR2-14 antibody and a light chain comprising the light chain CDRL1 to CDRL3 thereof, an antibody comprising the heavy and light chain variable regions of the rat FR2-13 antibody, an antibody comprising the heavy and light chain variable regions of the rat FR2-14 antibody, an antibody comprising the heavy and light chains of the rat FR2-13 antibody, and an antibody comprising the heavy and light chains of the rat FR2-14 antibody. Examples of such antibodies can include, but are not limited to, the rat FR2-13 antibody, the chimeric cFR2-13 antibody, the humanized FR2-13 antibodies, the rat FR2-14 antibody, the chimeric cFR2-14 antibody, and the humanized FR2-14 antibodies.

According to a preferred aspect, the composition for diagnosis of the present invention is for detection or assay of FGFR2, more preferably for detection or assay of human FGFR2 IIIb and/or human FGFR2 IIIc, even more preferably for detection or assay of human FGFR2 IIIb or human FGFR2 IIIb and human FGFR2 IIIc.

The present invention provides a method for detecting or assaying human FGFR2 IIIb in a test sample.

Alternatively, human FGFR2 IIIc in a test sample can be detected or assayed by: (i) detecting or assaying human FGFR2 IIIb and human FGFR2 IIIc in the test sample; (ii) detecting or assaying human FGFR2 IIIb in the sample; and (iii) comparing the results of detection or assay in the step (i) with the results of detection or assay in the step (ii) or subtracting the results of detection or assay in the step (ii) from the results of detection or assay in the step (i). Such a method for detecting or assaying human FGFR2 IIIc is also encompassed in the present invention.

The composition for diagnosis of the present invention can be used in these detection or assay methods. The present invention also encompasses such an assay method and a composition for diagnosis which are intended for diagnosis or testing of human FGFR2-positive cancer, preferably, human FGFR2 IIIb- and/or human FGFR2 IIIc-positive cancer.

The present invention also encompasses a method for identifying a recipient individual for the pharmaceutical composition of the present invention. This identification method involves assaying human FGFR2 in a sample derived from the individual. The individual can be determined to be positive when human FGFR2 is detected in the sample or when human FGFR2 is detected in a larger amount than that of human FGFR2 detected in a sample derived from a healthy individual. The human FGFR2 in the identification method is preferably human FGFR2 IIIb and/or human FGFR2 IIIc, more preferably human FGFR2 IIIb or human FGFR2 IIIb and human FGFR2 IIIc.

The composition for diagnosis of the present invention can be used in this method.

According to a preferred aspect, the individual in the identification method has cancer or is at risk thereof.

According to one aspect, the pharmaceutical composition of the present invention can be administered to an individual determined to be positive by the identification method.

7. Reagent

The antibody of the present invention or the functional fragment thereof, or the modified form of the antibody or functional fragment is also useful as a reagent. Such a reagent is used for testing or diagnosis as mentioned above, for research, and for any other use.

8. Screening Method

The present invention provides a method for identifying a substance having FGFR2-neutralizing activity. This method involves identifying a substance binding to a site on the antigen to which the antibody of the present invention binds. For example, a test substance is contacted with the human FGFR2 IIIb protein or its fragment. Subsequently, the distance is measured between the substance and amino acid residues constituting the epitope on the human FGFR IIIb to which any one of the rat FR2-14 antibody, the chimeric cFR2-14 antibody, and the humanized hFR2-14_H1/L1 to hFR2-14_H19/L1 antibodies binds. The substance can be determined to be positive when the substance has an interaction distance with each of the residues.

Such an identification method is also useful as a method for identifying a substance having antitumor activity. The antitumor activity of the substance confirmed to be positive by the method may be further assayed.

The test substance is preferably a peptide or an antibody or a functional fragment thereof, or a modified form of the antibody or functional fragment.

The peptide or the antibody or functional fragment thereof, or the modified form of the antibody or functional fragment confirmed to be positive by the method can also be prepared by gene recombination, peptide synthesis, or in vitro translation. The present invention also encompasses a method for producing such a peptide or an antibody, or the like.

EXAMPLES

Hereinafter, the present invention will be described further specifically with reference to the Examples. However, the present invention is not intended to be limited to them.

Procedures related to gene manipulation in the Examples below were performed according to the methods described in "Molecular Cloning" (Sambrook, J., Fritsch, E. F. and Maniatis, T., Cold Spring Harbor Laboratory Press, 1989) or the methods described in other experimental manuals used by those skilled in the art, or using commercially available reagents or kits according to the instruction manuals, unless otherwise specified.

Example 1

Preparation of Rat Anti-Human FGFR2 Antibody

1)-1 Immunization

Eight-week-old female WKY/Izm rats (Japan SLC, Inc.) and 7-week-old female Crlj:WI rats (Charles River Laboratories Japan Inc.) were used. At day 0, a mixture of 50 µg of Recombinant Human FGFR2β (IIIb)/Fc Chimera (manufactured by R&D Systems, Inc.) and Freund's Complete Adjuvant (manufactured by Wako Pure Chemicals Industries, Ltd.) (volume ratio: 1:2) was administered to the tail base of each WKY/Izm rat. At day 21, 50 µg of Recombinant Human FGFR2β (IIIb)/Fc Chimera was administered to the tail base of each rat. At day 35, the lymph node or the spleen was collected from the rat and used in hybridoma preparation. At day 0, a mixture of 50 µg of FGFR2β (IIIb)/Fc Chimera and Freund's Complete Adjuvant (volume ratio: 1:1) was subcutaneously or intradermally administered to each Crlj:WI rat. At days 7, 14, and 21, a mixture of 50 µg of FGFR2β (IIIb)/Fc Chimera and Freund's Incomplete Adjuvant (volume ratio: 1:1) was subcutaneously or intradermally administered to the rat. At day 38, 50 µg of FGFR2β (IIIb)/Fc Chimera was administered into the tail vein of the rat. At day 42, the lymph node or the spleen was collected from the rat and used in hybridoma preparation.

1)-2 Hybridoma Preparation

The lymph node cells or the spleen cells were electrically fused with mouse myeloma SP2/0-ag14 cells using Hybrimune Hybridoma Production System (manufactured by Cyto Pulse Sciences, Inc.). The fused cells were diluted with ClonaCell-HY Selection Medium D (manufactured by StemCell Technologies Inc.) and cultured. Hybridoma colonies that appeared were recovered to prepare monoclonal hybridomas. Each hybridoma colony thus recovered was cultured, and the obtained hybridoma culture supernatant was used to screen for an anti-FGFR2 antibody-producing hybridoma.

1)-3 Construction of Expression Vector for Screening for Antigen-Binding Antibody 1)-3-1 Construction of Human FGFR2 IIIb and FGFR2 IIIc Expression Vectors (pcDNA-DEST40-FGFR2 IIIb and pcDNA-DEST40-FGFR2 IIIc)

cDNAs encoding a human FGFR2 IIIb variant protein (isoform 2: NP_075259) and a human FGFR2 IIIc variant protein (isoform 1: NP_000132) were cloned into pcDNA-DEST40 vectors to construct vectors pcDNA-DEST40-FGFR2 IIIb and pcDNA-DEST40-FGFR2 IIIc for expression of each variant protein, respectively.

1)-3-2 Construction of Ig-Like Domain-Deficient FGFR2 IIIb Expression Vector

Vectors for expression of a mutant deficient in a region of amino acid positions 54 to 110 in the full-length amino acid sequence (1 to 822) of FGFR2 IIIb (hereinafter, referred to as an "IgD1-deletion mutant"), a mutant deficient in a region of amino acid positions 154 to 246 therein (hereinafter, referred to as an "IgD2-deletion mutant"), or a mutant deficient in a region of amino acid positions 263 to 358 therein (hereinafter, referred to as an "IgD3-deletion mutant") were constructed by PCR with pcDNA-DEST40-FGFR2 IIIb as a template.

1)-4 Antibody Screening by Cell-ELISA

1)-4-1 Preparation of Antigen Gene-Expressing Cell for Cell-ELISA

HEK293 cells were adjusted to $7.5 \times 10^5$ cells/ml in a DMEM medium containing 10% FBS. pcDNA-DEST40-FGFR2 IIIb or a control pcDNA-DEST40 was transfected thereto using Lipofectamine 2000 (manufactured by Life Technologies Corp.). The resulting cells were dispensed in an amount of 50 µl/well to a 96-well half area plate (manufactured by Corning Inc.) and cultured overnight at 37° C. under 5% $CO_2$ conditions in a DMEM medium containing 10% FBS. The obtained transfected cells were used in the attached state in Cell-ELISA.

1)-4-2 Cell-ELISA

After removal of the culture supernatant from the expression vector-transfected HEK293 cells prepared in Example 1)-4-1, each hybridoma culture supernatant was added to the pcDNA-DEST40-FGFR2 IIIb- or pcDNA-DEST40-transfected HEK293 cells, and the plate was left standing at 4° C. for 1 hour. The cells in the wells were washed once with PBS containing 5% FBS. Then, Anti-Rat IgG-Peroxidase antibody produced in rabbit (manufactured by Sigma-Aldrich Corp.) diluted 500-fold with PBS containing 5% FBS was added thereto, and the plate was left standing at 4° C. for 1 hour. The cells in the wells were washed 5 times with PBS containing 5% FBS. Then, an OPD chromogenic solution (OPD solution (o-phenylenediamine dihydrochloride (manufactured by Wako Pure Chemicals Industries, Ltd.) and $H_2O_2$ dissolved at concentrations of 0.4 mg/ml and 0.6% (v/v), respectively, in 0.05 M trisodium citrate and 0.1 M disodium hydrogen phosphate dodecahydrate, pH 4.5)) was added thereto at a concentration of 25 µl/well. Color reaction was performed with occasional stirring and stopped by the addition of 1 M HCl at a concentration of 25 µl/well. Then, the absorbance was measured at 490 nm using a plate reader (ENVISION; PerkinElmer, Inc.). In order to select a hybridoma producing an antibody specifically binding to FGFR2 expressed on cell membrane surface, hybridomas that yielded a culture supernatant exhibiting higher absorbance for the pcDNA-DEST40-FGFR2 IIIb expression vector-transfected HEK293 cells compared with the control pcDNA-DEST40-transfected HEK293 cells were selected as anti-FGFR2 antibody production-positive hybridomas.

1)-5 Antibody Screening by Flow Cytometry

1)-5-1 Preparation of Antigen Gene-Expressing Cell for Flow Cytometry Analysis

HEK293T cells were inoculated at a density of $5\times10^4$ cells/cm² to a 225-cm² flask (manufactured by Sumitomo Bakelite Co., Ltd.) and cultured overnight at 37° C. under 5% $CO_2$ conditions in a DMEM medium containing 10% FBS. On the next day, the pcDNA-DEST40-FGFR2 IIIb IgD1-deletion mutant deficient in the N-terminal IgD1 domain or a control pcDNA-DEST40 was transfected to the HEK293T cells using Lipofectamine 2000, and the cells were further cultured overnight at 37° C. under 5% $CO_2$ conditions. On the next day, the expression vector-transfected HEK293T cells were treated with TrypLE Express (manufactured by Life Technologies Corp.), washed with DMEM containing 10% FBS, and then suspended in PBS containing 5% FBS. The obtained cell suspension was used in flow cytometry analysis.

1)-5-2 Flow Cytometry Analysis

The FGFR2 IIIb binding specificity of the antibody produced by each hybridoma determined to be positive by Cell-ELISA in Example 1)-4 was further confirmed by flow cytometry. Each HEK293T cell suspension prepared in Example 1)-5-1 was centrifuged to remove a supernatant. Then, the pcDNA-DEST40-FGFR2 IIIb IgD1-deletion mutant-transfected HEK293T cells or the pcDNA-DEST40-transfected HEK293T cells were suspended by the addition of the hybridoma culture supernatant and left standing at 4° C. for 1 hour. The cells were washed twice with PBS containing 5% FBS, then suspended by the addition of Anti-Rat IgG FITC conjugate (manufactured by Sigma-Aldrich Corp.) diluted 320-fold with PBS containing 5% FBS, and left standing at 4° C. for 1 hour. The cells were washed 3 times with PBS containing 5% FBS and then resuspended in PBS containing 5% FBS and 2 µg/ml 7-aminoactinomycin D (manufactured by Molecular Probes, Inc.), followed by detection using a flow cytometer (FC500; manufactured by Beckman Coulter Inc.). The data was analyzed using Flowjo (manufactured by Tree Star Inc.). After removal of 7-aminoactinomycin D-positive dead cells by gating, the FITC fluorescence intensity of live cells was plotted to a histogram. Hybridomas that yielded a sample exhibiting a shift to stronger fluorescence intensity in the histogram of the pcDNA-DEST40-FGFR2 IIIb IgD1-deletion mutant-transfected HEK293T cells compared with the fluorescence intensity histogram of the control pcDNA-DEST40-transfected HEK293T cells were obtained as anti-FGFR2 IIIb antibody-producing hybridomas.

1)-6 Screening Based on Signal-Neutralizing Effect

In order to evaluate the signal-neutralizing effect of the anti-FGFR2 antibody produced by each obtained hybridoma, an Elk1 luciferase reporter gene assay system for detecting ERK (extracellular signal-regulated kinase) activation induced by FGFR2 activation via ligand FGF7 stimulation was constructed by a method shown below and used in the evaluation of the obtained antibody for its effect.

1)-6-1 Construction of Vector for Reporter Assay

First, a pFR-Luc2CP vector was constructed. pFR-Luc (Stratagene #219005) was cleaved with HindIII, blunt-ended using T4 DNA polymerase, and then cleaved with BamHI to isolate a 140-bp fragment comprising five GAL4 binding elements and a TATA box. Next, pGL4.12[luc2CP] (Promega #E6661) was cleaved with EcoICRI and BglII, dephosphorylated, and then ligated with the 140-bp fragment to prepare a pFR-Luc2CP vector.

1)-6-2 Elk1 Luciferase Reporter Gene Assay

The Elk1 luciferase reporter gene assay was carried out using each hybridoma culture supernatant selected in Example 1)-5. A cell line 293α, which was HEK293 cells stably transfected with integrin αv and integrin β3 expression vectors, was transiently cotransfected with pcDNA-DEST40-FGFR2 IIIb or pcDNA-DEST40, pFA2-Elk1 (manufactured by Stratagene Corp.), pFR-Luc2CP, and pGL4.74[hRluc/TK] (manufactured by Promega Corp.) according to transfection procedures using Lipofectamine 2000 (manufactured by Invitrogen Corp.), inoculated to a white 96-well cell culture plate (manufactured by Corning Inc.), and cultured overnight at 37° C. under 5% $CO_2$ conditions. On the next day, the culture supernatant was removed, and the hybridoma culture supernatant diluted 5-fold with DMEM containing 5% FBS was added at a concentration of 50 µl/well to the plate. After culture at 37° C. for 1 hour under 5% $CO_2$ conditions, a ligand human FGF7 (manufactured by R&D systems, Inc.) was added at a final concentration of 10 ng/ml to each well. After incubation for 6 hours, cell lysates were prepared and assayed for firefly luciferase activity (specific signal) and *Renilla* luciferase activity (signal for normalization) using Dual-luciferase reporter assay system (manufactured by Promega Corp.). The firefly/*Renilla* ratio was calculated to normalize data on each well. Hybridomas FR2-10, FR2-13, and FR2-14 were selected which produced anti-FGFR2 antibodies that reduced ligand FGF7 dependent reporter activation to a ligand-free level in the FGFR2-expressing HEK293 reporter cells.

1)-7 Isotyping of Antibody

The anti-FGFR2 antibody-producing hybridomas FR2-10, FR2-13, and FR2-14 were isotyped using Rat monoclonal isotyping test kit (manufactured by AbD Serotec). As a result, their isotypes were confirmed to be IgG2a and 78 chains for FR2-10 and IgG1 and κ chains for FR2-13 and FR2-14.

1)-8 Preparation of Monoclonal Antibody

Each monoclonal antibody was purified from the ascites (hereinafter, referred to as an "antibody purification material") of a hybridoma-transplanted mouse.

The mouse ascites was prepared as follows: first, 7- to 8-week-old BALB/cAJcl-nu/nu (Japan SLC, Inc.) was treated with pristane (manufactured by Sigma-Aldrich Corp.). Approximately 1 to 4 weeks later, each hybridoma washed with PBS was intraperitoneally transplanted in an amount of 1 to $2 \times 10^7$ cells per mouse. One to 2 weeks later, ascites accumulated intraperitoneally was collected, sterilized through a 0.22-μm filter, and used as an antibody purification material.

Each antibody was purified using Hitrap MabSelect SuRe (manufactured by GE Healthcare Bio-Sciences Corp.). The antibody purification material was applied to a column, which was then washed with PBS, followed by elution with 2 M arginine-HCl (pH 4.0). The eluted antibody solution was neutralized and then buffer-replaced with PBS. The concentration of the purified antibody was determined by the elution of the antibody bound with POROS G 20 μm Column PEEK, 4.6 mm×50 mm, 0.83 ml (manufactured by Applied Biosystems, Inc.) and the subsequent measurement of the absorbance (O.D. 280 nm) of the eluate. Specifically, the antibody sample diluted with PBS was applied to POROS G 20 μm equilibrated with an equilibration buffer (30.6 mM sodium dihydrogen phosphate dodecahydrate, 19.5 mM monopotassium phosphate, and 0.15 M NaCl, pH 7.0). The column was washed with an equilibration buffer, followed by the elution of the antibody bound with the column using an eluent (0.1% (v/v) HCl and 0.15 M NaCl). The peak area of the absorbance (O.D. 280 nm) of the eluate was measured, and the concentration was calculated according to the following expression: Antibody sample concentration (mg/ml)=(Peak area of the antibody sample)/(Peak area of a standard (human IgG1))×Concentration (mg/ml) of the standard×Dilution ratio of the sample. Also, the concentration of endotoxin contained in the obtained antibody was measured using Limulus ES-II Single Test Wako (Wako Pure Chemicals Industries, Ltd. 295-51030; containing control standard endotoxin) and Toxinometer (Wako Pure Chemicals Industries, Ltd. ET-301 or ET-5000) and confirmed to be 1 EU/mg or lower. The antibody was used in the subsequent experiments.

Example 2

In Vitro Evaluation of Rat Anti-Human FGFR2 Antibodies (FR2-10, FR2-13, and FR2-14)

2)-1 Study on Selective Binding Activity of Obtained Rat Anti-FGFR2 Antibodies (FR2-10, FR2-13, and FR2-14) Against Human FGFR2

2)-1-1 Construction of Human FGFR1 IIIc, Human FGFR3 IIIb, Human FGFR3 IIIc, and Human FGFR4 Expression Vectors cDNAs encoding a human FGFR1 IIIc variant protein (isoform 1: NP_075598), a human FGFR3 IIIb variant protein (isoform 3: NP_001156685), a human FGFR3 IIIc variant protein (isoform 1: NP_000133), and a human FGFR4 protein (isoform 1: NP_002002) were cloned into pcDNA-DEST40 vectors to construct vectors pcDNA-DEST40-FGFR1 IIIc, pcDNA-DEST40-FGFR3 IIIb, pcDNA-DEST40-FGFR3 IIIc, and pcDNA-DEST40-FGFR4 for expression of each variant protein, respectively.

2)-1-2 Flow Cytometry Analysis

Figure 1:
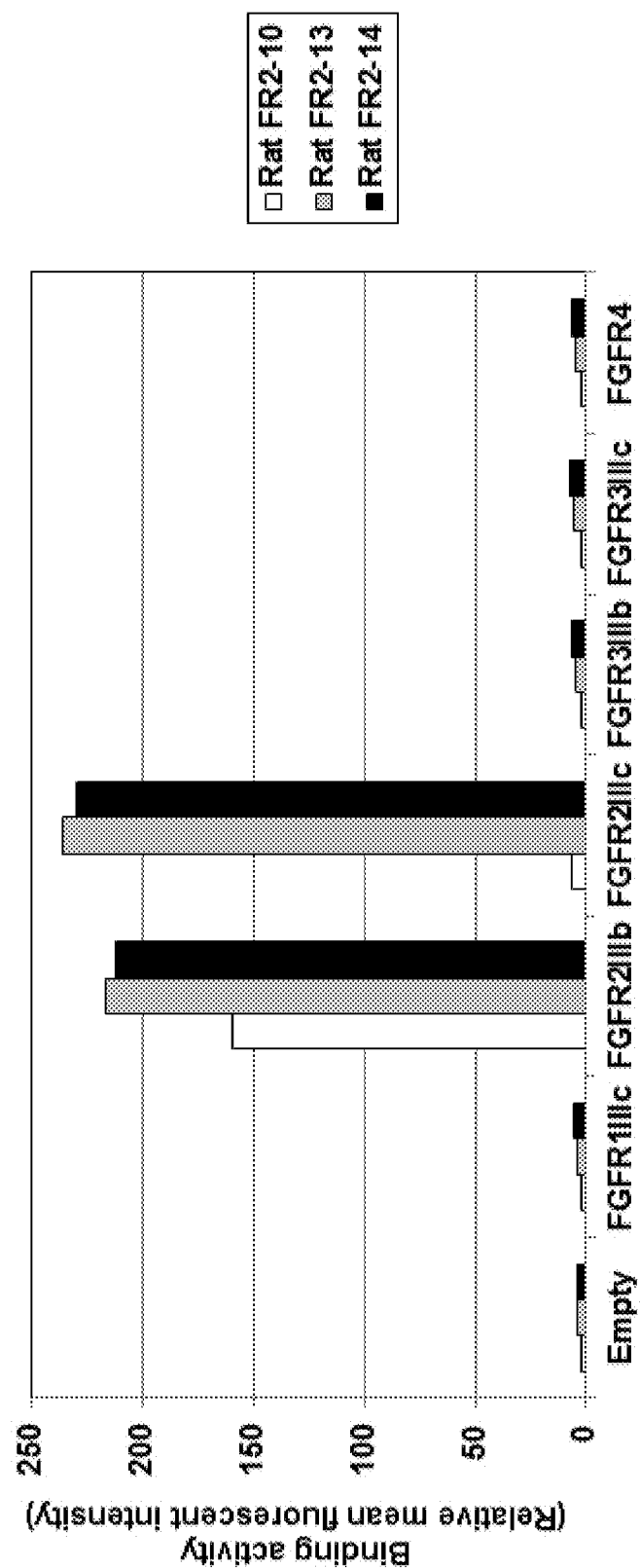
FIG. 1 is a diagram showing results of testing the binding activity of rat anti-FGFR2 antibodies (FR2-10, FR2-13, and FR2-14) against human FGFR2 by flow cytometry. The vertical axis represents a relative value of the average fluorescence intensity assayed by flow cytometry.

Each human FGFR expression vector constructed in Examples 1)-3-1 and 2)-1-1 was transfected to HEK293T cells by the method shown in Example 1)-5-1. The cell suspension was centrifuged to remove the supernatant. Then, these various human FGFR expression vector-transfected HEK293T cells and the pcDNA-DEST40-transfected HEK293T cells were separately suspended by the addition of the hybridoma culture supernatant containing the FR2-10, FR2-13, or FR2-14 antibody and left standing at 4° C. for 1 hour. The cells were washed twice with PBS containing 5% FBS, then suspended by the addition of Anti-Rat IgG FITC conjugate (manufactured by Sigma-Aldrich Corp.) diluted 320-fold with PBS containing 5% FBS, and left standing at 4° C. for 1 hour. The cells were washed 3 times with PBS containing 5% FBS and then resuspended in PBS containing 5% FBS and 2 μg/ml 7-aminoactinomycin D (manufactured by Molecular Probes, Inc.), followed by detection using a flow cytometer (FC500; manufactured by Beckman Coulter Inc.). The data was analyzed using Flowjo (manufactured by Tree Star Inc.). After removal of 7-aminoactinomycin D-positive dead cells by gating, the FITC fluorescence intensity of live cells was plotted to a histogram to calculate average fluorescence intensity (MFI). As seen from FIG. 1, the rat FR2-10 antibody was shown to selectively bind to human FGFR2 IIIb, while the rat FR2-13 and FR2-14 antibodies were shown to selectively bind to both human FGFR2 IIIb and FGFR2 IIIc.

2)-2 Identification of Epitope for Obtained Rat Anti-FGFR2 Antibodies (FR2-10, FR2-13, and FR2-14)

Figure 2:
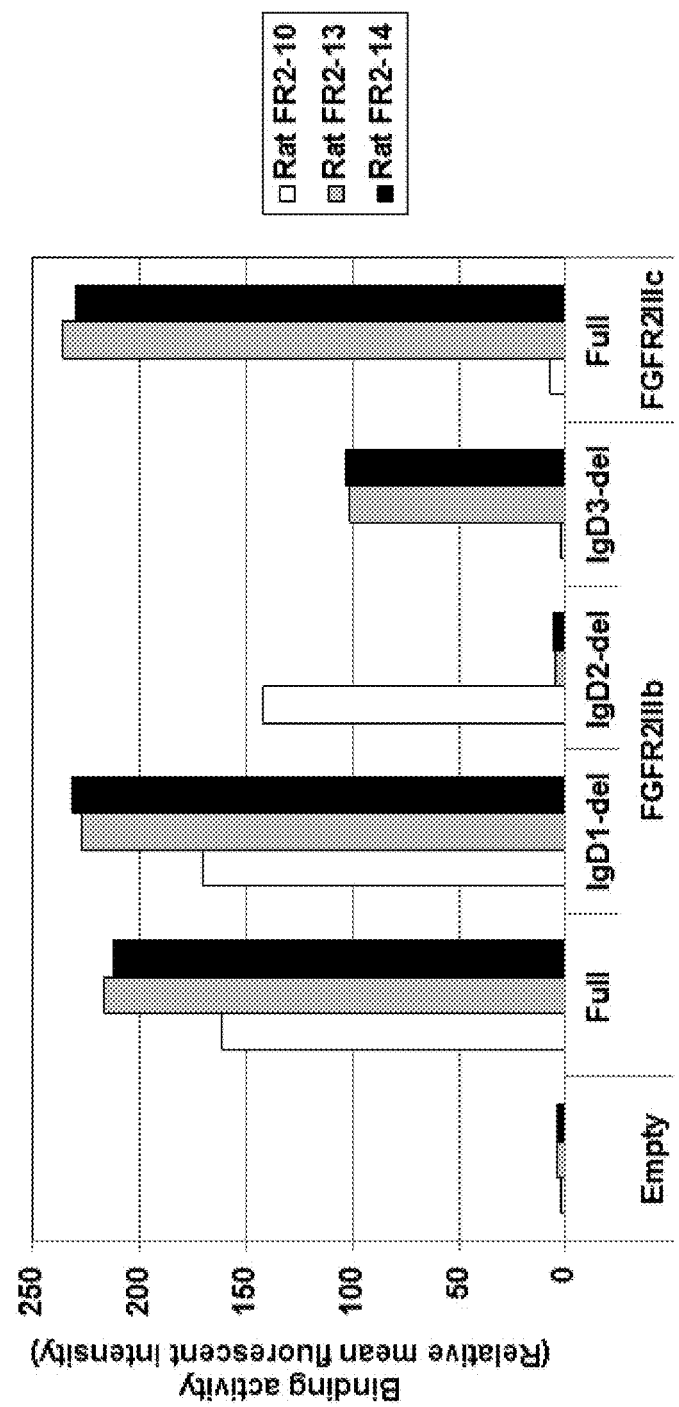
FIG. 2 is a diagram showing results of testing for epitopes on human FGFR2 to which the rat anti-FGFR2 antibodies (FR2-10, FR2-13, and FR2-14) bind by flow cytometry. The vertical axis represents a relative value of the average fluorescence intensity assayed by flow cytometry.

Epitopes bound by the obtained rat anti-FGFR2 antibodies were identified using vectors for expression of mutants lacking any one of the three Ig-like domains present in the FGFR2 extracellular region. The FGFR2 IIIb IgD1, IgD2, or IgD3-deletion mutant expression vector constructed in Example 1)-3-2 was transfected to HEK293T cells by the method shown in Example 1)-5-1. The cell suspension was centrifuged to remove a supernatant. Then, these various Ig-like domain-deficient FGFR2 IIIb expression vector-transfected HEK293T cells and the pcDNA-DEST40-transfected HEK293T cells were separately suspended by the addition of the hybridoma culture supernatant containing the FR2-10, FR2-13, or FR2-14 antibody and left standing at 4° C. for 1 hour. The cells were washed twice with PBS containing 5% FBS, then suspended by the addition of Anti-Rat IgG FITC conjugate (manufactured by Sigma-Aldrich Corp.) diluted 320-fold with PBS containing 5% FBS, and left standing at 4° C. for 1 hour. The cells were washed 3 times with PBS containing 5% FBS and then resuspended in PBS containing 5% FBS and 2 μg/ml 7-aminoactinomycin D (manufactured by Molecular Probes, Inc.), followed by detection using a flow cytometer (FC500; manufactured by Beckman Coulter Inc.). The data was analyzed using Flowjo (manufactured by Tree Star Inc.). After removal of 7-aminoactinomycin D-positive dead cells by gating, the FITC fluorescence intensity of live cells was plotted to a histogram to calculate average fluorescence intensity (MFI). As seen from FIG. 2, the rat FR2-10 antibody was shown to bind to the Ig-like domain 3 of human FGFR2 IIIb. By contrast, the rat FR2-13 and FR2-14 antibodies, which also exhibited binding activity against human FGFR2 IIIc, were shown to bind to the common Ig-like domain 2 of human FGFR2 IIIb and FGFR2 IIIc.

2)-3 Signal-Neutralizing Effects of Obtained Rat Anti-FGFR2 Antibodies (FR2-10, FR2-13, and FR2-14)

Figure 3A:
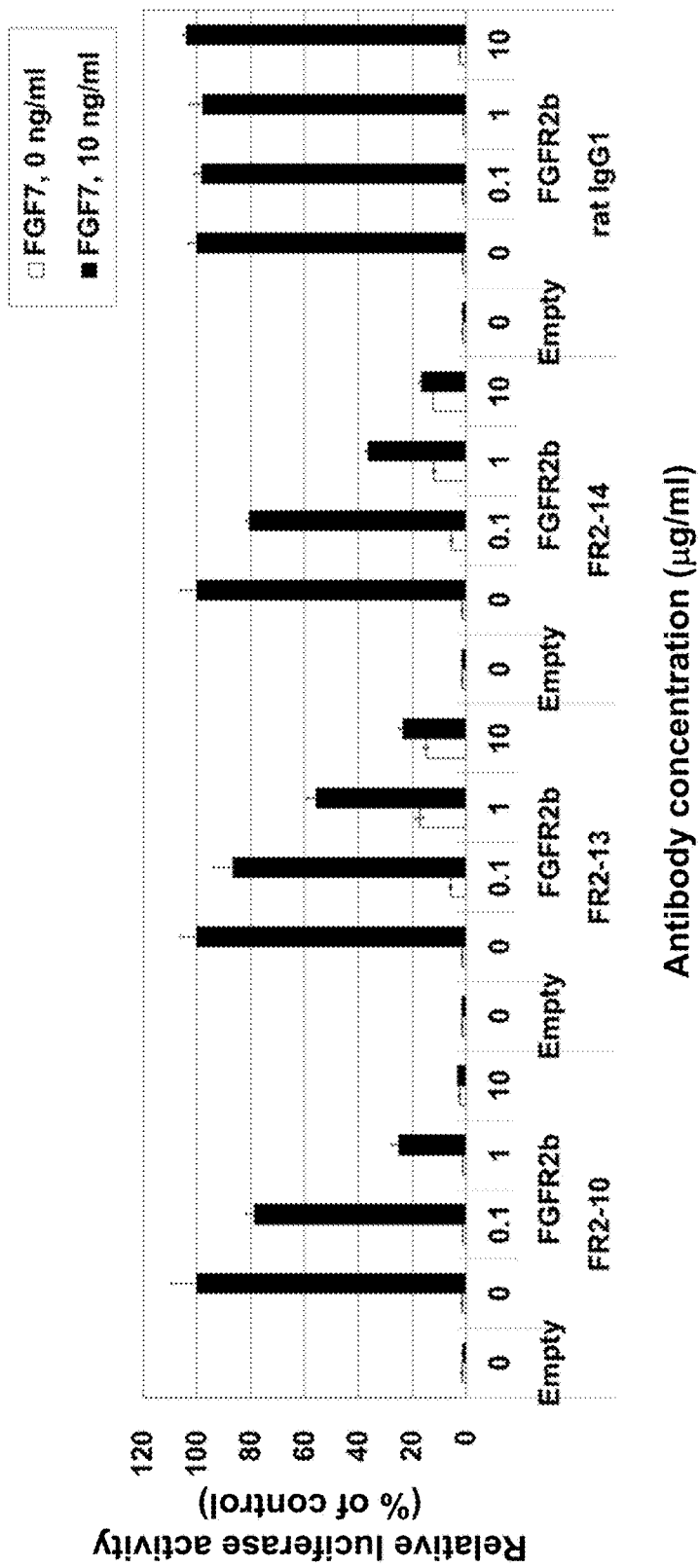
FIG. 3A is a diagram showing the signal-neutralizing activity of the rat anti-FGFR2 antibodies (FR2-10, FR2-13, and FR2-14) against human FGFR2 IIIb by Elk1 trans-reporter assay.
Figure 3B:
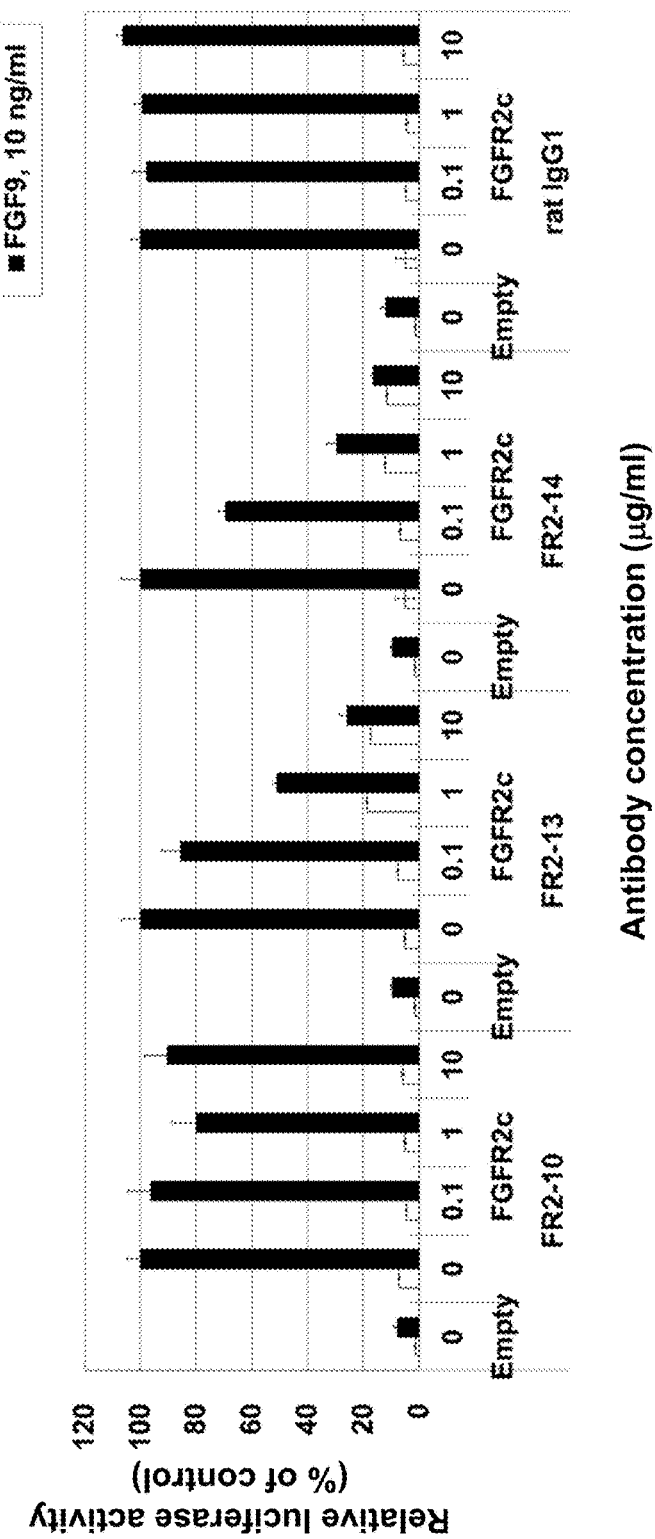
FIG. 3B is a diagram showing the signal-neutralizing activity of the rat anti-FGFR2 antibodies (FR2-10, FR2-13, and FR2-14) against human FGFR2 IIIc by Elk1 trans-reporter assay.

In order to evaluate the signal-neutralizing effects of the obtained antibodies by the Elk1 luciferase reporter gene assay, 293α cells were cotransfected with pcDNA-DEST40-FGFR2 IIIb or pcDNA-DEST40-FGFR2 IIIc constructed in Example 1)-3-1, pFA2-Elk1 (manufactured by Stratagene Corp.), pFR-Luc2CP, and pGL4.74[hRluc/TK] (manufactured by Promega Corp.) by the method shown in Example 1)-6-2, and cultured overnight at 37° C. under 5% $CO_2$ conditions. On the next day, the culture supernatant was removed, and the cells were then preincubated for 1 hour with the rat FR2-10, FR2-13, or FR2-14 antibody diluted with DMEM containing 2% FBS. Subsequently, a ligand human FGF7 (manufactured by R&D systems, Inc.) or human FGF9 (manufactured by PeproTech Inc.) was added at a final concentration of 10 ng/ml to each well. After incubation for 6 hours, firefly luciferase activity (specific signal) and *Renilla* luciferase activity (signal for normalization) were assayed using Dual-Glo Luciferase Assay System (manufactured by Promega Corp.). The firefly/*Renilla* ratio was calculated to normalize data on each well. As shown in FIG. 3A, the rat FR2-10, FR2-13, and FR2-14 antibodies inhibited ligand FGF7 dependent reporter activation in the FGFR2 IIIb-expressing cells. As shown in FIG. 3B, the rat FR2-13 and FR2-14 antibodies inhibited ligand FGF9 dependent reporter activity in the FGFR2 IIIc-expressing cells. These results demonstrated that these antibodies have the effect of inhibiting the activation of FGFR2 by its ligand.

Figure 4:
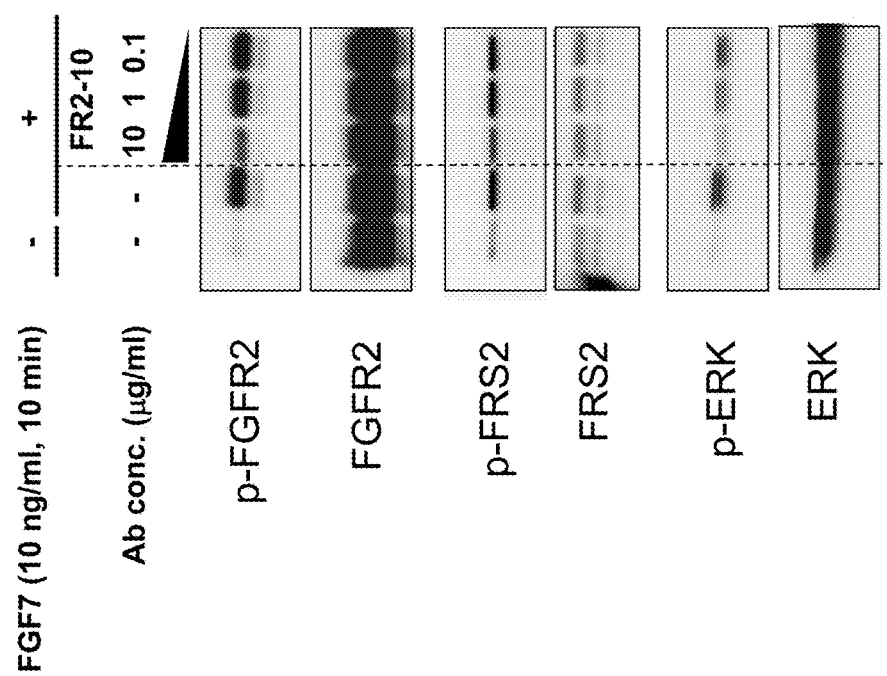
FIG. 4 is a diagram showing the signal inhibitory effect of the rat anti-FGFR2 antibody FR2-10 on FGFR2 by Western blotting. This diagram illustrates that the addition of the rat FR2-10 antibody inhibited FGFR2, FRS2, and ERK phosphorylation induced by the addition of FGF7 to a human stomach cancer cell line SNU-16.

2)-4 FGFR2 Signal Inhibitory Effect of Obtained Rat Anti-FGFR2 Antibody (FR2-10) on Human Cancer Cell Line The FGFR2 signal inhibitory effect of the obtained antibody was tested using a stomach cancer cell line SNU-16 endogenously expressing FGFR2. SNU-16 cells ($3 \times 10^6$) suspended in an RPMI medium containing 0.1% bovine serum albumin were seeded onto a 12-well plate and incubated overnight. The rat FR2-10 antibody was added thereto, and the cells were incubated at 37° C. for 1 hour. Then, 10 ng/ml FGF7 (manufactured by R&D systems, Inc.) was added thereto, and the cells were further incubated for 10 minutes. Subsequently, the cells were lysed with an RIPA buffer (1% NP-40, 0.5% sodium deoxycholate, and 0.1% SDS in PBS) containing Complete Mini (manufactured by Roche Applied Science) and a phosphatase inhibitor (manufactured by Nacalai Tesque Inc.). The lysates were centrifuged to obtain the cell lysis solution, and the protein concentration was determined using BCA protein assay (manufactured by Pierce Biotechnology, Inc.). The lysates were resuspended in a DTT-containing buffer and denatured at 99° C. for 5 minutes. The protein (20 µg/lane) was separated by SDS-PAGE on a 5 to 20% gel. The protein was blotted onto a PVDF membrane (manufactured by Bio-Rad Laboratories, Inc.). The membrane was blocked with TBS-T (2 mM Tris, 50 mM NaCl, and 0.1% Tween-20 (pH 7.4)) containing 5% skimmed milk (MEGMILK SNOW BRAND Co., Ltd.) at room temperature for 1 hour. Then, antibodies against FGFR2, phosphorylated FGFR2 (p-FGFR2), FRS2, phosphorylated FRS2 (p-FRS2), ERK, or phosphorylated ERK (p-ERK) were added thereto, followed by incubation overnight at 4° C. After washing, the membrane was incubated with a horseradish peroxidase-conjugated anti-rabbit secondary antibody (Amersham Biosciences Corp.). Immunoreactive bands were visualized with X-ray films using ECL plus substrate (GE Healthcare Bio-Sciences Corp.). As shown in FIG. 4, the ligand FGF7 stimulation increased the phosphorylation of FGFR2, FRS2, and ERK, whereas the rat FR2-10 antibody inhibited the increase in the phosphorylation of these molecules in a concentration dependent manner.

Example 3

Sequencing of cDNAs Encoding Variable Regions of Rat Anti-Human FGFR2 Antibodies (FR2-10, FR2-13, and FR2-14)

3)-1 Identification of N-Terminal Amino Acid Sequences of Heavy and Light Chains of Rat FR2-10, FR2-13, and FR2-14 Antibodies In order to identify the N-terminal amino acid sequences of the heavy and light chains of the rat FR2-10, FR2-13, and FR2-14 antibodies, the rat FR2-10, FR2-13, and FR2-14 antibodies purified in Example 1)-8 were each separated by SDS-PAGE. After the separation, each protein in the gel was transferred from the gel to Sequi-Blot PVDF membrane (Bio-Rad Laboratories, Inc.). The membrane was washed with a washing buffer (25 mM NaCl and 10 mM sodium borate buffer, pH 8.0), then stained by dipping in a staining solution (50% methanol, 20% acetic acid, and 0.05% Coomassie brilliant blue) for 5 minutes, and then decolorized with 90% methanol. Bands corresponding to the heavy chain (band with a smaller mobility) and light chain (band with a larger mobility) of each antibody visualized on the PVDF membrane were excised, and their respective N-terminal amino acid sequences were identified by the automatic Edman method (see Edman et al. (1967) Eur. J. Biochem. 1, 80) using Procise cLC protein sequencer Model 492cLC (Applied Biosystems, Inc.). As a result, the N-terminal amino acid sequence of the band corresponding to the heavy chain of FR2-10 was EVQLVESGGGLV (SEQ ID NO: 1 of the Sequence Listing; FIG. 9), and the N-terminal amino acid sequence of the band corresponding to the light chain thereof was DIQMTQSPSSLSA (SEQ ID NO: 2 of the Sequence Listing; FIG. 10).

The N-terminal amino acid sequence of the band corresponding to the heavy chain of FR2-13 was QVKLL (SEQ ID NO: 3 of the Sequence Listing; FIG. 11), and the N-terminal amino acid sequence of the band corresponding to the light chain thereof was DIQMTQSPASLSASLGE (SEQ ID NO: 4 of the Sequence Listing; FIG. 12).

The N-terminal amino acid sequence of the band corresponding to the heavy chain of FR2-14 was QVKLL (SEQ ID NO: 5 of the Sequence Listing; FIG. 13), and the N-terminal amino acid sequence of the band corresponding to the light chain thereof was DIQMTQSPASLSASLGE (SEQ ID NO: 6 of the Sequence Listing; FIG. 14).

3)-2 Preparation of mRNA from FR2-10-, FR2-13-, and FR2-14-Producing Hybridomas

In order to amplify cDNAs encoding the variable regions of FR2-10, FR2-13, and FR2-14, mRNAs were prepared from each of the FR2-10-, FR2-13-, and FR2-14-producing hybridoma cells using mRNA Isolation kit (Roche Applied Science).

3)-3 Synthesis of cDNA (5'-RACE-Ready cDNA)

cDNAs (5'-RACE-Ready cDNAs) were synthesized using 70 ng of each mRNA prepared in Example 3)-2, PrimeScript Reverse Transcriptase (Takara Bio Inc.), and SMART RACE cDNA Amplification Kit (Clontech Laboratories, Inc.).

3)-4 5'-RACE PCR Amplification and Sequencing of cDNAs Encoding FR2-10, FR2-13, and FR2-14 Heavy Chain Variable Regions Since the isotype of the FR2-10 heavy chain was IgG2a and the isotypes of the FR2-13 and FR2-14 heavy chains were IgG1 (Example 1)-7), the primers used for PCR amplification of the variable region-encoding cDNA of each heavy chain gene were oligonucleotides having the nucleotide sequences of UPM (Universal Primer A Mix; attached to SMART RACE cDNA Amplification Kit) and 5'-GAGTTACTTTTGAGAGCAGTTCCAGGAG-3' (RG1R1: SEQ ID NO: 7 of the Sequence Listing; FIG. 15). The UPM used was attached to SMART RACE cDNA Amplification Kit (Clontech Laboratories, Inc.), while RG1R1 was designed from the sequences of rat heavy chain (IgG2a and IgG1) constant regions registered in the database.

cDNAs encoding the heavy chain variable regions of FR2-10, FR2-13, and FR2-14 were each amplified by 5'-RACE PCR using this primer set and the cDNAs (5'-RACE-Ready cDNAs) synthesized in Example 3)-3 as templates. This PCR was carried out on the Touchdown PCR program according to the manual of SMART RACE cDNA Amplification Kit (Clontech Laboratories, Inc.) using polymerase KOD-Plus- (Toyobo Co., Ltd.).

Each heavy chain variable region-encoding cDNA amplified by 5'-RACE PCR was purified using MinElute PCR Purification Kit (Qiagen N.V.) and then analyzed by sequencing.

The sequencing primer used was an oligonucleotide having the nucleotide sequence 5'-GAGTTACTTTTGAGAGCAGTTCCAGGAG-3' (RG1R1: SEQ ID NO: 7 of the Sequence Listing; FIG. 15).

On the basis of the results of this sequencing analysis, a sequencing primer for a complementary strand of each cDNA was further designed as shown below and used in sequencing analysis.

Sequencing primer for FR2-10 5'-GGTTCTCCCACTCAGTAATC-3' (10HF: SEQ ID NO: 8 of the Sequence Listing; FIG. 16)

Sequencing primer for FR2-13 5'-CATATGATCAGTGTCCTCTC-3' (13HF: SEQ ID NO: 9 of the Sequence Listing; FIG. 17)

Sequencing primer for FR2-14 5'-ATATGATCAGTGTCCTCTCC-3' (14HF: SEQ ID NO: 10 of the Sequence Listing; FIG. 18)

The sequencing analysis was carried out using a gene sequence analyzer ("ABI PRISM 3700 DNA Analyzer; Applied Biosystems, Inc." or "Applied Biosystems 3730xl Analyzer; Applied Biosystems, Inc."). GeneAmp 9700 (Applied Biosystems, Inc.) was used in sequencing reaction.

The determined nucleotide sequences of the cDNAs encoding the heavy chain variable regions of FR2-10, FR2-13, and FR2-14 and the amino acid sequences of these variable regions are shown in SEQ ID NOs: 11, 13, and 15 and SEQ ID NOs: 12, 14, and 16 (FIGS. 19, 21, and 23 and FIGS. 20, 22, and 24), respectively, of the Sequence Listing.

The amino acid sequences of the FR2-10, FR2-13, and FR2-14 heavy chain variable regions determined on the basis of their nucleotide sequences were consistent with the N-terminal amino acid sequences determined in Example 3)-1.

3)-5 5'-RACE PCR Amplification and Aequencing of cDNA Encoding FR2-10 Light Chain Variable Region Since the isotype of the FR2-10 light chain was κ (Example 1)-7), the primers used for PCR amplification of the variable region-encoding cDNA of the light chain gene were oligonucleotides having the nucleotide sequences of UPM (Universal Primer A Mix; attached to SMART RACE cDNA Amplification Kit) and 5'-TTCATGAGGCACACGACTGAGGCACCTCC-3' (RKR3: SEQ ID NO: 17 of the Sequence Listing; FIG. 25). The UPM used was attached to SMART RACE cDNA Amplification Kit (Clontech Laboratories, Inc.), while RKR3 was designed from the sequences of rat light chain constant regions registered in the database.

A cDNA encoding the light chain variable region of FR2-10 was amplified by 5'-RACE PCR using this primer set and the cDNA (5'-RACE-Ready cDNA) synthesized in Example 3)-3 as a template. This PCR was carried out on the Touchdown PCR program according to the manual of SMART RACE cDNA Amplification Kit (Clontech Laboratories, Inc.) using polymerase KOD-Plus- (Toyobo Co., Ltd.). The light chain variable region-encoding cDNA amplified by 5'-RACE PCR was purified using MinElute PCR Purification Kit (Qiagen N.V.) and then analyzed by sequencing.

The sequencing primer used was an oligonucleotide having the nucleotide sequence 5'-TCCAGTTGCTAACTGTTCCG-3' (sqRK: SEQ ID NO: 18 of the Sequence Listing; FIG. 26) designed from the sequences of rat light chain constant regions registered in the database.

On the basis of the results of this sequencing analysis, a sequencing primer for a complementary strand of the cDNA was further designed as shown below and used in sequencing analysis.

Sequencing primer for FR2-10 5'-CAGTGGTATCAACGCAGAG-3' (10LF: SEQ ID NO: 19 of the Sequence Listing; FIG. 27)

Sequencing analysis and sequencing reaction were performed as mentioned above.

The determined nucleotide sequence of the cDNA encoding the light chain variable region of FR2-10 and the amino acid sequence of this variable region are shown in SEQ ID NO: 20 and SEQ ID NO: 21 (FIGS. 28 and 29), respectively, of the Sequence Listing.

The amino acid sequence of the FR2-10 light chain variable region determined on the basis of its nucleotide sequence was consistent with the N-terminal amino acid sequence determined in Example 3)-1.

3)-6 5'-RACE PCR Amplification and Sequencing of cDNAs Encoding FR2-13 and FR2-14 Light Chain Variable Regions Since the isotypes of the FR2-13 and FR2-14 light chains were κ (Example 1)-7), the primers used for PCR amplification of the variable region-encoding cDNA of each light chain gene were oligonucleotides having the nucleotide sequences of UPM (Universal Primer A Mix; attached to SMART RACE cDNA Amplification Kit) and 5'-TACGTGCTGTCTTTGCTGTCCTGATCAG-3' (RKR6: SEQ ID NO: 22 of the Sequence Listing; FIG. 30). The UPM used was attached to SMART RACE cDNA Amplification Kit (Clontech Laboratories, Inc.), while RKR6 was designed from the sequences of rat light chain constant regions registered in the database.

Variable region-encoding cDNAs of the light chain genes of FR2-13 and FR2-14 were each amplified by 5'-RACE PCR using this primer set and the cDNAs (5'-RACE-Ready cDNAs) synthesized in Example 3)-3 as templates. This PCR was carried out on the Touchdown PCR program according to the manual of SMART RACE cDNA Amplification Kit (Clontech Laboratories, Inc.) using polymerase KOD-Plus- (Toyobo Co., Ltd.).

Each light chain variable region-encoding cDNA amplified by 5'-RACE PCR was purified using MinElute PCR Purification Kit (Qiagen N.V.) and then cloned using Zero Blunt TOPO PCR Cloning Kit (Invitrogen Corp.). The cloned cDNAs encoding the light chain variable regions were analyzed by sequencing.

The sequencing primers used were an oligonucleotide having the nucleotide sequence 5'-TTCATGAGGCACAC-GACTGAGGCACCTCC-3' (RKR3: SEQ ID NO: 17 of the Sequence Listing; FIG. 25) designed from the sequences of rat light chain constant regions registered in the database, and NUP (Nested Universal Primer A: attached to SMART RACE cDNA Amplification Kit).

Sequencing analysis and sequencing reaction were performed as mentioned above.

The determined nucleotide sequences of the cDNAs encoding the light chain variable regions of FR2-13 and FR2-14 and the amino acid sequences of these variable regions are shown in SEQ ID NOs: 23 and 25 (FIGS. 31 and 33) and SEQ ID NOs: 24 and 26 (FIGS. 32 and 34), respectively, of the Sequence Listing.

The amino acid sequences of the FR2-13 and FR2-14 light chain variable regions determined on the basis of their nucleotide sequences were consistent with the N-terminal amino acid sequences determined in Example 3)-1.

Example 4

Preparation of Human Chimeric Anti-FGFR2 Antibodies (cFR2-10, cFR2-13, and cFR2-14)

4)-1 Construction of Chimeric and Humanized Light Chain Expression Vector pCMA-LK A plasmid pcDNA3.3-TOPO/LacZ (Invitrogen Corp.) was digested with restriction enzymes XbaI and PmeI. The obtained fragment of approximately 5.4 kb was ligated with a DNA fragment comprising a DNA sequence (shown in SEQ ID NO: 27 (FIG. 35) of the Sequence Listing) encoding a human κ chain secretory signal and a human κ chain constant region using In-Fusion Advantage PCR cloning kit (Clontech Laboratories, Inc.) to prepare pcDNA3.3/LK.

PCR was performed with pcDNA3.3/LK as a template using a primer set shown below. The obtained fragment of approximately 3.8 kb was phosphorylated and then self-ligated to construct a chimeric and humanized light chain expression vector pCMA-LK having a signal sequence, a cloning site, and the nucleotide sequence encoding the human κ chain constant region, downstream of the CMV promoter.

Primer Set

```
(3.3-F1: SEQ ID NO: 28 of the Sequence
Listing; FIG. 36)
5'-tataccgtcgacctctagctagagcttggc-3'

(3.3-R1: SEQ ID NO: 29 of the Sequence
Listing; FIG. 37)
5'-gctatggcagggcctgccgccccgacgttg-3'
```

4)-2 Construction of Chimeric and Humanized IgG1 Type Heavy Chain Expression Vector pCMA-G1 pCMA-LK was digested with XbaI and PmeI. The obtained DNA fragment except for the DNA sequence encoding the κ chain secretory signal and the human κ chain constant region was ligated with a DNA fragment comprising a DNA sequence (shown in SEQ ID NO: 30 (FIG. 38) of the Sequence Listing) encoding the amino acids of a human heavy chain signal sequence and a human IgG1 constant region using In-Fusion Advantage PCR cloning kit (Clontech Laboratories, Inc.) to construct a chimeric and humanized IgG1 type heavy chain expression vector pCMA-G1 having a signal sequence, a cloning site, and the nucleotide sequence encoding the human IgG1 heavy chain constant region, downstream of the CMV promoter.

4)-3 Construction of Human Chimeric FR2-10 Light Chain Expression Vector

A DNA fragment comprising a light chain variable region-encoding cDNA was amplified using the FR2-10 light chain variable region-encoding cDNA obtained in Example 3) as a template, KOD-Plus- (Toyobo Co., Ltd.), and a primer set shown below, and inserted to the restriction enzyme BsiWI-cleaved site of the general-purpose vector pCMA-LK for chimeric and humanized antibody light chain expression using In-Fusion Advantage PCR cloning kit (Clontech Laboratories, Inc.) to construct a human chimeric FR2-10 light chain expression vector. The obtained expression vector was designated as "pCMA-LK/cFR2-10". The nucleotide sequence of the human chimeric FR2-10 light chain and the amino acid sequence of this light chain are shown in SEQ ID NOs: 31 and 32 (FIGS. 39 and 40), respectively, of the Sequence Listing.

Primer set for human chimeric FR2-10 light chain
5'-atctccggcgcgtacggcgacatccagatgacccagtctccatcttcc-3'
(c10-LF: SEQ ID NO: 33 of the Sequence Listing; FIG. 41)
5'-ggaggggggcggccacagcccgtttatttccaacttcgtccctg-3' (c10-LR: SEQ ID NO: 34 of the Sequence Listing; FIG. 42)

4)-4 Construction of Human Chimeric FR2-10 Heavy Chain Expression Vector

A DNA fragment comprising a heavy chain variable region-encoding cDNA was amplified using the FR2-10 heavy chain variable region-encoding cDNA obtained in Example 3) as a template, KOD-Plus- (Toyobo Co., Ltd.), and a primer set shown below, and inserted to the restriction enzyme BlpI-cleaved site of the chimeric and humanized IgG1 type heavy chain expression vector pCMA-G1 using In-Fusion Advantage PCR cloning kit (Clontech Laboratories, Inc.) to construct a human chimeric FR2-10 heavy chain expression vector. The obtained expression vector was designated as "pCMA-G1/cFR2-10". The nucleotide sequence encoding the human chimeric FR2-10 heavy chain and the amino acid sequence of this heavy chain are shown in SEQ ID NOs: 35 and 36 (FIGS. 43 and 44), respectively, of the Sequence Listing.

Primer set for human chimeric FR2-10 heavy chain
5'-ccagatgggtgctgagcgaggtgcagctggtggagtctgggggaggc-3'
(c10-HF: SEQ ID NO: 37 of the Sequence Listing; FIG. 45)
5'-cttggtggaggctgagctgacagtgactgaagttccttgaccccaggc-3'
(c10-HR: SEQ ID NO: 38 of the Sequence Listing; FIG. 46)

4)-5 Construction of Human Chimeric FR2-13 Light Chain Expression Vector

A DNA fragment comprising a light chain variable region-encoding cDNA was amplified using the FR2-13 light chain variable region-encoding cDNA obtained in Example 3) as a template, KOD-Plus- (Toyobo Co., Ltd.), and a primer set shown below, and inserted to the restriction enzyme BsiWI-cleaved site of the general-purpose vector pCMA-LK for chimeric and humanized antibody light chain expression using In-Fusion Advantage PCR cloning kit (Clontech Laboratories, Inc.) to construct a human chimeric FR2-13 light chain expression vector. The obtained expression vector was designated as "pCMA-LK/cFR2-13". The nucleotide sequence encoding the human chimeric FR2-13 light chain and the amino acid sequence of this light chain are shown in SEQ ID NOs: 39 and 40 (FIGS. 47 and 48), respectively, of the Sequence Listing.

Primer set for human chimeric FR2-13 light chain
5'-atctccggcgcgtacggcgacatccagatgacacagtctccagcttcc-3' (c13-LF: SEQ ID NO: 41 of the Sequence Listing; FIG. 49)
5'-ggaggggggcggccacagcccgtttcagttccagcttggtcccaac-3' (c13-LR: SEQ ID NO: 42 of the Sequence Listing; FIG. 50)

4)-6 Construction of Human Chimeric FR2-13 Heavy Chain Expression Vector

A DNA fragment comprising a heavy chain variable region-encoding cDNA was amplified using the FR2-13 heavy chain variable region-encoding cDNA obtained in Example 3) as a template, KOD-Plus- (Toyobo Co., Ltd.), and a primer set shown below, and inserted to the restriction enzyme BlpI-cleaved site of the chimeric and humanized IgG1 type heavy chain expression vector pCMA-G1 using In-Fusion Advantage PCR cloning kit (Clontech Laboratories, Inc.) to construct a human chimeric FR2-13 heavy chain expression vector. The obtained expression vector was designated as "pCMA-G1/cFR2-13". The nucleotide sequence encoding the human chimeric FR2-13 heavy chain and the amino acid sequence of this heavy chain are shown in SEQ ID NOs: 43 and 44 (FIGS. 51 and 52), respectively, of the Sequence Listing.

Primer set for human chimeric FR2-13 heavy chain
5'-ccagatgggtgctgagccaggttaagctgctgcagtctggggctgag-3' (c13-HF: SEQ ID NO: 45 of the Sequence Listing; FIG. 53)
5'-cttggtggaggctgagctgacagtgaccagagtgccttggccccag-3' (c13-HR: SEQ ID NO: 46 of the Sequence Listing; FIG. 54)

4)-7 Construction of Human Chimeric FR2-14 Light Chain Expression Vector

A DNA fragment comprising a light chain variable region-encoding cDNA was amplified using the FR2-14 light chain variable region-encoding cDNA obtained in Example 3) as a template, KOD-Plus- (Toyobo Co., Ltd.), and a primer set shown below, and inserted to the restriction enzyme BsiWI-cleaved site of the general-purpose vector pCMA-LK for chimeric and humanized antibody light chain expression using In-Fusion Advantage PCR cloning kit (Clontech Laboratories, Inc.) to construct a human chimeric FR2-14 light chain expression vector. The obtained expression vector was designated as "pCMA-LK/cFR2-14". The nucleotide sequence encoding the human chimeric FR2-14 light chain and the amino acid sequence of this light chain are shown in SEQ ID NOs: 47 and 48 (FIGS. 55 and 56), respectively, of the Sequence Listing.

Primer set for human chimeric FR2-14 light chain
5'-atctccggcgcgtacggcgacatccagatgacacagtctccagcttcc-3' (c13-LF: SEQ ID NO: 41 of the Sequence Listing; FIG. 49)
5'-ggaggggggcggccacagcccgtttcagttccagcttggtcccagc-3' (c14-LR: SEQ ID NO: 49 of the Sequence Listing; FIG. 57)

4)-8 Construction of Human Chimeric FR2-14 Heavy Chain Expression Vector

A DNA fragment comprising a heavy chain variable region-encoding cDNA was amplified using the FR2-14 heavy chain variable region-encoding cDNA obtained in Example 3) as a template, KOD-Plus- (Toyobo Co., Ltd.), and a primer set shown below, and inserted to the restriction enzyme BlpI-cleaved site of the chimeric and humanized IgG1 type heavy chain expression vector pCMA-G1 using In-Fusion Advantage PCR cloning kit (Clontech Laboratories, Inc.) to construct a human chimeric FR2-14 heavy chain expression vector. The obtained expression vector was designated as "pCMA-G1/cFR2-14". The nucleotide sequence encoding the human chimeric FR2-14 heavy chain and the amino acid sequence of this heavy chain are shown in SEQ ID NOs: 50 and 51 (FIGS. 58 and 59), respectively, of the Sequence Listing.

Primer set for human chimeric FR2-14 heavy chain
5'-ccagatgggtgctgagccaggttaagctgctgcagtctggggctgag-3' (c13-HF: SEQ ID NO: 45 of the Sequence Listing; FIG. 53)
5'-cttggtggaggctgagctgacagtgaccagagtgccttggccccag-3' (c13-HR: SEQ ID NO: 46 of the Sequence Listing; FIG. 54)

4)-9 Preparation of Human Chimeric Anti-FGFR2 Antibody

4)-9-1 Production of Human Chimeric Anti-FGFR2 Antibody

FreeStyle 293F cells (Invitrogen Corp.) were subcultured and cultured according to the manual.

$1.2 \times 10^9$ FreeStyle 293F cells (Invitrogen Corp.) in the logarithmic growth phase were inoculated to a 3-L Fernbach Erlenmeyer Flask (Corning Inc.), adjusted to $1.0 \times 10^6$ cells/ml by dilution with FreeStyle 293 expression medium (Invitrogen Corp.), and then shake-cultured at 90 rpm at 37° C. for 1 hour in an 8% $CO_2$ incubator. 3.6 mg of polyethyleneimine (Polysciences #24765) was dissolved in 20 ml of Opti-Pro SFM medium (Invitrogen Corp.). Next, each H chain expression vector (0.4 mg) and each L chain expression vector (0.8 mg) prepared using PureLink HiPure Plasmid kit (Invitrogen Corp.) were suspended in 20 ml of Opti-Pro SFM medium (Invitrogen Corp.). 20 ml of the expression vector/Opti-Pro SFM mixed solution was added to 20 ml of the polyethyleneimine/Opti-Pro SFM mixed solution, and the mixture was gently stirred, left for 5 minutes, and then added to the FreeStyle 293F cells. The cells were shake-cultured at 90 rpm at 37° C. for 7 days in an 8% $CO_2$ incubator, and the obtained culture supernatant was filtered through Disposable Capsule Filter (ADVANTEC #CCS-045-E1H).

The human chimeric FR2-10 antibody obtained by the combination of pCMA-G1/cFR2-10 and pCMA-LK/cFR2-10 was designated as "cFR2-10". The human chimeric FR2-13 antibody obtained by the combination of pCMA-G1/cFR2-13 and pCMA-LK/cFR2-13 was designated as "cFR2-13". The human chimeric FR2-14 antibody obtained by the combination of pCMA-G1/cFR2-14 and pCMA-LK/cFR2-14 was designated as "cFR2-14".

4)-9-2 Purification of Human Chimeric Anti-FGFR2 Antibody

Each culture supernatant obtained in Example 4)-9-1 was purified by two steps using rProtein A affinity chromatography (at 4 to 6° C.) and ceramic hydroxyapatite (at room temperature). Buffer replacement steps after the rProtein A affinity chromatography purification and after the ceramic hydroxyapatite purification were carried out at room temperature. First, 1100 to 1200 ml of the culture supernatant was applied to MabSelect SuRe (manufactured by GE Healthcare Bio-Sciences Corp., HiTrap column; volume 1 ml×2 connected) equilibrated with PBS. After entry of the whole culture solution into the column, the column was washed with 15 to 30 ml of PBS. Next, antibody-containing fractions were collected by elution with a 2 M arginine hydrochloride solution (pH 4.0). The fractions were buffer-replaced with 5 mM sodium phosphate, 50 mM MES, and 20 mM NaCl (pH 6.5) using a desalting column (manufactured by GE Healthcare Bio-Sciences Corp., HiTrap Desalting column; volume 5 ml×2 connected). The buffer-replaced antibody solution was further applied to a ceramic hydroxyapatite column (Bio-Rad Laboratories, Inc., Bio-Scale CHT2-1 Hydroxyapatite Column; volume 2 ml) equilibrated with a buffer of 5 mM NaPi, 50 mM MES, and 20 mM NaCl (pH 6.5). Antibody-containing fractions were collected by linear concentration gradient elution using sodium chloride. The fractions were buffer-replaced with CBS (10 mM citrate buffer solution and 140 mM sodium chloride, pH 6.0) using a desalting column (manufactured by GE Healthcare BioSciences Corp., HiTrap Desalting column; volume 5 ml×2 connected). Finally, the fractions were concentrated and adjusted to an IgG concentration of 1.0 mg/ml or higher using Centrifugal UF Filter Device VIVASPIN 20 (molecular weight cutoff: 30K, Sartorius Japan K.K., at 4° C.), and used as a purified sample.

Example 5

In Vitro Activity of Human Chimeric Anti-FGFR2 Antibodies (cFR2-10, cFR2-13, and cFR2-14)

5)-1 Antigen Binding Activity of Human Chimeric Anti-FGFR2 Antibodies (cFR2-10, cFR2-13, and cFR2-14)

Figure 5:
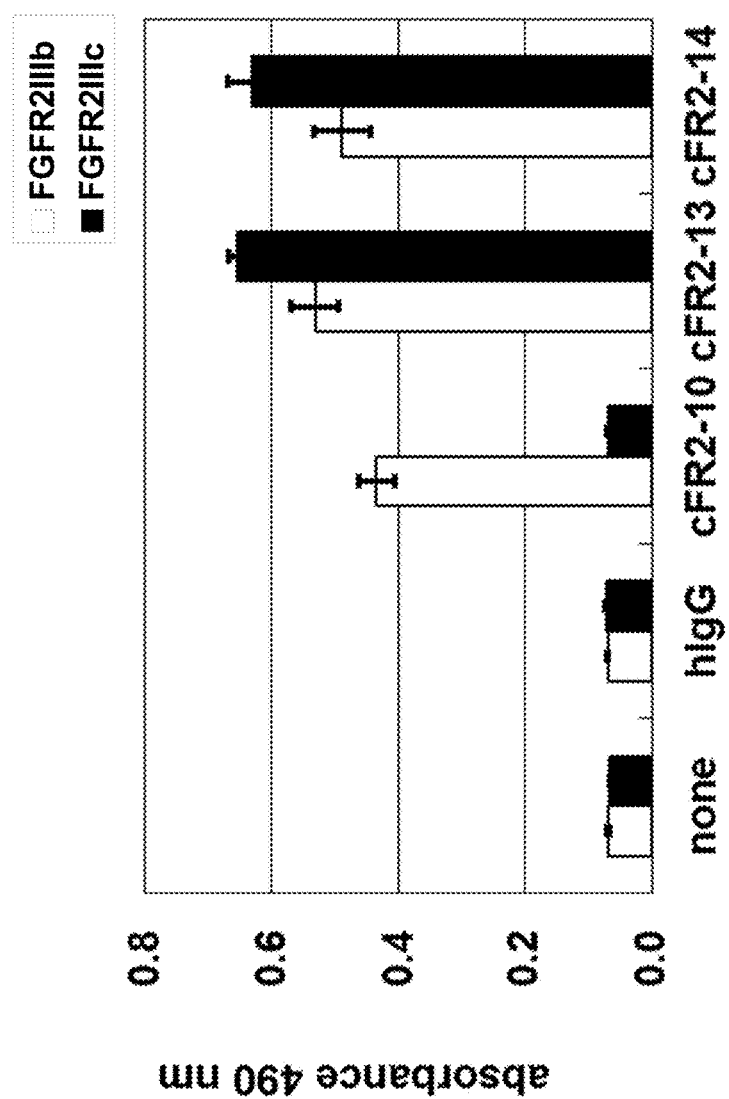
FIG. 5 is a diagram showing results of testing the binding activity of human chimeric anti-FGFR2 antibodies (cFR2-10, cFR2-13, and cFR2-14) against human FGFR2 by Cell-ELISA.

293α cells (described in Example 1)-6) were adjusted to $5 \times 10^5$ cells/ml in a DMEM medium containing 10% FBS. pcDNA-DEST40-FGFR2 IIIb or pcDNA-DEST40-FGFR2 IIIc was transfected thereto using Lipofectamine 2000 (manufactured by Invitrogen Corp.). The resulting cells were dispensed in an amount of 100 µl/well to a 96-well plate (manufactured by Corning Inc.) and cultured overnight at 37° C. under 5% $CO_2$ conditions in a DMEM medium containing 10% FBS. The obtained transfected cells were used in the attached state in Cell-ELISA. After removal of the culture supernatant, the cFR2-10, cFR2-13, or cFR2-14 antibody was added at a final concentration of 2 µg/ml to the pcDNA-DEST40-FGFR2 IIIb- or pcDNA-DEST40-FGFR2 IIIc-transfected cells, and the plate was left standing at 4° C. for 1 hour. The cells in the wells were washed once with PBS containing 5% FBS. Then, Anti-Human IgG-Peroxidase antibody produced in goat (manufactured by Sigma-Aldrich Corp.) diluted 500-fold with PBS containing 5% FBS was added thereto, and the plate was left standing at 4° C. for 1 hour. The cells in the wells were washed 5 times with PBS containing 5% FBS. Then, an OPD chromogenic solution (OPD solution (o-phenylenediamine dihydrochloride (manufactured by Wako Pure Chemicals Industries, Ltd.) and $H_2O_2$ dissolved at concentrations of 0.4 mg/ml and 0.6% (v/v), respectively, in 0.05 M trisodium citrate and 0.1 M disodium hydrogen phosphate dodecahydrate, pH 4.5)) was added thereto at a concentration of 100 µl/well. Color reaction was performed with occasional stirring and stopped by the addition of 1 M HCl at a concentration of 100 µl/well. Then, the absorbance was measured at 490 nm using a plate reader (ARVO; PerkinElmer, Inc.). As shown in FIG. 5, the cFR2-10 antibody selectively bound to FGFR2 IIIb, while the cFR2-13 and cFR2-14 antibodies bound to both FGFR2 IIIb and FGFR2 IIIc.

5)-2 Signal-Neutralizing Effects of Human Chimeric Anti-FGFR2 Antibodies (cFR2-10, cFR2-13, and cFR2-14)

Figure 6B:
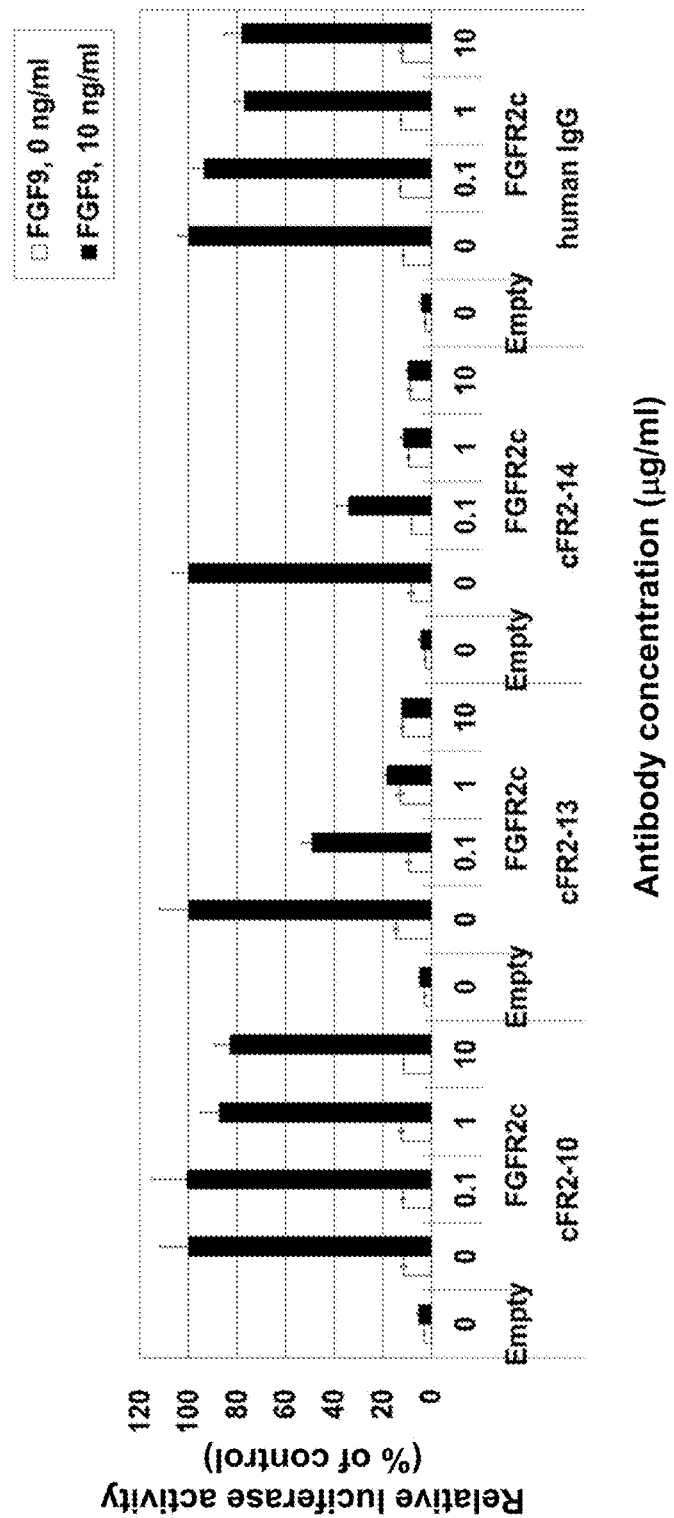
FIG. 6B is a diagram showing the signal-neutralizing activity of the human chimeric anti-FGFR2 antibodies (cFR2-10, cFR2-13, and cFR2-14) against human FGFR2 IIIc by Elk1 trans-reporter assay.

In order to evaluate the signal-neutralizing effects of the obtained antibodies by the Elk1 luciferase reporter gene assay, 293α cells were transfected with pcDNA-DEST40-FGFR2 IIIb or pcDNA-DEST40-FGFR2 IIIc constructed in Example 1)-3-1 by the method shown in Example 1)-6-2, and cultured overnight at 37° C. under 5% $CO_2$ conditions. On the next day, the culture supernatant was removed, and the cells were then preincubated for 1 hour with the cFR2-10, cFR2-13, or cFR2-14 antibody (final concentration: 0.05 to 5 µg/ml) diluted with DMEM containing 2% FBS. Subsequently, a ligand human FGF7 (manufactured by R&D systems, Inc.) or human FGF9 (manufactured by PeproTech Inc.) was added thereto at a final concentration of 10 ng/ml to each well. After incubation for 6 hours, cell lysates were prepared and assayed for firefly luciferase activity (specific signal) and Renilla luciferase activity (signal for normalization) using Dual-luciferase reporter assay system (manufactured by Promega Corp.). The firefly/Renilla ratio was calculated to normalize data on each well. As shown in FIG. 6A, cFR2-10, cFR2-13, and cFR2-14 inhibited ligand FGF7 dependent reporter activation in the FGFR2 IIIb-expressing cells. As shown in FIG. 6B, cFR2-13 and cFR2-14 inhibited ligand FGF9 dependent reporter activation in the FGFR2 IIIc-expressing cells. These results demonstrated that these antibodies have the effect of inhibiting the activation of FGFR2 by its ligand.

5)-3 ADCC Activity of Human Chimeric Anti-FGFR2 Antibodies (cFR2-10, cFR2-13, and cFR2-14)

5)-3-1 Preparation of Target Cell

293FT cells (Invitrogen Corp.) were cotransfected with pLenti6/V5-GW/lacZ and ViraPower™ Packaging Mix (Invitrogen Corp.) according to the attached protocols to prepare a recombinant lentivirus expressing the β-galactosidase gene. 293T cells were infected by the obtained recombinant lentivirus according to the protocol of ViraPower Lentiviral Expression Systems (Invitrogen Corp.). Virus-infected cells were selected using 10 µg/ml Blasticidin (Invitrogen Corp.) to obtain a line stably expressing β-galactosidase. These 293T cells stably expressing β-galactosidase were used as target cells in the assay of ADCC activity.

5)-3-2 Preparation of Target Cell

The stably β-galactosidase-expressing 293T cells (hereinafter, referred to as 293T-lacZ) obtained in Example 5)-3-1 were inoculated to a 225-cm² flask in an amount of $1 \times 10^7$ cells/ml in a DMEM medium containing 10% FBS. After overnight culture at 37° C., pcDNA-DEST40-FGFR2 IIIb was transfected to the cells using Lipofectamine 2000 (manufactured by Invitrogen Corp.), and the cells were cultured at 37° C. for 2 days under 5% $CO_2$ conditions in a DMEM medium containing 10% FBS and then dissociated and recovered from the flask using TrypLE Express (manufactured by Invitrogen Corp.). The cells were washed twice with phenol red-free RPMI1640 containing 5% FBS (hereinafter, referred to as a "medium for ADCC"). The number of live cells was counted by the trypan blue dye exclusion test. The cells were resuspended to $1 \times 10^5$ cells/ml in a medium for ADCC and used as target cells.

5)-3-3 Preparation of Effector Cell

Uncharacterized Cryopreserved PBMC (manufactured by Cellular Technology Ltd.) was suspended in a phenol red-free RPMI1640 medium (manufactured by Invitrogen Corp.) containing 10% FBS, centrifuged, and then resuspended. The number of live cells was counted by the trypan blue dye exclusion test. After centrifugation, the medium was removed, and the cells were suspended and adjusted to a live cell density of $2.3 \times 10^6$ cells/ml in a medium for ADCC and used as effector cells.

5)-3-4 ADCC Assay

The 293T-lacZ cells prepared in Example 5)-3-2 were added at a concentration of 50 µl/well to a 96-well U-bottomed microplate. The cFR2-10, cFR2-13, cFR2-14, or human control antibody (hIgG) diluted to 1 to 100 ng/ml (final concentration) with a medium for ADCC was added thereto at a concentration of 50 µl/well, and the plate was left standing at 4° C. for 1 hour. The effector cells prepared in Example 5)-3-3 were further added thereto at a concentration of 75 µl/well. The plate was centrifuged at 1200 rpm at room temperature for 5 minutes, followed by overnight culture at 37° C. under 5% $CO_2$ conditions. On the next day, 50 µl of the supernatant in each well was recovered into a white plate (manufactured by Corning Inc.). A solution of β-Glo assay system (manufactured by Promega Corp.) was added thereto at a concentration of 50 µl/well. The luminescence intensity was measured using a plate reader (ENVISION; manufactured by PerkinElmer, Inc.). The percentage of cells lysed by ADCC activity was calculated according to the following expression:

Percentage of cells lysed(%)=$(A-B)/(C-B)\times 100$

A: Count of sample well

B: Average of spontaneous release (wells supplemented with neither the antibody nor the effector cells) counts (n=3). The same operation as in the sample well was performed except that 50 µl and 75 µl of a medium for ADCC were added instead of the antibody and the effector cells, respectively.

C: Average of maximum release (wells containing target cells lysed in a surfactant) counts (n=3). 50 µl and 75 µl of a medium for ADCC were added instead of the antibody and the effector cells, respectively. For the assay, 175 µl of the β-Glo assay system solution was added to each well containing the target cells and mixed therewith. A 100 µl aliquot thereof was added to a white plate to carry out the assay.

As shown in FIG. 7, cFR2-10, cFR2-13, and cFR2-14 had ADCC activity against the FGFR2 IIIb-expressing cells.

Example 6

In Vivo Antitumor Activity of Human Chimeric Anti-FGFR2 Antibodies (cFR2-10, cFR2-13, and cFR2-14)

$5\times10^6$ cells of a human stomach cancer line SNU-16 (purchased from ATCC) were suspended in 50% Matrigel (purchased from Nippon Becton Dickinson Company, Ltd.) and subcutaneously transplanted to the axillary region of each nude mouse (CAnN.Cg-Foxnl$^{nu}$/CrlCrlj, purchased from Charles River Laboratories Japan Inc.). The mice were grouped according to their tumor volumes. Seven, 11, 14, and 18 days after transplantation, each human chimeric anti-FGFR2 antibody (cFR2-10, cFR2-13, or cFR2-14) was intraperitoneally administered at a dose of 1.5 or 15 mg/kg to the cancer-bearing mice (n=8). The major axis and minor axis of the transplanted tumor were measured twice a week using an electronic digital caliper (manufactured by Mitsutoyo Corp.). The tumor volume was calculated according to the following expression:

Tumor volume(mm$^3$)=½×Minor axis(mm)×Minor axis(mm)×Major axis(mm)

Figure 8:
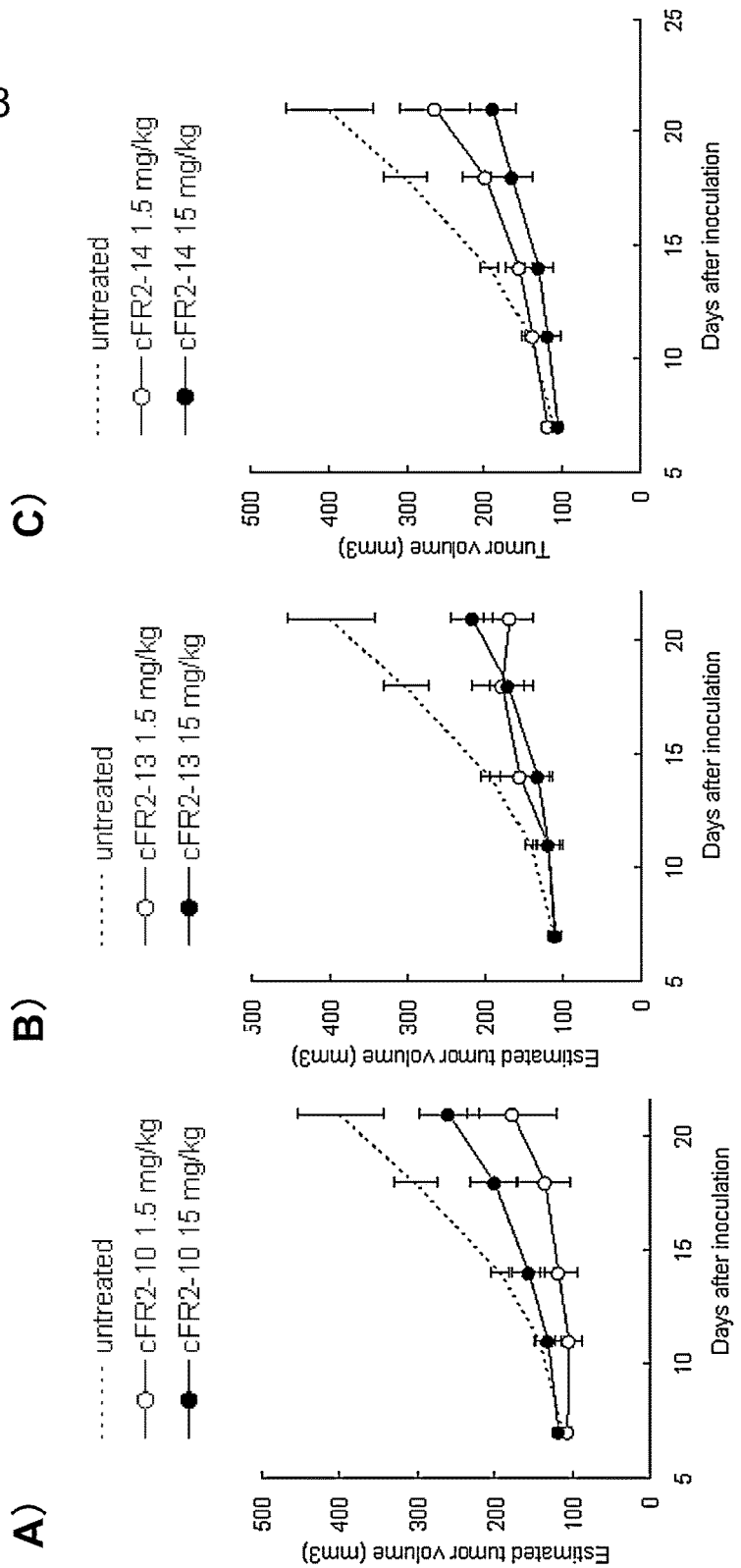
FIG. 8 is a diagram showing the in vivo antitumor activity of the human chimeric anti-FGFR2 antibodies (cFR2-10, cFR2-13, and cFR2-14) against human stomach cancer cell line SNU-16-transplanted nude mice.

The results on the cFR2-10 antibody are shown in FIG. 8-A. The percentage of tumor growth inhibition at 21 days after transplantation (final assay day) was 55% for the 1.5 mg/kg administration group and 35% for the 15 mg/kg administration group.

The results on the cFR2-13 antibody are shown in FIG. 8-B. The percentage of tumor growth inhibition at 21 days after transplantation (final assay day) was 57% for the 1.5 mg/kg administration group and 46% for the 15 mg/kg administration group.

The results on the cFR2-14 antibody are shown in FIG. 8-C. The percentage of tumor growth inhibition at 21 days after transplantation (final assay day) was 34% for the 1.5 mg/kg administration group and 53% for the 15 mg/kg administration group.

Example 7

Design of Humanized Version (hFR2-14) of Human Chimeric Anti-FGFR2 Antibody (cFR2-14)

7)-1 Molecular Modeling of FR2-14 Variable Region

The molecular modeling of the cFR2-14 variable regions was carried out by a method generally known as homology modeling (Methods in Enzymology, 203, 121-153, (1991)). The variable regions of FR2-14 determined above were compared with the primary sequences (three-dimensional structures derived from X-ray crystal structures are available) of human immunoglobulin variable regions registered in Protein Data Bank (Nuc. Acid Res. 28, 235-242 (2000)). As a result, 1ZAN was selected because it had the highest sequence homology to the light chain variable region of cFR2-14. Also, 1CT8 was selected because of its highest sequence homology to the heavy chain variable region of cFR2-14. The three-dimensional structures of framework regions were prepared as a "framework model" by combining the coordinates of 1ZAN and 1CT8 corresponding to the light and heavy chains of cFR2-14. The CDRs of cFR2-14 were assigned as clusters 11A, 7A, 10A, 10A, and 10A to CDRL1, CDRL2, CDRL3, CDRH1, and CDRH2, respectively, according to the classification of Thornton et al. (J. Mol. Biol., 263, 800-815, (1996)). Its CDRH3 was classified into k(6)-according to the H3 rule (FEBS letter, 399, 1-8 (1996)). Subsequently, the typical conformation of each CDR was incorporated into the framework model.

Finally, energy calculation for excluding disadvantageous interatomic contact was conducted in order to obtain possible molecular models of the cFR2-14 variable regions in terms of energy. These procedures were performed using a commercially available protein three-dimensional structure prediction program Prime and conformation search program MacroModel (Schrodinger, LLC).

7)-2 Design of Amino Acid Sequence of Humanized FR2-14

The humanized FR2-14 antibody was constructed by a method generally known as CDR grafting (Proc. Natl. Acad. Sci. USA 86, 10029-10033 (1989)). An acceptor antibody was selected on the basis of the homology of amino acids in framework regions.

The sequences of the cFR2-14 framework regions were compared with the sequences of all human frameworks registered in the Kabat database (Nuc. Acid Res., 29, 205-206 (2001)) of antibody amino acid sequences. As a result, an FV/IL-2'CL antibody was selected as an acceptor due to its 72% sequence homology as to framework regions. The amino acid residues of the framework regions in FV/IL-2'CL were aligned with the amino acid residues of the cFR2-14 framework regions to identify the positions of amino acids that did not match there between. The positions of these residues were analyzed using the three-dimensional model of cFR2-14 constructed above. Then, the donor residues to be grafted onto the acceptor were selected according to the criteria provided by Queen et al. (Proc. Natl. Acad. Sci. USA 86, 10029-10033 (1989)).

Some donor residues thus selected were transferred to the acceptor antibody to construct the humanized FR2-14 sequence as described in Examples below.

In addition, 1 to 3 amino acid residues in each CDR of cFR2-14 were substituted by different amino acid residues to construct a humanized FR2-14 sequence containing modified CDRs as described in Examples below.

7)-3 Humanization of FR2-14 Light Chain

7)-3-1 hFR2-14_L1 Type Light Chain:

A humanized FR2-14 light chain designed by the replacement of amino acid positions 29 (alanine), 35 (leucine), 37 (glutamic acid), 38 (threonine), 42 (glutamic acid), 62 (asparagine), 90 (glutamine), 92 (serine), 94 (lysine), 96 (asparagine), 100 (serine), 103 (valine), 105 (serine), 107 (phenylalanine), 121 (alanine), 125 (leucine), 127 (leucine), and 130 (alanine) in the cFR2-14 light chain shown in SEQ ID NO: 48 of the Sequence Listing with serine, valine, aspartic acid, arginine, threonine, lysine, aspartic acid, threonine, threonine, serine, proline, phenylalanine, threonine, tyrosine, glutamine, valine, isoleucine, and threonine, respectively, was designated as an "hFR2-14_L1 type light chain".

A nucleotide sequence encoding the hFR2-14_L1 type light chain is shown in SEQ ID NO: 72 of the Sequence Listing. Nucleotide positions 61 to 705 encode a mature light chain produced by the cleavage of the signal sequence. Also, the amino acid sequence of the hFR2-14_L1 type light chain is shown in SEQ ID NO: 73 of the Sequence Listing. Amino acid positions 21 to 235 represent a mature light chain produced by the cleavage of the signal sequence. The sequences of SEQ ID NOs: 72 and 73 are further described in FIGS. 80 and 81, respectively.

7)-4 Humanization of FR2-14 Heavy Chain

7)-4-1 hFR2-14_H1 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 62 (proline), 63 (serine), 64 (threonine), 67 (isoleucine), 86 (lysine), 87 (alanine), 94 (phenylalanine), 95 (serine), 101 (aspartic acid), 106 (threonine), 110 (alanine) and 114 (phenylalanine) in the cFR2-14 heavy chain shown in SEQ ID NO: 51 of the Sequence Listing with glutamine, valine, valine, lysine, valine, alanine, valine, arginine, alanine, glutamine, glycine, leucine, methionine, arginine, valine, serine, threonine, glutamic acid, arginine, threonine and tyrosine, respectively, was designated as an "hFR2-14_H1 type heavy chain".

A nucleotide sequence encoding the hFR2-14_H1 type heavy chain is shown in SEQ ID NO: 74 of the Sequence Listing. Nucleotide positions 58 to 1401 encode a mature heavy chain produced by the cleavage of the signal sequence. Also, the amino acid sequence of the hFR2-14_H1 type heavy chain is shown in SEQ ID NO: 75 of the Sequence Listing. Amino acid positions 20 to 467 represent a mature heavy chain produced by the cleavage of the signal sequence. The sequences of SEQ ID NOs: 74 and 75 are further described in FIGS. 82 and 83, respectively.

7)-4-2 hFR2-14_H2 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 62 (proline), 63 (serine), 64 (threonine), 67 (isoleucine), 86 (lysine), 87 (alanine), 91 (valine), 94 (phenylalanine), 95 (serine), 101 (aspartic acid), 106 (threonine), 110 (alanine) and 114 (phenylalanine) in the cFR2-14 heavy chain shown in SEQ ID NO: 51 of the Sequence Listing with glutamine, valine, valine, lysine, valine, alanine, valine, arginine, alanine, glutamine, glycine, leucine, methionine, arginine, valine, serine, threonine, glutamic acid, arginine, threonine and tyrosine, respectively, was designated as an "hFR2-14_H2 type heavy chain".

A nucleotide sequence encoding the hFR2-14_H2 type heavy chain is shown in SEQ ID NO: 76 of the Sequence Listing. Nucleotide positions 58 to 1401 encode a mature heavy chain produced by the cleavage of the signal sequence. Also, the amino acid sequence of the hFR2-14_H2 type heavy chain is shown in SEQ ID NO: 77 of the Sequence Listing. Amino acid positions 20 to 467 represent a mature heavy chain produced by the cleavage of the signal sequence. The sequences of SEQ ID NOs: 76 and 77 are further described in FIGS. 84 and 85, respectively.

7)-4-3 hFR2-14_H3 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine) and 114 (phenylalanine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine and tyrosine, respectively, was designated as an "hFR2-14_H3 type heavy chain".

A nucleotide sequence encoding the hFR2-14_H3 type heavy chain is shown in SEQ ID NO: 78 of the Sequence Listing. Nucleotide positions 58 to 1401 encode a mature heavy chain produced by the cleavage of the signal sequence. Also, the amino acid sequence of the hFR2-14_H3 type heavy chain is shown in SEQ ID NO: 79 of the Sequence Listing. Amino acid positions 20 to 467 represent a mature heavy chain produced by the cleavage of the signal sequence. The sequences of SEQ ID NOs: 78 and 79 are further described in FIGS. 86 and 87, respectively.

7)-4-4 hFR2-14_H4 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 64 (threonine), 67 (isoleucine), 86 (lysine), 87 (alanine), 94 (phenylalanine), 95 (serine), 101 (aspartic acid), 106 (threonine), 110 (alanine), 114 (phenylalanine) and 125 (threonine) in the cFR2-14 heavy chain shown in SEQ ID NO: 51 of the Sequence Listing with glutamine, valine, valine, lysine, valine, alanine, valine, arginine, alanine, isoleucine, methionine, arginine, valine, serine, threonine, glutamic acid, arginine, threonine, tyrosine and alanine, respectively, was designated as an "hFR2-14_H4 type heavy chain".

A nucleotide sequence encoding the hFR2-14_H4 type heavy chain is shown in SEQ ID NO: 80 of the Sequence Listing. Nucleotide positions 58 to 1401 encode a mature heavy chain produced by the cleavage of the signal sequence. Also, the amino acid sequence of the hFR2-14_H4 type heavy chain is shown in SEQ ID NO: 81 of the Sequence Listing. Amino acid positions 20 to 467 represent a mature heavy chain produced by the cleavage of the signal sequence. The sequences of SEQ ID NOs: 80 and 81 are further described in FIGS. 88 and 89, respectively.

7)-4-5 hFR2-14_H5 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 118 (aspartic acid) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and glutamic acid, respectively, was designated as an "hFR2-14_H5 type heavy chain".

A nucleotide sequence encoding the hFR2-14_H5 type heavy chain is shown in SEQ ID NO: 82 of the Sequence Listing. Nucleotide positions 58 to 1401 encode a mature heavy chain produced by the cleavage of the signal sequence. Also, the amino acid sequence of the hFR2-14_H5 type heavy chain is shown in SEQ ID NO: 83 of the Sequence Listing. Amino acid positions 20 to 467 represent a mature heavy chain produced by the cleavage of the signal sequence. The sequences of SEQ ID NOs: 82 and 83 are further described in FIGS. 90 and 91, respectively.

7)-4-6 hFR2-14_H6 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and alanine, respectively, was designated as an "hFR2-14_H6 type heavy chain".

A nucleotide sequence encoding the hFR2-14_H6 type heavy chain is shown in SEQ ID NO: 84 of the Sequence Listing. Nucleotide positions 58 to 1401 encode a mature heavy chain produced by the cleavage of the signal sequence. Also, the amino acid sequence of the hFR2-14_H6 type heavy chain is shown in SEQ ID NO: 85 of the Sequence Listing. Amino acid positions 20 to 467 represent a mature heavy chain produced by the cleavage of the signal sequence. The sequences of SEQ ID NOs: 84 and 85 are further described in FIGS. 92 and 93, respectively.

7)-4-7 hFR2-14_H7 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and glutamic acid, respectively, was designated as an "hFR2-14_H7 type heavy chain".

A nucleotide sequence encoding the hFR2-14_H7 type heavy chain is shown in SEQ ID NO: 86 of the Sequence Listing. Nucleotide positions 58 to 1401 encode a mature heavy chain produced by the cleavage of the signal sequence. Also, the amino acid sequence of the hFR2-14_H7 type heavy chain is shown in SEQ ID NO: 87 of the Sequence Listing. Amino acid positions 20 to 467 represent a mature heavy chain produced by the cleavage of the signal sequence. The sequences of SEQ ID NOs: 86 and 87 are further described in FIGS. 94 and 95, respectively.

7)-4-8 hFR2-14_H8 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and phenylalanine, respectively, was designated as an "hFR2-14_H8 type heavy chain".

A nucleotide sequence encoding the hFR2-14_H8 type heavy chain is shown in SEQ ID NO: 88 of the Sequence Listing. Nucleotide positions 58 to 1401 encode a mature heavy chain produced by the cleavage of the signal sequence. Also, the amino acid sequence of the hFR2-14_H8 type heavy chain is shown in SEQ ID NO: 89 of the Sequence Listing. Amino acid positions 20 to 467 represent a mature heavy chain produced by the cleavage of the signal sequence. The sequences of SEQ ID NOs: 88 and 89 are further described in FIGS. 96 and 97, respectively.

7)-4-9 hFR2-14_H9 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and histidine, respectively, was designated as an "hFR2-14_H9 type heavy chain".

A nucleotide sequence encoding the hFR2-14_H9 type heavy chain is shown in SEQ ID NO: 90 of the Sequence Listing. Nucleotide positions 58 to 1401 encode a mature heavy chain produced by the cleavage of the signal sequence. Also, the amino acid sequence of the hFR2-14_H9 type heavy chain is shown in SEQ ID NO: 91 of the Sequence Listing. Amino acid positions 20 to 467 represent a mature heavy chain produced by the cleavage of the signal sequence. The sequences of SEQ ID NOs: 90 and 91 are further described in FIGS. 98 and 99, respectively.

7)-4-10 hFR2-14_H10 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and isoleucine, respectively, was designated as an "hFR2-14_H10 type heavy chain".

A nucleotide sequence encoding the hFR2-14_H10 type heavy chain is shown in SEQ ID NO: 92 of the Sequence Listing. Nucleotide positions 58 to 1401 encode a mature heavy chain produced by the cleavage of the signal sequence. Also, the amino acid sequence of the hFR2-14_H10 type heavy chain is shown in SEQ ID NO: 93 of the Sequence Listing. Amino acid positions 20 to 467 represent a mature heavy chain produced by the cleavage of the signal sequence. The sequences of SEQ ID NOs: 92 and 93 are further described in FIGS. 100 and 101, respectively.

7)-4-11 hFR2-14_H11 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and lysine, respectively, was designated as an "hFR2-14_H11 type heavy chain".

A nucleotide sequence encoding the hFR2-14_H11 type heavy chain is shown in SEQ ID NO: 94 of the Sequence Listing. Nucleotide positions 58 to 1401 encode a mature heavy chain produced by the cleavage of the signal sequence. Also, the amino acid sequence of the hFR2-14_H11 type heavy chain is shown in SEQ ID NO: 95 of the Sequence Listing. Amino acid positions 20 to 467 represent a mature heavy chain produced by the cleavage of the signal sequence. The sequences of SEQ ID NOs: 94 and 95 are further described in FIGS. 102 and 103, respectively.

7)-4-12 hFR2-14_H12 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and leucine, respectively, was designated as an "hFR2-14_H12 type heavy chain".

A nucleotide sequence encoding the hFR2-14_H12 type heavy chain is shown in SEQ ID NO: 96 of the Sequence Listing. Nucleotide positions 58 to 1401 encode a mature heavy chain produced by the cleavage of the signal sequence. Also, the amino acid sequence of the hFR2-14_H12 type heavy chain is shown in SEQ ID NO: 97 of the Sequence Listing. Amino acid positions 20 to 467 represent a mature heavy chain produced by the cleavage of the signal sequence. The sequences of SEQ ID NOs: 96 and 97 are further described in FIGS. 104 and 105, respectively.

7)-4-13 hFR2-14_H13 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and methionine, respectively, was designated as an "hFR2-14_H13 type heavy chain".

A nucleotide sequence encoding the hFR2-14_H13 type heavy chain is shown in SEQ ID NO: 98 of the Sequence Listing. Nucleotide positions 58 to 1401 encode a mature heavy chain produced by the cleavage of the signal sequence. Also, the amino acid sequence of the hFR2-14_H13 type heavy chain is shown in SEQ ID NO: 99 of the Sequence Listing. Amino acid positions 20 to 467 represent a mature heavy chain produced by the cleavage of the signal sequence. The sequences of SEQ ID NOs: 98 and 99 are further described in FIGS. 106 and 107, respectively.

7)-4-14 hFR2-14_H14 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and glutamine, respectively, was designated as an "hFR2-14_H14 type heavy chain".

A nucleotide sequence encoding the hFR2-14_H14 type heavy chain is shown in SEQ ID NO: 100 of the Sequence Listing. Nucleotide positions 58 to 1401 encode a mature heavy chain produced by the cleavage of the signal sequence. Also, the amino acid sequence of the hFR2-14_H14 type heavy chain is shown in SEQ ID NO: 101 of the Sequence Listing. Amino acid positions 20 to 467 represent a mature heavy chain produced by the cleavage of the signal sequence. The sequences of SEQ ID NOs: 100 and 101 are further described in FIGS. 108 and 109, respectively.

7)-4-15 hFR2-14_H15 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and arginine, respectively, was designated as an "hFR2-14_H15 type heavy chain".

A nucleotide sequence encoding the hFR2-14_H15 type heavy chain is shown in SEQ ID NO: 102 of the Sequence Listing. Nucleotide positions 58 to 1401 encode a mature heavy chain produced by the cleavage of the signal sequence. Also, the amino acid sequence of the hFR2-14_H15 type heavy chain is shown in SEQ ID NO: 103 of the Sequence Listing. Amino acid positions 20 to 467 represent a mature heavy chain produced by the cleavage of the signal sequence. The sequences of SEQ ID NOs: 102 and 103 are further described in FIGS. 110 and 111, respectively.

7)-4-16 hFR2-14_H16 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and valine, respectively, was designated as an "hFR2-14_H16 type heavy chain".

A nucleotide sequence encoding the hFR2-14_H16 type heavy chain is shown in SEQ ID NO: 104 of the Sequence Listing. Nucleotide positions 58 to 1401 encode a mature heavy chain produced by the cleavage of the signal sequence. Also, the amino acid sequence of the hFR2-14_H16 type heavy chain is shown in SEQ ID NO: 105 of the Sequence Listing. Amino acid positions 20 to 467 represent a mature heavy chain produced by the cleavage of the signal sequence. The sequences of SEQ ID NOs: 104 and 105 are further described in FIGS. 112 and 113, respectively.

7)-4-17 hFR2-14_H17 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and tryptophan, respectively, was designated as an "hFR2-14_H17 type heavy chain".

A nucleotide sequence encoding the hFR2-14_H17 type heavy chain is shown in SEQ ID NO: 106 of the Sequence Listing. Nucleotide positions 58 to 1401 encode a mature heavy chain produced by the cleavage of the signal sequence. Also, the amino acid sequence of the hFR2-14_H17 type heavy chain is shown in SEQ ID NO: 107 of the Sequence Listing. Amino acid positions 20 to 467 represent a mature heavy chain produced by the cleavage of the signal sequence. The sequences of SEQ ID NOs: 106 and 107 are further described in FIGS. 114 and 115, respectively.

7)-4-18 hFR2-14_H18 Type Heavy Chain:

A humanized FR2-14 heavy chain designed by the replacement of amino acid positions 22 (lysine), 24 (leucine), 30 (leucine), 31 (valine), 39 (leucine), 43 (threonine), 56 (leucine), 57 (lysine), 59 (valine), 67 (isoleucine), 86 (lysine), 87 (alanine), 94 (phenylalanine), 95 (serine), 101 (aspartic acid), 106 (threonine), 110 (alanine), 114 (phenylalanine) and 119 (glycine) in the cFR2-14 heavy chain shown in SEQ ID NO: 51 of the Sequence Listing with glutamine, valine, valine, lysine, valine, alanine, valine, arginine, alanine, methionine, arginine, valine, serine, threonine, glutamic acid, arginine, threonine, tyrosine and tyrosine, respectively, was designated as an "hFR2-14_H18 type heavy chain".

A nucleotide sequence encoding the hFR2-14_H18 type heavy chain is shown in SEQ ID NO: 108 of the Sequence Listing. Nucleotide positions 58 to 1401 encode a mature heavy chain produced by the cleavage of the signal sequence. Also, the amino acid sequence of the hFR2-14_H18 type heavy chain is shown in SEQ ID NO: 109 of the Sequence Listing. Amino acid positions 20 to 467 represent a mature heavy chain produced by the cleavage of the signal sequence. The sequences of SEQ ID NOs: 108 and 109 are further described in FIGS. 116 and 117, respectively.

Example 8

Obtainment and Expression of Humanized Antibody (hFR2-14) of Rat Anti-Human FGFR2 Antibody FR2-14

8)-1 Construction of Light Chain Expression Vector for Humanized Antibody (hFR2-14) of Rat Anti-Human FGFR2 Antibody FR2-14

8)-1-1 Construction of hFR2-14_L1 Type Light Chain Expression Vector

A DNA comprising a gene encoding the hFR2-14_L1 type light chain variable region shown in amino acid positions 21 to 130 of SEQ ID NO: 73 was synthesized and cleaved with a restriction enzyme BsiWI. The resulting DNA fragment was inserted to the restriction enzyme BsiWI-cleaved site of the general-purpose vector (pCMA-LK) for chimeric and humanized antibody light chain expression to construct an hFR2-14_L1 type light chain expression vector. The obtained expression vector was designated as "pCMA-LK/hFR2-14_L1".

8)-2 Construction of Heavy Chain Expression Vector for Humanized Antibody (hFR2-14) of Rat Anti-Human FGFR2 Antibody FR2-14

8)-2-1 Construction of hFR2-14_H1, hFR2-14_H3, and hFR2-14_H4 Type Heavy Chain Expression Vectors A DNA comprising a gene encoding each of the hFR2-14_H1, hFR2-14_H3, and hFR2-14_H4 type heavy chain variable regions shown in amino acid positions 20 to 137 of SEQ ID NO: 75, amino acid positions 20 to 137 of SEQ ID NO: 79, and amino acid positions 20 to 137 of SEQ ID NO: 81, respectively, of the Sequence Listing was synthesized and cleaved with a restriction enzyme BlpI. The resulting DNA fragment was inserted to the restriction enzyme BlpI-cleaved site of the general-purpose vector (pCMA-G1) for humanized antibody heavy chain expression to construct hFR2-14_H1, hFR2-14_H3, and hFR2-14_H4 type heavy chain expression vectors. The obtained expression vectors were designated as "pCMA-G1/hFR2-14_H1", "pCMA-G1/hFR2-14_H3", and "pCMA-G1/hFR2-14_H4", respectively.

8)-2-2 Construction of hFR2-14_H2 Type Heavy Chain Expression Vector

An hFR2-14_H2 type heavy chain expression vector was constructed using pCMA-G1/hFR2-14_H1 constructed in Example 8)-2-1 as a template, a primer set shown below, and QuikChange XL Site-Directed Mutagenesis Kit (Agilent Technologies, Inc.). The obtained expression vector was designated a "pCMA-G1/hFR2-14_H2". The nucleotide sequence of the hFR2-14_H2 type heavy chain is shown in SEQ ID NO: 76 of the Sequence Listing, and its amino acid sequence is shown in SEQ ID NO: 77.

Primer Set (VH3A-F: SEQ ID NO: 110 of the Sequence Listing)
5'-ggcagagtgaccctgaccgccgacaagagcaccagcacc-3'

(VH3A-R: SEQ ID NO: 111 of the Sequence Listing)
5'-ggtgctggtgctcttgtcggcggtcagggtcactctgcc-3'

8)-2-3 Construction of hFR2-14_H5 Type Heavy Chain Expression Vector

The hFR2-14$_{13}$ H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H5 type heavy chain expression vector. The obtained expression vector was designated as "pCMA-G1/hFR2-14_H5". Primer set:

(H5-F: SEQ ID NO: 114 of the Sequence Listing)
5'-GAGGGCTACGGCGACTGGTTCACATAC-3'

(H-R, which is used as a common primer in the description below: SEQ ID NO: 115 of the Seqence Listing)
5'-GGTGGCGCAGTAGTACACGGCGGT-3'

8)-2-4 Construction of hFR2-14_H6 Type Heavy Chain Expression Vector

The hFR2-14_H3 type heavy chain expression vector pCMA-G1/hFR2-14H3 prepared in Example 8)-2-1 was used as a template and mutated using a primer set described below and KOD-Plus-Mutagenesis Kit (Toyobo Co., Ltd.) to construct an hFR2-14_H6 type heavy chain expression vector. The obtained expression vector was designated as "pCMA-G1/hFR2-14_H6". Primer set:

```
(H6-F: SEQ ID NO: 116 of the
Sequence Listing)
5'-GACGCCTACGGCGACTGGTTCACATAC-3'

(H-R: SEQ ID NO: 115 of the
Sequence Listing)
5'-GGTGGCGCAGTAGTACACGGCGGT-3'
```

8)-2-5 Construction of hFR2-14_H7 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H7 type heavy chain expression vector. The obtained expression vector was designated as "pCMA-G1/hFR2-14_H7". Primer set:

```
(H7-F: SEQ ID NO: 117 of the
Sequence Listing)
5'-GACGAGTACGGCGACTGGTTCACATAC-3'

(H-R: SEQ ID NO: 115 of the
Sequence Listing)
5'-GGTGGCGCAGTAGTACACGGCGGT-3'
```

8)-2-6 Construction of hFR2-14_H8 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H8 type heavy chain expression vector. The obtained expression vector was designated as "pCMA-G1/hFR2-14_H8".
Primer set:

```
(H8-F: SEQ ID NO: 118 of the
Sequence Listing)
5'-GACTTCTACGGCGACTGGTTCACATAC-3'

(H-R: SEQ ID NO: 115 of the
Sequence Listing)
5'-GGTGGCGCAGTAGTACACGGCGGT-3'
```

8)-2-7 Construction of hFR2-14_H9 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H9 type heavy chain expression vector. The obtained expression vector was designated as "pCMA-G1/hFR2-14_H9". Primer set:

```
(H9-F: SEQ ID NO: 119 of the
Sequence Listing)
5'-GACCACTACGGCGACTGGTTCACATAC-3'
```

```
(H-R: SEQ ID NO: 115 of the
Sequence Listing)
5'-GGTGGCGCAGTAGTACACGGCGGT-3'
```

8)-2-8 Construction of hFR2-14_H10 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H10 type heavy chain expression vector. The obtained expression vector was designated as "pCMA-G1/hFR2-14_H10". Primer set:

```
(H10-F: SEQ ID NO: 120 of the
Sequence Listing)
5'-GACATCTACGGCGACTGGTTCACATAC-3'

(H-R: SEQ ID NO: 115 of the
Sequence Listing)
5'-GGTGGCGCAGTAGTACACGGCGGT-3'
```

8)-2-9 Construction of hFR2-14_H11 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H11 type heavy chain expression vector. The obtained expression vector was designated as "pCMA-G1/hFR2-14_H11". Primer set:

```
(H11-F: SEQ ID NO: 121 of the
Sequence Listing)
5'-GACAAGTACGGCGACTGGTTCACATAC-3'

(H-R: SEQ ID NO: 115 of the
Sequence Listing)
5'-GGTGGCGCAGTAGTACACGGCGGT-3'
```

8)-2-10 Construction of hFR2-14_H12 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_hH12 type heavy chain expression vector. The obtained expression vector was designated as "pCMA-G1/hFR2-14_H12". Primer set:

```
(H12-F: SEQ ID NO: 122 of the
Sequence Listing)
5'-GACCTGTACGGCGACTGGTTCACATAC-3'

(H-R: SEQ ID NO: 115 of the
Sequence Listing)
5'-GGTGGCGCAGTAGTACACGGCGGT-3'
```

8)-2-11 Construction of hFR2-14_H13 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H13 type heavy chain expression vector. The obtained expression vector was designated as "pCMA-G1/hFR2-14_H13". Primer set:

```
(H13-F: SEQ ID NO: 123 of the
Sequence Listing)
5'-GACATGTACGGCGACTGGTTCACATAC-3'

(H-R: SEQ ID NO: 115 of the
Sequence Listing)
5'-GGTGGCGCAGTAGTACACGGCGGT-3'
```

8)-2-12 Construction of hFR2-14_H14 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H14 type heavy chain expression vector. The obtained expression vector was designated as "pCMA-G1/hFR2-14_H14". Primer set:

```
(H14-F: SEQ ID NO: 124 of the
Sequence Listing)
5'-GACCAGTACGGCGACTGGTTCACATAC-3'

(H-R: SEQ ID NO: 115 of the
Sequence Listing)
5'-GGTGGCGCAGTAGTACACGGCGGT-3'
```

8)-2-13 Construction of hFR2-14_H15 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H15 type heavy chain expression vector. The obtained expression vector was designated as "pCMA-G1/hFR2-14_H15". Primer set:

```
(H15-F: SEQ ID NO: 125 of the
Sequence Listing)
5'-GACCGGTACGGCGACTGGTTCACATAC-3'

(H-R: SEQ ID NO: 115 of the
Sequence Listing)
5'-GGTGGCGCAGTAGTACACGGCGGT-3'
```

8)-2-14 Construction of hFR2-14_H16 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H16 type heavy chain expression vector. The obtained expression vector was designated as "pCMA-G1/hFR2-14_H16". Primer set:

```
(H16-F: SEQ ID NO: 126 of the
Sequence Listing)
5'-GACGTGTACGGCGACTGGTTCACATAC-3'

(H-R: SEQ ID NO: 115 of the
Sequence Listing)
5'-GGTGGCGCAGTAGTACACGGCGGT-3'
```

8)-2-15 Construction of hFR2-14_H17 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H17 type heavy chain expression vector. The obtained expression vector was designated as "pCMA-G1/hFR2-14_H17". Primer set:

```
(H17-F: SEQ ID NO: 127 of the
Sequence Listing)
5'-GACTGGTACGGCGACTGGTTCACATAC-3'

(H-R: SEQ ID NO: 115 of the
Sequence Listing)
5'-GGTGGCGCAGTAGTACACGGCGGT-3'
```

8)-2-16 Construction of hFR2-14_H18 Type Heavy Chain Expression Vector

The hFR2-14_H3 type heavy chain expression vector pCMA-G1/hFR2-14_H3 prepared in Example 8)-2-1 was used as a template and mutated using a primer set described below and KOD-Plus-Mutagenesis Kit (Toyobo Co., Ltd.) to construct an hFR2-14_H18 type heavy chain expression vector. The obtained expression vector was designated as "pCMA-G1/hFR2-14_H18". Primer set:

```
(H18-F: SEQ ID NO: of the
Sequence Listing)
5'-GACTACTACGGCGACTGGTTCACATAC-3'

(H-R: SEQ ID NO: 115 of the
Sequence Listing)
5'-GGTGGCGCAGTAGTACACGGCGGT-3'
```

8)-3 Preparation of Humanized FR2-14 Antibody (FreeStyle 293F Cell)

8)-3-1 Production of Humanized FR2-14 Antibody

FreeStyle 293F cells (Invitrogen Corp.) were subcultured and cultured according to the manual.

$1.2 \times 10^9$ FreeStyle 293F cells (Invitrogen Corp.) in the logarithmic growth phase were inoculated to a 3-L Fernbach Erlenmeyer Flask (Corning Inc.), adjusted to $1.0 \times 10^6$ cells/mL by dilution with FreeStyle 293 expression medium (Invitrogen Corp.), and then shake-cultured at 90 rpm at 37° C. for 1 hour in an 8% $CO_2$ incubator. 3.6 mg of polyethyleneimine (Polysciences #24765) was dissolved in 20 ml of Opti-Pro SFM medium (Invitrogen Corp.). Next, each H chain expression vector (0.4 mg) and the L chain expression vector (0.8 mg) prepared using PureLink HiPure Plasmid kit (Invitrogen Corp.) were suspended in 20 ml of Opti-Pro SFM medium (Invitrogen Corp.). 20 ml of the expression vector/Opti-Pro SFM mixed solution was added to 20 ml of the polyethyleneimine/Opti-Pro SFM mixed solution, and the mixture was gently stirred, further left for 5 minutes, and then added to the FreeStyle 293F cells. The cells were shake-cultured at 90 rpm at 37° C. for 7 days in an 8% $CO_2$ incubator, and the obtained culture supernatant was filtered through Disposable Capsule Filter (ADVANTEC #CCS-045-E1H).

The humanized FR2-14 antibodies obtained by the combination of pCMA-G1/hFR2-14_H5, pCMA-G1/hFR2-14_H6, pCMA-G1/hFR2-14_H7, pCMA-G1/hFR2-14_H8, pCMA-G1/hFR2-14_H9, pCMA-G1/hFR2-14_H10, pCMA-G1/hFR2-14_H11, pCMA-G1/hFR2-14_H12, pCMA-G1/hFR2-14_H13, pCMA-G1/hFR2-14_H14, pCMA-G1/hFR2-14_H15, pCMA-G1/hFR2-14_H16, pCMA-G1/hFR2-14_H17 and pCMA-G1/hFR2-14_H18 with pCMA-LK/hFR2-14_L1 were designated as "hFR2-14_H5/L1", "hFR2-14_H6/L1", "hFR2-14_H7/L1", "hFR2-14_H8/L1", "hFR2-14_H9/L1", "hFR2-14_H10/L1", "hFR2-14_H11/L1", "hFR2-14_H12/L1", "hFR2-

14_H13/L1", "hFR2-14_H14/L1", "hFR2-14_H15/L1", "hFR2-14_H16/L1", "hFR2-14_H17/L1" and "hFR2-14_H18/L1, respectively.

8)-3-2 Purification of Humanized FR2-14 Antibody

Each antibody was purified from the culture supernatant obtained in Example 8)-3-1 by two steps using rProtein A affinity chromatography (at 4 to 6° C.) and ceramic hydroxyapatite (at room temperature). Buffer replacement steps after the rProtein A affinity chromatography purification and after the ceramic hydroxyapatite purification were carried out at 4 to 6° C. First, the culture supernatant was applied to MabSelect SuRe (manufactured by GE Healthcare Bio-Sciences Corp., HiTrap column) equilibrated with PBS. After entry of the whole culture solution in the column, the column was washed with PBS in an amount at least twice the column volume. Next, antibody-containing fractions were collected by elution with a 2 M arginine hydrochloride solution (pH 4.0). The fractions were buffer-replaced with PBS by dialysis (Thermo Fisher Scientific Inc., Slide-A-Lyzer Dialysis Cassette) and then diluted 5-fold with a buffer of 5 mM sodium phosphate and 50 mM MES (pH 7.0). The resulting antibody solution was applied to a ceramic hydroxyapatite column (Bio-Rad Laboratories, Inc., Bio-Scale CHT Type-I Hydroxyapatite Column) equilibrated with a buffer of 5 mM NaPi, 50 mM MES, and 30 mM NaCl (pH 7.0). Antibody-containing fractions were collected by linear concentration gradient elution using sodium chloride. The fractions were buffer-replaced with HBSor (25 mM histidine and 5% sorbitol, pH 6.0) by dialysis (Thermo Fisher Scientific Inc., Slide-A-Lyzer Dialysis Cassette). Finally, the fractions were concentrated and adjusted to an IgG concentration of 25 mg/ml or higher using Centrifugal UF Filter Device VIVASPIN 20 (molecular weight cutoff: UF10K, Sartorius Japan K.K., at 4° C.), and used as a purified sample.

Example 9

Preparation of Humanized FR2-14 Antibody with Regulated Sugar Chain Modification The humanized antibody comprising the heavy chain comprising amino acid positions 20 to 467 of the amino acid sequence represented by SEQ ID NO: 97 (FIG. 105), and the light chain comprising amino acid positions 21 to 235 of the amino acid sequence represented by SEQ ID NO: 73 (FIG. 81) was defucosylated according to a method known in the art to regulate the sugar chain modification of the antibody protein. The obtained antibody was designated as hFR2-14_H19/L1. This modified form was subjected to mass spectrometry. As a result, the peak of a fucose-containing H chain was equal to or lower than the detection limit. In the present invention, the antibody with regulated sugar chain modification, such as hFR2-14_H19/L1, is also referred to as an "antibody" or a "modified form of the antibody".

Example 10

Physical Property Evaluation of Humanized Anti-Human FGFR2 Antibody (hFR2-14)

10)-1 Biacore Assay of Antigen Binding Activity of Humanized Anti-Human FGFR2 Antibody (hFR2-14)

The antibody was assayed for its dissociation constant for an antigen (rhFGFR2 alpha (IIIb) Fc chimera or rhFGFR2 alpha (IIIc) Fc chimera) using Biacore 3000 (GE Healthcare Bio-Sciences Corp.) by the capture method, which involves capturing the antibody as a ligand onto an immobilized anti-human IgG(Fab) antibody and assaying the antigen as an analyte. Approximately 5000 RU of the anti-human IgG(Fab) antibody (Human Fab capture kit, GE Healthcare Bio-Sciences Corp.) was covalently bound to a sensor chip CM5 (BIAcore, Inc.) by the amine coupling method. Similarly, this antibody was immobilized onto a reference cell. The running buffer used was HBS-EP+ (10 mM HEPES (pH 7.4), 0.15 M NaCl, 3 mM EDTA, and 0.05% Surfactant P20). A 1 µg/mL antibody solution of the purified antibody was added onto the anti-human IgG(Fab) antibody-immobilized chip, at a flow rate of 10 µL/min for 60 seconds or the culture supernatant containing the antibody was added for 60 seconds. Then, serial dilutions (0.3 to 500 nM) of the antigen were added thereto at a flow rate of 30 µl/min for 180 seconds. Subsequently, the dissociation phase was monitored for 300 seconds. 10 mM Gly-HCl (pH 2.1) was added twice thereto as a regenerating solution at a flow rate of 10 µl/min for 60 seconds. The data was analyzed using the Bivalent binding model of analytical software (BIAevaluation software, version 4.1) to calculate an association rate constant kon, a dissociation rate constant koff, and a dissociation constant (KD; KD=koff/kon).

10)-1-1 Binding Activity Evaluation of 4 Types of Humanized Anti-FGFR2 Antibodies (hFR2-14_H1/L1 to hFR2-14_H4/L1) and Human Chimeric Anti-FGFR2 Antibody (cFR2-14)

Four types of humanized anti-FGFR2 antibodies (hFR2-14_H1/L1 to hFR2-14_H4/L1) and the human chimeric anti-FGFR2 antibody (cFR2-14) were expressed and purified by the methods of Examples 8)-3 and 4)-9 and evaluated for their binding activity against each human FGFR2 variant protein by the method shown in Example 10)-1. The Biacore assay results are shown in FIG. 122.

10)-1-2 Binding Activity Evaluation of 15 Types of Humanized Anti-FGFR2 Antibodies (hFR2-14_H3/L1 and hFR2-14_H5/L1 to hFR2-14_H18/L1)

Fifteen types of humanized anti-FGFR2 antibodies (hFR2-14_H3/L1 and hFR2-14_H5/L1 to hFR2-14_H18/L1) were expressed by the method of Example 8)-3, and the culture supernatant containing each antibody was used in the evaluation of binding activity against the FGFR2 IIIc protein by the method shown in Example 10)-1. The Biacore assay results are shown in FIG. 123.

10)-2 Study on Selective Binding Activity of Humanized Anti-Human FGFR2 Antibodies (hFR2-14_H3/L1, hFR2-14_H8/L1, and hFR2-14_H12/L1) Against Human FGFR2

10)-2-1 Construction of Human FGFR1 IIIb Expression Vector (pcDNA-DEST40-FGFR1 IIIb)

A cDNA encoding a human FGFR1 IIIb variant protein (protein comprising the amino acid sequence of the FGFR1 IIIb domain (AAB19502) between an amino acid sequence of positions 1 to 310 and an amino acid sequence of positions 359 to 820 of isoform 2 (NP_056934)) was cloned into a pcDNA-DEST40 vector to construct pcDNA-DEST40-FGFR1 IIIb.

10)-2-2 Cell-ELISA

Figure 124:
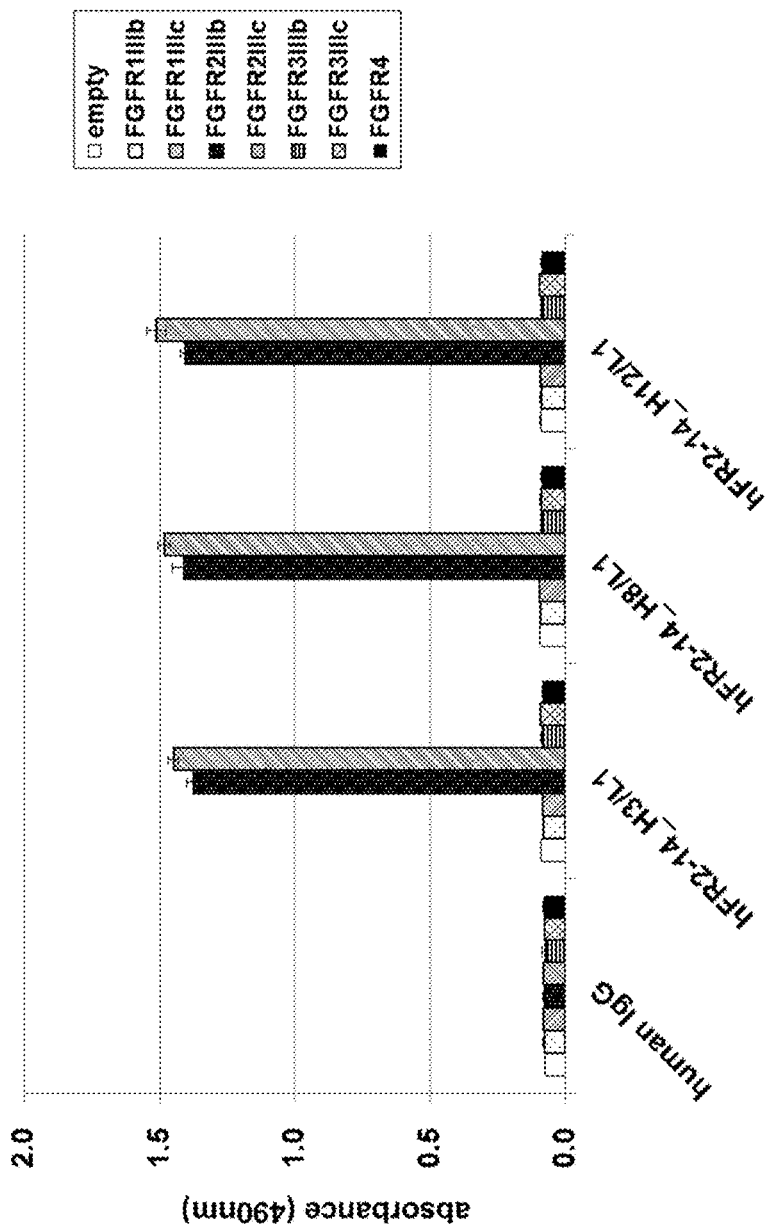

Various human FGFR expression vectors constructed in Examples 1)-3-1, 2)-1-1, and 10)-2-1 were separately transfected to 293α cells (described in Example 1)-6) using Lipofectamine 2000 (manufactured by Life Technologies Corp.). The resulting cells were dispensed in an amount of 100 µl/well to a 96-well plate (manufactured by Corning Inc.) and cultured overnight at 37° C. under 5% CO₂ conditions in a DMEM medium containing 10% FBS. After removal of the culture supernatant, a solution of hFR2-14_H3/L1, hFR2-14_H8/L1, or hFR2-14_H12/L1 diluted to 3 µg/ml with PBS containing 5% FBS was added at a concentration of 50 µl/well to the plate, and the plate was left standing at 4° C. for 1 hour. The cells in the wells were washed twice with PBS containing 5% FBS. Then, Anti-human IgG-Peroxidase conjugate antibody produced in goat (manufactured by Sigma-Aldrich Corp.) and diluted 2000-fold with PBS containing 5% FBS was added thereto, and the plate was left standing at 4° C. for 1 hour. The cells in the wells were washed 3 times with PBS containing 5% FBS. Then, an OPD chromogenic solution (OPD solution (o-phenylenediamine dihydrochloride (manufactured by Wako Pure Chemicals Industries, Ltd.) and $H_2O_2$ dissolved at concentrations of 0.4 mg/ml and 0.6% (v/v), respectively, in 0.05 M trisodium citrate and 0.1 M disodium hydrogen phosphate dodecahydrate, pH 4.5)) was added thereto at a concentration of 100 µl/well. Color reaction was performed with occasional stirring and stopped by the addition of 1 M HCl at a concentration of 100 µl/well. Then, the absorbance was measured at 490 nm using a plate reader (ARVO; PerkinElmer, Inc.). As seen from FIG. 124, the hFR2-14_H3/L1, hFR2-14_H8/L1, and hFR2-14_H12/L1 antibodies were shown to specifically bind to both human FGFR2 IIIb and FGFR2 IIIc.

10)-3 Thermal Stability Assay of Humanized Anti-Human FGFR2 Antibody (hFR2-14) Using Differential Scanning Calorimetry (DSC)

Figure 125A:
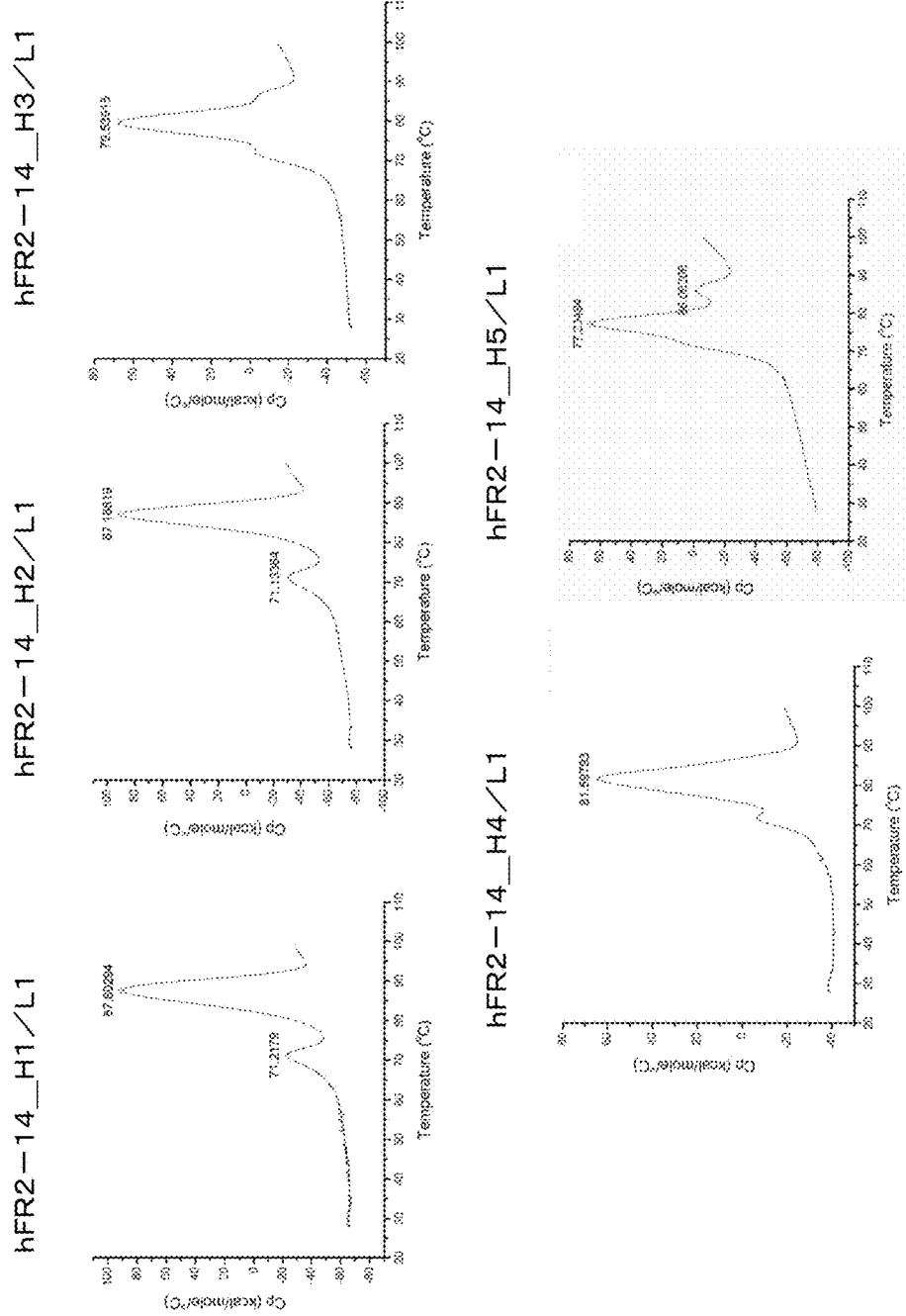
Figure 125B:
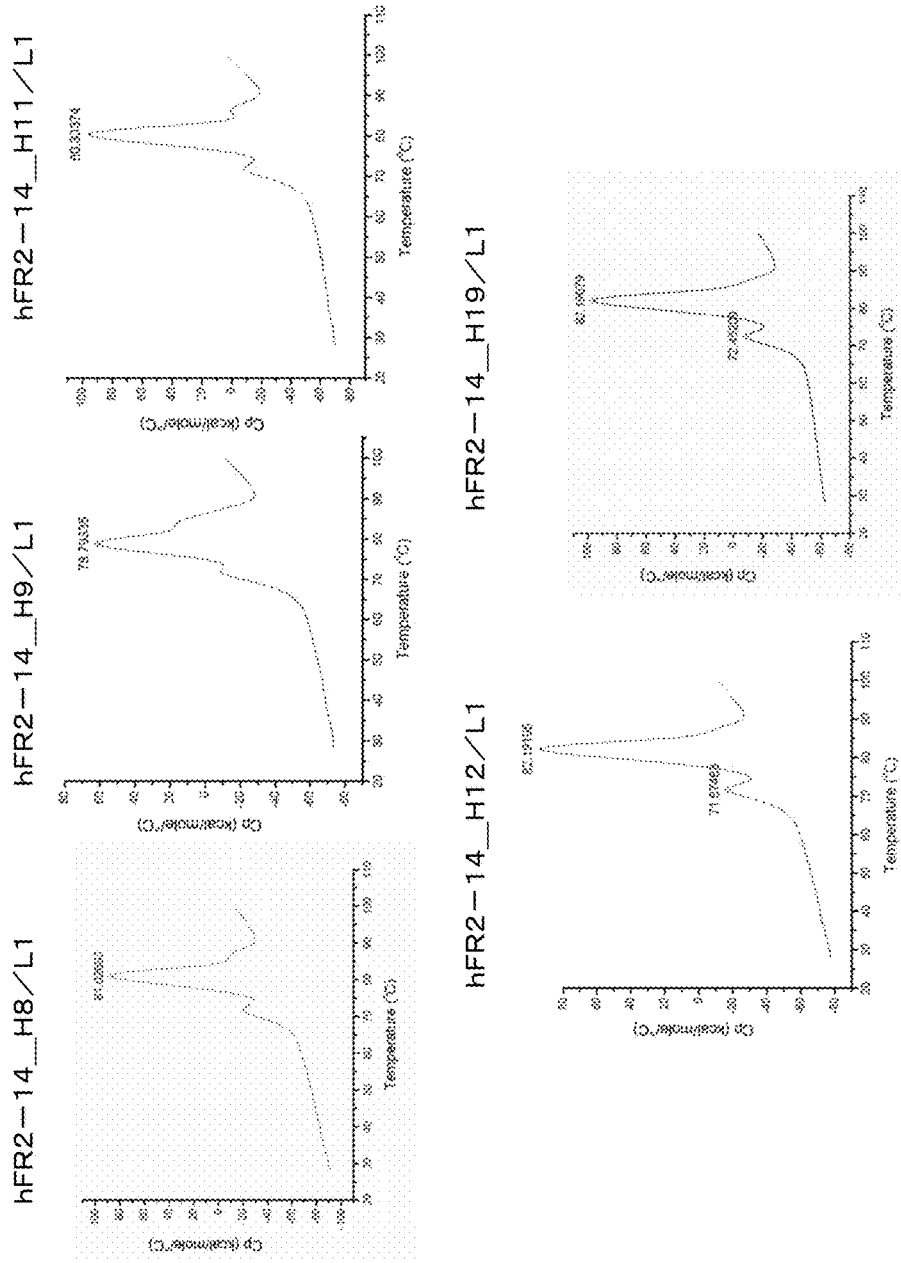

The thermal stability was assayed using differential scanning calorimetry (DSC). Each sample was dissolved at a concentration of 0.5 mg/mL in an HBSor buffer solution (prepared to contain 25 mM histidine (pH 6.0) and 5% sorbitol), and 400 µL of the sample solution was used in the DSC assay. The DSC assay conditions were set as follows: an initial temperature of 20° C.; a final temperature of 100° C.; a rate of temperature rise of 200° C./hour; a filtering time of 2 seconds; and a feedback mode of Low. The reference solution used was HBSor. VP-Capillary DSC Platform manufactured by GE Healthcare Bio-Sciences Corp. (USA) was used as a DSC assay apparatus in all experiments. Baseline correction was conducted by the subtraction of the baseline (scan curve obtained from the reference solution also charged into a sample cell) from a scan curve obtained from the sample solution. Next, concentration calibration was conducted using molar concentration calculated from the molecular weight of each sample. FIGS. 125A and 125B show the thermograms of various humanized FGFR2 antibodies. The thermal denaturation midpoint Tm is defined as the temperature at which the maximum peak in each thermogram exhibited a peak top. As shown in FIG. 125C, the hFR2-14_H1/L1 antibody had a Tm value of 87.6° C. The hFR2-14_H2/L1 antibody had a Tm value of 87.2° C. The hFR2-14_H3/L1 antibody had a Tm value of 79.5° C. The hFR2-14_H4/L1 antibody had a Tm value of 81.6° C. The hFR2-14_H5/L1 antibody had a Tm value of 77.2° C. The hFR2-14_H8/L1 antibody had a Tm value of 81.0° C. The hFR2-14_H9/L1 antibody had a Tm value of 78.8° C. The hFR2-14_H11/L1 antibody had a Tm value of 80.3° C. The hFR2-14_H12/L1 antibody had a Tm value of 82.2° C. The hFR2-14_H19/L1 antibody had a Tm value of 82.2° C.

10)-4 Binding Stability Test of Humanized Anti-Human FGFR2 Antibody (hFR2-14) Using Biacore The humanized anti-human FGFR2 antibody (hFR2-14) was evaluated for its antigen binding stability by a method described below.

Various humanized anti-FGFR2 antibodies (hFR2-14_H1/L1 to hFR2-14_H5/L1, hFR2-14_H8/L1, hFR2-14_H9/L1, hFR2-14_H11/L1, hFR2-14_H12/L1, and hFR2-14_H19/L1) and the human chimeric anti-FGFR2 antibody (cFR2-14) were expressed and purified by the methods of Examples 8)-3, 9), and 4)-9 and each dissolved at a concentration of 20 mg/mL in an HBSor buffer solution (prepared to contain 25 mM histidine (pH 6.0) and 5% sorbitol). The solutions were heated to 40° C. for 4 weeks to prepare degraded analytes. The analytes were assayed for their binding activity before and after degradation by the method shown in Example 10)-1 using Biacore. The Biacore assay results are shown in FIG. 126.

Example 11

Signal-Neutralizing Effect of Humanized Anti-Human FGFR2 Antibody (hFR2-14)

11)-1 Signal-Neutralizing Effects of Humanized Anti-FGFR2 Antibodies (hFR2-14_H1/L1, hFR2-14_H2/L1, hFR2-14_H3/L1, and hFR2-14_H4/L1) and Human Chimeric Anti-FGFR2 Antibody (cFR2-14)

Figure 127A:
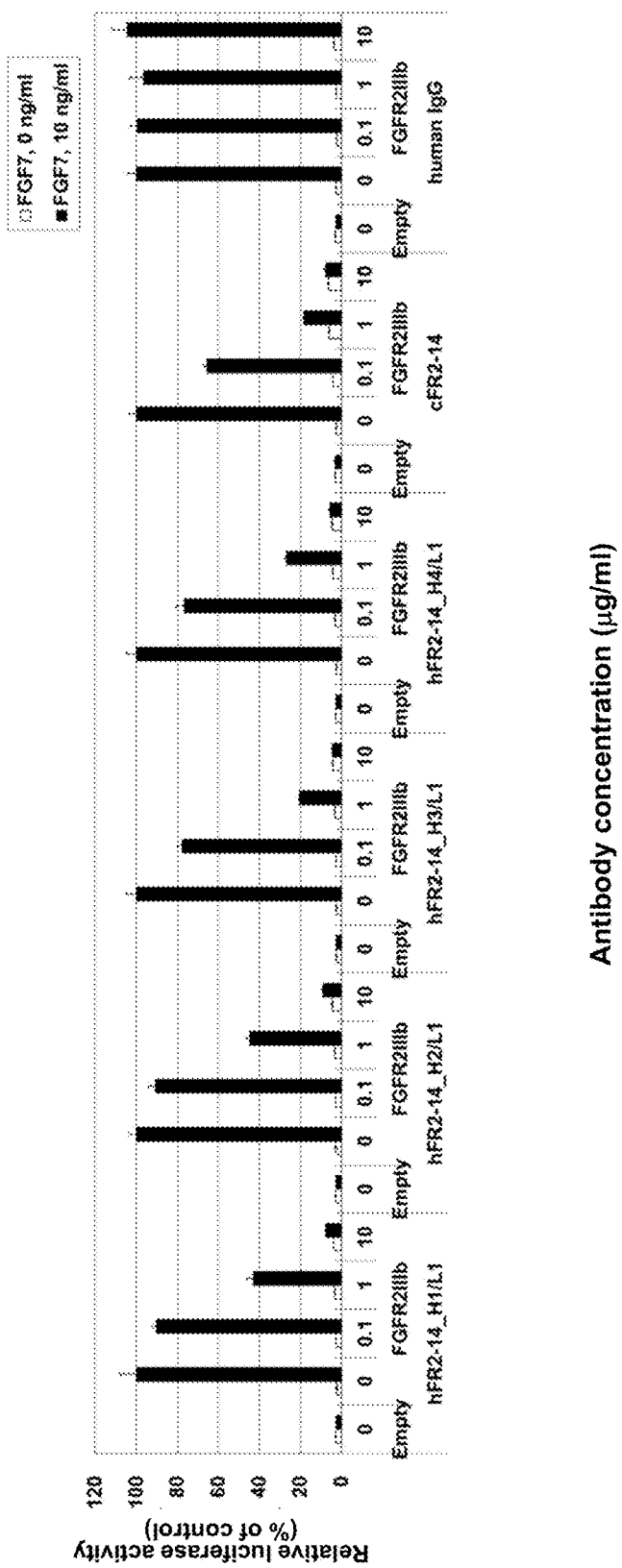

In order to evaluate the signal-neutralizing effects of the humanized antibodies by the Elk1 luciferase reporter gene assay, 293α cells were cotransfected with pcDNA-DEST40-FGFR2 IIIb or pcDNA-DEST40-FGFR2 IIIc, pFA2-Elk1 (manufactured by Stratagene Corp.), pFR-Luc2CP, and pGL4.74[hRluc/TK] (manufactured by Promega Corp.) by the method shown in Example 1)-6-2, and cultured overnight at 37° C. under 5% $CO_2$ conditions. On the next day, the culture supernatant was removed, and the cells were then preincubated for 1 hour with the hFR2-14_H1/L1, hFR2-14_H2/L1, hFR2-14_H3/L1, hFR2-14_H4/L1, or cFR2-14 antibody diluted with DMEM containing 2% FBS. Subsequently, a ligand (human FGF7 or human FGF9, manufactured by PeproTech Inc.) was added at a final concentration of 10 ng/ml to each well. After incubation for 6 hours, firefly luciferase activity (specific signal) and *Renilla* luciferase activity (signal for normalization) were assayed using Dual-Glo Luciferase Assay System (manufactured by Promega Corp.). The firefly/*Renilla* ratio was calculated to normalize data on each well. As shown in FIG. 127A, hFR2-14_H1/L1, hFR2-14_H2/L1, hFR2-14_H3/L1, hFR2-14_H4/L1, and cFR2-14 inhibited ligand FGF7 dependent reporter activation in the FGFR2 IIIb-expressing cells. As shown in FIG. 127B, hFR2-14_H1/L1, hFR2-14_H2/L1, hFR2-14_H3/L1, hFR2-14_H4/L1, and cFR2-14 inhibited ligand FGF9 dependent reporter activity in the FGFR2 IIIc-expressing cells. These results demonstrated that these antibodies have the effect of inhibiting the activation of FGFR2 by its ligand.

11)-2 Signal-Neutralizing Effects of Humanized Anti-FGFR2 Antibodies (hFR2-14_H3/L1, hFR2-14_H5/L1, hFR2-14_H6/L1, hFR2-14_H7/L1, hFR2-14_H8/L1, hFR2-14_H9/L1, hFR2-14_H10/L1, hFR2-14_H11/L1, hFR2-14_H12/L1, hFR2-14_H13/L1, hFR2-14_H14/L1, hFR2-14_H15/L1, hFR2-14_H16/L1, hFR2-14_H17/L1, and hFR2-14_H18/L1)

In order to evaluate the signal-neutralizing effects of the humanized antibodies by the Elk1 luciferase reporter gene assay, 293α cells were cotransfected with pcDNA-DEST40-FGFR2 IIIb or pcDNA-DEST40-FGFR2 IIIc, pFA2-Elk1 (manufactured by Stratagene Corp.), pFR-Luc2CP, and pGL4.74[hRluc/TK] (manufactured by Promega Corp.) by the method shown in Example 1)-6-2, and cultured overnight at 37° C. under 5% $CO_2$ conditions. On the next day, the culture supernatant was removed, and the cells were then preincubated for 1 hour with the culture supernatant of the 293 FreeStyle cells (manufactured by Invitrogen Corp.) producing the antibodies hFR2-14_H3/L1, hFR2-14_H5/L1, hFR2-14_H6/L1, hFR2-14_H7/L1, hFR2-14_H8/L1, hFR2-14_H9/L1, hFR2-14_H10/L1, hFR2-14_H11/L1, hFR2-14_H12/L1, hFR2-14_H13/L1, hFR2-14_H14/L1, hFR2-14_H15/L1, hFR2-14_H16/L1, hFR2-14_H17/L1, and hFR2-14_H18/L1 (prepared in Example 8)-3-1) diluted with DMEM containing 2% FBS. Subsequently, a ligand (human FGF7, manufactured by R&D systems, Inc.) was added at a final concentration of 10 ng/ml to each well. After incubation for 6 hours, firefly luciferase activity (specific signal) and Renilla luciferase activity (signal for normalization) were assayed using Dual-Glo Luciferase Assay System (manufactured by Promega Corp.). The firefly/Renilla ratio was calculated to normalize data on each well. As shown in FIGS. 128A, 128B, and 128C, hFR2-14_H3/L1, hFR2-14_H5/L1, hFR2-14_H6/L1, hFR2-14_H7/L1, hFR2-14_H8/L1, hFR2-14_H9/L1, hFR2-14_H10/L1, hFR2-14_H11/L1, hFR2-14_H12/L1, hFR2-14_H13/L1, hFR2-14_H14/L1, hFR2-14_H15/L1, hFR2-14_H16/L1, hFR2-14_H17/L1, and hFR2-14_H18/L1 inhibited ligand FGF7 dependent reporter activation in the FGFR2 IIIb-expressing cells.

11)-3 Signal-Neutralizing Effects of Humanized Anti-FGFR2 Antibodies (hFR2-14_H12/L1 and hFR2-14_H19/L1)

In order to evaluate the signal-neutralizing effects of the humanized antibodies by the Elk1 luciferase reporter gene assay, 293α cells were cotransfected with pcDNA-DEST40-FGFR2 IIIb or pcDNA-DEST40-FGFR2 IIIc, pFA2-Elk1 (manufactured by Stratagene Corp.), pFR-Luc2CP, and pGL4.74[hRluc/TK] (manufactured by Promega Corp.) by the method shown in Example 1)-6-2, and cultured overnight at 37° C. under 5% $CO_2$ conditions. On the next day, the culture supernatant was removed, and the cells were then preincubated for 1 hour with the hFR2-14_H12/L1 or hFR2-14_H19/L1 antibody (prepared in Examples 8) and 9)) diluted with DMEM containing 2% FBS. Subsequently, a ligand human FGF7 (manufactured by R&D systems, Inc.) or human FGF9 (manufactured by PeproTech Inc.) was added at a final concentration of 10 ng/ml to each well. After incubation for 6 hours, firefly luciferase activity (specific signal) and Renilla luciferase activity (signal for normalization) were assayed using Dual-Glo Luciferase Assay System (manufactured by Promega Corp.). The firefly/Renilla ratio was calculated to normalize data on each well. As shown in FIG. 129A, hFR2-14_H12/L1 and hFR2-14_H19/L1 inhibited ligand FGF7 dependent reporter activation in the FGFR2 IIIb-expressing cells. As shown in FIG. 129B, hFR2-14_H12/L1 and hFR2-14_H19/L1 inhibited ligand FGF9 dependent reporter activity in the FGFR2 IIIc-expressing cells. These results demonstrated that these antibodies have the effect of inhibiting the activation of FGFR2 by its ligand.

Example 12

ADCC Activity of Humanized Anti-Human FGFR2 Antibody (hFR2-14)

12)-1 ADCC Activity of Humanized Anti-FGFR2 Antibodies (hFR2-14_H1/L1, hFR2-14_H2/L1, hFR2-14_H3/L1, and hFR2-14_H4/L1) and Human Chimeric Anti-FGFR2 Antibody (cFR2-14) Against FGFR2-Overexpressing Cell The FGFR2 IIIb-expressing 293T-lacZ cells prepared by the method of Example 5)-3-2 were added at a concentration of 50 µl/well to a 96-well U-bottomed microplate. hFR2-14_H1/L1, hFR2-14_H2/L1, hFR2-14_H3/L1, hFR2-14_H4/L1, cFR2-14, or human IgG diluted to 1 to 100 ng/ml (final concentration) with a medium for ADCC described in Example 5)-3-2 was added thereto at a concentration of 50 µl/well, and the plate was left standing at 4° C. for 1 hour. The effector cells of Example 5)-3-3 were further added thereto at a concentration of 75 µl/well. The plate was centrifuged at 1200 rpm at room temperature for 5 minutes, followed by overnight culture at 37° C. under 5% $CO_2$ conditions. On the next day, 50 µl of the supernatant in each well was recovered into a white plate (manufactured by Corning Inc.). A solution of β-Glo assay system (manufactured by Promega Corp.) was added thereto at a concentration of 50 µl/well. The luminescence intensity was measured using a plate reader (ENVISION; manufactured by PerkinElmer, Inc.). The percentage of cells lysed by ADCC activity was calculated according to the following expression:

Percentage of cells lysed(%)=$(A-B)/(C-B)\times 100$

A: Count of sample well

B: Average of spontaneous release (wells supplemented with neither the antibody nor the effector cells) counts (n=3). The same operation as in the sample well was performed except that 50 µl and 75 µl of a medium for ADCC were added instead of the antibody and the effector cells, respectively.

C: Average of maximum release (wells containing target cells lysed in a surfactant) counts (n=3). 50 µl and 75 µl of a medium for ADCC were added instead of the antibody and the effector cells, respectively. For the assay, 175 µl of the β-Glo assay system solution was added to each well containing the target cells and mixed therewith. A 100 µl aliquot thereof was added to a white plate to carry out the assay.

As shown in FIGS. 130A and 130B, hFR2-14_H1/L1, hFR2-14_H2/L1, hFR2-14_H3/L1, hFR2-14_H4/L1, and cFR2-14 had ADCC activity against the FGFR2 IIIb-expressing cells.

12)-2 ADCC Activity of Humanized Anti-FGFR2 Antibodies (hFR2-14_H3/L1, hFR2-14_H8/L1, and hFR2-14_H12/L1) Against FGFR2-Expressing Cancer Cell Line 12)-2-1 Preparation of Target Cell KATO III, NCI-H716, or SNU16 cells were washed twice with a medium for ADCC and passed through a cell strainer (manufactured by Becton Dickinson and Company). Then, the number of live cells was counted by the trypan blue dye exclusion test. The cells were resuspended to $1\times10^5$ cells/ml and used as target cells.

12)-2-2 Preparation of PBMC Cell 25 ml of healthy human blood was gradually layered over 20 ml of Lymphosepar I (manufactured by Immuno-Biological Laboratories Co., Ltd.), followed by centrifugation at 1500 rpm at room temperature for 30 minutes. A cell layer located between plasma and Lymphosepar I (manufactured by Immuno-Biological Laboratories Co., Ltd.) was recovered using a dropper and suspended in 20 ml of a phenol red-free RPMI1640 medium (manufactured by Life Technologies Corp.) containing 10% FBS. The suspension was centrifuged at 1500 rpm for 5 minutes. After removal of the supernatant, the cells were washed twice by the addition of 20 ml of a medium for ADCC. The number of live cells was counted by the trypan blue dye exclusion test. After centrifugation, the medium was removed, and the cells were suspended in a medium for ADCC and used as effector cells.

12)-2-3 Evaluation of ADCC Activity

The NCI-H716 cells prepared by the method of Example 12)-2-1 were added at a concentration of 50 µl/well to a 96-well U-bottomed microplate. hFR2-14_H3/L1, hFR2-14_H8/L1, hFR2-14_H12/L1, or human IgG diluted to 1 to 1000 ng/ml (final concentration) with a medium for ADCC was added thereto at a concentration of 50 μl/well, and the plate was left standing at 4° C. for 1 hour. The PBMC cells (13.4×10$^6$ cells/ml) of Example 12)-2-2 were further added thereto at a concentration of 75 μl/well. The plate was centrifuged at 1200 rpm at room temperature for 5 minutes, followed by overnight culture at 37° C. under 5% CO$_2$ conditions. On the next day, 10× Lysis Solution attached to CytoTox 96 Non-Radioactive Cytotoxicity Assay (manufactured by Promega Corp.) kit was added at a concentration of 17.5 μl/well to the wells containing only the target cells and the medium and stirred, and the plate was then left standing at 37° C. for 45 minutes under 5% CO$_2$ conditions. After centrifugation at 200 g at room temperature for 4 minutes, 50 μl of the supernatant in each well was recovered into a 96-well flat-bottomed microplate (manufactured by Corning Inc.). Substrate Mix was added thereto at a concentration of 50 μl/well, and the plate was left standing at room temperature for 30 minutes while shielded from light. Stop Solution was further added thereto at a concentration of 50 μl/well. The absorbance was measured at 490 nm using a plate reader (ARVO; manufactured by PerkinElmer, Inc.). The percentage of cells lysed by ADCC activity was calculated according to the following expression:

Cytotoxicity(%)=$(A-B-C)/(D-C)\times 100$

A: Count of sample well

B: Average of spontaneous release (correction of culture solution-containing wells from effector cell-containing wells) counts from effector cells (n=3).

C: Average of spontaneous release (correction of culture solution-containing wells from target cell-containing wells) counts from target cells (n=3).

D: Average of maximum release (correction of wells containing a culture solution lysed in a surfactant from wells containing target cells lysed in a surfactant) counts (n=3).

As shown in FIG. 131, hFR2-14_H3/L1, hFR2-14_H8/L1, and hFR2-14_H12/L1 had ADCC activity against the FGFR2-expressing cancer cell line NCI-H716 cells.

12)-3 ADCC activity of humanized anti-FGFR2 antibodies (hFR2-14_H12/L1 and hFR2-14_H19/L1) against FGFR2-expressing cancer cell line The KATO III, NCI-H716, or SNU16 cells prepared by the method of Example 12)-2-1 were added at a concentration of 50 μl/well to a 96-well U-bottomed microplate. hFR2-14_H12/L1 or hFR2-14_H19/L1 (prepared in Examples 8) and 9)) or human IgG diluted to 1 to 1000 ng/ml (final concentration) with a medium for ADCC was added thereto at a concentration of 50 μl/well, and the plate was left standing at 4° C. for 1 hour. The effector cells (20×10$^6$ cells/ml) of Example 12)-2-2 were further added thereto at a concentration of 75 μl/well. The plate was centrifuged at 1200 rpm at room temperature for 5 minutes, followed by overnight culture at 37° C. under 5% CO$_2$ conditions. On the next day, 10× Lysis Solution attached to CytoTox 96 Non-Radioactive Cytotoxicity Assay (manufactured by Promega Corp.) kit was added at a concentration of 17.5 μl/well to the wells containing only the target cells and the medium and stirred, and the plate was then left standing at 37° C. for 45 minutes under 5% CO$_2$ conditions. After centrifugation at 200 g at room temperature for 4 minutes, 50 μl of the supernatant in each well was recovered into a 96-well flat-bottomed microplate (manufactured by Corning Inc.). Substrate Mix was added thereto at a concentration of 50 μl/well, and the plate was left standing at room temperature for 30 minutes while shielded from light. Stop Solution was further added thereto at a concentration of 50 μl/well. The absorbance was measured at 490 nm using a plate reader (ARVO; manufactured by PerkinElmer, Inc.). The percentage of cells lysed by ADCC activity was calculated according to the calculation method shown in Example 12)-2-3.

As shown in FIGS. 132A, 132B, and 132C, hFR2-14_H12/L1 and hFR2-14_H19/L1 had ADCC activity against the FGFR2-expressing cancer cell lines NCI-H716, SNU-16, and KATO III, and this activity was shown to be higher in hFR2-14_H19/L1.

Example 13

ADCP Activity of Humanized Anti-Human FGFR2 Antibody (hFR2-14)

13)-1 ADCP Activity of Humanized Anti-FGFR2 Antibodies (hFR2-14_H12/L1 and hFR2-14_H19/L1) Against FGFR2-Expressing Cancer Cell Line 13)-1-1 Preparation of Target Cell KATO III or NCI-H716 cells were recovered and washed 3 times with PBS. Then, the number of live cells was counted by the trypan blue dye exclusion test. 1×10$^6$ cells were separated, centrifuged, and then suspended in 200 μl of Diluent C attached to PKH26 Red Fluorescent Cell Linker Kit for General Cell Membrane Labeling (manufactured by Sigma-Aldrich Corp.). 1 mM PKH26 Linker was diluted as a labeling solution to 10 μM with Diluent C. Immediately thereafter, the cell suspension was mixed with an equal volume of the PKH26 Linker solution, and the mixture was left standing at room temperature for 5 minutes. The cells were washed twice by the addition of 5 ml of an RPMI1640 medium (manufactured by Life Technologies Corp.) containing 10% FBS, then resuspended to 5×10$^5$ cells/ml, and used as target cells.

13)-1-2 Preparation of PBMC Cell 25 ml of healthy human blood was gradually layered over 20 ml of Lymphosepar I (manufactured by Immuno-Biological Laboratories Co., Ltd.), followed by centrifugation at 1500 rpm at room temperature for 30 minutes. A cell layer located between plasma and Lymphosepar I (manufactured by Immuno-Biological Laboratories Co., Ltd.) was recovered using a dropper and suspended in 20 ml of an RPMI1640 medium (manufactured by Life Technologies Corp.) containing 10% FBS. The suspension was centrifuged at 1500 rpm for 5 minutes. After removal of the supernatant, the cells were washed twice by the addition of 20 ml of an RPMI1640 medium (manufactured by Life Technologies Corp.) containing 10% FBS. The number of live cells was counted by the trypan blue dye exclusion test. The resulting cells were used as effector cells.

13)-1-3 Preparation of Effector Cell

The PBMC cells prepared in Example 13)-1-2 was adjusted to 5×10$^7$ cells/ml with RoboSep buffer (manufactured by StemCell Technologies Inc.). 50 μl of EasySep human Monocyte enrichment cocktail attached to Human monocyte Enrichment Kit Without CD16 Depletion (manufactured by StemCell Technologies Inc.) was added per ml of the PBMC cell suspension. After reaction at 4° C. for 10 minutes, 50 μl of EasySep Magnetic Particles was added per ml of the PBMC cell suspension. After reaction at 4° C. for 5 minutes, RoboSep buffer (manufactured by StemCell Technologies Inc.) was added thereto up to 2.5 ml, and the reaction mixture was loaded to EasySep Magnet. After 2 minutes and 30 seconds, the supernatant was recovered and then centrifuged at 1200 rpm for 5 minutes to separate monocyte fractions. The fractions were washed once by the addition of an RPMI1640 medium (manufactured by Life Technologies Corp.) containing 10% FBS. Then, an RPMI1640 medium (manufactured by Life Technologies Corp.) containing 10% FBS, 10 ng/ml GM-CSF (manufactured by PeproTech Inc.), and 10 ng/ml M-CSF (manufactured by PeproTech Inc.) was added thereto, and the mixture was inoculated to a 225-cm² flask for suspension culture (manufactured by Sumitomo Bakelite Co., Ltd.). The cells were cultured at 37° C. for 14 days under 5% $CO_2$ conditions. During the culture period, the medium was replaced every 3 to 4 days with an RPMI1640 medium (manufactured by Life Technologies Corp.) containing 10% FBS, 10 ng/ml GM-CSF (manufactured by PeproTech Inc.), and 10 ng/ml M-CSF (manufactured by PeproTech Inc.). Fourteen days later, 0.05% trypsin-EDTA (manufactured by Life Technologies Corp.) was added to macrophages differentiated therefrom by induction. After reaction at 37° C. for 40 minutes, the cells were dissociated from the flask. The cells were washed twice by the addition of an RPMI1640 medium (manufactured by Life Technologies Corp.) containing 10% FBS, then resuspended to $5\times10^5$ cells/ml in an RPMI1640 medium (manufactured by Life Technologies Corp.) containing 10% FBS, 10 ng/ml M-CSF (manufactured by PeproTech Inc.), and 250 U/ml IFN-γ (manufactured by PeproTech Inc.), and used as effector cells.

13)-1-4 Evaluation of ADCP Activity

The target cells prepared by the method of Example 13)-1-1 were added at a concentration of 100 μl/well to Ultra-Low Attachment 96-well U-bottomed microplate (manufactured by Corning Inc.). hFR2-14_H12/L1 or hFR2-14_H19/L1 (prepared in Examples 8) and 9)) or human IgG diluted to 0.5 to 500 ng/ml (final concentration) with an RPMI1640 medium (manufactured by Life Technologies Corp.) containing 10% FBS was added thereto at a concentration of 100 μl/well, and the plate was left standing at 4° C. for 30 minutes. After centrifugation at 1200 rpm at room temperature for 5 minutes and removal of the supernatant, the cells were suspended in 100 μl/well of an RPMI1640 medium (manufactured by Life Technologies Corp.) containing 10% FBS. The effector cells ($5\times10^5$ cells/ml) prepared in Example 13)-1-3 were added thereto at a concentration of 100 μl/well, and the plate was then left standing at 37° C. for 3 hours under 5% $CO_2$ conditions. After centrifugation at 1200 rpm at 4° C. for 5 minutes and removal of the supernatant, the cells were washed with 200 μl/well of PBS containing 5% FBS. 45 μl/well of PBS containing 5% FBS and 5 μl/well of APC human CD11b (manufactured by Becton Dickinson and Company) were added to the cells, and the plate was left standing at 4° C. for 15 minutes. The cells were washed twice with 200 μl/well of PBS containing 5% FBS. The cells were suspended in 200 μl/well of PBS containing 1% paraformaldehyde, and the plate was left overnight at 4° C. On the next day, the cells were assayed by flow cytometry (FACS Canto II; manufactured by Becton Dickinson and Company). The data was analyzed using Flowjo (manufactured by Tree Star Inc.). After development on FSC (forward scatter)/SSC (side scatter), the number of PE-positive cells (A) and the number of cells positive for both APC and PE (B) were calculated. The cells positive for both APC and PE (B) mean that the macrophages englobed the target cells. The percentage of cells phagocytosed by ADCP activity was calculated according to the following expression:

Percentage of cells phagocytosed(%)=$B/(A+B)\times100$

As shown in FIGS. 133A and 133B, hFR2-14_H12/L1 and hFR2-14_H19/L1 had ADCP activity against the FGFR2-expressing cancer cell lines NCI-H716 and KATO III.

Example 14

In Vivo Antitumor Activity of Humanized Anti-FGFR2 Antibody (hFR2-14)

14)-1 In Vivo Antitumor Activity of Humanized Anti-FGFR2 Antibodies (hFR2-14_H1/L1, hFR2-14_H2/L1, hFR2-14_H3/L1, and hFR2-14_H4/L1) Against Human Stomach Cancer Cell Line SNU-16-Subcutaneously Transplanted Model $5\times10^6$ cells of a human stomach cancer line SNU-16 (purchased from ATCC) were suspended in 50% Matrigel (purchased from Nippon Becton Dickinson Company, Ltd.) and subcutaneously transplanted to the axillary region of each nude mouse (CAnN.Cg-Foxnl$^{nu}$/CrlCrlj, purchased from Charles River Laboratories Japan Inc.). The mice were grouped according to their tumor volumes. Seven, 10, 14, 17, and 21 days after transplantation, each humanized anti-FGFR2 antibody (hFR2-14_H1/L1, hFR2-14_H2/L1, hFR2-14_H3/L1, or hFR2-14_H4/L1) prepared in Example 8)-3 was intraperitoneally administered at a dose of 1.5 or 15 mg/kg to the cancer-bearing mice (n=8). The major axis and minor axis of the transplanted tumor were measured twice a week using an electronic digital caliper (manufactured by Mitsutoyo Corp.). The tumor volume was calculated according to the following expression:

Tumor volume(mm³)=½×Minor axis(mm)×Minor axis(mm)×Major axis(mm)

The results for the hFR2-14_H1/L1 antibody are shown in FIG. 134A. The percentage of tumor growth inhibition at 21 days after transplantation (final assay day) was 58% for the 1.5 mg/kg administration group and 53% for the 15 mg/kg administration group.

The results for the hFR2-14_H2/L1 antibody are shown in FIG. 134B. The percentage of tumor growth inhibition at 21 days after transplantation (final assay day) was 58% for the 1.5 mg/kg administration group and 58% for the 15 mg/kg administration group.

The results for the hFR2-14_H3/L1 antibody are shown in FIG. 134C. The percentage of tumor growth inhibition at 21 days after transplantation (final assay day) was 64% for the 1.5 mg/kg administration group and 41% for the 15 mg/kg administration group.

The results for the hFR2-14_H4/L1 antibody are shown in FIG. 134D. The percentage of tumor growth inhibition at 21 days after transplantation (final assay day) was 70% for the 1.5 mg/kg administration group and 39% for the 15 mg/kg administration group.

14)-2 In Vivo Antitumor Activity of Humanized Anti-FGFR2 Antibodies (hFR2-14_H5/L1, hFR2-14_H8/L1, hFR2-14_H9/L1, hFR2-14_H11/L1, hFR2-14_H12/L1, and hFR2-14_H19/L1) Against Human Stomach Cancer Cell Line SNU-16-Subcutaneously Transplanted Model $5\times10^6$ cells of a human stomach cancer line SNU-16 (purchased from ATCC) were suspended in 50% Matrigel (purchased from Nippon Becton Dickinson Company, Ltd.) and subcutaneously transplanted to the axillary region of each nude mouse (CAnN.Cg-Foxnl$^{nu}$/CrlCrlj, purchased from Charles River Laboratories Japan Inc.). The mice were grouped according to their tumor volumes. Seven, 10 (or 11), 14, and 17 (or 18) days after transplantation, each humanized antibody (hFR2-14_H5/L1, hFR2-14_H8/L1, hFR2-14_H9/L1, hFR2-14_H11/L1, or hFR2-14_H12/L1) prepared in Example 8)-3 or the humanized antibody (hFR2-14_H19/L1) prepared in Example 9) was intraperitoneally administered at a dose of 2 or 20 mg/kg to the cancer-bearing mice (n =8 or 9). The major axis and minor axis of the transplanted tumor were measured twice a week using an electronic digital caliper (manufactured by Mitsutoyo Corp.). The tumor volume was calculated according to the following expression:

Tumor volume(mm$^3$)=½×Minor axis(mm)×Minor axis(mm)×Major axis(mm)

The results on hFR2-14_H5/L1 are shown in FIG. 135A. The percentage of tumor growth inhibition at 21 days after transplantation (final assay day) was 41% for the 2 mg/kg administration group and 51% for the 20 mg/kg administration group.

The results for hFR2-14_H8/L1 are shown in FIG. 135B. The percentage of tumor growth inhibition at 21 days after transplantation (final assay day) was 30% for the 2 mg/kg administration group and 30% for the 20 mg/kg administration group.

The results for hFR2-14_H9/L1 are shown in FIG. 135C. The percentage of tumor growth inhibition at 21 days after transplantation (final assay day) was 1% for the 2 mg/kg administration group and 23% for the 20 mg/kg administration group.

The results for hFR2-14_H11/L1 are shown in FIG. 135D. The percentage of tumor growth inhibition at 21 days after transplantation (final assay day) was 61% for the 2 mg/kg administration group and 42% for the 20 mg/kg administration group.

The results for hFR2-14_H12/L1 are shown in FIG. 135E. The percentage of tumor growth inhibition at 21 days after transplantation (final assay day) was 36% for the 2 mg/kg administration group and 58% for the 20 mg/kg administration group.

The results for hFR2-14_H19/L1 are shown in FIG. 135F. The percentage of tumor growth inhibition at 21 days after transplantation (final assay day) was 70% for the 2 mg/kg administration group and 40% for the 20 mg/kg administration group.

14)-3 In Vivo Antitumor Activity of Humanized Anti-FGFR2 Antibodies (hFR2-14_H12/L1 and hFR2-14_H19/L1) Against Human Colorectal Cancer Cell Line NCI-H716 Block-Transplanted Model A tumor block (5×5×5 mm$^3$) of a human colorectal cancer line NCI-H716 (purchased from ATCC) was subcutaneously transplanted to the axillary region of each nude mouse (CAnN.Cg-Foxnl$^{nu}$/CrlCrlj, purchased from Charles River Laboratories Japan Inc.). On the transplantation day and 3, 7, 10, 14, 17, 21, and 24 days after transplantation, each humanized antibody (hFR2-14_H12/L1 or hFR2-14_H19/L1) prepared in Example 8) or 9) was intraperitoneally administered at a dose of 20 mg/kg to the cancer-bearing mice (n=11). The major axis and minor axis of the transplanted tumor were measured twice a week using an electronic digital caliper (manufactured by Mitsutoyo Corp.). The tumor volume was calculated according to the following expression:

Tumor volume(mm$^3$)=½×Minor axis(mm)×Minor axis(mm)×Major axis(mm)

The results for hFR2-14_H12/L1 are shown in FIG. 136A. The percentage of tumor growth inhibition at 28 days after transplantation (final assay day) was 99%.

The results for hFR2-14_H19/L1 are shown in FIG. 136B. The percentage of tumor growth inhibition at 28 days after transplantation (final assay day) was 99%.

14)-4 In Vivo Antitumor Activity of Humanized Anti-FGFR2 Antibodies (hFR2-14_H12/L1 and hFR2-14_H19/L1) Against Human Colorectal Cancer Cell Line NCI-H716-Luc-Peritoneally Disseminated Model 3×10$^6$ cells of luciferase gene-expressing human colorectal cancer line NCI-H716-luc (NCI-H716 (purchased from ATCC) transfected with the luciferase gene) were suspended in saline (purchased from Otsuka Pharmaceutical Co., Ltd.) and intraperitoneally transplanted to each NOG mouse (NOD/Shi-SCID, IL-2Rγnull, purchased from Central Institute for Experimental Animals). One day after transplantation, the mice were grouped according to their weights. One, 5, 8, 12, 16, 19, and 26 days after transplantation, each humanized antibody (hFR2-14_H12/L1 or hFR2-14_H19/L1) prepared in Examples 8) and 9) was intraperitoneally administered at a dose of 20 mg/kg to the cancer-bearing mice (n=11). The date of death of a mouse was recorded, and the survival rate (%) was calculated. Thirty-seven days after transplantation, VivoGlo Luciferin (purchased from Promega Corp.) was administered at a dose of 150 mg/kg to the tail veins of the cancer-bearing mice. Ten minutes after administration, the luciferase activity of the cancer-bearing mice was assayed using IVIS (manufactured by Caliper, A PerkinElmer Company). The luciferase activity (p/s/cm$^2$/sr) was quantified using Living Image (manufactured by Caliper, A PerkinElmer Company).

FIG. 137(A) shows the tumor growth inhibitory effects of the humanized antibodies. The percentage of tumor growth inhibition relative to the non-administered group, with the luciferase activity as an index, at 37 days after transplantation was 98% for the hFR2-14_H12/L1-administered group and 98% for the hFR2-14_H19/L1-administered group.

FIG. 137(B) shows the life prolonging effects of the humanized antibodies. The survival rate at 93 days after transplantation was 0% for the non-administered group, whereas the survival rate was 64% for the hFR2-14_H12/L1 antibody-administered group and 91% for the hFR2-14_H19/L1 antibody-administered group.

Example 15

X-Ray Structural Analysis of Complex of Humanized Anti-FGFR2 Antibody (hFR2-14_H3/L1) and FGFR2 Protein 15)-1 Preparation of FGFR2 Protein for Crystallization 15)-1-1 Preparation of FGFR2 Protein Expression Vector for Crystallization In order to construct a vector for expression of a region consisting of an amino acid sequence of amino acid positions 148 to 249 in the common portion of human FGFR2 IIIb and IIIc (FIG. 78; SEQ ID NO: 70 and FIG. 79; SEQ ID NO: 71) (hereinafter, this region is referred to as "D2"), PCR reaction was performed using a primer set shown below and a vector plasmid comprising amino acid positions 126 to 313 of human FGFR2 (FIG. 78; SEQ ID NO: 70 and FIG. 79; SEQ ID NO: 71) as a template.

Primer Set for Gene Amplification of D2:

```
D23fw:
                              (FIG. 120; SEQ ID NO: 112)
5'-CTGTTTCAAGGTCCGAGCAATAACAAACGTGCACCGTATTGG-3'
and D23rv:
                              (FIG. 121; SEQ ID NO: 113)
5'-CGCAAGCTTGTCGACTCAAACAACATCCAGATGATAGGTATG-3'.
```

The obtained PCR product was inserted to pET24b(+) (manufactured by Merck KGaA (Novagen)) preliminarily containing nucleotide sequences encoding a His tag and an HRV3c protease cleavage site using In-Fusion HD Cloning Kit (manufactured by Takara Bio Inc.) (hereinafter, the resulting vector is referred to as "pET24b(+)-D2", and hereinafter and in the drawings, the recombinant protein expressed by "pET24b(+)-D2" is referred to as FGFR2D2).

15)-1-2 Preparation of FGFR2 Protein (FGFR2D2) for Crystallization

*E. coli* Origami 2 (DE3) (manufactured by Merck KGaA (Novagen)) was transformed with the expression plasmid pET24b(+)-D2 and precultured overnight at 200 rpm at 37° C. in 50 mL of Terrific medium (manufactured by ForMedium Ltd.) supplemented with 25 µg/ml kanamycin (manufactured by Wako Pure Chemicals Industries, Ltd.) and 12 µg/ml tetracycline (manufactured by Wako Pure Chemicals Industries, Ltd.). 50 mL of the precultured solution was added to 1 L of Terrific medium also supplemented with 25 µg/ml kanamycin and 12 µg/ml tetracycline, and cultured at 250 rpm at 37° C. for 1 hour. Then, the temperature was lowered to 16° C., and the expression of FGFR2D2 was induced by the addition of 1 mM IPTG, followed by culture for 26 hours. The bacterial cells were collected by centrifugation at 4500 rpm for 30 minutes, suspended in a binding buffer (50 mM Tris-HCl (pH 8.0), 400 mM NaCl, and 20 mM imidazole) containing Inhibitor Cocktail (manufactured by Roche Applied Science) dissolved therein, and then sonicated on ice. After centrifugation at 25000 rpm for 20 minutes, the supernatant was recovered and applied to HisTrap FF crude column (manufactured by GE Healthcare Bio-Sciences Corp.). The column was washed with the binding buffer, followed by gradient elution with an elution buffer (50 mM Tris-HCl (pH 8.0), 400 mM NaCl, and 500 mM imidazole) to collect fractions containing the protein of interest. The collected sample was diluted with a buffer (50 mM Tris-HCl (pH 7.5) and 0.1 mM EDTA) and then applied to HiTrap SP HP, followed by gradient elution with a buffer (50 mM Tris-HCl (pH 7.5), 1 M NaCl, and 0.1 mM EDTA) to collect fractions containing the protein of interest. The obtained sample was applied to a gel filtration column (HiLoad 16/600 Superdex 75 pg; manufactured by GE Healthcare Bio-Sciences Corp.) equilibrated with a buffer (25 mM HEPES (pH 7.5), 300 mM NaCl, and 0.1 mM EDTA) to collect fractions containing the protein of interest. The obtained FGFR2D2 was concentrated into 15 mg/mL using Amicon Ultra-4 (manufactured by Merck Millipore).

15)-2 Preparation of Fab Fragment of Humanized Anti-FGFR2 Antibody (hFR2-14_H3/L1)

hFR2-14_H3/L1 was dialyzed against 20 mM phosphate and 10 mM EDTA (pH 7.0) and then concentrated into 24 mg/ml using Amicon Ultra-15 MWCO 10K (manufactured by Merck Millipore) to prepare 1.9 ml of a concentrate. 5.5 ml of cysteine (manufactured by Sigma-Aldrich Corp.) adjusted to 0.005 mM with 20 mM phosphate and 10 mM EDTA (pH 7.0), and 0.19 ml of papain (manufactured by Sigma-Aldrich Corp.) diluted 1/100 with 20 mM phosphate and 10 mM EDTA (pH 7.0) were added to the concentrate and reacted at 37° C. for 18 hours. After 18 hours, the reaction was stopped by the addition of 2.53 ml of N-ethylmaleimide (manufactured by Tokyo Chemical Industry Co., Ltd.) dissolved at a concentration of 120 mM in 20 mM phosphate and 10 mM EDTA (pH 7.0). The reaction solution was applied to MabSelect SuRe 5 ml (manufactured by GE Healthcare Bio-Sciences Corp.) equilibrated with PBS to recover 18 ml of a flow-through fraction corresponding to the Fab fragment. The fraction was concentrated using Amicon Ultra-15 MWCO 10K (manufactured by Merck Millipore) and applied to Superdex 200 16/60 (manufactured by GE Healthcare Bio-Sciences Corp.) equilibrated with 50 mM Tris-HCl and 20 mM NaCl (pH 7.5) to recover 18 ml of a fraction corresponding to the Fab fragment (hereinafter, the resulting fragment is referred to as an "H3L1Fab fragment").

15)-3 Preparation of H3L1Fab Fragment/FGFR2D2 Complex Sample 0.5 mL of 15 mg/mL FGFR2D2 was mixed per mL of 12.5 mg/mL H3L1Fab fragment, and the mixture was left overnight at 4° C. and then applied to HisTrap FF crude equilibrated with a binding buffer (50 mM Tris-HCl (pH 8.0), 400 mM NaCl, and 20 mM imidazole). The column was washed with the binding buffer, followed by elution with an elution buffer (50 mM Tris-HCl (pH 8.0), 400 mM NaCl, and 500 mM imidazole). The eluted sample was applied to a gel filtration column (HiLoad 16/600 Superdex 200 pg; manufactured by GE Healthcare Bio-Sciences Corp.) equilibrated with a buffer (25 mM Tris-HCl (pH 7.5) and 50 mM NaCl) to recover 11 mL of a fraction corresponding to the complex.

15)-4 Crystallization and Structural Analysis of H3L1Fab Fragment/FGFR2D2 Complex The obtained complex of H3L1Fab and FGFR2D2 was concentrated into 22 mg/mL and used in crystallization. The vapor diffusion method was used for the crystallization. To 0.5 to 0.7 µL of the protein solution, an equal amount of a precipitant solution (1.225 M ammonium sulfate and 0.15 M Tris-HCl, pH 8.5) was added, and the resulting solution was placed in a sealed container containing 0.45 mL of a precipitant solution such that these solutions had no contact with each other. The container was left standing at 20° C. Three days later, 0.2 mm×0.2 mm×0.2 mm single crystals were obtained.

The obtained crystals were dipped in a precipitant solution supplemented with 30% (v/v) ethylene glycol and subsequently frozen under nitrogen stream of −180° C. X-ray diffraction data was collected under nitrogen stream of 95 K using BL5A of Photon Factory, Institute of Materials Structure Science, High Energy Accelerator Research Organization. Diffraction intensity was digitized from the obtained diffraction image using software HKL2000 (manufactured by HKL Research Inc.) to determine crystal structure factors. The crystals were in the tetragonal system with a space group of P41212 and unit cells of a=b=60.57 angstroms and c=331.2 angstroms.

The molecular replacement method was performed using the obtained structure factors and the three-dimensional structure coordinates of FGFR2 (the portion concerned was extracted from PDB code: 3OJ2) and Fab (the antibody structure previously subjected to crystal structural analysis was utilized) to determine a phase. Software phaser (CCP4: Collaborative Computational Project No. 4) was used in calculation. The crystals each contained 1 complex in the asymmetric unit.

Structure refinement was performed using software refmac5 (CCP4), and model correction was performed using software coot. This operation was repetitively performed to obtain a final R factor of 21.8% and a free R factor of 25.8% with a resolution of 2.3 angstroms. The model is composed of 1 complex and contains amino acid residues 1 to 215 of the H3L1Fab L chain, amino acid residues 1 to 221 of the H3L1Fab H chain, amino acid residues 150 to 249 of FGFR2D2, 1 sulfate ion, and 285 water molecules. The C-terminal 1 residue of the H3L1Fab L chain, the C-terminal 4 residues of the H3L1Fab H chain, and N-terminal 20 residues comprising the His tag and protease cleavage site of FGFR2D2 were not included in the model because of their obscure electric density.

The determined amino acid residues of FGFR2D2 within 4 angstroms from H3L1Fab are as follows: Tyr155, Thr157, Lys176, Ala181, Gly182, Gly183, Asn184, Pro185, Met186, Thr188, Gln200, Glu201, Gly205, Gly206, Lys208, Val209, Arg210, Asn211, Gln212, His213, Trp214, and Ile217. FIG. 138 shows a ribbon model of the whole complex. FIG. 139 shows a diagram showing the superposition of the D2 region in the FGFR2D2/H3L1Fab complex onto the corresponding region of an FGFR2/FGF1 complex structure (PDB code: 3OJ2).

Example 16

Immunostaining Using Rat Anti-FGFR2 Antibody FR2-10

16)-1 Preparation of Sample for Immunostaining

16)-1-1 Preparation of Cell Line Expressing Each Molecule of FGFR Family

293α cells (described in Example 1)-6) were adjusted to $6 \times 10^6$ cells/225-cm$^2$ flask (manufactured by Sumitomo Bakelite Co., Ltd.) in a DMEM medium containing 10% FBS and cultured overnight at 37° C. under 5% $CO_2$ conditions. The cells were transfected with the FGFR1 IIIb, FGFR1 IIIc, FGFR2 IIIb, FGFR2 IIIc, FGFR3 IIIb, FGFR3 IIIc, or FGFR4 expression vector constructed in Examples 1)-3-1, 2)-1-1, and 10)-2-1 or an empty vector, i.e., pcDNA-DEST04-FGFR1 IIIb, pcDNA-DEST40-FGFR1 IIIc, pcDNA-DEST40-FGFR2 IIIb, pcDNA-DEST40-FGFR2 IIIc, pcDNA-DEST40-FGFR3 IIIb, pcDNA-DEST40-FGFR3 IIIc, pcDNA-DEST40-FGFR4, or pcDNA-DEST40 using FuGENE 6 (manufactured by Roche Diagnostics K.K.) and cultured for two nights at 37° C. under 5% $CO_2$ conditions. The obtained cells were recovered using TrypLE Express (manufactured by Life Technologies Corp.) and centrifuged to obtain a pellet, which was then washed once with PBS and centrifuged. The resulting pellet was fixed in 20% neutral buffered formalin.

16)-1-2 Preparation of FGFR2-Expressing Cancer Cell Line

A human stomach cancer line SNU-16 and a human colorectal cancer line NCI-H716 (purchased from ATCC) cultured in RPMI containing 10% FBS were each recovered and centrifuged to obtain pellet, which was then fixed in 20% neutral buffered formalin. A human stomach cancer line KATO III (purchased from ATCC) cultured in DMEM containing 10% FBS was recovered and centrifuged to obtain a pellet, which was then fixed in 20% neutral buffered formalin.

16)-1-3 Preparation of Tumor Sample of FGFR2-Expressing Cancer Cell Line Xenograft Model $5 \times 10^6$ cells of SNU-16 were suspended in 50% Matrigel (manufactured by Nippon Becton Dickinson Company, Ltd.) and subcutaneously transplanted to the axillary region of each nude mice (CAnN.Cg-Foxnl$^{nu}$/CrlCrlj, purchased from Charles River Laboratories Japan Inc.). Twenty days after transplantation, tumor was recovered and fixed in Mildform (manufactured by Wako Pure Chemicals Industries, Ltd.).

$3 \times 10^5$ cells of KATO III were suspended in 100% Matrigel (manufactured by Nippon Becton Dickinson Company, Ltd.) and subcutaneously transplanted to the axillary region of each SCID mouse (CB17/lcr-Prkdc$^{scid}$/CrlCrlj, purchased from Charles River Laboratories Japan Inc.). Thirty days after transplantation, tumor was recovered and fixed in Mildform (manufactured by Wako Pure Chemicals Industries, Ltd.).

$2.5 \times 10^6$ cells of NCI-H716 were suspended in 100% Matrigel (manufactured by Nippon Becton Dickinson Company, Ltd.) and subcutaneously transplanted to the axillary region of each nude mice (CAnN.Cg-Foxnl$^{nu}$/CrlCrlj, purchased from Charles River Laboratories Japan Inc.). Twenty-one days after transplantation, tumor was recovered.

16)-2 Paraffin Embedding and Sectioning

Paraffin embedding and sectioning are general approaches, and any tool or instrument can be used without particular limitations.

The cells of each line prepared in Examples 16)-1-1 and 16)-1-2 were recovered into a 15-mL tube and centrifuged at 1500 rpm for 5 minutes to remove a supernatant. 3 mL of 20% neutral buffered formalin (manufactured by Wako Pure Chemicals Industries, Ltd.) was layered over the cell pellet and left standing at room temperature for 30 minutes or longer for fixation. Then, 5 mL of chloroform was added thereto. Immediately thereafter, the tube was centrifuged at 1000 rpm for 10 minutes, and the formalin layer was immediately removed. Then, the cell pellet formed between the formalin layer and the chloroform layer was recovered. The cell pellet was put in a nylon mesh bag, which was then placed in a cassette for tissue preparation (Unicassette Standard, manufactured by Sakura Finetek Japan Co., Ltd.). The cell pellet, together with the cassette, was dipped in ethanol to wash off the chloroform. Each xenograft tissue prepared in Example 16)-1-3 was fixed in Mildform (purchased from Wako Pure Chemicals Industries, Ltd.), then trimmed at the cutout portion, and placed in a cassette.

The cell pellet and the xenograft tissue were paraffin-embedded by a conventional method. Dehydration, delipidation, and paraffin impregnation were performed using an automatic fixation and embedding apparatus (Tissue-Tek VIP5 Jr.; manufactured by Sakura Finetek Japan Co., Ltd.). The cassette was taken out of the automatic fixation and embedding apparatus and transferred to the paraffin bath of a paraffin-embedded block preparation apparatus (Tissue-Tek TEC Plus; manufactured by Sakura Finetek Japan Co., Ltd.). A small amount of melted paraffin was injected into an embedding dish loaded to this apparatus. The cell pellet or the tissue was separated with tweezers from the cassette container or the nylon mesh taken out of the paraffin bath, and loaded into the paraffin in this embedding dish. Subsequently, a cassette was placed as an embedding frame on the embedding dish, and melted paraffin was poured over the cell pellet or the tissue within the cassette. The embedding dish containing the embedding frame integrated with the cells or the tissue was placed on a cooling unit and cooled. After solidification of paraffin, the embedded block was taken out of the embedding dish and subjected to sectioning. The sectioning was performed by the slicing of the embedded block thus prepared into sections with a thickness of 3 μm using a microtome (IVS-410; manufactured by Sakura Finetek Japan Co., Ltd.). Each section thus obtained was applied to an antistripping glass slide (Platinum; manufactured by Matsunami Glass Ind., Ltd.). The glass slide was dried overnight on a paraffin stretcher (manufactured by Sakura Finetek Japan Co., Ltd.) at 50° C., accommodated in a slide case, and stored in a desiccator.

16)-3 Staining

Each sample was stained using an automatic staining apparatus (Discovery Ultra; manufactured by Ventana Medical Systems, Inc.). The reaction temperature during the staining process was set to 37° C., unless otherwise specified. The amounts of various reagents added were all set to one drop. The sample was deparaffinized by 3 incubation runs each involving 68° C. for 4 minutes using fresh EZ buffer (manufactured by Ventana Medical Systems, Inc.). The sample was washed with EZ buffer. Cell conditioning was carried out by 4 runs each involving 95° C. using fresh CC1 buffer (manufactured by Ventana Medical Systems, Inc.) (a total of 52 minutes). The sample was washed 4 times with a reaction buffer (manufactured by Ventana Medical Systems, Inc.). The rat anti-FGFR2 antibody FR2-10 and a commercially available antibody Anti-Human K-sam Rabbit IgG Affinity Purify (manufactured by IBL Co., Ltd.) were diluted to 10 µg/mL and 210 µg/mL, respectively, with an antibody diluent dedicated to Discovery (manufactured by Ventana Medical Systems, Inc.), and reacted with the sample for 1 hour. After washing 4 times with a reaction buffer, a solution of biotinylated goat anti-rat IgG (manufactured by Jackson ImmunoResearch Laboratories, Inc.) diluted 500-fold with an antibody diluent dedicated to Discovery and Discovery Universal Secondary Antibody (manufactured by Ventana Medical Systems, Inc.) were reacted therewith for 32 minutes. The sample was washed twice with a reaction buffer. Inhibitor D (DAB Map kit; manufactured by Ventana Medical Systems, Inc.) was reacted therewith for 8 minutes, and the sample was then washed twice with a reaction buffer. SA-HRP D (DAB Map kit; manufactured by Ventana Medical Systems, Inc.) was reacted therewith for 16 minutes, and the sample was washed twice with a reaction buffer. DAB D (DAB Map kit; manufactured by Ventana Medical Systems, Inc.) was reacted therewith for 4 minutes. Then, DAB $H_2O_2$ (DAB Map kit; manufactured by Ventana Medical Systems, Inc.) was added thereto, followed by reaction with 8 minutes. The sample was washed twice with a reaction buffer. Copper-D (DAB Map kit; manufactured by Ventana Medical Systems, Inc.) was reacted therewith for 4 minutes, and the sample was washed 3 times with a reaction buffer. Hematoxylin nuclear staining reagent II (manufactured by Ventana Medical Systems, Inc.) was reacted therewith for 4 minutes, and the sample was washed twice with a reaction buffer. A lithium carbonate reagent (manufactured by Ventana Medical Systems, Inc.) was reacted therewith for 4 minutes, and the sample was washed once with a reaction buffer.

The completely stained preparations were dehydrated with ethanol series, cleared with xylene series, and then mounted on glass covers together with mounting agents. The preparations were observed under an optical microscope and evaluated for brown stains representing positive reaction products.

As shown in FIG. 140, the rat anti-FGFR2 antibody FR2-10 exhibited very strong stains only on some cells in the blocks of cells forced to express FGFR2 IIIb. No positive stain was observed in other forcedly expressing cells or empty vector-transfected cells. Thus, it was concluded that the rat anti-FGFR2 antibody FR2-10 is capable of specifically staining FGFR2 IIIb.

As shown in FIG. 141, the commercially available anti-FGFR2 antibody exhibited clear positive stains on many cells in the blocks of SNU-16 cells (FIG. 141-D), KATO III cells (FIG. 141-E), and NCI-H716 cells (FIG. 141-F), demonstrating that these cell lines expressed the FGFR2 protein. On the other hand, the rat anti-FGFR2 antibody FR2-10 exhibited clear positive stains on many cells in the blocks of SNU-16 cells (FIG. 141-A) and KATO III cells (FIG. 141-B), but exhibited no positive stain on the NCI-H716 cells (FIG. 141-C), demonstrating that the NCI-H716 cells did not express the FGFR2 IIIb protein.

As shown in FIG. 142, the rat anti-FGFR2 antibody FR2-10 exhibited clear positive stains on many cells in the xenograft tumors derived from SNU-16 cells (FIG. 142-A) and KATO III cells (FIG. 142-B), but exhibited no stain on the xenograft tumor derived from NCI-H716 cells (FIG. 142-C).

Example 17

Inhibitory Activity of Humanized Anti-Human FGFR2 Antibody (hFR2-14) Against Ligand-Receptor Binding The binding of the ligand FGF7 to the antigen (C-terminally His-tagged rhFGFR2 alpha (IIIb)) was detected by ELISA. rhFGFR2 alpha (IIIb) was diluted to 2 µg/ml with PBS and added at a concentration of 100 µl/well to 96 well Clear Polystyrene High Bind Stripwell Microplate (manufactured by Corning Inc.), and the plate was left overnight at 4° C. On the next day, the solution was removed using an aspirator, and the contents in the wells were washed 3 times with PBS containing 0.05% Tween-20 (manufactured by Bio-Rad Laboratories, Inc.). Then, PBS containing 1% BSA (manufactured by Sigma-Aldrich Corp.) was added thereto at a concentration of 200 µl/well, and the plate was left at room temperature for 1 hour. After removal of the solution, the contents in the wells were washed 3 times with PBS containing 0.05% Tween-20. FGF7 diluted to 9 ng/ml with PBS containing 1% BSA, heparin (manufactured by Sigma-Aldrich Corp.) diluted to 300 µg/ml, and the cFR2-10 (prepared in Example 4)), hFR2-14_H12/L1 (prepared in Example 8)), or hFR2-14_H19/L1 antibody (prepared in Example 9)) diluted to 0.3 to 30 µg/ml were each added thereto at a concentration of 50 µl/well, and the plate was left at room temperature for 2 hours. After removal of the solution, the contents in the wells were washed 3 times with PBS containing 0.05% Tween-20. A biotinylated anti-FGF-7 antibody (Human KGF/FGF-7 DuoSet, manufactured by R&D Systems, Inc.) diluted 180-fold with PBS containing 1% BSA was added thereto at a concentration of 100 µl/well, and the plate was left at room temperature for 2 hours. After removal of the solution, the contents in the wells were washed 3 times with PBS containing 0.05% Tween-20. Streptavidin-HRP (Human KGF/FGF-7 DuoSet, manufactured by R&D Systems, Inc.) diluted 200-fold with PBS containing 1% BSA was added thereto at a concentration of 100 µl/well, and the plate was left at room temperature for 20 minutes while shielded from light. After removal of the solution, the contents in the wells were washed 3 times with PBS containing 0.05% Tween-20. A substrate solution containing Reagent A and Reagent B mixed in equal amounts (Substrate Reagent Pack, manufactured by R&D Systems, Inc.) was added thereto at a concentration of 100 µl/well, and the plate was left at room temperature for 20 minutes for color reaction while shielded from light. The reaction was stopped by the addition of Stop solution (manufactured by R&D Systems, Inc.) at a concentration of 50 μl/well. Then, the absorbance was measured at 450 nm and 570 nm using a plate reader. The measurement value at 570 nm was subtracted from the measurement value at 450 nm to determine a value. As shown in FIG. 143, the cFR2-10, hFR2-14_H12/L1, and hFR2-14_H19/L1 antibodies all had the activity of inhibiting the binding of the ligand to the receptor.

INDUSTRIAL APPLICABILITY

Use of the antibody provided by the present invention enables treatment or prevention of various cancers and testing or diagnosis of various cancers.

SEQUENCE LISTING FREE TEXT

SEQ ID NO: 1: N-terminal amino acid sequence of a band corresponding to the heavy chain of a rat anti-FGFR2 antibody FR2-10 (FIG. 9).
SEQ ID NO: 2: N-terminal amino acid sequence of a band corresponding to the light chain of a rat anti-FGFR2 antibody FR2-10 (FIG. 10).
SEQ ID NO: 3: N-terminal amino acid sequence of a band corresponding to the heavy chain of a rat anti-FGFR2 antibody FR2-13 (FIG. 11).
SEQ ID NO: 4: N-terminal amino acid sequence of a band corresponding to the light chain of a rat anti-FGFR2 antibody FR2-13 (FIG. 12).
SEQ ID NO: 5: N-terminal amino acid sequence of a band corresponding to the heavy chain of a rat anti-FGFR2 antibody FR2-14 (FIG. 13).
SEQ ID NO: 6: N-terminal amino acid sequence of a band corresponding to the light chain of a rat anti-FGFR2 antibody FR2-14 (FIG. 14).
SEQ ID NO: 7: Primer for gene amplification of a rat heavy chain (FIG. 15).
SEQ ID NO: 8: Sequencing primer for the heavy chain of FR2-10 (FIG. 16).
SEQ ID NO: 9: Sequencing primer for the heavy chain of FR2-13 (FIG. 17).
SEQ ID NO: 10: Sequencing primer for the heavy chain of FR2-14 (FIG. 18).
SEQ ID NO: 11: Nucleotide sequence of a cDNA encoding the heavy chain variable region of a rat anti-FGFR2 antibody FR2-10 (FIG. 19).
SEQ ID NO: 12: Amino acid sequence of the heavy chain variable region of the rat anti-FGFR2 antibody FR2-10 (FIG. 20).
SEQ ID NO: 13: Nucleotide sequence of a cDNA encoding the heavy chain variable region of a rat anti-FGFR2 antibody FR2-13 (FIG. 21).
SEQ ID NO: 14: Amino acid sequence of the heavy chain variable region of the rat anti-FGFR2 antibody FR2-13 (FIG. 22).
SEQ ID NO: 15: Nucleotide sequence of a cDNA encoding the heavy chain variable region of a rat anti-FGFR2 antibody FR2-14 (FIG. 23).
SEQ ID NO: 16: Amino acid sequence of the heavy chain variable region of the rat anti-FGFR2 antibody FR2-14 (FIG. 24).
SEQ ID NO: 17: Primer for gene amplification of a rat light chain (FIG. 25).
SEQ ID NO: 18: Sequencing primer for a rat light chain (FIG. 26).
SEQ ID NO: 19: Sequencing primer for the light chain of FR2-10 (FIG. 27).
SEQ ID NO: 20: Nucleotide sequence of a cDNA encoding the light chain variable region of a rat anti-FGFR2 antibody FR2-10 (FIG. 28).
SEQ ID NO: 21: Amino acid sequence of the light chain variable region of the rat anti-FGFR2 antibody FR2-10 (FIG. 29).
SEQ ID NO: 22: Primer for gene amplification of the rat FR2-13 or FR2-14 light chain (FIG. 30).
SEQ ID NO: 23: Nucleotide sequence of a cDNA encoding the light chain variable region of a rat anti-FGFR2 antibody FR2-13 (FIG. 31).
SEQ ID NO: 24: Amino acid sequence of the light chain variable region of the rat anti-FGFR2 antibody FR2-13 (FIG. 32).
SEQ ID NO: 25: Nucleotide sequence of a cDNA encoding the light chain variable region of a rat anti-FGFR2 antibody FR2-14 (FIG. 33).
SEQ ID NO: 26: Amino acid sequence of the light chain variable region of the rat anti-FGFR2 antibody FR2-14 (FIG. 34).
SEQ ID NO: 27: DNA fragment comprising a DNA sequence encoding the amino acids of a human κ chain secretory signal sequence and a human κ chain constant region (FIG. 35).
SEQ ID NO: 28: Primer F for a light chain expression vector (FIG. 36).
SEQ ID NO: 29: Primer R for a light chain expression vector (FIG. 37).
SEQ ID NO: 30: DNA fragment comprising a DNA sequence encoding the amino acids of a human heavy chain signal sequence and a human IgG1 constant region (FIG. 38).
SEQ ID NO: 31: Nucleotide sequence of the light chain of human chimeric FR2-10 (cFR2-10) (FIG. 39). In this sequence, nucleotide positions 1 to 60 represent a signal sequence, which is usually not contained in the nucleotide sequences of most of mature cFR2-10 light chains.
SEQ ID NO: 32: Amino acid sequence of the light chain of human chimeric FR2-10 (cFR2-10) (FIG. 40). In this sequence, amino acid positions 1 to 20 represent a signal sequence, which is usually not contained in the amino acid sequences of most of mature cFR2-10 light chains.
SEQ ID NO: 33: Primer set F for the light chain of human chimeric FR2-10 (FIG. 41).
SEQ ID NO: 34: Primer set R for the light chain of human chimeric FR2-10 (FIG. 42).
SEQ ID NO: 35: Nucleotide sequence of the heavy chain of human chimeric FR2-10 (cFR2-10) (FIG. 43). In this sequence, nucleotide positions 1 to 57 represent a signal sequence, which is usually not contained in the nucleotide sequences of most of mature cFR2-10 heavy chains.
SEQ ID NO: 36: Amino acid sequence of the heavy chain of human chimeric FR2-10 (cFR2-10) (FIG. 44). In this sequence, amino acid positions 1 to 19 represent a signal sequence, which is usually not contained in the amino acid sequences of most of mature cFR2-10 heavy chains.
SEQ ID NO: 37: Primer set F for the heavy chain of human chimeric FR2-10 (FIG. 45).
SEQ ID NO: 38: Primer set R for the heavy chain of human chimeric FR2-10 (FIG. 46).
SEQ ID NO: 39: Nucleotide sequence of the light chain of human chimeric FR2-13 (cFR2-13) (FIG. 47). In this sequence, nucleotide positions 1 to 60 represent a signal sequence, which is usually not contained in the nucleotide sequences of most of mature cFR2-13 light chains.
SEQ ID NO: 40: Amino acid sequence of the light chain of human chimeric FR2-13 (cFR2-13) (FIG. 48). In this sequence, amino acid positions 1 to 20 represent a signal sequence, which is usually not contained in the amino acid sequences of most of mature cFR2-13 light chains.

SEQ ID NO: 41: Primer F for the light chain of human chimeric FR2-13 (FIG. 49).

SEQ ID NO: 42: Primer R for the light chain of human chimeric FR2-13 (FIG. 50).

SEQ ID NO: 43: Nucleotide sequence of the heavy chain of human chimeric FR2-13 (cFR2-13) (FIG. 51). In this sequence, nucleotide positions 1 to 57 represent a signal sequence, which is usually not contained in the nucleotide sequences of most of mature cFR2-13 heavy chains.

SEQ ID NO: 44: Amino acid sequence of the heavy chain of human chimeric FR2-13 (cFR2-13) (FIG. 52). In this sequence, amino acid positions 1 to 19 represent a signal sequence, which is usually not contained in the amino acid sequences of most of mature cFR2-13 heavy chains.

SEQ ID NO: 45: Primer F for the heavy chain of human chimeric FR2-13 (FIG. 53).

SEQ ID NO: 46: Primer R for the heavy chain of human chimeric FR2-13 (FIG. 54).

SEQ ID NO: 47: Nucleotide sequence of the light chain of human chimeric FR2-14 (cFR2-14) (FIG. 55). In this sequence, nucleotide positions 1 to 60 represent a signal sequence, which is usually not contained in the nucleotide sequences of most of mature cFR2-14 light chains.

SEQ ID NO: 48: Amino acid sequence of the light chain of human chimeric FR2-14 (cFR2-14) (FIG. 56). In this sequence, amino acid positions 1 to 20 represent a signal sequence, which is usually not contained in the amino acid sequences of most of mature cFR2-14 light chains.

SEQ ID NO: 49: Primer for the light chain of human chimeric FR2-14 (FIG. 57).

SEQ ID NO: 50: Nucleotide sequence of the heavy chain of human chimeric FR2-14 (cFR2-14) (FIG. 58). In this sequence, nucleotide positions 1 to 57 represent a signal sequence, which is usually not contained in the nucleotide sequences of most of mature cFR2-14 heavy chains.

SEQ ID NO: 51: Amino acid sequence of the heavy chain of human chimeric FR2-14 (cFR2-14) (FIG. 59). In this sequence, amino acid positions 1 to 19 represent a signal sequence, which is usually not contained in the amino acid sequences of most of mature cFR2-14 heavy chains.

SEQ ID NO: 52: Amino acid sequence of the heavy chain CDR1 of the rat anti-FGFR2 antibody FR2-10 (FIG. 60).

SEQ ID NO: 53: Amino acid sequence of the heavy chain CDR2 of the rat anti-FGFR2 antibody FR2-10 (FIG. 61).

SEQ ID NO: 54: Amino acid sequence of the heavy chain CDR3 of the rat anti-FGFR2 antibody FR2-10 (FIG. 62).

SEQ ID NO: 55: Amino acid sequence of the heavy chain CDR1 of the rat anti-FGFR2 antibody FR2-13 (FIG. 63).

SEQ ID NO: 56: Amino acid sequence of the heavy chain CDR2 of the rat anti-FGFR2 antibody FR2-13 (FIG. 64).

SEQ ID NO: 57: Amino acid sequence of the heavy chain CDR3 of the rat anti-FGFR2 antibody FR2-13 (FIG. 65).

SEQ ID NO: 58: Amino acid sequence of the heavy chain CDR1 of the rat anti-FGFR2 antibody FR2-14 (FIG. 66).

SEQ ID NO: 59: Amino acid sequence of the heavy chain CDR2 of the rat anti-FGFR2 antibody FR2-14 (FIG. 67).

SEQ ID NO: 60: Amino acid sequence of the heavy chain CDR3 of the rat anti-FGFR2 antibody FR2-14 (FIG. 68).

SEQ ID NO: 61: Amino acid sequence of the light chain CDR1 of the rat anti-FGFR2 antibody FR2-10 (FIG. 69).

SEQ ID NO: 62: Amino acid sequence of the light chain CDR2 of the rat anti-FGFR2 antibody FR2-10 (FIG. 70).

SEQ ID NO: 63: Amino acid sequence of the light chain CDR3 of the rat anti-FGFR2 antibody FR2-10 (FIG. 71).

SEQ ID NO: 64: Amino acid sequence of the light chain CDR1 of the rat anti-FGFR2 antibody FR2-13 (FIG. 72).

SEQ ID NO: 65: Amino acid sequence of the light chain CDR2 of the rat anti-FGFR2 antibody FR2-13 (FIG. 73).

SEQ ID NO: 66: Amino acid sequence of the light chain CDR3 of the rat anti-FGFR2 antibody FR2-13 (FIG. 74).

SEQ ID NO: 67: Amino acid sequence of the light chain CDR1 of the rat anti-FGFR2 antibody FR2-14 (FIG. 75).

SEQ ID NO: 68: Amino acid sequence of the light chain CDR2 of the rat anti-FGFR2 antibody FR2-14 (FIG. 76).

SEQ ID NO: 69: Amino acid sequence of the light chain CDR3 of the rat anti-FGFR2 antibody FR2-14 (FIG. 77).

SEQ ID NO: 70: Amino acid sequence of human FGFR2 IIIb (FIG. 78).

SEQ ID NO: 71: Amino acid sequence of human FGFR2 IIIc (FIG. 79).

SEQ ID NO: 72: Nucleotide sequence of a humanized FR2-14 light chain (hFR2-14_L1) (FIG. 80). In this sequence, nucleotide positions 1 to 60 represent a signal sequence, which is usually not contained in the nucleotide sequences of most of mature light chains hFR2-14_L1.

SEQ ID NO: 73: Amino acid sequence of the humanized FR2-14 light chain (hFR2-14_L1) (FIG. 81). In this sequence, amino acid positions 1 to 20 represent a signal sequence, which is usually not contained in the amino acid sequences of most of mature light chains hFR2-14_L1.

SEQ ID NO: 74: Nucleotide sequence of a humanized FR2-14 heavy chain (hFR2-14_H1) (FIG. 82). In this sequence, nucleotide positions 1 to 57 represent a signal sequence, which is usually not contained in the nucleotide sequences of most of mature heavy chains hFR2-14_H1.

SEQ ID NO: 75: Amino acid sequence of the humanized FR2-14 heavy chain (hFR2-14_H1) (FIG. 83). In this sequence, amino acid positions 1 to 19 represent a signal sequence, which is usually not contained in the amino acid sequences of most of mature heavy chains hFR2-14_H1.

SEQ ID NO: 76: Nucleotide sequence of a humanized FR2-14 heavy chain (hFR2-14_H2) (FIG. 84). In this sequence, nucleotide positions 1 to 57 represent a signal sequence, which is usually not contained in the nucleotide sequences of most of mature heavy chains hFR2-14_H2.

SEQ ID NO: 77: Amino acid sequence of the humanized FR2-14 heavy chain (hFR2-14_H2) (FIG. 85). In this sequence, amino acid positions 1 to 19 represent a signal sequence, which is usually not contained in the amino acid sequences of most of mature heavy chains hFR2-14_H2.

SEQ ID NO: 78: Nucleotide sequence of a humanized FR2-14 heavy chain (hFR2-14_H3) (FIG. 86). In this sequence, nucleotide positions 1 to 57 represent a signal sequence, which is usually not contained in the nucleotide sequences of most of mature heavy chains hFR2-14_H3.

SEQ ID NO: 79: Amino acid sequence of the humanized FR2-14 heavy chain (hFR2-14_H3) (FIG. 87). In this sequence, amino acid positions 1 to 19 represent a signal sequence, which is usually not contained in the amino acid sequences of most of mature heavy chains hFR2-14_H3.

SEQ ID NO: 80: Nucleotide sequence of a humanized FR2-14 heavy chain (hFR2-14_H4) (FIG. 88). In this sequence, nucleotide positions 1 to 57 represent a signal sequence, which is usually not contained in the nucleotide sequences of most of mature heavy chains hFR2-14_H4.

SEQ ID NO: 81: Amino acid sequence of the humanized FR2-14 heavy chain (hFR2-14_H4) (FIG. 89). In this sequence, amino acid positions 1 to 19 represent a signal sequence, which is usually not contained in the amino acid sequences of most of mature heavy chains hFR2-14_H4.

SEQ ID NO: 82: Nucleotide sequence of a humanized FR2-14 heavy chain (hFR2-14_H5) (FIG. 90). In this sequence, nucleotide positions 1 to 57 represent a signal sequence, which is usually not contained in the nucleotide sequences of most of mature heavy chains hFR2-14_H5.

SEQ ID NO: 83: Amino acid sequence of the humanized FR2-14 heavy chain (hFR2-14_H5) (FIG. 91). In this sequence, amino acid positions 1 to 19 represent a signal sequence, which is usually not contained in the amino acid sequences of most of mature heavy chains hFR2-14_H5.

SEQ ID NO: 84: Nucleotide sequence of a humanized FR2-14 heavy chain (hFR2-14_H6) (FIG. 92). In this sequence, nucleotide positions 1 to 57 represent a signal sequence, which is usually not contained in the nucleotide sequences of most of mature heavy chains hFR2-14_H6.

SEQ ID NO: 85: Amino acid sequence of the humanized FR2-14 heavy chain (hFR2-14_H6) (FIG. 93). In this sequence, amino acid positions 1 to 19 represent a signal sequence, which is usually not contained in the amino acid sequences of most of mature heavy chains hFR2-14_H6.

SEQ ID NO: 86: Nucleotide sequence of a humanized FR2-14 heavy chain (hFR2-14_H7) (FIG. 94). In this sequence, nucleotide positions 1 to 57 represent a signal sequence, which is usually not contained in the nucleotide sequences of most of mature heavy chains hFR2-14_H7.

SEQ ID NO: 87: Amino acid sequence of the humanized FR2-14 heavy chain (hFR2-14_H7) (FIG. 95). In this sequence, amino acid positions 1 to 19 represent a signal sequence, which is usually not contained in the amino acid sequences of most of mature heavy chains hFR2-14_H7.

SEQ ID NO: 88: Nucleotide sequence of a humanized FR2-14 heavy chain (hFR2-14_H8) (FIG. 96). In this sequence, nucleotide positions 1 to 57 represent a signal sequence, which is usually not contained in the nucleotide sequences of most of mature heavy chains hFR2-14_H8.

SEQ ID NO: 89: Amino acid sequence of the humanized FR2-14 heavy chain (hFR2-14_H8) (FIG. 97). In this sequence, amino acid positions 1 to 19 represent a signal sequence, which is usually not contained in the amino acid sequences of most of mature heavy chains hFR2-14_H8.

SEQ ID NO: 90: Nucleotide sequence of a humanized FR2-14 heavy chain (hFR2-14_H9) (FIG. 98). In this sequence, nucleotide positions 1 to 57 represent a signal sequence, which is usually not contained in the nucleotide sequences of most of mature heavy chains hFR2-14_H9.

SEQ ID NO: 91: Amino acid sequence of the humanized FR2-14 heavy chain (hFR2-14_H9) (FIG. 99). In this sequence, amino acid positions 1 to 19 represent a signal sequence, which is usually not contained in the amino acid sequences of most of mature heavy chains hFR2-14_H9.

SEQ ID NO: 92: Nucleotide sequence of a humanized FR2-14 heavy chain (hFR2-14_H10) (FIG. 100). In this sequence, nucleotide positions 1 to 57 represent a signal sequence, which is usually not contained in the nucleotide sequences of most of mature heavy chains hFR2-14_H10.

SEQ ID NO: 93: Amino acid sequence of the humanized FR2-14 heavy chain (hFR2-14_H10) (FIG. 101). In this sequence, amino acid positions 1 to 19 represent a signal sequence, which is usually not contained in the amino acid sequences of most of mature heavy chains hFR2-14_H10.

SEQ ID NO: 94: Nucleotide sequence of a humanized FR2-14 heavy chain (hFR2-14_H11) (FIG. 102). In this sequence, nucleotide positions 1 to 57 represent a signal sequence, which is usually not contained in the nucleotide sequences of most of mature heavy chains hFR2-14_H11.

SEQ ID NO: 95: Amino acid sequence of the humanized FR2-14 heavy chain (hFR2-14_H11) (FIG. 103). In this sequence, amino acid positions 1 to 19 represent a signal sequence, which is usually not contained in the amino acid sequences of most of mature heavy chains hFR2-14_H11.

SEQ ID NO: 96: Nucleotide sequence of a humanized FR2-14 heavy chain (hFR2-14_H12 or hFR2-14_H19) (FIG. 104). In this sequence, nucleotide positions 1 to 57 represent a signal sequence, which is usually not contained in the nucleotide sequences of most of mature heavy chains hFR2-14_H12 or hFR2-14_H19.

SEQ ID NO: 97: Amino acid sequence of the humanized FR2-14 heavy chain (hFR2-14_H12 or hFR2-14_H19) (FIG. 105). In this sequence, amino acid positions 1 to 19 represent a signal sequence, which is usually not contained in the amino acid sequences of most of mature heavy chains hFR2-14_H12 or hFR2-14_H19.

SEQ ID NO: 98: Nucleotide sequence of a humanized FR2-14 heavy chain (hFR2-14_H13) (FIG. 106). In this sequence, nucleotide positions 1 to 57 represent a signal sequence, which is usually not contained in the nucleotide sequences of most of mature heavy chains hFR2-14_H13.

SEQ ID NO: 99: Amino acid sequence of the humanized FR2-14 heavy chain (hFR2-14_H13) (FIG. 107). In this sequence, amino acid positions 1 to 19 represent a signal sequence, which is usually not contained in the amino acid sequences of most of mature heavy chains hFR2-14_H13.

SEQ ID NO: 100: Nucleotide sequence of a humanized FR2-14 heavy chain (hFR2-14_H14) (FIG. 108). In this sequence, nucleotide positions 1 to 57 represent a signal sequence, which is usually not contained in the nucleotide sequences of most of mature heavy chains hFR2-14_H14.

SEQ ID NO: 101: Amino acid sequence of the humanized FR2-14 heavy chain (hFR2-14_H14) (FIG. 109). In this sequence, amino acid positions 1 to 19 represent a signal sequence, which is usually not contained in the amino acid sequences of most of mature heavy chains hFR2-14_H14.

SEQ ID NO: 102: Nucleotide sequence of a humanized FR2-14 heavy chain (hFR2-14_H15) (FIG. 110). In this sequence, nucleotide positions 1 to 57 represent a signal sequence, which is usually not contained in the nucleotide sequences of most of mature heavy chains hFR2-14_H15.

SEQ ID NO: 103: Amino acid sequence of the humanized FR2-14 heavy chain (hFR2-14_H15) (FIG. 111). In this sequence, amino acid positions 1 to 19 represent a signal sequence, which is usually not contained in the amino acid sequences of most of mature heavy chains hFR2-14_H15.

SEQ ID NO: 104: Nucleotide sequence of a humanized FR2-14 heavy chain (hFR2-14_H16) (FIG. 112). In this sequence, nucleotide positions 1 to 57 represent a signal sequence, which is usually not contained in the nucleotide sequences of most of mature heavy chains hFR2-14_H16.

SEQ ID NO: 105: Amino acid sequence of the humanized FR2-14 heavy chain (hFR2-14_H16) (FIG. 113). In this sequence, amino acid positions 1 to 19 represent a signal sequence, which is usually not contained in the amino acid sequences of most of mature heavy chains hFR2-14_H16.

SEQ ID NO: 106: Nucleotide sequence of a humanized FR2-14 heavy chain (hFR2-14_H17) (FIG. 114). In this sequence, nucleotide positions 1 to 57 represent a signal sequence, which is usually not contained in the nucleotide sequences of most of mature heavy chains hFR2-14_H17.

SEQ ID NO: 107: Amino acid sequence of the humanized FR2-14 heavy chain (hFR2-14_H17) (FIG. 115). In this sequence, amino acid positions 1 to 19 represent a signal sequence, which is usually not contained in the amino acid sequences of most of mature heavy chains hFR2-14_H17.

SEQ ID NO: 108: Nucleotide sequence of a humanized FR2-14 heavy chain (hFR2-14_H18) (FIG. 116). In this sequence, nucleotide positions 1 to 57 represent a signal sequence, which is usually not contained in the nucleotide sequences of most of mature heavy chains hFR2-14_H18.

SEQ ID NO: 109: Amino acid sequence of the humanized FR2-14 heavy chain (hFR2-14_H18) (FIG. 117). In this sequence, amino acid positions 1 to 19 represent a signal sequence, which is usually not contained in the amino acid sequences of most of mature heavy chains hFR2-14_H18.

SEQ ID NO: 110: Primer VH3A-F for an hFR2-14_H2 type heavy chain (FIG. 118).

SEQ ID NO: 111: Primer VH3A-R for an hFR2-14_H2 type heavy chain (FIG. 119).

SEQ ID NO: 112: Primer D23fw for gene amplification of D2 (FIG. 120).

SEQ ID NO: 113: Primer D23rv for gene amplification of D2 (FIG. 121).

The invention claimed is:

1. An antibody or a functional fragment thereof, comprising a heavy chain and a light chain, the heavy chain comprising:
   (i) a CDRH1 comprising SEQ ID NO: 58;
   (ii) a CDRH2 comprising SEQ ID NO: 59; and
   (iii) a CDRH3 comprising SEQ ID NO: 60 or an amino acid sequence derived from SEQ ID NO: 60 by one amino acid substitution at the first amino acid position and/or one amino acid substitution at the second amino acid position;
   and the light chain comprising
   (i) a CDRL1 comprising SEQ ID NO: 67;
   (ii) a CDRL2 comprising SEQ ID NO: 68; and
   (iii) a CDRL3 comprising SEQ ID NO: 69, wherein the antibody or functional fragment thereof has antibody-dependent cellular cytotoxic activity and binds to human fibroblast growth factor receptor 2 (human FGFR2) IIIb and human fibroblast growth factor receptor 2 (human FGFR2) IIIc.

2. The antibody or functional fragment thereof according to claim 1, wherein the antibody or functional fragment thereof binds to one or more immunoglobulin-like domains of human fibroblast growth factor receptor 2.

3. The antibody or functional fragment thereof according to claim 1, wherein the antibody or functional fragment thereof binds to immunoglobulin-like domain 2 of human fibroblast growth factor receptor 2.

4. The antibody or functional fragment thereof according to claim 1, wherein the antibody or functional fragment thereof has neutralizing activity against human fibroblast growth factor receptor 2 (human FGFR2) IIIb and/or human fibroblast growth factor receptor 2 (human FGFR2) IIIc.

5. The antibody or functional fragment thereof according to claim 1, wherein the antibody or functional fragment thereof has neutralizing activity against human fibroblast growth factor receptor 2 (human FGFR2) IIIb and human fibroblast growth factor receptor 2 (human FGFR2) IIIc.

6. The antibody or functional fragment thereof according to claim 1, wherein the antibody or functional fragment thereof has antitumor activity.

7. The antibody or functional fragment thereof according to claim 6, wherein the antibody or functional fragment thereof exhibits antitumor activity in vivo.

8. An antibody or a functional fragment thereof which has antibody-dependent cellular cytotoxic activity and binds to a fibroblast growth factor receptor (FGFR), wherein the antibody comprises a heavy chain comprising:
   (i) a CDRH1 comprising SEQ ID NO: 52;
   (ii) a CDRH2 comprising SEQ ID NO: 53; and
   (iii) a CDRH3 comprising SEQ ID NO: 54;
   and a light chain comprising:
   (i) a CDRL1 comprising SEQ ID NO: 61;
   (ii) a CDRL2 comprising SEQ ID NO: 62; and
   (iii) a CDRL3 comprising SEQ ID NO: 63, and binds to human FGFR2.

9. An antibody or a functional fragment thereof which has antibody-dependent cellular cytotoxic activity and binds to a fibroblast growth factor receptor (FGFR), wherein the antibody comprises a heavy chain comprising:
(i) a CDRH1 comprising ID NO: 55;
(ii) a CDRH2 comprising SEQ ID NO: 56; and
(iii) a CDRH3 comprising SEQ ID NO: 57;
and a light chain comprising:
(i) a CDRL1 comprising SEQ ID NO: 64;
(ii) a CDRL2 comprising SEQ ID NO: 65; and
(iii) a CDRL3 comprising SEQ ID NO: 66, and binds to human FGFR2.

10. The antibody or functional fragment thereof according to claim 1, wherein the CDRH3 comprises amino acids 118 to 126 of SEQ ID NO: 97.

11. The antibody or functional fragment thereof according to claim 1, wherein the antibody is a monoclonal antibody.

12. The antibody or functional fragment thereof according to claim 1, wherein the antibody is a chimeric antibody.

13. The antibody or functional fragment thereof according to claim 1, wherein the antibody is a humanized antibody.

14. An antibody or a functional fragment thereof which has antibody-dependent cellular cytotoxic activity and binds to human fibroblast growth factor receptor 2 (human FGFR2) IIIb and human fibroblast growth factor receptor 2 (human FGFR2) IIIc, wherein the antibody is selected from the following (i) to (xix):
a. a humanized antibody (hFR2-14_H19/L1) comprising a light chain comprising amino acid positions 21 to 235 of SEQ ID NO: 73, and a heavy chain comprising amino acid positions 20 to 467 of SEQ ID NO: 97;
b. a humanized antibody (hFR2-14_H12/L1) comprising a light chain comprising amino acid positions 21 to 235 of SEQ ID NO: 73, and a heavy chain comprising amino acid positions 20 to 467 of SEQ ID NO: 97;
c. a humanized antibody (hFR2-14_H8/L1) comprising a light chain comprising amino acid positions 21 to 235 of SEQ ID NO: 73, and a heavy chain comprising amino acid positions 20 to 467 of SEQ ID NO: 89;
d. a humanized antibody (hFR2-141411/L1) comprising a light chain comprising amino acid positions 21 to 235 of SEQ ID NO: 73, and a heavy chain comprising amino acid positions 20 to 467 of SEQ ID NO: 95;
e. a humanized antibody (hFR2-14_H5/L1) comprising a light chain comprising amino acid positions 21 to 235 of SEQ ID NO: 73, and a heavy chain comprising amino acid positions 20 to 467 of SEQ ID NO: 83;
f. a humanized antibody (hFR2-14_H1/L1) comprising a light chain comprising amino acid positions 21 to 235 of SEQ ID NO: 73, and a heavy chain comprising amino acid positions 20 to 467 of SEQ ID NO: 75;
g. a humanized antibody (hFR2-14_H2/L1) comprising a light chain comprising amino acid positions 21 to 235 of SEQ ID NO: 73, and a heavy chain comprising amino acid positions 20 to 467 of SEQ ID NO: 77;
h. a humanized antibody (hFR2-14_H3/L1) comprising a light chain comprising amino acid positions 21 to 235 of SEQ ID NO: 73, and a heavy chain comprising amino acid positions 20 to 467 of SEQ ID NO: 79;
i. a humanized antibody (hFR2-14 H4/L1) comprising a light chain comprising amino acid positions 21 to 235 of SEQ ID NO: 73, and a heavy chain comprising amino acid positions 20 to 467 of SEQ ID NO: 81;
j. a humanized antibody (hFR2-14_H6/L1) comprising a light chain comprising amino acid positions 21 to 235 of SEQ ID NO: 73, and a heavy chain comprising amino acid positions 20 to 467 of SEQ ID NO: 85;
k. a humanized antibody (hFR2-14_H7/L1) comprising a light chain comprising amino acid positions 21 to 235 of SEQ ID NO: 73, and a heavy chain comprising amino acid positions 20 to 467 of SEQ ID NO: 87;
l. a humanized antibody (hFR2-14_H9/L1) comprising a light chain comprising amino acid positions 21 to 235 of SEQ ID NO: 73, and a heavy chain comprising amino acid positions 20 to 467 of SEQ ID NO: 91;
m. a humanized antibody (hFR2-14_H10/L1) comprising a light chain comprising amino acid positions 21 to 235 of SEQ ID NO: 73, and a heavy chain comprising amino acid positions 20 to 467 of SEQ ID NO: 93;
n. a humanized antibody (hFR2-14_H13/L1) comprising a light chain comprising amino acid positions 21 to 235 of SEQ ID NO: 73, and a heavy chain comprising amino acid positions 20 to 467 of SEQ ID NO: 99;
o. a humanized antibody (hFR2-14 H14/L1) comprising a light chain comprising amino acid positions 21 to 235 of SEQ ID NO: 73, and a heavy chain comprising amino acid positions 20 to 467 of SEQ ID NO: 101;
p. a humanized antibody (hFR2-14_H15/L1) comprising a light chain comprising amino acid positions 21 to 235 of SEQ ID NO: 73, and a heavy chain comprising amino acid positions 20 to 467 of SEQ ID NO: 103;
q. a humanized antibody (hFR2-14_H16/L1) comprising a light chain comprising amino acid positions 21 to 235 of SEQ ID NO: 73, and a heavy chain comprising amino acid positions 20 to 467 of SEQ ID NO: 105;
r. a humanized antibody (hFR2-14_H17/L1) comprising a light chain comprising amino acid positions 21 to 235 of SEQ ID NO: 73, and a heavy chain comprising amino acid positions 20 to 467 of SEQ ID NO: 107; and
s. a humanized antibody (hFR2-14_H18/L1) comprising a light chain comprising amino acid positions 21 to 235 of SEQ ID NO: 73, and a heavy chain comprising amino acid positions 20 to 467 of SEQ ID NO: 109.

15. An antibody or a functional fragment thereof which has antibody-dependent cellular cytotoxic activity, wherein the antibody or functional fragment thereof binds to a site on FGFR2IIIb or IIIc that is recognized by an antibody according to claim 14.

16. An antibody or a functional fragment thereof which has antibody-dependent cellular cytotoxic activity, wherein the antibody or functional fragment thereof competes with an antibody according to claim 14 for binding to human FGFR2 IIIb or IIIc.

17. The antibody or functional fragment thereof according to claim 1, wherein the antibody or functional fragment thereof binds to an epitope on human FGFR2, the epitope being constituted by tyrosine (Tyr) at residue 155, threonine (Thr) at residue 157, lysine (Lys) at residue 176, alanine (Ala) at residue 181, glycine (Gly) at residue 182, glycine (Gly) at residue 183, asparagine (Asn) at residue 184, proline (Pro) at residue 185, methionine (Met) at residue 186, threonine (Thr) at residue 188, glutamine (Gin) at residue 200, glutamic acid (Glu) at residue 201, glycine (Gly) at residue 205, glycine (Gly) at residue 206, lysine (Lys) at residue 208, valine (Val) at residue 209, arginine (Arg) at residue 210, asparagine (Asn) at residue 211, glutamine (Gln) at residue 212, histidine (His) at residue 213, tryptophan (Trp) at residue 214, and isoleucine (Ile) at residue 217 in the amino acid sequence represented by SEQ ID NO: 70.

18. The antibody or functional fragment thereof according to claim 1, wherein the antibody or functional fragment thereof has an interaction distance of 8angstroms or shorter with each of tyrosine (Tyr) at residue 155, threonine (Thr) at residue 157, lysine (Lys) at residue 176, alanine (Ala) at residue 181, glycine (Gly) at residue 182, glycine (Gly) at residue 183, asparagine (Asn) at residue 184, proline (Pro) at residue 185, methionine (Met) at residue 186, threonine (Thr) at residue 188, glutamine (Gln) at residue 200, glutamic acid (Glu) at residue 201, glycine (Gly) at residue 205, glycine (Gly) at residue 206, lysine (Lys) at residue 208, valine (Val) at residue 209, arginine (Arg) at residue 210, asparagine (Asn) at residue 211, glutamine (Gln) at residue 212, histidine (His) at residue 213, tryptophan (Trp) at residue 214, and isoleucine (Ile) at residue 217 in the amino acid sequence represented by SEQ ID NO: 70.

19. The antibody or functional fragment thereof according to claim 18, wherein the interaction distance is 6 angstroms or shorter.

20. The antibody or functional fragment thereof according to claim 18, wherein the interaction distance is 4 angstroms or shorter.

21. The antibody or functional fragment thereof according to claim 1, wherein the antibody is a human antibody.

22. The antibody or functional fragment thereof according to claim 1, wherein the antibody or functional fragment thereof inhibits the binding of FGF to human FGFR2.

23. The antibody or functional fragment thereof according to claim 1, wherein the antibody or functional fragment thereof has antibody-dependent cellular cytotoxic activity and antibody-dependent cell phagocytosis activity.

24. The antibody or a functional fragment thereof according to claim 14, wherein the antibody or functional fragment thereof is defucosylated or has been modified such that the antibody or functional fragment has reduced fucose.

25. The antibody or functional fragment thereof according to claim 14 or 24, wherein 1 to 5 amino acids are deleted from the amino terminus or carboxyl terminus of the heavy or light chain.

26. A pharmaceutical composition comprising an antibody or a functional fragment thereof according to claim 1 as an active ingredient.

27. The pharmaceutical composition according to claim 26, wherein the pharmaceutical composition is an anticancer agent.

28. The pharmaceutical composition according to claim 27, wherein the cancer is FGFR2-positive.

29. A composition for testing or diagnosis of cancer, comprising an antibody or a functional fragment thereof according to claim 1.

30. A composition comprising an antibody or a functional fragment thereof which has human FGFR2 IIIb selectivity, the antibody comprising a heavy chain comprising SEQ ID NO: 52, SEQ ID NO: 53, or SEQ ID NO: 54 and a light chain comprising SEQ ID NO: 61, SEQ ID NO: 62, or SEQ ID NO: 63 or a modified form of the antibody or functional fragment thereof, wherein the modified form of the antibody or functional fragment thereof comprising a heavy chain comprising SEQ ID NO: 52, SEQ ID NO: 53, or SEQ ID NO: 54 and a light chain comprising SEQ ID NO: 61, SEQ ID NO: 62, or SEQ ID NO: 63 comprises one or more modifications selected from the group consisting of defucosylation, reduced fucose, N-linked glycosylation, O-linked glycosylation, N-terminal processing, C-terminal processing, deamidation, isomerization of aspartic acid, oxidation of methionine, and amidation of a proline residue.

31. The composition according to claim 30, wherein the antibody comprises a heavy chain variable region having the amino acid sequence represented by SEQ ID NO: 12 and a light chain variable region having the amino acid sequence represented by SEQ ID NO: 21.

32. The composition according to claim 30, wherein the antibody is a chimeric antibody or a rat antibody.

33. The composition according to claim 30, wherein the composition is for detection or assay of human FGFR2 IIIb.

34. A reagent comprising an antibody or a functional fragment thereof according to claim 1.

35. The pharmaceutical composition according to claim 26, further comprising an additional drug.

36. The antibody or functional fragment thereof according claim 1, wherein the antibody or functional fragment is conjugated with an additional compound.

37. The pharmaceutical composition according to claim 36, wherein the pharmaceutical composition further comprises an additional drug.

38. The antibody or functional fragment thereof according to claim 1, wherein the CDRH3 comprises amino acids 118-126 of an amino acid sequence selected from the group consisting of SEQ ID NOs. 97, 89, 91, 95, and 83.

39. A modified form of an antibody or a functional fragment thereof according to claim 1, wherein the antibody or a functional fragment thereof comprises one or more modifications selected from the group consisting of N-linked glycosylation, O-linked glycosylation, N-terminal processing, C-terminal processing, deamidation, isomerization of aspartic acid, oxidation of methionine, and amidation of a proline residue.

40. A method for treating cancer in a subject in need thereof comprising, administering to the subject with cancer a therapeutically effective amount of the antibody or functional fragment of claim 38.

41. The method for treating cancer according to claim 40, wherein the cancer is FGFR2-positive.

42. The method for treating cancer according to claim 40, wherein the cancer is selected from the group consisting of breast cancer, pancreatic cancer, cervical cancer, non-small cell lung cancer, endometrial cancer, ovary cancer, lung cancer, stomach cancer, colorectal cancer, prostate cancer, and kidney cancer.

43. The method for treating cancer according to claim 42, wherein the cancer is stomach cancer.

44. The method for treating cancer according to claim 40, wherein the antibody or functional fragment is administered in a pharmaceutical composition.

45. The method for treating cancer according to claim 44, wherein the pharmaceutical composition comprises a pharmaceutically acceptable diluent, vehicle, solubilizer, emulsifier, preservative, or additive.

46. The method for treating cancer according to claim 44, wherein the pharmaceutical composition is administered by intravenous administration, intraarterial administration, intramuscular administration, intradermal administration, hypodermic administration, intraperitoneal administration, transdermal administration, intraosseous administration, or intraarticular administration.

* * * * *